US011085090B2

(12) United States Patent
Reddington et al.

(10) Patent No.: US 11,085,090 B2
(45) Date of Patent: Aug. 10, 2021

(54) DIAGNOSTIC METHOD FOR BACTERIAL ORGANISMS USING THE SMPB GENE

(71) Applicant: National University of Ireland, Galway, Galway (IE)

(72) Inventors: Kate Mary Reddington, Westport (IE); Nina Tuite, Newcastle (IE); Elizabeth Minogue, Whitegate (IE); Thomas Gerard Barry, Kinvara (IE)

(73) Assignee: National University of Ireland, Galway, Galway (IE)

( * ) Notice: Subject to any disclaimer, the term of this patent is extended or adjusted under 35 U.S.C. 154(b) by 276 days.

(21) Appl. No.: 15/576,176

(22) PCT Filed: May 23, 2016

(86) PCT No.: PCT/EP2016/061599
§ 371 (c)(1),
(2) Date: Nov. 21, 2017

(87) PCT Pub. No.: WO2016/188962
PCT Pub. Date: Dec. 1, 2016

(65) Prior Publication Data

US 2018/0155766 A1 Jun. 7, 2018

(30) Foreign Application Priority Data

May 22, 2015 (GB) ...................................... 1508860

(51) Int. Cl.
*C12Q 1/68* (2018.01)
*C12Q 1/689* (2018.01)

(52) U.S. Cl.
CPC ....... *C12Q 1/689* (2013.01); *C12Q 2600/156* (2013.01); *C12Q 2600/16* (2013.01)

(58) Field of Classification Search
None
See application file for complete search history.

(56) References Cited

FOREIGN PATENT DOCUMENTS

| | | |
|---|---|---|
| EP | 1227152 | 7/2002 |
| WO | 0070086 | 11/2000 |
| WO | 2005019249 | 3/2005 |
| WO | 2006110413 | 10/2006 |
| WO | 2007012131 | 2/2007 |
| WO | 2010003765 | 1/2010 |
| WO | 2016188962 | 12/2016 |

OTHER PUBLICATIONS

Moreira et al. (BMC Microbiology, 2012, 12:268, p. 1-14) (Year: 2012).*
O'Connor et al. (PNAS, 2011, vol. 108(36):: 14733-14740) (Year: 2011).*
Lowe et al. (Nucleic Acids Research, 1990, 18(7): 1757-1761) (Year: 1990).*
Holden et al. (Veterinary Microbiology, 2006, 109-116) (Year: 2006).*
Schroeder et al. (J of Bacteriology, 2010, vol. 192, No. 22; 192(22):6001-6016) (Year: 2010).*
Ansong et al. (PLoS One 2009, 4(3):e4809, p. 1-13) (Year: 2009).*
Mignard et al. (Int Journal of Systematic and Evolutionary Microbiol, 2009, 58, 1432-1441) (Year: 2009).*
Guidelines for the Prevention and Control of Infection from Water Systems in Healthcare Facilities, Health Protection Surveillance Centre, Prepared by the Prevention and Control of Infection from Water Systems in Healthcare Facilities Sub-Committee of the HPSC Scientific Advisory Committee, Aug. 12, 2015, 100 pages.
Acinas et al., Divergence and Redundancy of 16S rRNA Sequences in Genomes with Multiple rrn Operons, Journal of Bacteriology, vol. 186, No. 9, May 2004, pp. 2629-2635.
Adjemian et al., Prevalence of Nontuberculous Mycobacterial Lung Disease in U.S. Medicare Beneficiaries, American Journal of Respiratory and Critical Care Medicine, vol. 185, No. 8, Apr. 15, 2012, pp. 881-886.
Atkinson et al., Epidemiology, Clinical manifestations, Pathogenesis and Laboratory Detection of Mycoplasma Pneumoniae Infections, FEMS Microbiology Reviews, vol. 32, No. 6, Nov. 2008, pp. 956-973.
Baum et al., Mycoplasma Pneumoniae Pneumonia Revisited Within the German Competence Network for Community-acquired Pneumonia (CAPNETZ), BMC Infectious Diseases, vol. 9, No. 62, May 13, 2009, 10 pages.
Baumann, Isolation of Acinetobacter from Soil and Water, Journal of Bacteriology, vol. 96, No. 1, Jul. 1968, pp. 39-42.
Binks et al., Molecular Surveillance of True Nontypeable Haemophilus influenzae: An Evaluation of PCR Screening Assays, PLoS One, vol. 7, Issue 3, e34083, Molecular Detection of Haemophilus influenzae, Mar. 28, 2012, 8 pages.
Brosch et al., A New Evolutionary Scenario for the *Mycobacterium tuberculosis* Complex, Proceedings of the national academy of Sciences, vol. 99, No. 6, Mar. 2002, pp. 3684-3689.
Bruin et al., Identification of Haemophilus Influenzae and Haemophilus Haemolyticus by Matrix-assisted Laser Desorption Ionization-Time of Flight Mass Spectrometry, European Journal of Clinical Microbiology & Infectious Diseases, vol. 33, Issue 2, Feb. 2014, pp. 279-284.
Cassidy et al., Nontuberculous Mycobacterial Disease Prevalence and Risk Factors: A Changing Epidemiology, Clinical Infectious Diseases, vol. 49, Issue 12, Dec. 15, 2009, pp. e124-e129.
Cherry, Computer manipulation of DNA and protein sequences, Current Protocols in Molecular Biology, Chapter 7:Unit7.7, Supplement 30, 1995, pp. 7.7.1-7.7.23.

(Continued)

*Primary Examiner* — Stephanie K Mummert
(74) *Attorney, Agent, or Firm* — Kilpatrick Townsend & Stockton LLP

(57) ABSTRACT

A method for determining the presence or absence of a member of a group of bacterial organisms in a sample, wherein the method comprises determining whether a target region of the smpB gene is present in said sample is provided. Primers, probes and kits for use in these methods also form part of the invention, as does the use of an smpB gene target region to detect the presence or absence of a member of a group of bacterial organisms in a sample, in a range of clinical and non-clinical applications.

19 Claims, 83 Drawing Sheets

Specification includes a Sequence Listing.

(56) References Cited

OTHER PUBLICATIONS

Couturier et al., Identification of HACEK Clinical Isolates by Matrix-Assisted Laser Desorption Ionization-Time of Flight Mass Spectrometry, Journal of Clinical Microbiology, vol. 49, No. 3, Mar. 2011, pp. 1104-1106.
Covert et al., Occurrence of Nontuberculous Mycobacteria in Environmental Samples, Applied and Environmental Microbiology, vol. 65, No. 6, Jun. 1999, pp. 2492-2496.
Crago et al., Surveillance and Molecular Characterization of Nontuberculous Mycobacteria in a Hospital Water Distribution System Over a Three-year Period, Journal of Hospital Infection, vol. 87, Issue 1, May 2014, pp. 59-62.
Cunha, The Atypical Pneumonias: Clinical Diagnosis and Importance, Clinical Microbiology and Infection, Suppl 3, May 2006, pp. 12-24.
Daxboeck et al., Laboratory Diagnosis of Mycoplasma Pneumoniae Infection, Clinical Microbiology and Infection, vol. 9, No. 4, Apr. 2003, pp. 263-273.
Dille et al., Amplification of Chlamydia trachomatis Dna by Ligase Chain Reaction, Journal of Clinical Microbiology, vol. 31, No. 3, Mar. 1993, pp. 729-731.
Dulebohn et al., Role of Conserved Surface Amino Acids in Binding of SmpB Protein to SsrA RNA*, Journal of Biological Chemistry, vol. 281, No. 39, Sep. 29, 2006, pp. 28536-28545.
Enne et al., A High Prevalence of Antimicrobial Resistant *Escherichia coli* Isolated From Pigs and a Low Prevalence of Antimicrobial Resistant *E. coli* from Cattle and Sheep in Great Britain at Slaughter, FEMS Microbiology Letters, vol. 278, Issue 2, Jan. 1, 2008, pp. 193-199.
EUCAST, European Committee on Antimicrobial Susceptibility Testing, Breakpoint tables for interpretation of MICs and zone diameters Version 4.0, Available on internet at: http://www.eucast.org, Jan. 1, 2014, 80 pages.
Falkinham, Surrounded by Mycobacteria: Nontuberculous Mycobacteria in the Human Environment, Journal of Applied Microbiology, vol. 107, No. 2, Aug. 2009, pp. 356-367.
Fleischmann et al., Whole-Genome Random Sequencing and Assembly of Haemophilus Influenzae Rd, Science, Research Articles, vol. 269, Issue 5223, Jul. 28, 1995, pp. 496-512.
Flint et al., The RD1 virulence locus of *Mycobacterium tuberculosis* regulates DNA transfer in *Mycobacterium smegmatis*, Proceedings of the National Academy of Sciences of the United States of America, vol. 101, Issue 34, Aug. 24, 2004, pp. 12598-12603.
Unite Kingdom Application No. 1508860.2, Search Report dated Feb. 23, 2016, 2 pages.
Gil et al., Determination of the Core of a Minimal Bacterial Gene Set, Microbiol Mol Biol Rev., vol. 68, No. 3, Sep. 2004, pp. 518-537.
Griffith et al., An Official ATS/IDSA Statement: Diagnosis, Treatment, and Prevention of Nontuberculous Mycobacterial Diseases, American Thoracic Society Documents, American Journal of Respiratory and Critical Care Medicine, vol. 175, No. 4, Feb. 15, 2007, pp. 367-416.
Halse et al., Combined Real-Time PCR and rpoB Gene Pyrosequencing for Rapid Identification of *Mycobacterium tuberculosis* and Determination of Rifampin Resistance Directly in Clinical Specimens, Journal of Clinical Microbiology, vol. 48, No. 4, Apr. 2010, pp. 1182-1188.
Hidalgo et al., Characterization and Epidemiological Relationships of Spanish Brachyspira Hyodysenteriae Field Isolates, Epidemiol Infect, vol. 138, No. 1, Jan. 2010, pp. 76-85.
Hoefsloot et al., Prevalence of Nontuberculous Mycobacteria in COPD Patients with Exacerbations, J Infect. , vol. 66, No. 6, Jun. 2013, pp. 542-545.
Hoefsloot et al., The Geographic Diversity of Nontuberculous Mycobacteria Isolated From Pulmonary Samples, Eur. Respir J. vol. 42, No. 6, Original Article Respiratory Infections, Dec. 2013, pp. 1604-1613.
Holden et al., SmpB: A Novel Outer Membrane Protein Present in Some Brachyspira Hyodysenteriae Strains, Vet Microbiol. , vol. 113, No. (1-2), Mar. 10, 2006, pp. 109-116.
Hoorfar et al., Practical Considerations in Design of Internal Amplification Controls for Diagnostic PCR Assays, J Clin. Microbiol. vol. 42, No. 5, May 2004, pp. 1863-1868.
Huang et al., Non-tuberculous Mycobacterium Infection After Lung Transplantation is Associated with Increased Mortality, J Heart Lung Transplant., vol. 30, No. 7, Jul. 2011, pp. 790-798.
Huard et al., PCR-Based Method to Differentiate the Subspecies of the *Mycobacterium tuberculosis* Complex on the Basis of Genomic Deletions, Journal of Clinical Microbiology, vol. 41, No. 4, Apr. 2003, pp. 1637-1650.
Hussein et al., Detection of Non-tuberculous Mycobacteria in Hospital Water by Culture and Molecular Methods, International Journal of Medical Microbiology, vol. 299, No. 4, Apr. 2009, pp. 281-290.
Ingen et al., Clinical Relevance of Non-Tuberculous Mycobacteria Isolated in The Nijmegen-Arnhem Region, The Netherlands, Thorax, vol. 64, No. 6, Jun. 2009, pp. 502-506.
Janda et al., 16S rRNA Gene Sequencing for Bacterial Identification in the Diagnostic Laboratory: Pluses, Perils, and Pitfalls, Journal of Clinical Microbiology, vol. 45, No. 9, Sep. 2007, pp. 2761-2764.
Karzai et al., SmpB,A Unique RNA-binding Protein Essential for the Peptide-tagging Activity of SsrA (tmRNA), EMBO J. vol. 18, No. 13, Jul. 1, 1999, pp. 3793-3799.
Karzai et al., The SsrA—SmpB System for Protein Tagging, Directed Degradation and Ribosome Rescue, nature structural biology, vol. 7 , No. 6, Jun. 2000, pp. 449-455.
Kiers et al., Transmission of *Mycobacterium pinnipedii* to Humans in a Zoo with Marine Mammals, Int J Tuberc Lung Dis, vol. 12, No. 12, Dec. 2008, pp. 1469-1473.
Kilian , A Taxonomic Study of the Genus Haemophilus, with the Proposal of a New Species, Journal of General Microbiology , vol. 93, No. 1, Mar. 1976, pp. 9-62.
Lipuma, The Changing Microbial Epidemiology in Cystic Fibrosis, Clinical Microbiology Reviews, vol. 23, No. 2, Apr. 2010, pp. 299-323.
Livni et al., Outbreak of *Mycobacterium mucogenicum* Bacteraemia Due to Contaminated Water Supply in a Paediatric Haematologyeoncology Department, Journal of Hospital Infection, vol. 70, Issue 3, Nov. 2008, pp. 253-258.
Maaroufi et al., Real-Time PCR for Determining Capsular Serotypes of Haemophilus influenzae, Journal of Clinical Microbiology, vol. 45, No. 7, Jul. 2007, pp. 2305-2308.
Marras et al., Epidemiology of Human Pulmonary Infection with Nontuberculous Mycobacteria, Clinics in Chest Medicine 23, vol. 23, No. 3, Sep. 2002, pp. 553-567.
Marras et al., Pulmonary Nontuberculous Mycobacterial Disease, Ontario, Canada, 1998-2010, Emerging Infectious Diseases, vol. 19, No. 11, Nov. 2013, pp. 1889-1891.
McCrea et al., Relationships of Nontypeable Haemophilus Influenzae Strains to Hemolytic and Nonhemolytic Haemophilus Haemolyticus Strains, Journal of Clinical Microbiology, vol. 46, No. 2, Feb. 2008, pp. 406-416.
McDade et al., Legionnaires' Disease: Isolation of a Bacterium and Demonstration of Its Role in Other Respiratory Disease, The New England Journal of Medicine, vol. 297, No. 22, Dec. 1, 1977, pp. 1197-1203.
Meyler et al., Development of a Diagnostic Real-time Polymerase Chain Reaction Assay for the Detection of Invasive Haemophilus Influenzae in Clinical Samples, Diagnostic Microbiology and Infectious Disease, vol. 74, No. 4, Dec. 1, 2012, pp. 356-362.
Mignard et al., A Seven-gene, Multilocus, Genus-wide Approach to the Phylogeny of Mycobacteria Using Supertrees, International Journal of Systematic and Evolutionary Microbiology, vol. 58, No. Pt 6, Jun. 2008, pp. 1432-1441.
Millan et al., β-Lactam Resistance in Haemophilus Parasuis is Mediated by Plasmid pB1000 Bearing blaROB-1, Antimicrobial Agents and Chemotherapy, vol. 51, No. 6, Jun. 2007, pp. 2260-2264.

(56) References Cited

OTHER PUBLICATIONS

Moore et al., Increasing Reports of Non-Tuberculous Mycobacteria in England, Wales and Northern Ireland, 1995-2006, BMC Public Health, vol. 10, No. 612, Oct. 15, 2010, pp. 1-6.

Nallur et al., Signal Amplification by Rolling Circle Amplification on Dna Microarrays, Nucleic Acids Res., vol. 29, Issue 23, Dec. 1, 2001, pp. 1-9.

O' Grady et al., Rapid Real-time PCR Detection of Food Samples Based on the ssrA Gene, A Novel Diagnostic Target Listeria Monocytogenes in Enriched, Food Microbiology, vol. 25, No. 1, Feb. 2008, pp. 75-84.

Perez et al., Global Challenge of Multidrug-Resistant Acinetobacter Baumannii, Antimicrobial Agents and Chemotherapy, vol. 51, No. 10, Oct. 2007, pp. 3471-3484.

Phelippeau et al., Prevalence of Mycobacterium Lentiflavum in Cystic Fibrosis Patients, France, BMC Pulmonary Medicine, vol. 15, No. 131, Oct. 26, 2015, 5 pages.

Qin et al., The Highly Conserved LepA Is a Ribosomal Elongation Factor that Back-Translocates the Ribosome, Cell, vol. 127, No. 4, Nov. 17, 2006, pp. 721-733.

Reddington et al., Comparison of Established Diagnostic Methodologies and a Novel Bacterial smpB Real-Time PCR Assay for Specific Detection of Haemophilus Influenzae Isolates Associated with Respiratory Tract Infections., Journal of Clinical Microbiology, vol. 53, No. 9, Sep. 2015, pp. 2854-2860.

Reddington et al., Novel Multiplex Real-Time PCR Diagnostic Assay for Identification and Differentiation of *Mycobacterium tuberculosis, Mycobacterium canettii*, and *Mycobacterium tuberculosis* Complex Strains, Journal of Clinical Microbiology, vol. 49, No. 2, Feb. 2011, pp. 651-657.

Ridderberg et al., Haemophilus Influenzae May Be Untypable by the Multilocus Sequence Typing Scheme Due to a Complete Deletion of the Fucose Operon, J Med Microbiol., vol. 59, No. Pt 6, Jun. 2010, pp. 740-742.

Rodríguez et al., A Molecular Beacon-based Real-time Nasba Assay for Detection of *Mycobacterium avium* Subsp. Paratuberculosis in Water and Milk, FEMS Microbiology Letters, vol. 237, No. 1, Aug. 1, 2004, pp. 119-126.

Scheler et al., Fluorescent Labeling of Nasba Amplified Tmrna Molecules for Microarray Applications, BMC Biotechnology, vol. 9, No. 45, May 15, 2009, 6 pages.

Schönhuber et al., Utilization of tmRNA Sequences for Bacterial Identification, BMC Microbiology, vol. 1, No. 20, Sep. 7, 2001, 8 pages.

Seng et al., Ongoing Revolution in Bacteriology: Routine Identification of Bacteria by Matrix-Assisted Laser Desorption Ionization Time-of-Flight Mass Spectrometry, Clinical Infectious Diseases, vol. 49, No. 4, Aug. 15, 2009, pp. 543-551.

Shin et al., Prevalence of Non-tuberculous Mycobacteria in a Hospital Environment, Journal of Hospital Infection, vol. 65, No. 2, Feb. 2007, pp. 143-148.

Smith et al., Comparison of Biosequences, Advances in Applied Mathematics, vol. 2, Issue 4, Dec. 1981, pp. 482-489.

Theodore et al., Evaluation of New Biomarker Genes for Differentiating Haemophilus Influenzae from Haemophilus Haemolyticus, Journal of Clinical Microbiology, vol. 50, No. 4, Apr. 2012, pp. 1422-1424.

Tortoli et al., Evaluation of a Commercial Ligase Chain Reaction Kit (Abbott LCx) for Direct Detection of *Mycobacterium tuberculosis* in Pulmonary and Extrapulmonary Specimens, Journal of Clinical Microbiology, vol. 35, No. 9, Sep. 1997, pp. 2424-2426.

Vetrovsky et al., The Variability of the 16S rRNA Gene in Bacterial Genomes and Its Consequences for Bacterial Community Analyses, PLoS One, vol. 8, No. 2, e57923, Feb. 2013, 10 pages.

Voelkerding et al., Next-Generation Sequencing: From Basic Research to Diagnostics, Clinical Chemistry, vol. 55, Issue 4, Feb. 2009, pp. 641-658.

Wang et al., Detection of Bacterial Pathogens in Mongolia Meningitis Surveillance With a New Real-time PCR Assay to Detect Haemophilus Influenzae, International Journal of Medical Microbiology, vol. 301, No. 4, Apr. 2011, pp. 303-309.

Werf et al., Inventory Study of Non-tuberculous Mycobacteria in the European Union, BMC Infectious Diseases, vol. 14, No. 62, Feb. 6, 2014, 9 pages.

Yun et al., Genomic DNA Functions as a Universal External Standard in Quantitative Real-time PCR, Nucleic Acids Research, vol. 34, No. 12, e85, Jul. 13, 2006, 10 pages.

Zhu et al., MALDI-TOF MS Distinctly Differentiates Nontypable Haemophilus Influenzae from Haemophilus Haemolyticus, PLoS One, vol. 8, No. 2,e56139, Feb. 2013, 7 pages.

International Search Report and Written Opinion for PCT/EP2016/061599 dated Aug. 26, 2016.

Jacob et al.; 2005 *Journal of Biological Chemistry* 280(7):5503-5509.

* cited by examiner

Amplification Curves

FIG. 1(contd.)
Amplification Curves
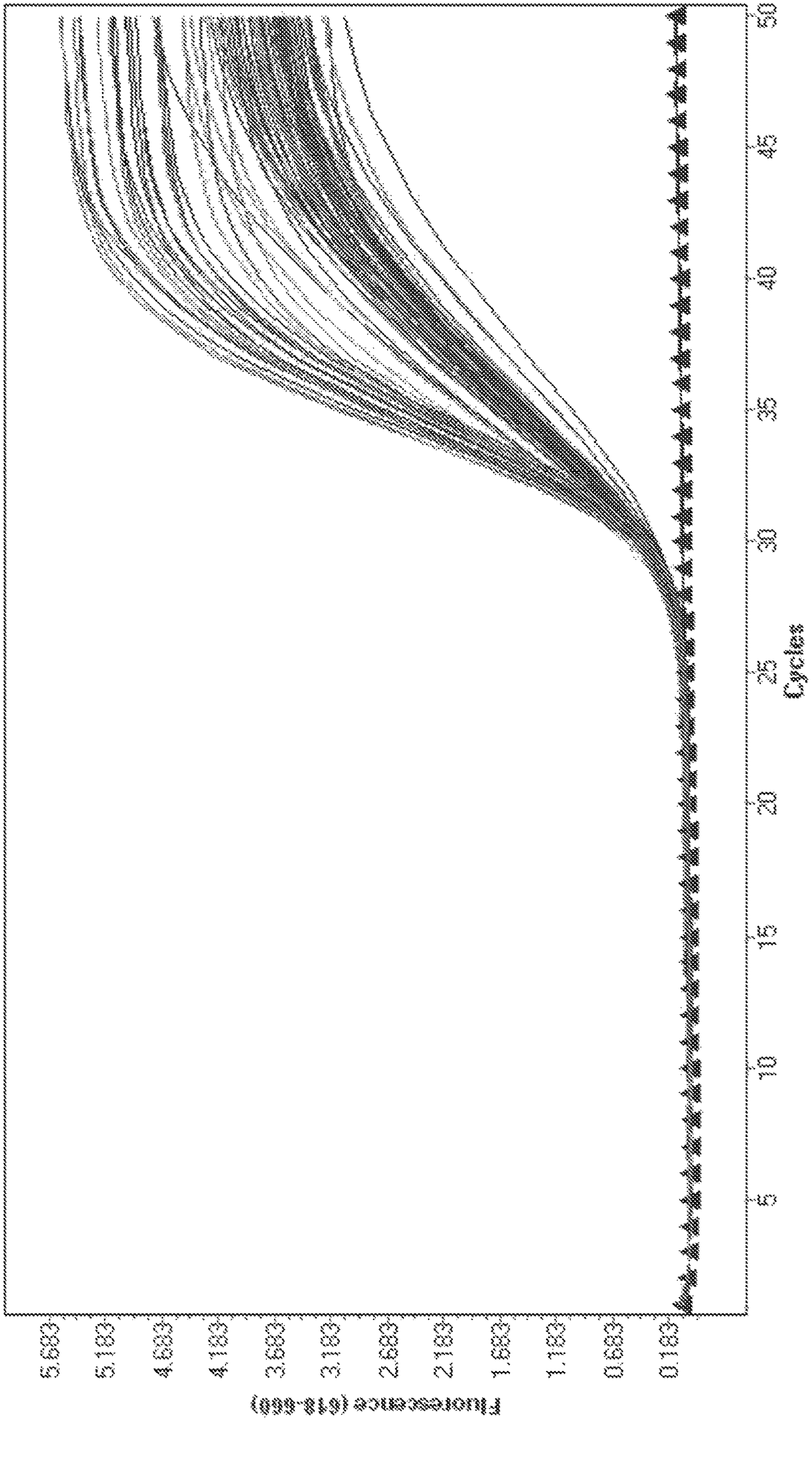

FIG. 2A

```
SEQ ID
NO:
 44 L.pneumophila_Paris   ATGACTACCAAAAAACAACCAGATTCCACCATAGCCTTGAATAGAAAAGCTGGTTTTGAT 60
 45 L.pneumophila_Corby   ATGACTACCAAAAAACAACCAGATTCCACCATAGCCTTGAATAGAAAAGCTGGTTTTGAT 60
 46 L.pneumophila_Pneu    ATGACTACCAAAAAACAACCAGATTCCACCATAGCCTTGAATAGAAAAGCTGGTTTTGAT 60
 47 L.pneumophila_Lens    ATGACTACCAAAAAACAACCAGATTCCACCATAGCTTTGAATAGAAAAGCTGGTTTTGAT 60
 48 L.pneumophila_Alcoy   ATGACTACCAAAAAACAACCAGATTCCACCATAGCCTTGAATAGAAAAGCTGGTTTTGAT 60
 49 L.pneumophila_2868    ATGACTACCAAAAAACAACCAGATTCCACCATAGCCTTGAATAGAAAAGCTGGTTTTGAT 60
 50 L.pneumophila_3140    ATGACTACCAAAAAACAACCAGATTCAACCATAGCTTTGAATAGAAAAGCTGGTTTTGAT 60
 51 L.pneumophila_3194    ATGACTACCAAAAAACAACCAGATTCCACCATAGCCTTGAATAGAAAAGCTGGTTTTGAT 60
 52 L.pneumophila_00189   ATGACTACCAAAAAACAACCAGATTCCACCATAGCCTTGAATAGAAAAGCTGGTTTTGAT 60
 53 L.pneumophila_2829    ATGACTACCAAAAAACAACCAGATTCCACCATAGCCTTGAATAGAAAAGCTGGTTTTGAT 60
                          ************************* ********* ************************

SEQ ID
NO:
 44 L.pneumophila_Paris   TATTTTATTGAAGATCAATACGAAGCAGGCCTGGTTTTGGAGGGCTGGGAAGTAAAAAGT 120
 45 L.pneumophila_Corby   TACTTTATTGAAGATCAATACGAAGCAGGCCTGGTTTTGGAAGGCTGGGAAGTAAAAAGT 120
 46 L.pneumophila_Pneu    TACTTTATTGAAGATCAATACGAAGCAGGCCTGGTTTTGGAAGGCTGGGAAGTAAAAAGT 120
 47 L.pneumophila_Lens    TACTTTATTGAAGATCAATACGAAGCAGGCCTGGTTTTGGAAGGCTGGGAAGTAAAAAGT 120
 48 L.pneumophila_Alcoy   TACTTTATTGAAGATCAATACGAAGCAGGCCTGGTTTTGGAAGGCTGGGAAGTAAAAAGT 120
 49 L.pneumophila_2868    TACTTTATTGAAGATCAATACGAAGCAGGCCTGGTTTTGGAAGGCTGGGAAGTAAAAAGT 120
 50 L.pneumophila_3140    TACTTTATTGAAGATCAATACGAAGCAGGCCTGGTTTTGGAAGGCTGGGAAGTAAAAAGT 120
 51 L.pneumophila_3194    TACTTTATTGAAGATCAATACGAAGCAGGCCTGGTTTTGGAAGGCTGGGAAGTAAAAAGT 120
 52 L.pneumophila_00189   TACTTTATTGAAGATCAATACGAAGCAGGCCTGGTTTTGGAAGGCTGGGAAGTAAAAAGT 120
 53 L.pneumophila_2829    TACTTTATTGAAGATCAATACGAAGCAGGCCTGGTTTTGGAAGGCTGGGAAGTAAAAAGT 120
                          ** ************************************** ******************
```

FIG. 2A(contd.)

```
SEQ ID
NO:
  44 L.pneumophila_Paris   CTGCGTGCTGGGAAAATCAATTTGTCGGATTCACACGTGATAATCAAATACGGTGAGGCA 180
  45 L.pneumophila_Corby   CTGCGTGCTGGAAAAATCAATTTGTCGGATTCACACGTGATAATCAAATACGGTGAGGCA 180
  46 L.pneumophila_Pneu    CTGCGTGCTGGAAAAATCAATTTGTCGGATTCACACGTGATAATCAAATACGGTGAGGCA 180
  47 L.pneumophila_Lens    CTGCGTGCTGGAAAAATCAATTTGTCGGATTCACACGTGATAATCAAATACGGTGAGGCA 180
  48 L.pneumophila_Alcoy   CTGCGTGCTGGAAAAATCAATTTGTCGGATTCACACGTGATAATCAAATACGGTGAGGCA 180
  49 L.pneumophila_2868    CTGCGTGCTGGAAAAATCAATTTGTCGGATTCACACGTGATAATCAAATACGGTGAGGCA 180
  50 L.pneumophila_3140    CTGCGTGCTGGAAAAATCAATTTGTCGGATTCACACGTGATAATCAAATACGGTGAGGCA 180
  51 L.pneumophila_3194    CTGCGTGCTGGAAAAATCAATTTGTCGGATTCACACGTGATAATCAAATACGGTGAGGCA 180
  52 L.pneumophila_00189   CTGCGTGCTGGAAAAATCAATTTGTCGGATTCACACGTGATAATCAAATACGGTGAGGCA 180
  53 L.pneumophila_2829    CTGCGTGCTGGAAAAATCAATTTGTCGGATTCACACGTGATAATCAAATACGGTGAGGCA 180
                           *********** ************************************************
SEQ ID
NO:
  44 L.pneumophila_Paris   TTCCTATTGGGCGCCCAAATACAGCCTCTTCCCACCGCATCCACTCATTTTATTCCTGAT 240
  45 L.pneumophila_Corby   TTCCTATTGGGCGCCCAAATACAGCCGCTTCCCACCGCATCCACTCATTTTATTCCTGAT 240
  46 L.pneumophila_Pneu    TTCCTATTGGGCGCCCAAATACAGCCTCTTCCCACCGCATCCACTCATTTTATTCCTGAT 240
  47 L.pneumophila_Lens    TTCCTATTGGGCGCCCAAATACAGCCTCTTCCAACCGCATCCACTCATTTTATTCCTGAT 240
  48 L.pneumophila_Alcoy   TTCCTATTGGGCGCCCAAATACAGCCGCTTCCCACCGCATCCACTCATTTTATTCCTGAT 240
  49 L.pneumophila_2868    TTCCTATTGGGCGCCCAAATACAGCCTCTTCCCACCGCATCCACTCATTTTATTCCTGAT 240
  50 L.pneumophila_3140    TTCCTATTGGGCGCCCAAATACAGCCTCTTCCCACCGCATCCACTCATTTTATTCCTGAT 240
  51 L.pneumophila_3194    TTCCTATTGGGCGCCCAAATACAGCCTCTTCCCACCGCATCCACTCATTTTATTCCTGAT 240
  52 L.pneumophila_00189   TTCCTATTGGGCGCCCAAATACAGCCTCTTCCCACCGCATCCACTCATTTTATTCCTGAT 240
  53 L.pneumophila_2829    TTCCTATTGGGCGCCCAAATACAGCCTCTTCCCACCGCATCCACTCATTTTATTCCTGAT 240
                           ************************** ***** ***************************
```

| SEQ ID NO: | | | |
|---|---|---|---|
| 44 | L.pneumophila_Paris | CCGGTCAGGACGCGCAAGCTATTGATGAATAAAAAAGAATTAAACCATCTCATTGGAAGT | 300 |
| 45 | L.pneumophila_Corby | CCGATCAGGACGCGCAAGCTATTGATGAATAAAAAAGAATTAAACCATCTCATAGGAAGT | 300 |
| 46 | L.pneumophila_Pneu | CCGATCAGGACGCGCAAGCTATTGATGAATAAAAAAGAATTAAACCATCTCATAGGAAGT | 300 |
| 47 | L.pneumophila_Lens | CCGGTCAGGACGCGCAAGCTATTGATGAATAAAAAAGAATTAAACCATCTCATTGGAAGT | 300 |
| 48 | L.pneumophila_Alcoy | CCGATCAGGACGCGCAAGCTATTGATGAATAAAAAAGAATTAAACCATCTCATAGGAAGT | 300 |
| 49 | L.pneumophila_2868 | CCGATCAGGACGCGCAAGCTATTGATGAATAAAAAAGAATTAAACCATCTCATAGGAAGT | 300 |
| 50 | L.pneumophila_3140 | CCGGTCAGGACGCGCAAGCTATTGATGAATAAAAAAGAATTAAACCATCTCATAGGAAGT | 300 |
| 51 | L.pneumophila_3194 | CCGCTGAGGACGCGCAAGCTATTGATGAATAAAAGAGAATTAAACCATCTCATAGGAAGT | 300 |
| 52 | L.pneumophila_00189 | CCGATCAGGACGCGCAAGCTATTGATGAATAAAAAAGAATTAAACCATCTCATAGGAAGT | 300 |
| 53 | L.pneumophila_2829 | CCGATCAGGACGCGCAAGCTATTGATGAATAAAAAAGAATTAAACCATCTCATAGGAAGT | 300 |
| | | *** * **************************** ****************** ****** | |

```
SEQ ID
NO:
  44 L.pneumophila_Paris   GTTGAAAGGCAAGGCTATACCATAGTCCCTCTTTCTTTGTATTGGAAAAAAAATAAAATT 360
  45 L.pneumophila_Corby   GTTGAAAGGCAAGGCTATACCATAGTCCCTCTTTCTTTGTATTGGAAAAAAAATAAAATT 360
  46 L.pneumophila_Pneu    GTTGAAAGGCAAGGCTATACCATAGTCCCTCTTTCTTTGTATTGGAAAAAAAATAAAATT 360
  47 L.pneumophila_Lens    GTTGAAAGGCAAGGCTATACCATAGTCCCTCTTTCTTTGTATTGGAAAAAAAATAAAATT 360
  48 L.pneumophila_Alcoy   GTTGAAAGGCAAGGCTATACCATAGTCCCTCTTTCTTTGTATTGGAAAAAAAATAAAATT 360
  49 L.pneumophila_2868    GTTGAAAGGCAAGGCTATACCATAGTCCCTCTTTCTTTGTATTGGAAAAAAAATAAAATT 360
  50 L.pneumophila_3140    GTTGAAAGGCAAGGCTATACCATAGTCCCTCTTTCTTTGTATTGGAAAAAAAATAAAATT 360
  51 L.pneumophila_3194    GTTGAAAGGCAAGGCTATACCATAGTCCCTCTTTCTTTGTATTGGAAAAAAAATAAAATT 360
  52 L.pneumophila_00189   GTTGAAAGGCAAGGCTATACCATAGTCCCTCTTTCTTTGTATTGGAAAAAAAATAAAATT 360
  53 L.pneumophila_2829    GTTGAAAGGCAAGGCTATACCATAGTCCCTCTTTCTTTGTATTGGAAAAAAAATAAAATT 360
                           ************************************************************
SEQ ID
NO:
  44 L.pneumophila_Paris   AAAATAAAAATTGCTCTGGCCAAAGGAAAAAAAGAGCATGACAAAAGAGACACGATCAAA 420
  45 L.pneumophila_Corby   AAAATAAAAATTGCTCTGGCCAAAGGAAAAAAAGAGCATGACAAAAGAGACACGATCAAA 420
  46 L.pneumophila_Pneu    AAAATAAAAATTGCTCTGGCTAAAGGAAAAAAAGAGCA---------------------- 398
  47 L.pneumophila_Lens    AAAATAAAAATTGCTCTGGCCAAAGGAAAAAAAGAGCATGACAAAAGAGACACGATCAAA 420
  48 L.pneumophila_Alcoy   AAAATAAAAATTGCTCTGGCCAAAGGAAAAAAAGAGCATGACAAAAGAGACACGATCAAA 420
  49 L.pneumophila_2868    AAAATAAAAATTGCTCTGGCTAAAGGAAAAAAAGAGCATGACAAAAGAGACACGATCAAA 420
  50 L.pneumophila_3140    AAAATAAAAATTGCTCTGGCCAAAGGAAAAAAAGAGCATGACAAAAGAGACACGATCAAA 420
  51 L.pneumophila_3194    AAAATAAAAATTGCTCTGGCCAAAGGAAAAAAAGAGCATGACAAAAGAGACACGATCAAA 420
  52 L.pneumophila_00189   AAAATAAAAATTGCTCTGGCTAAAGGAAAAAAAGAGCATGACAAAAGAGACACGATCAAA 420
  53 L.pneumophila_2829    AAAATAAAAATTGCTCTGGCTAAAGGAAAAAAAGAGCATGACAAAAGAGACACGATCAAA 420
                           ******************** *****************
```

| SEQ ID NO: | | | |
|---|---|---|---|
| 44 | L.pneumophila_Paris | GACAGAGAATGGCAAAGAGATCGTTCAAGAATAATGAAAAAGAACACTTGA | 471 |
| 45 | L.pneumophila_Corby | GACAGAGAATGGCAAAGGGATCGTTCAAGAATAATGAAAAAGAACACTTGA | 471 |
| 46 | L.pneumophila_Pneu | --------------------------------------------------- | |
| 47 | L.pneumophila_Lens | GACAGAGAATGGCAAAGAGATCGTTCAAGAATAATGAAAAAGAACACTTGA | 471 |
| 48 | L.pneumophila_Alcoy | GACAGAGAATGGCAAAGGGATCGTTCAAGAATAATGAAAAAGAACACTTGA | 471 |
| 49 | L.pneumophila_2868 | GACAGAGAATGGCAAAGGGATCGTTCAAGAATAATGAAAAAGAACACTTGA | 471 |
| 50 | L.pneumophila_3140 | GACAGAGAATGGCAAAGGGATCGTTCAAGAATAATGAAAAAGAACACTTGA | 471 |
| 51 | L.pneumophila_3194 | GACAGAGAATGGCAAAGGGATCGTTCAAGAATAATGAAAAAGAACACTTGA | 471 |
| 52 | L.pneumophila_00189 | GACAGAGAATGGCAAAGGGATCGTTCAAGAATAATGAAAAAGAACACTTGA | 471 |
| 53 | L.pneumophila_2829 | GACAGAGAATGGCAAAGGGATCGTTCAAGAATAATGAAAAAGAACACTTGA | 471 |

```
SEQ ID
NO:
  54 L.pneumophila_NCTC11986  GATCAATACGAAGCAGGCCTGGTTTTGGAGGGCTGGGAAGTAAAAAGTCT 50
  55 L.pneumophila_NCTC12000  GATCAATACGAAGCAGGCCTGGTTTTGGAAGGCTGGGAAGTAAAAAGTCT 50
  56 L.pneumophila_NCTC12179  GATCAATACGAAGCAGGCCTGGTTTTGGAAGGCTGGGAAGTAAAAAGTCT 50
  57 L.pneumophila_DSM7513    GATCAATACGAAGCAGGCCTGGTTTTGGAAGGCTGGGAAGTAAAAAGTCT 50
  58 L.pneumophilaDSM7514     GATCAATACGAAGCAGGCTTGGTTTTGGAAGGCTGGGAAGTAAAAAGTCT 50
  59 L.pneumophilaDSM7515     GATCAATACGAAGCAGGCTTGGTTTTGGAAGGCTGGGAAGTAAAAAGTCT 50
  60 L.pneumophila_NCTC11191  GATCAATACGAAGCAGGCCTGGTTTTGGAAGGCTGGGAAGTAAAAAGTCT 50
  61 L.pneumophila_NCTC11230  GATCAATACGAAGCAGGCCTGGTTTTGGAAGGCTGGGAAGTAAAAAGTCT 50
  62 L.pneumophila_NCTC11232  GATCAATACGAAGCAGGCCTGGTTTTGGAAGGCTGGGAAGTAAAAAGTCT 50
  63 L.pneumophila_NCTC11287  GATCAATACGAAGCAGGCCTGGTTTTGGAAGGCTGGGAAGTAAAAAGTCT 50
  64 L.pneumophila_NCTC11984  GATCAATACGAAGCAGGCCTGGTTTTGGAAGGCTGGGAAGTAAAAAGTCT 50
  65 L.pneumophila_NCTC11985  GATCAATACGAAGCAGGCCTGGTTTTGGAAGGCTGGGAAGTAAAAAGTCT 50
                              ****************** ********** ********************
```

FIG. 3A(contd.)

```
SEQ ID
NO:
  54 L.pneumophila_NCTC11986  GCGTGCTGGGAAAATCAATTTGTCGGATTCACACGTGATAATCAAATACG 100
  55 L.pneumophila_NCTC12000  GCGTGCTGGAAAAATCAATTTGTCGGATTCACACGTGATAATCAAATACG 100
  56 L.pneumophila_NCTC12179  GCGTGCTGGAAAAATCAATTTGTCGGATTCACACGTGATAATCAAATACG 100
  57 L.pneumophila_DSM7513    GCGTGCTGGAAAAATCAATTTGTCGGATTCACACGTGATAATCAAATACG 100
  58 L.pneumophilaDSM7514     GCGGGCAGGAAAAATCAATTTGTCAGATGCACACGTGATAATCAAATACG 100
  59 L.pneumophilaDSM7515     GCGTGCAGGAAAAATCAATTTGTCGGATGCACACGTGATAATAAAATACG 100
  60 L.pneumophila_NCTC11191  GCGTGCTGGGAAAATCAATTTGTCGGATTCACACGTGATAATCAAATACG 100
  61 L.pneumophila_NCTC11230  GCGTGCTGGAAAAATCAATTTGTCGGATTCACACGTGATAATCAAATACG 100
  62 L.pneumophila_NCTC11232  GCGTGCTGGAAAAATCAATTTGTCGGATTCACACGTGATAATCAAATACG 100
  63 L.pneumophila_NCTC11287  GCGTGCTGGAAAAATCAATTTGTCGGATTCACACGTGATAATCAAATACG 100
  64 L.pneumophila_NCTC11984  GCGTGCTGGAAAAATCAATTTGTCGGATTCACACGTGATAATCAAATACG 100
  65 L.pneumophila_NCTC11985  GCGTGCTGGAAAAATCAATTTGTCGGATTCACACGTGATAATCAAATACG 100
                              *** ** ** ************** *** ************* *******
```

FIG. 3A(contd.)

```
SEQ ID
NO:
   54 L.pneumophila_NCTC11986  GTGAGGCATTCCTATTGGGCGCCCAAATACAGCCTCTTCCCACCGCATCC 150
   55 L.pneumophila_NCTC12000  GTGAGGCATTCCTATTGGGCGCCCAAATACAGCCGCTTCCCACCGCATCC 150
   56 L.pneumophila_NCTC12179  GTGAGGCATTCCTATTGGGCGCCCAAATACAGCCTCTTCCCACCGCATCC 150
   57 L.pneumophila_DSM7513    GTGAGGCATTCCTATTGGGCGCCCAAATACAGCCTCTTCCCACCGCATCC 150
   58 L.pneumophilaDSM7514     GTGAGGCATTCCTGTTAGGAGCTCAAATACAGCCTCTTCCTACTGCATCC 150
   59 L.pneumophilaDSM7515     GTGAGGCATTCCTGTTAGGAGCCCAAATACAGCCTCTTCCTACTGCATCC 150
   60 L.pneumophila_NCTC11191  GTGAAGCATTCCTATTGGGCGCCCAAATACAGCCTCTTCCCACCGCATCC 150
   61 L.pneumophila_NCTC11230  GTGAGGCATTCCTATTGGGCGCCCAAATACAGCCTCTTCCCACCGCATCC 150
   62 L.pneumophila_NCTC11232  GTGAGGCATTCCTATTGGGCGCCCAAATACAGCCTCTTCCCACCGCATCC 150
   63 L.pneumophila_NCTC11287  GTGAGGCATTCCTATTGGGCGCCCAAATACAGCCTCTTCCCACCGCATCC 150
   64 L.pneumophila_NCTC11984  GTGAGGCATTCCTATTGGGCGCCCAAATACAGCCTCTTCCCACCGCATCC 150
   65 L.pneumophila_NCTC11985  GTGAGGCATTCCTATTGGGCGCCCAAATACAGCCTCTTCCCACCGCATCC 150
                               **** ******** ** ** ** *********** ***** ** ******
```

FIG. 3A(contd.)

```
SEQ ID
NO:
  54 L.pneumophila_NCTC11986  ACTCATTTTATTCCTGATCCGGTCAGGACGCGCAAGCTATTGATGAATAA 200
  55 L.pneumophila_NCTC12000  ACTCATTTTATTCCTGATCCGATCAGGACGCGCAAGCTATTGATGAATAA 200
  56 L.pneumophila_NCTC12179  ACTCATTTTATTCCTGATCCGGTCAGGACGCGCAAGCTATTGATGAATAA 200
  57 L.pneumophila_DSM7513    ACTCATTTTATTCCTGATCCGATCAGGACGCGCAAGCTATTGATGAATAA 200
  58 L.pneumophilaDSM7514     ACTCATTTTATTCCTGATCCGGTCAGGACACGCAAGCTATTGATGAATAA 200
  59 L.pneumophilaDSM7515     ACTCATTTTATTCCTGATCCAGTCAGGACACGCAAGCTGTTGATGAATAA 200
  60 L.pneumophila_NCTC11191  ACTCATTTTATTCCTGATCCGGTCAGGACGCGCAAGCTATTGATGAATAA 200
  61 L.pneumophila_NCTC11230  ACTCATTTTATTCCTGATCCGATCAGGACGCGCAAGCTATTGATGAATAA 200
  62 L.pneumophila_NCTC11232  ACTCATTTTATTCCTGATCCGCTGAGGACGCGCAAGCTATTGATGAATAA 200
  63 L.pneumophila_NCTC11287  ACTCATTTTATTCCTGATCCGCTGAGGACGCGCAAGCTATTGATGAATAA 200
  64 L.pneumophila_NCTC11984  ACTCATTTTATTCCTGATCCGCTGAGGACGCGCAAGCTATTGATGAATAA 200
  65 L.pneumophila_NCTC11985  ACTCATTTTATTCCTGATCCGGTCAGGACGCGCAAGCTATTGATGAATAA 200
                              ********************  * ***** ******** ***********
```

```
SEQ ID
NO:
   54 L.pneumophila_NCTC11986  AAAAGAATTAAACCATCTCATTGGAAGTGTTGAAAGGCAAGGCTATACCA 250
   55 L.pneumophila_NCTC12000  AAAAGAATTAAACCATCTCATAGGAAGTGTTGAAAGGCAAGGCTATACCA 250
   56 L.pneumophila_NCTC12179  AAAAGAATTAAACCATCTCATTGGAAGTGTTGAAAGGCAAGGCTATACCA 250
   57 L.pneumophila_DSM7513    AAAAGAATTAAACCATCTCATAGGAAGTGTTGAAAGGCAAGGCTATACCA 250
   58 L.pneumophilaDSM7514     AAAAGAATTAAACCATCTCATCGGAAGTGTTGAAAGACAAGGCTATACCA 250
   59 L.pneumophilaDSM7515     AAAAGAATTAAACCATCTTATCGGAAGTGTTGAAAGACAAGGCTATACCA 250
   60 L.pneumophila_NCTC11191  AAAAGAATTAAACCATCTCATTGGAAGTGTTGAAAGGCAAGGCTATACCA 250
   61 L.pneumophila_NCTC11230  AAAAGAATTAAACCATCTCATAGGAAGTGTTGAAAGGCAAGGCTATACCA 250
   62 L.pneumophila_NCTC11232  AAGAGAATTAAACCATCTCATAGGAAGTGTTGAAAGGCAAGGCTATACCA 250
   63 L.pneumophila_NCTC11287  AAGAGAATTAAACCATCTCATAGGAAGTGTTGAAAGGCAAGGCTATACCA 250
   64 L.pneumophila_NCTC11984  AAGAGAATTAAACCATCTCATAGGAAGTGTTGAAAGGCAAGGCTATACCA 250
   65 L.pneumophila_NCTC11985  AAAAGAATTAAACCATCTCATAGGAAGTGTTGAAAGGCAAGGCTATACCA 250
                               ** *************** ** ************** *************
```

```
SEQ ID
NO:
   54 L.pneumophila_NCTC11986  TAGTCCCTCTTTCTTTGTATTGGAAAAAAAATAAAATTAAAATAAAAATT 300
   55 L.pneumophila_NCTC12000  TAGTCCCTCTTTCTTTGTATTGGAAAAAAAATAAAATTAAAATAAAAATT 300
   56 L.pneumophila_NCTC12179  TAGTCCCTCTTTCTTTGTATTGGAAAAAAAATAAAATTAAAATAAAAATT 300
   57 L.pneumophila_DSM7513    TAGTCCCTCTTTCTTTGTATTGGAAAAAAAATAAAATTAAAATAAAAATT 300
   58 L.pneumophilaDSM7514     TAGTGCCTCTTTCTTTGTATTGGAAAAAGAATAAAATTAAAATAAAAATC 300
   59 L.pneumophilaDSM7515     TAGTTCCTCTTTCTTTGTATTGGAAAAAGAATAAAATTAAAATAAAAATC 300
   60 L.pneumophila_NCTC11191  TAGTCCCTCTTTCTTTGTATTGGAAAAAAAATAAAATTAAAATAAAAATT 300
   61 L.pneumophila_NCTC11230  TAGTCCCTCTTTCTTTGTATTGGAAAAAAAATAAAATTAAAATAAAAATT 300
   62 L.pneumophila_NCTC11232  TAGTCCCTCTTTCTTTGTATTGGAAAAAAAATAAAATTAAAATAAAAATT 300
   63 L.pneumophila_NCTC11287  TAGTCCCTCTTTCTTTGTATTGGAAAAAAAATAAAATTAAAATAAAAATT 300
   64 L.pneumophila_NCTC11984  TAGTCCCTCTTTCTTTGTATTGGAAAAAAAATAAAATTAAAATAAAAATT 300
   65 L.pneumophila_NCTC11985  TAGTCCCTCTTTCTTTGTATTGGAAAAAAAATAAAATTAAAATAAAAATT 300
                               **** *********************** ********************
```

FIG. 3B(contd.)

```
SEQ ID
NO:
 54 L.pneumophila_NCTC11986  GCTCTGGCCAAAGGAAAAAAAGAGCATGACAAAAGAGACACGATCAAAGA 350
 55 L.pneumophila_NCTC12000  GCTCTGGCCAAAGGAAAAAAAGAGCATGACAAAAGAGACACGATCAAAGA 350
 56 L.pneumophila_NCTC12179  GCTCTGGCCAAAGGAAAAAAAGAGCATGACAAAAGAGACACGATCAAAGA 350
 57 L.pneumophila_DSM7513    GCTCTGGCTAAAGGAAAAAAAGAGCATGACAAAAGAGACACGATCAAAGA 350
 58 L.pneumophilaDSM7514     GCTCTGGCTAAAGGAAAAAAAGAGCATGACAAAAGAGACACGATCAAAGA 350
 59 L.pneumophilaDSM7515     GCACTGGCCAAAGGAAAGAAAGAGCATGACAAAAGAGACACGATCAAAGA 350
 60 L.pneumophila_NCTC11191  GCTCTGGCCAAAGGAAAAAAAGAGCATGACAAAAGAGACACGATCAAAGA 350
 61 L.pneumophila_NCTC11230  GCTCTGGCTAAAGGAAAAAAAGAGCATGACAAAAGAGACACGATCAAAGA 350
 62 L.pneumophila_NCTC11232  GCTCTGGCCAAAGGAAAAAAAGAGCATGACAAAAGAGACACGATCAAAGA 350
 63 L.pneumophila_NCTC11287  GCTCTGGCCAAAGGAAAAAAAGAGCATGACAAAAGAGACACGATCAAAGA 350
 64 L.pneumophila_NCTC11984  GCTCTGGCCAAAGGAAAAAAAGAGCATGACAAAAGAGACACGATCAAAGA 350
 65 L.pneumophila_NCTC11985  GCTCTGGCCAAAGGAAAAAAAGAGCATGACAAAAGAGACACGATCAAAGA 350
                             ** ***** ******** ********************************
```

| SEQ ID NO: | | | |
|---|---|---|---|
| 54 | L.pneumophila_NCTC11986 | CAGAGAATGGC | 361 |
| 55 | L.pneumophila_NCTC12000 | CAGAGAATGGC | 361 |
| 56 | L.pneumophila_NCTC12179 | CAGAGAATGGC | 361 |
| 57 | L.pneumophila_DSM7513 | CAGAGAATGGC | 361 |
| 58 | L.pneumophilaDSM7514 | CAGAGAATGGC | 361 |
| 59 | L.pneumophilaDSM7515 | CAGAGAATGGC | 361 |
| 60 | L.pneumophila_NCTC11191 | CAGAGAATGGC | 361 |
| 61 | L.pneumophila_NCTC11230 | CAGAGAATGGC | 361 |
| 62 | L.pneumophila_NCTC11232 | CAGAGAATGGC | 361 |
| 63 | L.pneumophila_NCTC11287 | CAGAGAATGGC | 361 |
| 64 | L.pneumophila_NCTC11984 | CAGAGAATGGC | 361 |
| 65 | L.pneumophila_NCTC11985 | CAGAGAATGGC | 361 |
| | | *********** | |

| SEQ ID NO: | | | |
|---|---|---|---|
| 44 | L.pneumophila_Paris | ATGACTACCAAAAAACAACCAGATTCCACCATAGCCTTGAATAGAAAAGC | 50 |
| 45 | L.pneumophila_Corby | ATGACTACCAAAAAACAACCAGATTCCACCATAGCCTTGAATAGAAAAGC | 50 |
| 46 | L.pneumophila_Pneu | ATGACTACCAAAAAACAACCAGATTCCACCATAGCCTTGAATAGAAAAGC | 50 |
| 47 | L.pneumophila_Lens | ATGACTACCAAAAAACAACCAGATTCCACCATAGCTTTGAATAGAAAAGC | 50 |
| 48 | L.pneumophila_Alcoy | ATGACTACCAAAAAACAACCAGATTCCACCATAGCCTTGAATAGAAAAGC | 50 |
| 49 | L.pneumophila_2868 | ATGACTACCAAAAAACAACCAGATTCCACCATAGCCTTGAATAGAAAAGC | 50 |
| 50 | L.pneumophila_3140 | ATGACTACCAAAAAACAACCAGATTCAACCATAGCTTTGAATAGAAAAGC | 50 |
| 51 | L.pneumophila_3194 | ATGACTACCAAAAAACAACCAGATTCCACCATAGCCTTGAATAGAAAAGC | 50 |
| 52 | L.pneumophila_00189 | ATGACTACCAAAAAACAACCAGATTCCACCATAGCCTTGAATAGAAAAGC | 50 |
| 53 | L.pneumophila_2829 | ATGACTACCAAAAAACAACCAGATTCCACCATAGCCTTGAATAGAAAAGC | 50 |
| 54 | L.pneumophila_NCTC11986 | -------------------------------------------------- | |
| 55 | L.pneumophila_NCTC12000 | -------------------------------------------------- | |
| 56 | L.pneumophila_NCTC12179 | -------------------------------------------------- | |
| 57 | L.pneumophila_DSM7513 | -------------------------------------------------- | |
| 58 | L.pneumophilaDSM7514 | -------------------------------------------------- | |
| 59 | L.pneumophilaDSM7515 | -------------------------------------------------- | |
| 60 | L.pneumophila_NCTC11191 | -------------------------------------------------- | |
| 61 | L.pneumophila_NCTC11230 | -------------------------------------------------- | |
| 62 | L.pneumophila_NCTC11232 | -------------------------------------------------- | |
| 63 | L.pneumophila_NCTC11287 | -------------------------------------------------- | |
| 64 | L.pneumophila_NCTC11984 | -------------------------------------------------- | |
| 65 | L.pneumophila_NCTC11985 | -------------------------------------------------- | |

FIG. 4A(contd.)

| SEQ ID NO: | | | LgensmpB_F | | |
|---|---|---|---|---|---|
| 44 | L.pneumophila_Paris | TGGTTTTGATTATTTTATTGAA | GATCAATACGAAGCAGGC | CTGGTTTTGG | 100 |
| 45 | L.pneumophila_Corby | TGGTTTTGATTACTTTATTGAA | GATCAATACGAAGCAGGC | CTGGTTTTGG | 100 |
| 46 | L.pneumophila_Pneu | TGGTTTTGATTACTTTATTGAA | GATCAATACGAAGCAGGC | CTGGTTTTGG | 100 |
| 47 | L.pneumophila_Lens | TGGTTTTGATTACTTTATTGAA | GATCAATACGAAGCAGGC | CTGGTTTTGG | 100 |
| 48 | L.pneumophila_Alcoy | TGGTTTTGATTACTTTATTGAA | GATCAATACGAAGCAGGC | CTGGTTTTGG | 100 |
| 49 | L.pneumophila_2868 | TGGTTTTGATTACTTTATTGAA | GATCAATACGAAGCAGGC | CTGGTTTTGG | 100 |
| 50 | L.pneumophila_3140 | TGGTTTTGATTACTTTATTGAA | GATCAATACGAAGCAGGC | CTGGTTTTGG | 100 |
| 51 | L.pneumophila_3194 | TGGTTTTGATTACTTTATTGAA | GATCAATACGAAGCAGGC | CTGGTTTTGG | 100 |
| 52 | L.pneumophila_00189 | TGGTTTTGATTACTTTATTGAA | GATCAATACGAAGCAGGC | CTGGTTTTGG | 100 |
| 53 | L.pneumophila_2829 | TGGTTTTGATTACTTTATTGAA | GATCAATACGAAGCAGGC | CTGGTTTTGG | 100 |
| 54 | L.pneumophila_NCTC11986 | ---------------------- | GATCAATACGAAGCAGGC | CTGGTTTTGG | 28 |
| 55 | L.pneumophila_NCTC12000 | ---------------------- | GATCAATACGAAGCAGGC | CTGGTTTTGG | 28 |
| 56 | L.pneumophila_NCTC12179 | ---------------------- | GATCAATACGAAGCAGGC | CTGGTTTTGG | 28 |
| 57 | L.pneumophila_DSM7513 | ---------------------- | GATCAATACGAAGCAGGC | CTGGTTTTGG | 28 |
| 58 | L.pneumophilaDSM7514 | ---------------------- | GATCAATACGAAGCAGGC | TTGGTTTTGG | 28 |
| 59 | L.pneumophilaDSM7515 | ---------------------- | GATCAATACGAAGCAGGC | TTGGTTTTGG | 28 |
| 60 | L.pneumophila_NCTC11191 | ---------------------- | GATCAATACGAAGCAGGC | CTGGTTTTGG | 28 |
| 61 | L.pneumophila_NCTC11230 | ---------------------- | GATCAATACGAAGCAGGC | CTGGTTTTGG | 28 |
| 62 | L.pneumophila_NCTC11232 | ---------------------- | GATCAATACGAAGCAGGC | CTGGTTTTGG | 28 |
| 63 | L.pneumophila_NCTC11287 | ---------------------- | GATCAATACGAAGCAGGC | CTGGTTTTGG | 28 |
| 64 | L.pneumophila_NCTC11984 | ---------------------- | GATCAATACGAAGCAGGC | CTGGTTTTGG | 28 |
| 65 | L.pneumophila_NCTC11985 | ---------------------- | GATCAATACGAAGCAGGC | CTGGTTTTGG | 28 |
| | | | ***************** | ********* | |

| SEQ ID NO: | | | |
|---|---|---|---|
| 44 | L.pneumophila_Paris | AGGGCTGGGAAGTAAAAAGTCTGCGTGCTGGGAAAATCAATTTGTCGGAT | 150 |
| 45 | L.pneumophila_Corby | AAGGCTGGGAAGTAAAAAGTCTGCGTGCTGGAAAAATCAATTTGTCGGAT | 150 |
| 46 | L.pneumophila_Pneu | AAGGCTGGGAAGTAAAAAGTCTGCGTGCTGGAAAAATCAATTTGTCGGAT | 150 |
| 47 | L.pneumophila_Lens | AAGGCTGGGAAGTAAAAAGTCTGCGTGCTGGAAAAATCAATTTGTCGGAT | 150 |
| 48 | L.pneumophila_Alcoy | AAGGCTGGGAAGTAAAAAGTCTGCGTGCTGGAAAAATCAATTTGTCGGAT | 150 |
| 49 | L.pneumophila_2868 | AAGGCTGGGAAGTAAAAAGTCTGCGTGCTGGAAAAATCAATTTGTCGGAT | 150 |
| 50 | L.pneumophila_3140 | AAGGCTGGGAAGTAAAAAGTCTGCGTGCTGGAAAAATCAATTTGTCGGAT | 150 |
| 51 | L.pneumophila_3194 | AAGGCTGGGAAGTAAAAAGTCTGCGTGCTGGAAAAATCAATTTGTCGGAT | 150 |
| 52 | L.pneumophila_00189 | AAGGCTGGGAAGTAAAAAGTCTGCGTGCTGGAAAAATCAATTTGTCGGAT | 150 |
| 53 | L.pneumophila_2829 | AAGGCTGGGAAGTAAAAAGTCTGCGTGCTGGAAAAATCAATTTGTCGGAT | 150 |
| 54 | L.pneumophila_NCTC11986 | AGGGCTGGGAAGTAAAAAGTCTGCGTGCTGGGAAAATCAATTTGTCGGAT | 78 |
| 55 | L.pneumophila_NCTC12000 | AAGGCTGGGAAGTAAAAAGTCTGCGTGCTGGAAAAATCAATTTGTCGGAT | 78 |
| 56 | L.pneumophila_NCTC12179 | AAGGCTGGGAAGTAAAAAGTCTGCGTGCTGGAAAAATCAATTTGTCGGAT | 78 |
| 57 | L.pneumophila_DSM7513 | AAGGCTGGGAAGTAAAAAGTCTGCGTGCTGGAAAAATCAATTTGTCGGAT | 78 |
| 58 | L.pneumophilaDSM7514 | AAGGCTGGGAAGTAAAAAGTCTGCGGGCAGGAAAAATCAATTTGTCAGAT | 78 |
| 59 | L.pneumophilaDSM7515 | AAGGCTGGGAAGTAAAAAGTCTGCGTGCAGGAAAAATCAATTTGTCGGAT | 78 |
| 60 | L.pneumophila_NCTC11191 | AAGGCTGGGAAGTAAAAAGTCTGCGTGCTGGGAAAATCAATTTGTCGGAT | 78 |
| 61 | L.pneumophila_NCTC11230 | AAGGCTGGGAAGTAAAAAGTCTGCGTGCTGGAAAAATCAATTTGTCGGAT | 78 |
| 62 | L.pneumophila_NCTC11232 | AAGGCTGGGAAGTAAAAAGTCTGCGTGCTGGAAAAATCAATTTGTCGGAT | 78 |
| 63 | L.pneumophila_NCTC11287 | AAGGCTGGGAAGTAAAAAGTCTGCGTGCTGGAAAAATCAATTTGTCGGAT | 78 |
| 64 | L.pneumophila_NCTC11984 | AAGGCTGGGAAGTAAAAAGTCTGCGTGCTGGAAAAATCAATTTGTCGGAT | 78 |
| 65 | L.pneumophila_NCTC11985 | AAGGCTGGGAAGTAAAAAGTCTGCGTGCTGGAAAAATCAATTTGTCGGAT | 78 |
| | | * ********************** ** ** ************* *** | |

| SEQ ID NO: | Strain | LegPneuF1 | |
|---|---|---|---|
| 44 | L.pneumophila_Paris | TCACACGTGATAATCAAATACGGTGAGGCATTCCTATTGGGCGCCCAAAT | 200 |
| 45 | L.pneumophila_Corby | TCACACGTGATAATCAAATACGGTGAGGCATTCCTATTGGGCGCCCAAAT | 200 |
| 46 | L.pneumophila_Pneu | TCACACGTGATAATCAAATACGGTGAGGCATTCCTATTGGGCGCCCAAAT | 200 |
| 47 | L.pneumophila_Lens | TCACACGTGATAATCAAATACGGTGAGGCATTCCTATTGGGCGCCCAAAT | 200 |
| 48 | L.pneumophila_Alcoy | TCACACGTGATAATCAAATACGGTGAGGCATTCCTATTGGGCGCCCAAAT | 200 |
| 49 | L.pneumophila_2868 | TCACACGTGATAATCAAATACGGTGAGGCATTCCTATTGGGCGCCCAAAT | 200 |
| 50 | L.pneumophila_3140 | TCACACGTGATAATCAAATACGGTGAGGCATTCCTATTGGGCGCCCAAAT | 200 |
| 51 | L.pneumophila_3194 | TCACACGTGATAATCAAATACGGTGAGGCATTCCTATTGGGCGCCCAAAT | 200 |
| 52 | L.pneumophila_00189 | TCACACGTGATAATCAAATACGGTGAGGCATTCCTATTGGGCGCCCAAAT | 200 |
| 53 | L.pneumophila_2829 | TCACACGTGATAATCAAATACGGTGAGGCATTCCTATTGGGCGCCCAAAT | 200 |
| 54 | L.pneumophila_NCTC11986 | TCACACGTGATAATCAAATACGGTGAGGCATTCCTATTGGGCGCCCAAAT | 128 |
| 55 | L.pneumophila_NCTC12000 | TCACACGTGATAATCAAATACGGTGAGGCATTCCTATTGGGCGCCCAAAT | 128 |
| 56 | L.pneumophila_NCTC12179 | TCACACGTGATAATCAAATACGGTGAGGCATTCCTATTGGGCGCCCAAAT | 128 |
| 57 | L.pneumophila_DSM7513 | TCACACGTGATAATCAAATACGGTGAGGCATTCCTATTGGGCGCCCAAAT | 128 |
| 58 | L.pneumophilaDSM7514 | GCACACGTGATAATCAAATACGGTGAGGCATTCCTGTTAGGAGCTCAAAT | 128 |
| 59 | L.pneumophilaDSM7515 | GCACACGTGATAATAAAATACGGTGAGGCATTCCTGTTAGGAGCCCAAAT | 128 |
| 60 | L.pneumophila_NCTC11191 | TCACACGTGATAATCAAATACGGTGAAGCATTCCTATTGGGCGCCCAAAT | 128 |
| 61 | L.pneumophila_NCTC11230 | TCACACGTGATAATCAAATACGGTGAGGCATTCCTATTGGGCGCCCAAAT | 128 |
| 62 | L.pneumophila_NCTC11232 | TCACACGTGATAATCAAATACGGTGAGGCATTCCTATTGGGCGCCCAAAT | 128 |
| 63 | L.pneumophila_NCTC11287 | TCACACGTGATAATCAAATACGGTGAGGCATTCCTATTGGGCGCCCAAAT | 128 |
| 64 | L.pneumophila_NCTC11984 | TCACACGTGATAATCAAATACGGTGAGGCATTCCTATTGGGCGCCCAAAT | 128 |
| 65 | L.pneumophila_NCTC11985 | TCACACGTGATAATCAAATACGGTGAGGCATTCCTATTGGGCGCCCAAAT | 128 |
| | | ************* ************ ******** ** ** ** ***** | |

FIG. 4B(contd.)

LegPneuP3

| SEQ ID NO: | Strain | Sequence | |
|---|---|---|---|
| 44 | L.pneumophila_Paris | ACAGCCTCTTCCCACCGCATCCACTCATTTTATTCCTGATCCGGTCAGGA | 250 |
| 45 | L.pneumophila_Corby | ACAGCCGCTTCCCACCGCATCCACTCATTTTATTCCTGATCCGATCAGGA | 250 |
| 46 | L.pneumophila_Pneu | ACAGCCTCTTCCCACCGCATCCACTCATTTTATTCCTGATCCGATCAGGA | 250 |
| 47 | L.pneumophila_Lens | ACAGCCTCTTCCAACCGCATCCACTCATTTTATTCCTGATCCGGTCAGGA | 250 |
| 48 | L.pneumophila_Alcoy | ACAGCCGCTTCCCACCGCATCCACTCATTTTATTCCTGATCCGATCAGGA | 250 |
| 49 | L.pneumophila_2868 | ACAGCCTCTTCCCACCGCATCCACTCATTTTATTCCTGATCCGATCAGGA | 250 |
| 50 | L.pneumophila_3140 | ACAGCCTCTTCCCACCGCATCCACTCATTTTATTCCTGATCCGGTCAGGA | 250 |
| 51 | L.pneumophila_3194 | ACAGCCTCTTCCCACCGCATCCACTCATTTTATTCCTGATCCGCTGAGGA | 250 |
| 52 | L.pneumophila_00189 | ACAGCCTCTTCCCACCGCATCCACTCATTTTATTCCTGATCCGATCAGGA | 250 |
| 53 | L.pneumophila_2829 | ACAGCCTCTTCCCACCGCATCCACTCATTTTATTCCTGATCCGATCAGGA | 250 |
| 54 | L.pneumophila_NCTC11986 | ACAGCCTCTTCCCACCGCATCCACTCATTTTATTCCTGATCCGGTCAGGA | 178 |
| 55 | L.pneumophila_NCTC12000 | ACAGCCGCTTCCCACCGCATCCACTCATTTTATTCCTGATCCGATCAGGA | 178 |
| 56 | L.pneumophila_NCTC12179 | ACAGCCTCTTCCCACCGCATCCACTCATTTTATTCCTGATCCGGTCAGGA | 178 |
| 57 | L.pneumophila_DSM7513 | ACAGCCTCTTCCCACCGCATCCACTCATTTTATTCCTGATCCGATCAGGA | 178 |
| 58 | L.pneumophilaDSM7514 | ACAGCCTCTTCCTACTGCATCCACTCATTTTATTCCTGATCCGGTCAGGA | 178 |
| 59 | L.pneumophilaDSM7515 | ACAGCCTCTTCCTACTGCATCCACTCATTTTATTCCTGATCCAGTCAGGA | 178 |
| 60 | L.pneumophila_NCTC11191 | ACAGCCTCTTCCCACCGCATCCACTCATTTTATTCCTGATCCGGTCAGGA | 178 |
| 61 | L.pneumophila_NCTC11230 | ACAGCCTCTTCCCACCGCATCCACTCATTTTATTCCTGATCCGATCAGGA | 178 |
| 62 | L.pneumophila_NCTC11232 | ACAGCCTCTTCCCACCGCATCCACTCATTTTATTCCTGATCCGCTGAGGA | 178 |
| 63 | L.pneumophila_NCTC11287 | ACAGCCTCTTCCCACCGCATCCACTCATTTTATTCCTGATCCGCTGAGGA | 178 |
| 64 | L.pneumophila_NCTC11984 | ACAGCCTCTTCCCACCGCATCCACTCATTTTATTCCTGATCCGCTGAGGA | 178 |
| 65 | L.pneumophila_NCTC11985 | ACAGCCTCTTCCCACCGCATCCACTCATTTTATTCCTGATCCGGTCAGGA | 178 |
| | | ****** ***** ** ************************** * **** | |

| SEQ ID NO: | | LegPneuR1 | |
|---|---|---|---|
| 44 | L.pneumophila_Paris | CGCGCAAGCTATTGATGAATAAAAAAGAATTAAACCATCTCATTGGAAGT | 300 |
| 45 | L.pneumophila_Corby | CGCGCAAGCTATTGATGAATAAAAAAGAATTAAACCATCTCATAGGAAGT | 300 |
| 46 | L.pneumophila_Pneu | CGCGCAAGCTATTGATGAATAAAAAAGAATTAAACCATCTCATAGGAAGT | 300 |
| 47 | L.pneumophila_Lens | CGCGCAAGCTATTGATGAATAAAAAAGAATTAAACCATCTCATTGGAAGT | 300 |
| 48 | L.pneumophila_Alcoy | CGCGCAAGCTATTGATGAATAAAAAAGAATTAAACCATCTCATAGGAAGT | 300 |
| 49 | L.pneumophila_2868 | CGCGCAAGCTATTGATGAATAAAAAAGAATTAAACCATCTCATAGGAAGT | 300 |
| 50 | L.pneumophila_3140 | CGCGCAAGCTATTGATGAATAAAAAAGAATTAAACCATCTCATAGGAAGT | 300 |
| 51 | L.pneumophila_3194 | CGCGCAAGCTATTGATGAATAAAAGAGAATTAAACCATCTCATAGGAAGT | 300 |
| 52 | L.pneumophila_00189 | CGCGCAAGCTATTGATGAATAAAAAAGAATTAAACCATCTCATAGGAAGT | 300 |
| 53 | L.pneumophila_2829 | CGCGCAAGCTATTGATGAATAAAAAAGAATTAAACCATCTCATAGGAAGT | 300 |
| 54 | L.pneumophila_NCTC11986 | CGCGCAAGCTATTGATGAATAAAAAAGAATTAAACCATCTCATTGGAAGT | 228 |
| 55 | L.pneumophila_NCTC12000 | CGCGCAAGCTATTGATGAATAAAAAAGAATTAAACCATCTCATAGGAAGT | 228 |
| 56 | L.pneumophila_NCTC12179 | CGCGCAAGCTATTGATGAATAAAAAAGAATTAAACCATCTCATTGGAAGT | 228 |
| 57 | L.pneumophila_DSM7513 | CGCGCAAGCTATTGATGAATAAAAAAGAATTAAACCATCTCATAGGAAGT | 228 |
| 58 | L.pneumophilaDSM7514 | CACGCAAGCTATTGATGAATAAAAAAGAATTAAACCATCTCATCGGAAGT | 228 |
| 59 | L.pneumophilaDSM7515 | CACGCAAGCTGTTGATGAATAAAAAAGAATTAAACCATCTTATCGGAAGT | 228 |
| 60 | L.pneumophila_NCTC11191 | CGCGCAAGCTATTGATGAATAAAAAAGAATTAAACCATCTCATTGGAAGT | 228 |
| 61 | L.pneumophila_NCTC11230 | CGCGCAAGCTATTGATGAATAAAAAAGAATTAAACCATCTCATAGGAAGT | 228 |
| 62 | L.pneumophila_NCTC11232 | CGCGCAAGCTATTGATGAATAAAAGAGAATTAAACCATCTCATAGGAAGT | 228 |
| 63 | L.pneumophila_NCTC11287 | CGCGCAAGCTATTGATGAATAAAAGAGAATTAAACCATCTCATAGGAAGT | 228 |
| 64 | L.pneumophila_NCTC11984 | CGCGCAAGCTATTGATGAATAAAAGAGAATTAAACCATCTCATAGGAAGT | 228 |
| 65 | L.pneumophila_NCTC11985 | CGCGCAAGCTATTGATGAATAAAAAAGAATTAAACCATCTCATAGGAAGT | 228 |
| | | * ******** ************ ************** ** ****** | |

```
SEQ ID
NO: 44 L.pneumophila_Paris        GTTGAAAGGCAAGGCTATACCATAGTCCCTCTTTCTTTGTATTGGAAAAA 350
    45 L.pneumophila_Corby        GTTGAAAGGCAAGGCTATACCATAGTCCCTCTTTCTTTGTATTGGAAAAA 350
    46 L.pneumophila_Pneu         GTTGAAAGGCAAGGCTATACCATAGTCCCTCTTTCTTTGTATTGGAAAAA 350
    47 L.pneumophila_Lens         GTTGAAAGGCAAGGCTATACCATAGTCCCTCTTTCTTTGTATTGGAAAAA 350
    48 L.pneumophila_Alcoy        GTTGAAAGGCAAGGCTATACCATAGTCCCTCTTTCTTTGTATTGGAAAAA 350
    49 L.pneumophila_2868         GTTGAAAGGCAAGGCTATACCATAGTCCCTCTTTCTTTGTATTGGAAAAA 350
    50 L.pneumophila_3140         GTTGAAAGGCAAGGCTATACCATAGTCCCTCTTTCTTTGTATTGGAAAAA 350
    51 L.pneumophila_3194         GTTGAAAGGCAAGGCTATACCATAGTCCCTCTTTCTTTGTATTGGAAAAA 350
    52 L.pneumophila_00189        GTTGAAAGGCAAGGCTATACCATAGTCCCTCTTTCTTTGTATTGGAAAAA 350
    53 L.pneumophila_2829         GTTGAAAGGCAAGGCTATACCATAGTCCCTCTTTCTTTGTATTGGAAAAA 350
    54 L.pneumophila_NCTC11986    GTTGAAAGGCAAGGCTATACCATAGTCCCTCTTTCTTTGTATTGGAAAAA 278
    55 L.pneumophila_NCTC12000    GTTGAAAGGCAAGGCTATACCATAGTCCCTCTTTCTTTGTATTGGAAAAA 278
    56 L.pneumophila_NCTC12179    GTTGAAAGGCAAGGCTATACCATAGTCCCTCTTTCTTTGTATTGGAAAAA 278
    57 L.pneumophila_DSM7513      GTTGAAAGGCAAGGCTATACCATAGTCCCTCTTTCTTTGTATTGGAAAAA 278
    58 L.pneumophilaDSM7514       GTTGAAAGACAAGGCTATACCATAGTGCCTCTTTCTTTGTATTGGAAAAA 278
    59 L.pneumophilaDSM7515       GTTGAAAGACAAGGCTATACCATAGTTCCTCTTTCTTTGTATTGGAAAAA 278
    60 L.pneumophila_NCTC11191    GTTGAAAGGCAAGGCTATACCATAGTCCCTCTTTCTTTGTATTGGAAAAA 278
    61 L.pneumophila_NCTC11230    GTTGAAAGGCAAGGCTATACCATAGTCCCTCTTTCTTTGTATTGGAAAAA 278
    62 L.pneumophila_NCTC11232    GTTGAAAGGCAAGGCTATACCATAGTCCCTCTTTCTTTGTATTGGAAAAA 278
    63 L.pneumophila_NCTC11287    GTTGAAAGGCAAGGCTATACCATAGTCCCTCTTTCTTTGTATTGGAAAAA 278
    64 L.pneumophila_NCTC11984    GTTGAAAGGCAAGGCTATACCATAGTCCCTCTTTCTTTGTATTGGAAAAA 278
    65 L.pneumophila_NCTC11985    GTTGAAAGGCAAGGCTATACCATAGTCCCTCTTTCTTTGTATTGGAAAAA 278
                                  ******** ***************** ***********************
```

FIG. 4C(contd.)

| SEQ ID NO: | | | |
|---|---|---|---|
| 44 | L.pneumophila_Paris | AAATAAAATTAAAATAAAAATTGCTCTGGCCAAAGGAAAAAAAGAGCATG | 400 |
| 45 | L.pneumophila_Corby | AAATAAAATTAAAATAAAAATTGCTCTGGCCAAAGGAAAAAAAGAGCATG | 400 |
| 46 | L.pneumophila_Pneu | AAATAAAATTAAAATAAAAATTGCTCTGGCTAAAGGAAAAAAAGAGCA-- | 398 |
| 47 | L.pneumophila_Lens | AAATAAAATTAAAATAAAAATTGCTCTGGCCAAAGGAAAAAAAGAGCATG | 400 |
| 48 | L.pneumophila_Alcoy | AAATAAAATTAAAATAAAAATTGCTCTGGCCAAAGGAAAAAAAGAGCATG | 400 |
| 49 | L.pneumophila_2868 | AAATAAAATTAAAATAAAAATTGCTCTGGCTAAAGGAAAAAAAGAGCATG | 400 |
| 50 | L.pneumophila_3140 | AAATAAAATTAAAATAAAAATTGCTCTGGCCAAAGGAAAAAAAGAGCATG | 400 |
| 51 | L.pneumophila_3194 | AAATAAAATTAAAATAAAAATTGCTCTGGCCAAAGGAAAAAAAGAGCATG | 400 |
| 52 | L.pneumophila_00189 | AAATAAAATTAAAATAAAAATTGCTCTGGCTAAAGGAAAAAAAGAGCATG | 400 |
| 53 | L.pneumophila_2829 | AAATAAAATTAAAATAAAAATTGCTCTGGCTAAAGGAAAAAAAGAGCATG | 400 |
| 54 | L.pneumophila_NCTC11986 | AAATAAAATTAAAATAAAAATTGCTCTGGCCAAAGGAAAAAAAGAGCATG | 328 |
| 55 | L.pneumophila_NCTC12000 | AAATAAAATTAAAATAAAAATTGCTCTGGCCAAAGGAAAAAAAGAGCATG | 328 |
| 56 | L.pneumophila_NCTC12179 | AAATAAAATTAAAATAAAAATTGCTCTGGCCAAAGGAAAAAAAGAGCATG | 328 |
| 57 | L.pneumophila_DSM7513 | AAATAAAATTAAAATAAAAATTGCTCTGGCTAAAGGAAAAAAAGAGCATG | 328 |
| 58 | L.pneumophilaDSM7514 | GAATAAAATTAAAATAAAAATCGCTCTGGCTAAAGGAAAAAAAGAGCATG | 328 |
| 59 | L.pneumophilaDSM7515 | GAATAAAATTAAAATAAAAATCGCACTGGCCAAAGGAAAGAAAGAGCATG | 328 |
| 60 | L.pneumophila_NCTC11191 | AAATAAAATTAAAATAAAAATTGCTCTGGCCAAAGGAAAAAAAGAGCATG | 328 |
| 61 | L.pneumophila_NCTC11230 | AAATAAAATTAAAATAAAAATTGCTCTGGCTAAAGGAAAAAAAGAGCATG | 328 |
| 62 | L.pneumophila_NCTC11232 | AAATAAAATTAAAATAAAAATTGCTCTGGCCAAAGGAAAAAAAGAGCATG | 328 |
| 63 | L.pneumophila_NCTC11287 | AAATAAAATTAAAATAAAAATTGCTCTGGCCAAAGGAAAAAAAGAGCATG | 328 |
| 64 | L.pneumophila_NCTC11984 | AAATAAAATTAAAATAAAAATTGCTCTGGCCAAAGGAAAAAAAGAGCATG | 328 |
| 65 | L.pneumophila_NCTC11985 | AAATAAAATTAAAATAAAAATTGCTCTGGCCAAAGGAAAAAAAGAGCATG | 328 |
| | | ******************** ** ***** ******** ******** | |

FIG. 4C(contd.)

| SEQ ID NO: | | LgensmpB_R | |
|---|---|---|---|
| 44 | L.pneumophila_Paris | ACAAAAGAGACACGATCAAAGACAGAGAATGGCAAAGAGATCGTTCAAGA | 450 |
| 45 | L.pneumophila_Corby | ACAAAAGAGACACGATCAAAGACAGAGAATGGCAAAGGGATCGTTCAAGA | 450 |
| 46 | L.pneumophila_Pneu | -------------------------------------------------- | |
| 47 | L.pneumophila_Lens | ACAAAAGAGACACGATCAAAGACAGAGAATGGCAAAGAGATCGTTCAAGA | 450 |
| 48 | L.pneumophila_Alcoy | ACAAAAGAGACACGATCAAAGACAGAGAATGGCAAAGGGATCGTTCAAGA | 450 |
| 49 | L.pneumophila_2868 | ACAAAAGAGACACGATCAAAGACAGAGAATGGCAAAGGGATCGTTCAAGA | 450 |
| 50 | L.pneumophila_3140 | ACAAAAGAGACACGATCAAAGACAGAGAATGGCAAAGGGATCGTTCAAGA | 450 |
| 51 | L.pneumophila_3194 | ACAAAAGAGACACGATCAAAGACAGAGAATGGCAAAGGGATCGTTCAAGA | 450 |
| 52 | L.pneumophila_00189 | ACAAAAGAGACACGATCAAAGACAGAGAATGGCAAAGGGATCGTTCAAGA | 450 |
| 53 | L.pneumophila_2829 | ACAAAAGAGACACGATCAAAGACAGAGAATGGCAAAGGGATCGTTCAAGA | 450 |
| 54 | L.pneumophila_NCTC11986 | ACAAAAGAGACACGATCAAAGACAGAGAATGGC----------------- | 361 |
| 55 | L.pneumophila_NCTC12000 | ACAAAAGAGACACGATCAAAGACAGAGAATGGC----------------- | 361 |
| 56 | L.pneumophila_NCTC12179 | ACAAAAGAGACACGATCAAAGACAGAGAATGGC----------------- | 361 |
| 57 | L.pneumophila_DSM7513 | ACAAAAGAGACACGATCAAAGACAGAGAATGGC----------------- | 361 |
| 58 | L.pneumophilaDSM7514 | ACAAAAGAGACACGATCAAAGACAGAGAATGGC----------------- | 361 |
| 59 | L.pneumophilaDSM7515 | ACAAAAGAGACACGATCAAAGACAGAGAATGGC----------------- | 361 |
| 60 | L.pneumophila_NCTC11191 | ACAAAAGAGACACGATCAAAGACAGAGAATGGC----------------- | 361 |
| 61 | L.pneumophila_NCTC11230 | ACAAAAGAGACACGATCAAAGACAGAGAATGGC----------------- | 361 |
| 62 | L.pneumophila_NCTC11232 | ACAAAAGAGACACGATCAAAGACAGAGAATGGC----------------- | 361 |
| 63 | L.pneumophila_NCTC11287 | ACAAAAGAGACACGATCAAAGACAGAGAATGGC----------------- | 361 |
| 64 | L.pneumophila_NCTC11984 | ACAAAAGAGACACGATCAAAGACAGAGAATGGC----------------- | 361 |
| 65 | L.pneumophila_NCTC11985 | ACAAAAGAGACACGATCAAAGACAGAGAATGGC----------------- | 361 |

FIG. 4D

| SEQ ID NO: | | | |
|---|---|---|---|
| 44 | L.pneumophila_Paris | ATAATGAAAAAGAACACTTGA | 471 |
| 45 | L.pneumophila_Corby | ATAATGAAAAAGAACACTTGA | 471 |
| 46 | L.pneumophila_Pneu | --------------------- | |
| 47 | L.pneumophila_Lens | ATAATGAAAAAGAACACTTGA | 471 |
| 48 | L.pneumophila_Alcoy | ATAATGAAAAAGAACACTTGA | 471 |
| 49 | L.pneumophila_2868 | ATAATGAAAAAGAACACTTGA | 471 |
| 50 | L.pneumophila_3140 | ATAATGAAAAAGAACACTTGA | 471 |
| 51 | L.pneumophila_3194 | ATAATGAAAAAGAACACTTGA | 471 |
| 52 | L.pneumophila_00189 | ATAATGAAAAAGAACACTTGA | 471 |
| 53 | L.pneumophila_2829 | ATAATGAAAAAGAACACTTGA | 471 |
| 54 | L.pneumophila_NCTC11986 | --------------------- | |
| 55 | L.pneumophila_NCTC12000 | --------------------- | |
| 56 | L.pneumophila_NCTC12179 | --------------------- | |
| 57 | L.pneumophila_DSM7513 | --------------------- | |
| 58 | L.pneumophilaDSM7514 | --------------------- | |
| 59 | L.pneumophilaDSM7515 | --------------------- | |
| 60 | L.pneumophila_NCTC11191 | --------------------- | |
| 61 | L.pneumophila_NCTC11230 | --------------------- | |
| 62 | L.pneumophila_NCTC11232 | --------------------- | |
| 63 | L.pneumophila_NCTC11287 | --------------------- | |
| 64 | L.pneumophila_NCTC11984 | --------------------- | |
| 65 | L.pneumophila_NCTC11985 | --------------------- | |

Amplification Curves

FIG. 7A

```
SEQ ID NO:
 66 A.baumannii_AB307-0294          TGATATGTGGGAAAAAACTTCACCTTGGCATCAGTTTACGGCACAATAGG 50
 67 A.baumannii_MRY10-0558          TGATATGTGGGAAAAAACTTCACCTTGGCATCAGTTTACGGCACAATAGG 50
 68 A.baumannii_MDR-TJ              TGATATGTGGGAAAAAACTTCACCTTGGCATCAGTTTACGGCACAATAGG 50
 69 A.baumannii_D1279779            --ATATGTGGGAAAAAACTTCACCTTGGCATCAGTTTACGGCACAATAGG 48
 70 A.baumannii_Naval-82            TGATATGTGGGAAAAAACTTCACCTTGGCATCAGTTTACGGCACAATAGG 50
 71 A.baumannii_UMB002              TGATATGTGGGAAAAAACTTCACCTTGGCATCAGTTTACGGCACAATAGG 50
 72 Acinetobacter_sp.ADP1           -CATTAAAATGAAAAAACTTCACCTCGGTCGTTGTTTAAGGCACAATAAG 49
 73 Acinetobacter_sp.RUH2624        TGATATGTGGGAAAAAACTTCACCTTGGCATCAGTTTACGGCACAATAGG 50
 74 Acinetobacter_sp.SH024          ------------AAAAACTTCACCTTAGCATCAGTTTACGGCACAATAGG 38
 75 A.calcoaceticus_PHEA-2B         --------------------------------------------------
 76 A.calcoaceticus_PHEA-2          --GACGTGCAGGAAAAACTTCACCTTAGCATCAGTTTACGGCACAATAGG 48
 77 A.calcoaceticus.anitratus_XM15  ------------AAAAACTTCACCTTAGCATCAGTTTACGGCACAATAGG 38
 78 A.calcoaceticus_TG19585         ------------AAAAACTTCACCTTAGCATCAGTTTACGGCACAATAGG 38
 79 A.calcoaceticus_RUH2202         ------------AAAAACTTCACCTTAGCATCAGTTTACGGCACAATAGG 38
 80 A.calcoaceticus_ANC3811         ------------AAAAACTTCACCTTAGCATCAGTTTACGGCACAATAGG 38
 81 A.calcoaceticus_ANC3680         --------------------------------------------------
 82 A.calcoaceticus_TG19593         ------------AAAAACTTCACCTTAGCATCAGTTTACGGCACAATAGG 38
 83 A.calcoaceticus_TG19588         ------------AAAAACTTCACCTTAGCATCAGTTTACGGCACAATAGG 38
 84 A.calcoaceticus_DSM30006        ------------AAAAACTTCACCTTAGCATCAGTTTACGGCACAATAGG 38
 85 A.calcoaceticus_NIPH_13         ------------AAAAACTTCACCTTAGCATCAGTTTACGGCACAATAGG 38
 86 A.nosocomialis_TG21145          --------------------------------------------------
 87 A.nosocomialis_TG19596          --------------------------------------------------
 88 A.nosocomialis_M2c_7            TGATATGTGGGAAAAAACTTCACCTTGGCATCAGTTTACGGCACAATAGG 50
 89 A.nosocomialis_NIPH2119         TGATATGTGGGAAAAAACTTCACCTTGGCATCAGTTTACGGCACAATAGG 50
 90 A.nosocomialis_NIPH386          --------------------------------------------------
 91 A.nosocomialis_Ab22222          --------------------------------------------------
 92 A.genomosp.3.str.DSM21653       ------------AAAAACTTCACCTTAGCATCAGTTTACGGCACAATAGG 38
 93 A.genomosp.3str.DSM9306         ------------AAAAACTTCACCTTAGCATCAGTTTACGGCACAATAGG 38
 94 A.oleivorans_DR1                TTCATGTGCAGGAAAAACTTCACCTTAGCATCAGTTTACGGCACAATAGG 50
 95 A.pittii_ANC4050                ------------AAAAACTTCACCTTAGCATCAGTTTACGGCACAATAGA 38
 96 A.pittii_ANC3678                ------------AAAAACTTCACCTTAGCATCAGTTTACGGCACAATAGG 38
 97 A.pittii_D499                   ------------AAAAACTTCACCTTAGCATCAGTTTACGGCACAATAGG 38
 98 A.pittii_CIP70.29               ------------AAAAACTTCACCTTAGCATCAGTTTACGGCACAATAGG 38
 99 A.pittii_TG6411                 ------------AAAAACTTCACCTTAGCATCAGTTTACGGCACAATAGG 38
100 A.pittii_ANC4052                ------------AAAAACTTCACCTTAGCATCAGTTTACGGCACAATAGG 38
101 A.junii_SH205                   ----------------------------------TTTACGGCACAATAGA 16
102 A.junii_NIPH182                 ----------------------------------TTTACGGCACAATAGA 16
103 A.junii_CIP64.5                 ----------------------------------TTTACGGCACAATAGA 16
104 A.junii_TG19608                 ----------------------------------TTTACGGCACAATAGA 16
105 A.junii_MTCC11364               ----------------------------------TTTACGGCACAATAGA 16
106 A.junii_CIP107470               ----------------------------------TTTACGGCACAATAGA 16
107 A.gyllenbergii_CIP110306        ----------------------------------TTTACGGCACAATAGA 16
108 A.gyllenbergii_MTCC11365        ----------------------------------TTTACGGCACAATAGA 16
109 A.beijerinckii_ANC3835          ----------------------------------TTTACGGCACAATAGG 16
110 A.beijerinckii_CIP110307        ----------------------------------TTTACGGCACAATAGG 16
111 A.brisouii_ANC4119              ------------AAAAGCTTCACCTTGGGAAAAGTTTGCGGCACAATAGA 38
112 A.lwoffii_WJ10621               ----------GAAAAAACTTCACCTTAACCATGCTTTAAGGCACAATAGG 40
113 A.lwoffii_CIP70.31              -----------AAAAAACTTCACCTTATTTCTAGTT-GCGGTACAATAGC 38
114 A.lwoffii_NIPH715               -----------AAAAAACTTCACCTTATTTCTAGTT-GCGGTACAATAGC 38
115 A.lwoffii_SH145                 -----------AAAAAACTTCACCTTATTTCTAGTT-GCGGTACAATAGC 38
116 A.lwoffii_TG19636               -----------AAAAAACTTCACCTTATTTCTAGTT-GCGGTACAATAGC 38
117 A.lwoffii_NCTC5866              -----------AAAAAACTTCACCTTATTTCTAGTT-GCGGTACAATAGC 38
118 A.lwoffii_NIPH478               -----------AAAAAACTTCACCTTATTTCTAGTT-GCGGTACAATAGC 38
```

FIG. 7B

```
SEQ ID NO:
 66  A.baumannii_AB307-0294        GACAATTGTGGAA-GTTTGAATTATGGCGAAAGCA---ACAGTAGTAAAG 96
 67  A.baumannii_MRY10-0558        GACAATTGTGGAA-GTTTGAATTATGGCGAAAGCA---ACAGTAGTAAAG 96
 68  A.baumannii_MDR-TJ            GACAATTGTGGAA-GTTTGAATTATGGCGAAAGCA---ACAGTAGTAAAG 96
 69  A.baumannii_D1279779          GACAATTGTGGAA-GTTTGAATTATGGCGAAAGCA---ACAGTAGTAAAG 94
 70  A.baumannii_Naval-82          GACAATTGTGGAA-GTTTGAATTATGGCGAAAGCA---ACAGTAGTAAAG 96
 71  A.baumannii_UMB002            GACAATTGTGGAA-GTTTGAATTATGGCGAAAGCA---ACAGTAGTAAAG 96
 72  Acinetobacter_sp.ADP1         CATAACTTTGGAATTTTAAGATTATGTCGAAAGCA---GTAGTAGTTAAA 96
 73  Acinetobacter_sp.RUH2624      GGCAATTGTGGAA-GTTTGAATTATGGCGAAAGCA---ACAGTAGTAAAG 96
 74  Acinetobacter_sp.SH024        GGCAATTGTGGAA-GTTTGAATTATGGCGAAAGCA---ACAGTAGTGAAA 84
 75  A.calcoaceticus_PHEA-2B       -----------------------ATGGCGAAAGCA---ACAGTAGTAAAG 24
 76  A.calcoaceticus_PHEA-2        GGCAATTGTGGAA-GTTTGAATTATGGCGAAAGCA---ACAGTAGTAAAG 94
 77  A.calcoaceticus.anitratus_XM15 GGCAATTGTGGAA-GTTTGAATTATGGCGAAAGCA---ACAGTAGTGAAA 84
 78  A.calcoaceticus_TG19585       CATAATTGTGGAA-GTTTGAATTATGGCGAAAGCA---ACAGTAGTAAAG 84
 79  A.calcoaceticus_RUH2202       CATAATTGTGGAA-GTTTGAATTATGGCGAAAGCA---ACAGTAGTAAAG 84
 80  A.calcoaceticus_ANC3811       CATAATTGTGGAA-GTTTGAATTATGGCGAAAGCA---ACAGTAGTGAAA 84
 81  A.calcoaceticus_ANC3680       -----------------------ATGGCGAAAGCA---ACAGTAGTGAAA 24
 82  A.calcoaceticus_TG19593       CATAATTGTGGAA-GTTTGAATTATGGCGAAAGCA---ACAGTAGTGAAA 84
 83  A.calcoaceticus_TG19588       CATAATTGTGGAA-GTTTGAATTATGGCGAAAGCA---ACAGTAGTGAAA 84
 84  A.calcoaceticus_DSM30006      CATAATTGTGGAA-GTTTGAATTATGGCGAAAGCA---ACAGTAGTGAAA 84
 85  A.calcoaceticus_NIPH_13       CATAATTGTGGAA-GTTTGAATTATGGCGAAAGCA---ACAGTAGTGAAA 84
 86  A.nosocomialis_TG21145        ----------------------------------------AGTTGTAAAG 10
 87  A.nosocomialis_TG19596        ----------------------------------------AGTTGTAAAG 10
 88  A.nosocomialis_M2c_7          GACAATTGTGGAA-GTTTGAATTATGGCGAAAGCA---ACAGTAGTAAAG 96
 89  A.nosocomialis_NIPH2119       GGCAATTGTGGAA-GTTTGAATTATGGCGAAAGCA---ACTGTAGTAAAG 96
 90  A.nosocomialis_NIPH386        ----------------------------------------AGTTGTAAAG 10
 91  A.nosocomialis_Ab22222        ----------------------------------------AGTTGTAAAG 10
 92  A.genomosp.3.str.DSM21653     GGCAATTGTGGAA-GTTTGAATTATGGCGAAAGCA---ACAGTAGTAAAG 84
 93  A.genomosp.3str.DSM9306       CATAATTGTGGAA-GTTTGAATTATGGCGAAAGCA---ACAGTAGTAAAG 84
 94  A.oleivorans_DR1              CATAATTGTGGAA-GTTTGAATTATGGCGAAAGCA---ACAGTAGTAAAG 96
 95  A.pittii_ANC4050              GGCAATTGTGGAA-GTTTGAATTATGGCGAAAGCA---ACAGTAGTAAAG 84
 96  A.pittii_ANC3678              GGCAATTGTGGAA-GTTTGAATTATGGCGAAAGCG---ACAGTAGTGAAA 84
 97  A.pittii_D499                 GGCAATTGTGGAA-GTTTGAATTATGGCGAAAGCA---ACAGTAGTGAAA 84
 98  A.pittii_CIP70.29             GGCAATTGTGGAA-GTTTGAATTATGGCGAAAGCA---ACAGTAGTAAAG 84
 99  A.pittii_TG6411               GGCAATTGTGGAA-GTTTGAATTATGGCGAAAGCG---ACAGTAGTGAAA 84
100  A.pittii_ANC4052              GGCAATTGTGGAA-GTTTGAATTATGGCGAAAGCA---ACAGTAGTAAAG 84
101  A.junii_SH205                 TGCAATTGTGGAA-GTTTGAATTATGGCGCAAGCA---ACAGTTGTAAAA 62
102  A.junii_NIPH182               TGCAATTGTGGAA-GTTTGAATTATGGCGCAAGCA---ACAGTTGTAAAA 62
103  A.junii_CIP64.5               TGCAATTGTGGAA-GTTTGAATTATGGCGCAAGCA---ACAGTTGTAAAA 62
104  A.junii_TG19608               TGCAATTGTGGAA-GTTTGAATTATGGCGCAAGCA---ACAGTTGTAAAA 62
105  A.junii_MTCC11364             TGCAATTGTGGAA-GTTTGAATTATGGCGCAAGCA---ACAGTTGTAAAA 62
106  A.junii_CIP107470             TGCAATTGTGGAA-GTTTGAATTATGGCGCAAGCA---ACAGTTGTAAAA 62
107  A.gyllenbergii_CIP110306      GCCAATTGTGGAA-GTTTAAATTATGGCGCAAGCA---ACAGTTGTAAAA 62
108  A.gyllenbergii_MTCC11365      GCCAATTGTGGAA-GTTTAAATTATGGCGCAAGCA---ACAGTTGTAAAA 62
109  A.beijerinckii_ANC3835        CATAATTGTGGAA-GTTTGAATTATGGCGAAAGCA---ACTGTAGTTAAA 62
110  A.beijerinckii_CIP110307      CATAATTGTGGAA-GTTTGAATTATGGCGAAAGCA---ACTGTAGTTAAA 62
111  A.brisouii_ANC4119            TACAGTTTTGGAATGATTTAATTATGGCGAAAGCA---ACTGTAGTCAAG 85
112  A.lwoffii_WJ10621             TACATTGTTGGAAGTAATTGATTATGGCGAAAGCA---ACTGTAGTTAAA 87
113  A.lwoffii_CIP70.31            AGCACGTTTGGAAGTATCAGATTATGGCGAAAGCATCTATTGTAGTAAAA 88
114  A.lwoffii_NIPH715             AGCACGTTTGGAAGTATCAGATTATGGCGAAAGCATCTATTGTAGTAAAA 88
115  A.lwoffii_SH145               AGCACGTTTGGAAGTATCAGATTATGGCGAAAGCATCTATTGTAGTAAAA 88
116  A.lwoffii_TG19636             AGCACGTTTGGAAGTATCAGATTATGGCGAAAGCATCTATTGTAGTAAAA 88
117  A.lwoffii_NCTC5866            AGCACGTTTGGAAGTATCAGATTATGGCGAAAGCATCTATTGTAGTAAAA 88
118  A.lwoffii_NIPH478             AGCACGTTTGGAAGTATCAGATTATGGCGAAAGCATCTATTGTAGTAAAA 88
                                                                      ** ** **
```

FIG. 7C

```
SEQ ID NO:
 66 A.baumannii_AB307-0294          AAACATAATGGCGGAACCATCGCACAAAACAAACGTGCCCGTCATGATTA 146
 67 A.baumannii_MRY10-0558          AAACATAATGGCGGAACCATTGCACAAAACAAACGTGCCCGTCATGATTA 146
 68 A.baumannii_MDR-TJ              AAACATAATGGCGGAACCATTGCACAAAACAAACGTGCCCGTCATGATTA 146
 69 A.baumannii_D1279779            AAACATAATGGCGGAACCATTGCACAAAACAAACGTGCCCGTCATGATTA 144
 70 A.baumannii_Naval-82            AAACATAATGGCGGAACCATCGCACAAAACAAACGTGCCCGTCATGATTA 146
 71 A.baumannii_UMB002              AAACATAATGGCGGAACCATCGCACAAAACAAACGTGCCCGTCATGATTA 146
 72 Acinetobacter_sp.ADP1           AAAAATAATGGCGGTACCATTGCGCAGAATAAACGCGCCCGACACGATTA 146
 73 Acinetobacter_sp.RUH2624        AAACATAATGGCGGAACCATCGCACAAAATAAACGTGCCCGTCATGATTA 146
 74 Acinetobacter_sp.SH024          AAACATAATGGTGGAACCATCGCACAAAACAAACGTGCCCGCCATGATTA 134
 75 A.calcoaceticus_PHEA-2B         AAACATAATGGCGGAACCATCGCACAAAATAAACGTGCCCGTCATGATTA 74
 76 A.calcoaceticus_PHEA-2          AAACATAATGGCGGAACCATCGCACAAAATAAACGTGCCCGTCATGATTA 144
 77 A.calcoaceticus.anitratus_XM15 AAACATAATGGTGGAACCATCGCACAAAACAAACGTGCCCGCCATGATTA 134
 78 A.calcoaceticus_TG19585         AAACATAATGGCGGAACAATCGCACAAAATAAACGTGCCCGTCATGATTA 134
 79 A.calcoaceticus_RUH2202         AAACATAATGGCGGAACAATCGCACAAAATAAACGTGCCCGTCATGATTA 134
 80 A.calcoaceticus_ANC3811         AAACACAATGGCGGAACAATCGCACAAAACAAACGTGCCCGTCATGATTA 134
 81 A.calcoaceticus_ANC3680         AAACACAATGGCGGAACAATCGCACAAAATAAACGTGCCCGTCATGATTA 74
 82 A.calcoaceticus_TG19593         AAACACAATGGCGGAACAATCGCACAAAATAAACGTGCCCGTCATGATTA 134
 83 A.calcoaceticus_TG19588         AAACACAATGGCGGAACAATCGCACAAAATAAACGTGCCCGTCATGATTA 134
 84 A.calcoaceticus_DSM30006        AAACACAATGGCGGAACAATCGCACAAAATAAACGTGCCCGTCATGATTA 134
 85 A.calcoaceticus_NIPH_13         AAACACAATGGCGGAACAATCGCACAAAATAAACGTGCCCGTCATGATTA 134
 86 A.nosocomialis_TG21145          AAACATAATGGCGGAACCATCGCACAAAATAAACGTGCCCGTCATGATTA 60
 87 A.nosocomialis_TG19596          AAACATAATGGCGGAACCATCGCACAAAATAAACGTGCCCGTCATGATTA 60
 88 A.nosocomialis_M2c_7            AAACATAATGGCGGAACCATCGCACAAAATAAACGTGCCCGTCATGATTA 146
 89 A.nosocomialis_NIPH2119         AAACATAATGGCGGAACCATCGCACAAAATAAACGTGCCCGTCATGATTA 146
 90 A.nosocomialis_NIPH386          AAACATAATGGCGGAACCATCGCACAAAATAAGCGTGCCCGTCATGATTA 60
 91 A.nosocomialis_Ab22222          AAACATAATGGCGGAACCATCGCACAAAATAAGCGTGCCCGTCATGATTA 60
 92 A.genomosp.3.str.DSM21653       AAACATAATGGCGGAACCATCGCACAAAATAAACGTGCCCGTCATGATTA 134
 93 A.genomosp.3str.DSM9306         AAACATAATGGCGGAACCATCGCACAAAACAAACGTGCCCGCCATGATTA 134
 94 A.oleivorans_DR1                AAACATAATGGCGGAACAATCGCACAAAATAAGCGTGCCCGTCATGATTA 146
 95 A.pittii_ANC4050                AAACATAATGGCGGAACCATCGCACAAAATAAACGTGCCCGTCATGATTA 134
 96 A.pittii_ANC3678                AAACATAATGGCGGAACCATCGCACAAAACAAACGTGCCCGCCATGATTA 134
 97 A.pittii_D499                   AAACATAATGGTGGAACCATCGCACAAAACAAACGTGCCCGCCATGATTA 134
 98 A.pittii_CIP70.29               AAACATAATGGCGGAACCATCGCACAAAATAAACGTGCCCGTCATGATTA 134
 99 A.pittii_TG6411                 AAACATAATGGCGGAACCATCGCACAAAACAAACGTGCCCGCCATGATTA 134
100 A.pittii_ANC4052                AAACATAATGGCGGAACCATCGCACAAAACAAACGTGCCCGCCATGATTA 134
101 A.junii_SH205                   AAACATAATGGTGGCACGATTGCTCAAAATAAAAGAGCGCGTCACGATTA 112
102 A.junii_NIPH182                 AAACATAATGGTGGCACGATTGCTCAAAATAAAAGAGCGCGTCACGATTA 112
103 A.junii_CIP64.5                 AAACATAATGGTGGCACGATTGCTCAGAATAAAAGAGCGCGTCACGATTA 112
104 A.junii_TG19608                 AAACATAATGGTGGCACGATTGCTCAGAATAAAAGAGCGCGTCACGATTA 112
105 A.junii_MTCC11364               AAACATAATGGTGGCACGATTGCTCAGAATAAAAGAGCGCGTCACGATTA 112
106 A.junii_CIP107470               AAACATAATGGTGGCACGATTGCTCAGAATAAAAGAGCGCGTCACGATTA 112
107 A.gyllenbergii_CIP110306        AAACATAATGGTGGCACGATTGCTCAAAATAAAAGAGCGCGCCACGATTA 112
108 A.gyllenbergii_MTCC11365        AAACATAATGGTGGCACGATTGCTCAAAATAAAAGAGCGCGCCACGATTA 112
109 A.beijerinckii_ANC3835          AAAAATAATGGTGGAACGATTGCTCAAAACAAAAGAGCGCGTCACGATTA 112
110 A.beijerinckii_CIP110307        AAAAATAATGGTGGAACGATTGCTCAAAACAAAAGAGCGCGTCACGATTA 112
111 A.brisouii_ANC4119              AAAAATAATGGCGGAACTATTGCACAAAATAAGCGTGCCCGTCATGATTA 135
112 A.lwoffii_WJ10621               AAAAATACCAGCGGGACGATTGCACAGAATAAACGTGCACGTCACGACTA 137
113 A.lwoffii_CIP70.31              AAAAATAATGGCGGTACCATTGCACTGAATAAACGTGCCCGCCACGATTA 138
114 A.lwoffii_NIPH715               AAAAATAATGGCGGTACCATTGCACTGAATAAACGTGCCCGCCACGATTA 138
115 A.lwoffii_SH145                 AAAAATAATGGCGGTACCATTGCACTGAATAAACGTGCCCGCCACGATTA 138
116 A.lwoffii_TG19636               AAAAATAATGGCGGTACCATTGCACTGAATAAACGTGCCCGCCACGATTA 138
117 A.lwoffii_NCTC5866              AAAA-TAATGGCGGTACCATTGCACTGAATAAACGTGCCCGCCACGATTA 137
118 A.lwoffii_NIPH478               AAAAATAATGGCGGTACCATTGCACTGAATAAACGTGCCCGCCACGATTA 138
                                    ***   *   * ** ** ** ** *  ** **  * ** ** ** ** **
```

FIG. 7D

A.baum smpB F1

| SEQ ID NO: | | | |
|---|---|---|---|
| 66 | A.baumannii_AB307-0294 | TTTTATCGAAGAAAAATTTGAAGCTGGCATGTCTTTACTAGGCTGGGAAG | 196 |
| 67 | A.baumannii_MRY10-0558 | TTTTATCGAAGAAAAATTTGAAGCTGGCATGTCTTTACTAGGCTGGGAAG | 196 |
| 68 | A.baumannii_MDR-TJ | TTTTATCGAAGAAAAATTTGAAGCTGGCATGTCTTTACTAGGCTGGGAAG | 196 |
| 69 | A.baumannii_D1279779 | TTTTATCGAAGAAAAATTTGAAGCTGGCATGTCTTTACTAGGCTGGGAAG | 194 |
| 70 | A.baumannii_Naval-82 | TTTTATCGAAGAAAAATTTGAAGCTGGCATGTCTTTACTAGGCTGGGAAG | 196 |
| 71 | A.baumannii_UMB002 | TTTTATCGAAGAAAAATTTGAAGCTGGCATGTCTTTACTAGGCTGGGAAG | 196 |
| 72 | Acinetobacter_sp.ADP1 | TTTTATTGAAGAAAAATTTGAAGCAGGTATGTCTTTGCAAGGCTGGGAAG | 196 |
| 73 | Acinetobacter_sp.RUH2624 | TTTTATCGAAGAAAAATTTGAAGCTGGCATGTCTTTACTCGGCTGGGAAG | 196 |
| 74 | Acinetobacter_sp.SH024 | TTTTATCGAAGAAAAATTTGAAGCTGGTATGTCTTTACTCGGCTGGGAAG | 184 |
| 75 | A.calcoaceticus_PHEA-2B | TTTTATCGAAGAAAAATTTGAAGCTGGTATGTCTTTACTCGGCTGGGAAG | 124 |
| 76 | A.calcoaceticus_PHEA-2 | TTTTATCGAAGAAAAATTTGAAGCTGGTATGTCTTTACTCGGCTGGGAAG | 194 |
| 77 | A.calcoaceticus.anitratus_XM15 | TTTTATCGAAGAAAAATTTGAAGCTGGTATGTCTTTACTCGGCTGGGAAG | 184 |
| 78 | A.calcoaceticus_TG19585 | TTTTATCGAAGAAAAATTTGAAGCGGGCATGTCACTTCAAGGTTGGGAAG | 184 |
| 79 | A.calcoaceticus_RUH2202 | TTTTATCGAAGAAAAATTTGAAGCAGGCATGTCACTTCAAGGTTGGGAAG | 184 |
| 80 | A.calcoaceticus_ANC3811 | TTTTATCGAAGAAAAATTTGAAGCAGGCATGTCACTTCAAGGTTGGGAAG | 184 |
| 81 | A.calcoaceticus_ANC3680 | TTTTATTGAAGAAAAATTTGAAGCTGGTATGTCACTTCAAGGTTGGGAAG | 124 |
| 82 | A.calcoaceticus_TG19593 | TTTTATCGAAGAAAAATTTGAAGCGGGTATGTCACTTCAAGGTTGGGAAG | 184 |
| 83 | A.calcoaceticus_TG19588 | TTTTATCGAAGAAAAATTTGAAGCGGGTATGTCACTTCAAGGTTGGGAAG | 184 |
| 84 | A.calcoaceticus_DSM30006 | TTTTATCGAAGAAAAATTTGAAGCGGGTATGTCACTTCAAGGTTGGGAAG | 184 |
| 85 | A.calcoaceticus_NIPH_13 | TTTTATCGAAGAAAAATTTGAAGCGGGTATGTCACTTCAAGGTTGGGAAG | 184 |
| 86 | A.nosocomialis_TG21145 | TTTTATCGAAGAAAAATTTGAAGCTGGCATGTCTTTACTCGGCTGGGAAG | 110 |
| 87 | A.nosocomialis_TG19596 | TTTTATCGAAGAAAAATTTGAAGCTGGCATGTCTTTACTCGGCTGGGAAG | 110 |
| 88 | A.nosocomialis_M2c_7 | TTTTATCGAAGAAAAATTTGAAGCTGGCATGTCTTTACTCGGCTGGGAAG | 196 |
| 89 | A.nosocomialis_NIPH2119 | TTTTATCGAAGAAAAATTTGAAGCTGGCATGTCTTTACTCGGCTGGGAAG | 196 |
| 90 | A.nosocomialis_NIPH386 | TTTTATCGAAGAAAAATTTGAAGCTGGCATGTCTTTACTCGGCTGGGAAG | 110 |
| 91 | A.nosocomialis_Ab22222 | TTTTATCGAAGAAAAATTTGAAGCTGGCATGTCTTTACTCGGCTGGGAAG | 110 |
| 92 | A.genomosp.3.str.DSM21653 | TTTTATCGAAGAAAAATTTGAAGCTGGTATGTCTTTACTCGGCTGGGAAG | 184 |
| 93 | A.genomosp.3str.DSM9306 | TTTTATCGAAGAAAAATTTGAAGCTGGTATGTCTTTACTCGGTTGGGAAG | 184 |
| 94 | A.oleivorans_DR1 | TTTTATCGAAGAAAAATTTGAAGCAGGCATGTCACTTCAAGGTTGGGAAG | 196 |
| 95 | A.pittii_ANC4050 | TTTTATCGAAGAAAAATTTGAAGCTGGTATGTCTTTACTCGGCTGGGAAG | 184 |
| 96 | A.pittii_ANC3678 | TTTTATCGAAGAAAAATTTGAAGCTGGTATGTCTTTACTAGGCTGGGAAG | 184 |
| 97 | A.pittii_D499 | TTTTATCGAAGAAAAATTTGAAGCTGGTATGTCTTTACTCGGCTGGGAAG | 184 |
| 98 | A.pittii_CIP70.29 | TTTTATCGAAGAAAAATTTGAAGCTGGTATGTCTTTACTCGGCTGGGAAG | 184 |
| 99 | A.pittii_TG6411 | TTTTATCGAAGAAAAATTTGAAGCTGGTATGTCTTTACTCGGCTGGGAAG | 184 |
| 100 | A.pittii_ANC4052 | TTTTATCGAAGAAAAATTTGAAGCTGGTATGTCTTTACTCGGCTGGGAAG | 184 |
| 101 | A.junii_SH205 | CTTTATCGAAGAAAAATTTGAAGCAGGCATGTCACTTCAGGGTTGGGAAG | 162 |
| 102 | A.junii_NIPH182 | TTTTATCGAAGAAAAATTTGAAGCAGGCATGTCACTTCAGGGTTGGGAAG | 162 |
| 103 | A.junii_CIP64.5 | CTTTATCGAAGAAAAATTTGAAGCAGGCATGTCACTTCAGGGTTGGGAAG | 162 |
| 104 | A.junii_TG19608 | CTTTATCGAAGAAAAATTTGAAGCAGGCATGTCACTTCAGGGTTGGGAAG | 162 |
| 105 | A.junii_MTCC11364 | CTTTATCGAAGAAAAATTTGAAGCAGGCATGTCACTTCAGGGTTGGGAAG | 162 |
| 106 | A.junii_CIP107470 | CTTTATCGAAGAAAAATTTGAAGCAGGCATGTCACTTCAGGGTTGGGAAG | 162 |
| 107 | A.gyllenbergii_CIP110306 | CTTTATCGAAGAAAAATTTGAAGCAGGCATGTCCCTACAAGGTTGGGAAG | 162 |
| 108 | A.gyllenbergii_MTCC11365 | CTTTATCGAAGAAAAATTTGAAGCAGGCATGTCCCTACAAGGTTGGGAAG | 162 |
| 109 | A.beijerinckii_ANC3835 | CTTTATTGAAGAAAAAATTGAAGCTGGTATGTCTTTACAAGGCTGGGAAG | 162 |
| 110 | A.beijerinckii_CIP110307 | CTTTATTGAAGAAAAAATTGAAGCTGGTATGTCTTTACAAGGCTGGGAAG | 162 |
| 111 | A.brisouii_ANC4119 | TTTTATCGAAGAAAAATTTGAAGCGGGTCTTTCCCTACAGGGTTGGGAAG | 185 |
| 112 | A.lwoffii_WJ10621 | TTTTATTGAAGAAAAATTTGAAGCTGGCCTGTCACTGCAAGGCTGGGAAG | 187 |
| 113 | A.lwoffii_CIP70.31 | TTTTATTGAAGAGAAATTTGAAGCGGGGCTGTCATTAAAGGGCTGGGAAG | 188 |
| 114 | A.lwoffii_NIPH715 | TTTTATTGAAGAGAAATTTGAAGCGGGGCTTTCATTAAAAGGCTGGGAAG | 188 |
| 115 | A.lwoffii_SH145 | TTTTATTGAAGAGAAATTTGAAGCGGGGCTTTCATTAAAAGGCTGGGAAG | 188 |
| 116 | A.lwoffii_TG19636 | TTTTATTGAAGAGAAATTTGAAGCGGGGCTTTCATTAAAAGGCTGGGAAG | 188 |
| 117 | A.lwoffii_NCTC5866 | TTTTATTGAAGAGAAATTTGAAGCGGGGCTTTCATTAAAAGGCTGGGAAG | 187 |
| 118 | A.lwoffii_NIPH478 | TTTTATTGAAGAGAAATTTGAAGCGGGGCTTTCATTAAAAGGTTGGGAAG | 188 |
| | | ***** ***** *** ******* ** * ** * ** ******* | |

FIG. 7E

```
SEQ ID NO:
 66 A.baumannii_AB307-0294         TAAAATCTTTACGTGCCGGTCGTATGAGT-TTGACAGAAAGTTATGTCAT 245
 67 A.baumannii_MRY10-0558         TAAAATCTTTACGTGCCGGTCGTATGAGT-TTGACAGAAAGTTATGTCAT 245
 68 A.baumannii_MDR-TJ             TAAAATCTTTACGTGCCGGTCGTATGAGT-TTGACAGAAAGTTATGTCAT 245
 69 A.baumannii_D1279779           TAAAATCTTTACGTGCCGGTCGTATGAGT-TTGACAGAAAGTTATGTCAT 243
 70 A.baumannii_Naval-82           TAAAATCTTTACGTGCCGGTCGTATGAGT-TTGACAGAAAGTTATGTCAT 245
 71 A.baumannii_UMB002             TAAAATCTTTACGTGCCGGTCGTATGAGT-TTGACAGAAAGTTATGTCAT 245
 72 Acinetobacter_sp.ADP1          TAAAATCCTTGCGTGCAGGTCGTATGAGC-CTTACCGAAAGCTATATCAT 245
 73 Acinetobacter_sp.RUH2624       TAAAGTCTTTACGTGCTGGTCGTATGAGT-TTGACAGAAAGTTATGTCAT 245
 74 Acinetobacter_sp.SH024         TAAAGTCTTTACGTGCTGGTCGCATGAGT-TTGACAGAAAGTTATGTCAT 233
 75 A.calcoaceticus_PHEA-2B        TAAAGTCTTTACGTGCTGGTCGCATGAGT-TTGACAGAAAGTTATGTCAT 173
 76 A.calcoaceticus_PHEA-2         TAAAGTCTTTACGTGCTGGTCGCATGAGT-TTGACAGAAAGTTATGTCAT 243
 77 A.calcoaceticus.anitratus_XM15 TAAAGTCTTTACGTGCTGGTCGCATGAGT-TTGACAGAAAGTTATGTCAT 233
 78 A.calcoaceticus_TG19585        TAAAATCCTTACGTGCTGGGCGCATGACT-TTGACGGAAAGTTATGTCAT 233
 79 A.calcoaceticus_RUH2202        TAAAATCCTTACGTGCTGGGCGTATGACT-TTGACGGAAAGTTATGTCAT 233
 80 A.calcoaceticus_ANC3811        TAAAATCCTTACGTGCTGGACGTATGACT-TTGACTGAAAGTTATGTGAT 233
 81 A.calcoaceticus_ANC3680        TAAAATCCTTACGTGCTGGGCGTATGACT-TTGACGGAAAGTTATGTCAT 173
 82 A.calcoaceticus_TG19593        TAAAATCCTTACGCGCTGGGCGCATGACT-TTGACGGAAAGTTATGTCAT 233
 83 A.calcoaceticus_TG19588        TAAAATCCTTACGTGCTGGGCGTATGACT-TTGACGGAAAGTTATGTCAT 233
 84 A.calcoaceticus_DSM30006       TAAAATCCTTACGTGCTGGGCGTATGACT-TTGACGGAAAGTTATGTCAT 233
 85 A.calcoaceticus_NIPH_13        TAAAATCCTTACGTGCTGGGCGTATGACT-TTGACGGAAAGTTATGTCAT 233
 86 A.nosocomialis_TG21145         TAAAGTCTTTACGTGCTGGTCGTATGAGT-TTGACAGAAAGTTATGTCAT 159
 87 A.nosocomialis_TG19596         TAAAGTCTTTACGTGCTGGTCGTATGAGT-TTGACAGAAAGTTATGTCAT 159
 88 A.nosocomialis_M2c_7           TAAAGTCTTTACGTGCTGGTCGTATGAGT-TTGACAGAAAGTTATGTCAT 245
 89 A.nosocomialis_NIPH2119        TAAAGTCTTTACGTGCTGGTCGTATGAGT-TTGACAGAAAGTTATGTCAT 245
 90 A.nosocomialis_NIPH386         TAAAGTCTTTACGTGCCGGTCGTATGAGT-TTGACAGAAAGTTATGTCAT 159
 91 A.nosocomialis_Ab22222         TAAAGTCTTTACGTGCCGGTCGTATGAGT-TTGACAGAAAGTTATGTCAT 159
 92 A.genomosp.3.str.DSM21653      TAAAGTCTTTACGTGCTGGTCGCATGAGT-TTGACAGAAAGTTATGTCAT 233
 93 A.genomosp.3str.DSM9306        TAAAGTCTTTACGTGCTGGTCGCATGAGT-TTGACAGAAAGTTATGTCAT 233
 94 A.oleivorans_DR1               TAAAATCCTTACGTGCTGGGCGTATGACT-TTGACGGAAAGTTATGTCAT 245
 95 A.pittii_ANC4050               TAAAGTCTTTACGTGCTGGTCGCATGAGT-TTGACAGAAAGTTATGTCAT 233
 96 A.pittii_ANC3678               TAAAGTCTTTACGTGCTGGTCGGATGAGC-TTGACAGAAAGTTATGTCAT 233
 97 A.pittii_D499                  TAAAGTCTTTACGTGCTGGTCGCATGAGT-TTGACAGAAAGTTATGTCAT 233
 98 A.pittii_CIP70.29              TAAAGTCTTTACGTGCTGGTCGCATGAGT-TTGACAGAAAGTTATGTCAT 233
 99 A.pittii_TG6411                TAAAGTCTTTACGTGCTGGTCGGATGAGC-TTGACAGAAAGTTATGTCAT 233
100 A.pittii_ANC4052               TAAAGTCTTTACGTGCTGGTCGCATGAGT-TTGACAGAAAGTTATGTCAT 233
101 A.junii_SH205                  TAAAATCCTTACGTGCTGGACGTATGACC-TTGTCTGAAAGTTATGTCAT 211
102 A.junii_NIPH182                TAAAATCCTTACGCGCTGGACGTATGACC-TTGTCTGAAAGTTATGTCAT 211
103 A.junii_CIP64.5                TAAAATCCTTACGTGCTGGACGTATGACA-TTGTCTGAAAGTTATGTCAT 211
104 A.junii_TG19608                TAAAATCCTTACGTGCTGGACGTATGACA-TTGTCTGAAAGTTATGTCAT 211
105 A.junii_MTCC11364              TAAAATCCTTACGTGCTGGACGGATGACT-TTGTCTGAAAGTTATGTCAT 211
106 A.junii_CIP107470              TAAAATCCTTACGTGCTGGACGGATGACT-TTGTCTGAAAGTTATGTCAT 211
107 A.gyllenbergii_CIP110306       TAAAATCCCTACGTGCTGGGCGTATGAGC-TTGACTGAAAGTTATGTCAT 211
108 A.gyllenbergii_MTCC11365       TAAAATCCCTACGTGCTGGGCGTATGAGC-TTGACTGAAAGTTATGTCAT 211
109 A.beijerinckii_ANC3835         TGAAATCACTTCGTGCCGGTCGTATGACT-CTGACTGAAAGCTATGTCAT 211
110 A.beijerinckii_CIP110307       TGAAGTCACTTCGTGCCGGTCGTATGACG-CTGACTGAAAGCTATGTCAT 211
111 A.brisouii_ANC4119             TCAAATCCTTGCGTGCTGGGCGTATGAGT-CTGGTTGAGAGCTATATTAT 234
112 A.lwoffii_WJ10621              TGAAATCATTACGTGCAGGTCGTATGAC-GCTGTCTGAGAGTTATATCAC 236
113 A.lwoffii_CIP70.31             TCAAATCAATGCGTGCCGGTCGTATGACCATTGTA-GAAAGCTATATTAC 237
114 A.lwoffii_NIPH715              TCAAATCAATGCGTGCTGGTCGCATGACCATCGTA-GAAAGTTATATTAC 237
115 A.lwoffii_SH145                TCAAATCAATGCGTGCTGGTCGCATGACCATCGTA-GAAAGTTATATTAC 237
116 A.lwoffii_TG19636              TCAAATCAATGCGCGCTGGTCGCATGACCATTGTA-GAAAGTTATATTAC 237
117 A.lwoffii_NCTC5866             TCAAATCAATGCGCGCTGGTCGCATGACCATTGTA-GAAAGTTATATTAC 236
118 A.lwoffii_NIPH478              TCAAATCAATGCGTGCTGGTCGCATGACCATCGTA-GAAAGTTATATTAC 237
                                   * ** **  * ** ** ** ** ****         ** ** *** * *
```

A.baum smpB P FIG. 7F

```
SEQ ID NO:
 66 A.baumannii_AB307-0294          TTTTAAAAATGGTGAAGCATTCTTATTTGGTGCTCAGATTCAACCACTCC 295
 67 A.baumannii_MRY10-0558          TTTTAAAAATGGTGAAGCATTCTTATTTGGTGCTCAGATTCAACCACTCC 295
 68 A.baumannii_MDR-TJ              TTTTAAAAATGGTGAAGCATTCTTATTTGGTGCTCAGATTCAACCACTCC 295
 69 A.baumannii_D1279779            TTTTAAAAATGGTGAAGCATTCTTATTTGGTGCTCAGATTCAACCACTCC 293
 70 A.baumannii_Naval-82            TTTTAAAAATGGTGAAGCATTCTTATTTGGTGCTCAGATTCAACCACTCC 295
 71 A.baumannii_UMB002              TTTTAAAAATGGTGAAGCATTCTTATTTGGTGCTCAGATTCAACCACTCC 295
 72 Acinetobacter_sp.ADP1           CTTTAAAAATGGTGAAGCCTACCTATTTGGTGCTCAAATTCAACCGTTGC 295
 73 Acinetobacter_sp.RUH2624        TTTTAAAAACGGTGAAGCATTTTTATTTGGTGCGCAAATTCAACCGCTCC 295
 74 Acinetobacter_sp.SH024          TTTTAAGAATGGTGAAGCGTTTTTATTTGGTGCACAAATTCAACCGCTCC 283
 75 A.calcoaceticus_PHEA-2B         TTTTAAGAATGGTGAAGCGTTTTTATTTGGTGCACAAATTCAACCGCTCC 223
 76 A.calcoaceticus_PHEA-2          TTTTAAGAATGGTGAAGCGTTTTTATTTGGTGCACAAATTCAACCGCTCC 293
 77 A.calcoaceticus.anitratus_XM15  TTTTAAGAATGGTGAAGCGTTTTTATTTGGTGCACAAATTCAACCGCTCC 283
 78 A.calcoaceticus_TG19585         TTTCAAGAATGGCGAAGCATTTTTACTTGGCTCACAAATTCAGCCTTTAT 283
 79 A.calcoaceticus_RUH2202         TTTCAAGAATAGCGAAGCATTTTTACTTGGTTCACAAATTCAGCCTTTAT 283
 80 A.calcoaceticus_ANC3811         TTTCAAAAATGGCGAAGCATTTTTACTTGGCTCACAAATTCAGCCTTTAT 283
 81 A.calcoaceticus_ANC3680         TTTCAAGAATAGCGAAGCATTTTTACTTGGTTCACAAATTCAGCCTTTAT 223
 82 A.calcoaceticus_TG19593         TTTCAAGAATGGCGAAGCATTTTTACTTGGCTCACAAATTCAGCCTTTAT 283
 83 A.calcoaceticus_TG19588         TTTCAAGAATGGCGAAGCATTTTTACTTGGCTCACAAATTCAGCCTTTAT 283
 84 A.calcoaceticus_DSM30006        TTTCAAGAATGGCGAAGCATTTTTACTTGGCTCACAAATTCAGCCTTTAT 283
 85 A.calcoaceticus_NIPH_13         TTTCAAGAATGGCGAAGCATTTTTACTTGGCTCACAAATTCAGCCTTTAT 283
 86 A.nosocomialis_TG21145          TTTTAAAAACGGTGAAGCATTTTTATTTGGTGCACAAATTCAACCGCTCC 209
 87 A.nosocomialis_TG19596          TTTTAAAAACGGTGAAGCATTTTTATTTGGTGCACAAATTCAACCGCTCC 209
 88 A.nosocomialis_M2c_7            TTTTAAAAACGGTGAAGCATTTTTATTTGGTGCACAAATTCAACCGCTCC 295
 89 A.nosocomialis_NIPH2119         TTTTAAAAACGGTGAAGCATTTTTATTTGGTGCACAAATTCAACCGCTCC 295
 90 A.nosocomialis_NIPH386          TTTTAAAAACGGTGAAGCATTTTTATTTGGTGCACAAATTCAACCGCTTC 209
 91 A.nosocomialis_Ab22222          TTTTAAAAACGGTGAAGCATTTTTATTTGGTGCACAAATTCAACCGCTTC 209
 92 A.genomosp.3.str.DSM21653       TTTTAAGAATGGTGAAGCGTTTTTATTTGGTGCACAAATTCAACCGCTCC 283
 93 A.genomosp.3str.DSM9306         TTTTAAGAATGGTGAAGCGTTTTTATTTGGTGCACAAATTCAACCGCTCC 283
 94 A.oleivorans_DR1                TTTCAAAAATGGCGAAGCATTTTTACTTGGTTCACAAATTCAGCCTTTAT 295
 95 A.pittii_ANC4050                TTTTAAGAATGGTGAAGCGTTTTTATTTGGTGCACAAATTCAACCGCTCC 283
 96 A.pittii_ANC3678                TTTTAAGAATGGTGAAGCGTTTTTATTTGGTGCACAAATTCAACCGCTCC 283
 97 A.pittii_D499                   TTTTAAGAATGGTGAAGCGTTTTTATTTGGTGCACAAATTCAACCGCTCC 283
 98 A.pittii_CIP70.29               TTTTAAGAATGGTGAAGCGTTTTTATTTGGTGCACAAATTCAACCGCTCC 283
 99 A.pittii_TG6411                 TTTTAAGAATGGTGAAGCGTTTTTATTTGGTGCACAAATTCAACCGCTCC 283
100 A.pittii_ANC4052                TTTTAAGAATGGTGAAGCGTTTTTATTTGGTGCACAAATTCAACCGCTCC 283
101 A.junii_SH205                   TTTTAAAAATGGTGAAGCCTTTTTATTTGGTTCACAGATTCAGCCTTTAT 261
102 A.junii_NIPH182                 TTTTAAAAATGGTGAAGCCTTTTTATTTGGTTCACAGATTCAGCCTTTAT 261
103 A.junii_CIP64.5                 TTTTAAAAATGGTGAAGCCTTTTTATTTGGTTCACAGATTCAGCCTTTAT 261
104 A.junii_TG19608                 TTTTAAAAATGGTGAAGCCTTTTTATTTGGTTCACAGATTCAGCCTTTAT 261
105 A.junii_MTCC11364               TTTTAAAAATGGTGAAGCCTTTTTATTTGGTTCACAGATTCAGCCTTTAT 261
106 A.junii_CIP107470               TTTTAAAAATGGTGAAGCCTTTTTATTTGGTTCACAGATTCAGCCTTTAT 261
107 A.gyllenbergii_CIP110306        TTTTAAAAATGGTGAAGCTTTTTTATTGGGCTCACAAATTCAGCCCTTGT 261
108 A.gyllenbergii_MTCC11365        TTTTAAAAATGGTGAAGCTTTTTTATTGGGCTCACAAATTCAGCCCTTGT 261
109 A.beijerinckii_ANC3835          TTTTAAAAATGGTGAAGCATTTTTACTGGGTTCACAAATTCAGCCTTTAT 261
110 A.beijerinckii_CIP110307        TTTTAAAAATGGTGAAGCATTTTTACTGGGTTCACAAATTCAGCCTTTAT 261
111 A.brisouii_ANC4119              TTTTAAAAATAATGAAGCGTTTTTATTTGGCGCACAGATTCAGCCACTCT 284
112 A.lwoffii_WJ10621               CTTTAAAAATGGTGAAGCTTTCCTGTTCGGTGCTCAAATTCAGCCTTTAC 286
113 A.lwoffii_CIP70.31              CTTTAAAAATGGTGAAGCTTTCCTGTTTGGTGCGCAAGTTCAGCCTTTGC 287
114 A.lwoffii_NIPH715               CTTTAAAAATGGTGAAGCGTTCTTGTTTGGTGCACAGGTTCAGCCCTTGT 287
115 A.lwoffii_SH145                 CTTTAAAAATGGTGAAGCGTTCTTGTTTGGTGCACAGGTTCAGCCCTTGT 287
116 A.lwoffii_TG19636               CTTTAAAAATGGTGAAGCGTTCTTGTTTGGTGCACAGGTTCAGCCCTTGT 287
117 A.lwoffii_NCTC5866              CTTTAAAAATGGTGAAGCGTTCTTGTTTGGTGCACAGGTTCAGCCCTTGT 286
118 A.lwoffii_NIPH478               CTTTAAAAATGGTGAAGCGTTCTTGTTTGGTGCACAGGTTCAGCCCTTGT 287
                                     ** ** **    ***** *   *  * **  * **  **** **  *
```

FIG. 7G

A.baum smpB R1

| SEQ ID NO: | | | |
|---|---|---|---|
| 66 | A.baumannii_AB307-0294 | TTTCTGCATCTACACATATTGTGCCGGAAGCTACACGTACACGAAAATTA | 345 |
| 67 | A.baumannii_MRY10-0558 | TTTCTGCATCTACACATATTGTGCCGGAAGCTACACGTACACGAAAATTA | 345 |
| 68 | A.baumannii_MDR-TJ | TTTCTGCATCTACACATATTGTGCCGGAAGCTACACGTACACGAAAATTA | 345 |
| 69 | A.baumannii_D1279779 | TTTCTGCATCTACACATATTGTGCCGGAAGCTACACGTACACGAAAATTA | 343 |
| 70 | A.baumannii_Naval-82 | TTTCTGCATCTACACATATTGTGCCGGAAGCTACACGTACACGAAAATTA | 345 |
| 71 | A.baumannii_UMB002 | TTTCTGCATCTACACATATTGTGCCGGAAGCTACGCGTACACGAAAATTA | 345 |
| 72 | Acinetobacter_sp.ADP1 | TTACCGCATCGAGCCATGTTGTGCCTGAAGCCACACGGACACGTAAATTA | 345 |
| 73 | Acinetobacter_sp.RUH2624 | TTTCTGCATCTACACATATCGTGCCGGAAGCTACACGTACACGTAAATTA | 345 |
| 74 | Acinetobacter_sp.SH024 | TTTCAGCATCTACTCATGTAGTACCTGAAGCTACACGTACACGTAAATTA | 333 |
| 75 | A.calcoaceticus_PHEA-2B | TTTCGGCATCTACTCATGTAGTACCTGAAGCTACACGTACACGTAAATTA | 273 |
| 76 | A.calcoaceticus_PHEA-2 | TTTCGGCATCTACTCATGTAGTACCTGAAGCTACACGTACACGTAAATTA | 343 |
| 77 | A.calcoaceticus.anitratus_XM15 | TTTCAGCATCTACTCATGTAGTACCTGAAGCTACACGTACACGTAAATTA | 333 |
| 78 | A.calcoaceticus_TG19585 | TATCGGCTTCGACCCATGTGGTACCTGAAGCAACACGCACCCGTAAGTTA | 333 |
| 79 | A.calcoaceticus_RUH2202 | TATCGGCTTCGACCCATGTGGTACCTGAAGCAACACGTACCCGTAAGTTA | 333 |
| 80 | A.calcoaceticus_ANC3811 | TATCAGCTTCGACTCATGTTGTACCTGAAGCAACACGTACCCGTAAGTTA | 333 |
| 81 | A.calcoaceticus_ANC3680 | TATCGGCTTCGACCCATGTGGTACCTGAAGCAACACGTACCCGTAAGTTA | 273 |
| 82 | A.calcoaceticus_TG19593 | TATCGGCTTCGACCCATGTGGTACCTGAAGCAACACGCACCCGTAAGTTA | 333 |
| 83 | A.calcoaceticus_TG19588 | TATCGGCTTCGACCCATGTGGTACCTGAAGCAACACGCACCCGTAAGTTA | 333 |
| 84 | A.calcoaceticus_DSM30006 | TATCGGCTTCGACCCATGTGGTACCTGAAGCAACACGCACCCGTAAGTTA | 333 |
| 85 | A.calcoaceticus_NIPH_13 | TATCGGCTTCAACTCATGTGGTACCTGAAGCAACACGCACCCGTAAGTTA | 333 |
| 86 | A.nosocomialis_TG21145 | TTTCTGCATCTACACATATCGTGCCGGAAGCTACACGTACACGTAAATTA | 259 |
| 87 | A.nosocomialis_TG19596 | TTTCTGCATCTACACATATCGTGCCGGAAGCTACACGTACACGTAAATTA | 259 |
| 88 | A.nosocomialis_M2c_7 | TTTCTGCATCTACACATATCGTGCCGGAAGCTACACGTACACGTAAATTA | 345 |
| 89 | A.nosocomialis_NIPH2119 | TTTCTGCATCTACACATATCGTGCCGGAAGCTACACGTACACGTAAATTA | 345 |
| 90 | A.nosocomialis_NIPH386 | TTTCTGCATCTACACATATTGTGCCGGAGGCTACACGTACACGTAAATTA | 259 |
| 91 | A.nosocomialis_Ab22222 | TTTCTGCATCTACACATATTGTGCCGGAGGCTACACGTACACGTAAATTA | 259 |
| 92 | A.genomosp.3.str.DSM21653 | TTTCGGCATCTACTCATGTAGTACCTGAAGCTACACGTACACGTAAATTA | 333 |
| 93 | A.genomosp.3str.DSM9306 | TTTCAGCATCTACTCATGTAGTACCTGAAGCTACACGTACACGTAAATTA | 333 |
| 94 | A.oleivorans_DR1 | TATCGGCTTCGACCCATGTTGTACCTGAGGCAACACGTACCCGTAAACTA | 345 |
| 95 | A.pittii_ANC4050 | TTTCGGCGTCTACTCATGTAGTACCTGAAGCTACACGTACACGTAAATTA | 333 |
| 96 | A.pittii_ANC3678 | TTTCAGCATCTACTCATGTAGTACCTGAAGCTACACGTACACGTAAATTA | 333 |
| 97 | A.pittii_D499 | TTTCAGCATCTACTCATGTAGTACCTGAAGCTACACGTACACGTAAATTA | 333 |
| 98 | A.pittii_CIP70.29 | TTTCGGCATCTACTCATGTAGTACCTGAAGCTACACGTACACGTAAATTA | 333 |
| 99 | A.pittii_TG6411 | TTTCAGCATCTACTCATGTAGTACCTGAAGCTACACGTACACGTAAATTA | 333 |
| 100 | A.pittii_ANC4052 | TTTCTGCCTCTACTCATGTAGTACCTGAAGCTACACGTACACGTAAATTA | 333 |
| 101 | A.junii_SH205 | TGTCTGCATCAACCCATGTCGTACCTGAATCGACACGTACACGAAAGTTA | 311 |
| 102 | A.junii_NIPH182 | TGTCTGCATCAACCCATGTCGTACCTGAATCAACACGTACACGAAAGTTA | 311 |
| 103 | A.junii_CIP64.5 | TGTCTGCATCAACCCATGTCGTACCTGAATCGACACGTACACGAAAGTTA | 311 |
| 104 | A.junii_TG19608 | TGTCTGCATCAACCCATGTCGTACCTGAATCGACACGTACACGAAAGTTA | 311 |
| 105 | A.junii_MTCC11364 | TGTCTGCATCAACCCATGTCGTACCTGAATCAACACGTACACGAAAGTTA | 311 |
| 106 | A.junii_CIP107470 | TGTCTGCATCAACCCATGTCGTACCTGAATCAACACGTACACGAAAGTTA | 311 |
| 107 | A.gyllenbergii_CIP110306 | TGTCTGCCTCAACTCATGTGGTTCCAGAAGCAACACGTACGCGTAAATTA | 311 |
| 108 | A.gyllenbergii_MTCC11365 | TGTCTGCCTCAACTCATGTGGTTCCAGAAGCAACACGTACGCGTAAATTA | 311 |
| 109 | A.beijerinckii_ANC3835 | TGTCAGCATCAAGTCATGTGGTTCCTGAGGCAACTCGTACACGTAAGTTA | 311 |
| 110 | A.beijerinckii_CIP110307 | TATCAGCATCAAGTCATGTGGTTCCTGAGGCAACTCGTACACGTAAGTTA | 311 |
| 111 | A.brisouii_ANC4119 | TGTCTGCCTCAACTCATGTCGTACCCGAAGCCACTCGCACTCGCAAACTA | 334 |
| 112 | A.lwoffii_WJ10621 | TCAGTGCATCTACGCACATTGTTCCTGAAGCGACCCGTACCCGTAAGTTA | 336 |
| 113 | A.lwoffii_CIP70.31 | TGAGTGCTTCAACACACGTGGTGCCTGAAGCGACCCGTACCCGAAAACTG | 337 |
| 114 | A.lwoffii_NIPH715 | TAAGTGCTTCGACCCATGTGGTGCCTGAAGCAACCCGTACCCGCAAACTG | 337 |
| 115 | A.lwoffii_SH145 | TAAGTGCTTCGACCCATGTGGTGCCTGAAGCAACCCGTACCCGCAAACTG | 337 |
| 116 | A.lwoffii_TG19636 | TAAGTGCTTCGACCCATGTGGTGCCTGAAGCAACCCGTACCCGCAAACTG | 337 |
| 117 | A.lwoffii_NCTC5866 | TAAGTGCTTCGACCCATGTGGTGCCTGAAGCAACCCGTACCCGCAAACTG | 336 |
| 118 | A.lwoffii_NIPH478 | TAAGCGCTTCGACCCATGTGGTGCCTGAAGCAACCCGTACTCGCAAGCTG | 337 |
| | | * ** ** * ** * ** ** ** * ** ** ** ** ** * | |

FIG. 7H

```
SEQ ID NO:
 66 A.baumannii_AB307-0294         TTATTATCTCGTCGTGAACTTGAAAAGCTTATGGGTGCGGTGAACCAAAA 395
 67 A.baumannii_MRY10-0558         TTATTATCTCGTCGTGAACTTGAAAAGCTTATGGGTGCAGTGAACCAAAA 395
 68 A.baumannii_MDR-TJ             TTATTATCTCGTCGTGAACTTGAAAAGCTTATGGGTGCAGTGAACCAAAA 395
 69 A.baumannii_D1279779           TTATTATCTCGTCGTGAACTTGAAAAGCTTATGGGTGCGGTGAACCAAAA 393
 70 A.baumannii_Naval-82           TTATTATCTCGTCGTGAACTTGAAAAGCTTATGGGTGCGGTGAACCAAAA 395
 71 A.baumannii_UMB002             TTATTATCTCGTCGTGAACTTGAAAAGCTTATGGGTGCGGTGAACCAAAA 395
 72 Acinetobacter_sp.ADP1          CTACTGTCACGTCGTGAAATTGGTCAACTACTAGGTGCTGTCAATCAGAA 395
 73 Acinetobacter_sp.RUH2624       TTATTATCTCGTCGTGAACTTGAAAAGCTTATGGGTGCAGTGAACCAAAA 395
 74 Acinetobacter_sp.SH024         TTATTATCACGCCGAGAACTAGAAAAGCTAACAGGTTCAGTTAACCAAAA 383
 75 A.calcoaceticus_PHEA-2B        TTATTATCACGCCGAGAACTAGAAAAGCTAACGGGTTCAGTGAACCAAAA 323
 76 A.calcoaceticus_PHEA-2         TTATTATCACGCCGAGAACTAGAAAAGCTAACGGGTTCAGTGAACCAAAA 393
 77 A.calcoaceticus.anitratus_XM15 TTATTATCACGCCGAGAACTAGAAAAGCTAACAGGTTCAGTTAACCAAAA 383
 78 A.calcoaceticus_TG19585        TTGCTCTCCCGACGTCAGCTTGAACACCTAATGGGTGCAGTTAACCAAAA 383
 79 A.calcoaceticus_RUH2202        TTGCTCTCCCGCCGTCAGCTTGAACACCTGATGGGTGCAGTTAACCAAAA 383
 80 A.calcoaceticus_ANC3811        TTGCTCTCCCGACGTCAGCTTGAACACCTAATGGGTGCAGTTAACCAGAA 383
 81 A.calcoaceticus_ANC3680        TTACTCTCCAGACGTCAGCTTGAACACCTAATGGGTGCAGTTAACCAAAA 323
 82 A.calcoaceticus_TG19593        TTACTCTCCCGACGTCAGCTTGAACACCTAATGGGTGCAGTTAACCAAAA 383
 83 A.calcoaceticus_TG19588        TTGCTCTCCCGACGTCAGCTTGAACACCTAATGGGCGCAGTTAACCAAAA 383
 84 A.calcoaceticus_DSM30006       TTGCTCTCCCGACGTCAGCTTGAACACCTAATGGGCGCAGTTAACCAAAA 383
 85 A.calcoaceticus_NIPH_13        TTGCTCTCCCGACGTCAGCTTGAACACCTAATGGGTGCAGTTAACCAAAA 383
 86 A.nosocomialis_TG21145         TTATTATCTCGTCGTGAACTTGAAAAGCTTATGGGTGCAGTGAACCAAAA 309
 87 A.nosocomialis_TG19596         TTATTATCTCGTCGTGAACTTGAAAAGCTTATGGGTGCAGTGAACCAAAA 309
 88 A.nosocomialis_M2c_7           TTATTATCTCGTCGTGAACTTGAAAAGCTTATGGGTGCAGTGAACCAAAA 395
 89 A.nosocomialis_NIPH2119        TTATTATCTCGTCGTGAACTTGAAAAGCTTATGGGTGCAGTGAACCAAAA 395
 90 A.nosocomialis_NIPH386         TTATTATCTCGTCGTGAACTTGAAAAGCTTATGGGTGCAGTGAACCAAAA 309
 91 A.nosocomialis_Ab22222         TTATTATCTCGTCGTGAACTTGAAAAGCTTATGGGTGCAGTGAACCAAAA 309
 92 A.genomosp.3.str.DSM21653      TTATTATCACGCCGAGAACTAGAAAAGCTAACGGGTTCAGTTAACCAAAA 383
 93 A.genomosp.3str.DSM9306        TTATTATCGCGCCGAGAACTAGAAAAGCTAACAGGTTCAGTTAACCAAAA 383
 94 A.oleivorans_DR1               TTGCTCTCCCGACGTCAGCTTGAACATCTAATGGGTGCAGTTAACCAGAA 395
 95 A.pittii_ANC4050               TTATTATCACGCCGAGAACTAGAAAAGCTAACAGGTTCAGTGAACCAAAA 383
 96 A.pittii_ANC3678               TTATTATCACGCCGAGAACTAGAAAAGCTAACAGGTTCAGTTAACCAAAA 383
 97 A.pittii_D499                  TTATTATCACGCCGAGAACTAGAAAAGCTAACAGGTTCAGTTAACCAAAA 383
 98 A.pittii_CIP70.29              TTATTATCACGCCGAGAACTAGAAAAGCTAACGGGTTCAGTTAACCAAAA 383
 99 A.pittii_TG6411                TTATTATCACGCCGAGAACTAGAAAAGCTAACAGGTTCAGTTAACCAAAA 383
100 A.pittii_ANC4052               TTATTATCACGCCGAGAACTAGAAAAGTTAACAGGTTCAGTTAACCAAAA 383
101 A.junii_SH205                  TTATTATCTCGTCGTGAACTAGAAAAGTTACTAGGTGCTGTGAACCAAAA 361
102 A.junii_NIPH182                TTATTATCTCGTCGTGAACTAGAAAAGTTACTAGGCGCAGTGAACCAAAA 361
103 A.junii_CIP64.5                TTATTATCTCGTCGTGAACTAGAAAAGTTACTAGGCGCAGTGAACCAAAA 361
104 A.junii_TG19608                TTATTATCTCGTCGTGAACTAGAAAAGTTACTAGGCGCAGTGAACCAAAA 361
105 A.junii_MTCC11364              TTATTATCTCGTCGCGAACTAGAAAAGTTACTAGGCGCAGTGAACCAAAA 361
106 A.junii_CIP107470              TTATTATCTCGTCGCGAACTAGAAAAGTTACTAGGCGCAGTGAACCAAAA 361
107 A.gyllenbergii_CIP110306       CTGCTCTCTCGTCGTGAGCTAGAAAAGCTTTTGGGTGCAGTGAATCAAAA 361
108 A.gyllenbergii_MTCC11365       CTGCTCTCTCGTCGTGAGCTAGAAAAGCTTTTGGGTGCAGTGAATCAAAA 361
109 A.beijerinckii_ANC3835         CTACTTTCTCGCCGTGAGATAGATAGACTAATGGGCGCAGTGAATCAGAA 361
110 A.beijerinckii_CIP110307       CTACTTTCTCGCCGTGAGATAGATAGACTAATGGGCGCAGTGAATCAGAA 361
111 A.brisouii_ANC4119             TTACTGTCACGCCGTGAACTGGAACAGCTCACAGGCGCAGTAAATCAAAA 384
112 A.lwoffii_WJ10621              CTGTTGAACCGTCGTGAACTGGATAAGCTACTCGGCGCAGTGAATCAAAA 386
113 A.lwoffii_CIP70.31             TTGTTGAATCGCCGTGAAATTGAAAAGCTGATGGGCGCGATTAACCAGAA 387
114 A.lwoffii_NIPH715              TTGCTGAATCGCCGTGAAATTGAAAAGTTGATGGGTGCGATTAACCAGAA 387
115 A.lwoffii_SH145                TTGCTGAATCGCCGTGAAATTGAAAAGTTGATGGGTGCGATTAACCAGAA 387
116 A.lwoffii_TG19636              TTGCTGAATCGCCGTGAAATTGAAAAGTTGATGGGTGCGATTAACCAGAA 387
117 A.lwoffii_NCTC5866             TTGCTGAATCGCCGTGAAATTGAAAAGTTGATGGGTGCGATTAACCAGAA 386
118 A.lwoffii_NIPH478              TTGCTGAATCGCCGTGAAATTGAAAAGCTGATGGGTGCGATTAACCAGAA 387
                                    *  *     * **  *  * *      *    **  *  * ** ** **
```

FIG. 7I

```
SEQ ID NO:
 66 A.baumannii_AB307-0294          AGGTTATTCTTGCGTTCCATTAGCATGTTACTGGAAAGGTCATCTGGTTA 445
 67 A.baumannii_MRY10-0558          AGGTTATTCGTGCGTTCCATTAGCATGTTACTGGAAAGGTCATCTGGTTA 445
 68 A.baumannii_MDR-TJ              AGGTTATTCGTGCGTTCCATTAGCATGTTACTGGAAAGGTCATCTGGTTA 445
 69 A.baumannii_D1279779            AGGTTATTCGTGCGTTCCATTAGCATGTTACTGGAAAGGTCATCTGGTTA 443
 70 A.baumannii_Naval-82            AGGTTATTCGTGCGTTCCATTAGCATGTTACTGGAAAGGTCATCTGGTTA 445
 71 A.baumannii_UMB002              AGGTTATTCGTGCGTTCCATTAGCATGTTACTGGAAAGGTCATCTGGTTA 445
 72 Acinetobacter_sp.ADP1           AGGTTATTCGTGTGTACCTTTGGCATGTTACTGGAAAGGTCACTTGGTCA 445
 73 Acinetobacter_sp.RUH2624        AGGTTATTCGTGCGTTCCATTAGCATGTTACTGGAAAGGTCATCTGGTCA 445
 74 Acinetobacter_sp.SH024          AGGTTACTCATGTGTTCCTTTAGCATGTTACTGGAAAGGTCACTTGGTTA 433
 75 A.calcoaceticus_PHEA-2B         AGGTTACTCATGTGTTCCTTTGGCATGTTATTGGAAAGGTCACTTGGTGA 373
 76 A.calcoaceticus_PHEA-2          AGGTTACTCATGTGTTCCTTTGGCATGTTATTGGAAAGGTCACTTGGTGA 443
 77 A.calcoaceticus.anitratus_XM15  AGGTTACTCATGTGTTCCTTTAGCATGTTACTGGAAAGGTCACTTGGTTA 433
 78 A.calcoaceticus_TG19585         AGGTTACTCATGTGTTCCTTTGGCGTGTTACTGGAAAGGTCACTTGGTTA 433
 79 A.calcoaceticus_RUH2202         AGGTTACTCGTGCGTTCCTTTGGCGTGTTACTGGAAAGGTCACTTGGTTA 433
 80 A.calcoaceticus_ANC3811         AGGTTACTCATGCGTTCCTTTAGCGTGTTACTGGAAGGGTCATTTAGTCA 433
 81 A.calcoaceticus_ANC3680         AGGTTACTCATGCGTTCCTTTGGCGTGTTACTGGAAAGGTCATTTAGTCA 373
 82 A.calcoaceticus_TG19593         AGGTTACTCATGCGTTCCTTTGGCGTGTTACTGGAAAGGTCATTTAGTCA 433
 83 A.calcoaceticus_TG19588         AGGTTACTCATGTGTTCCTTTGGCGTGTTACTGGAAAGGTCACTTGGTTA 433
 84 A.calcoaceticus_DSM30006        AGGTTACTCATGTGTTCCTTTGGCGTGTTACTGGAAAGGTCACTTGGTTA 433
 85 A.calcoaceticus_NIPH_13         AGGTTACTCATGCGTTCCTTTGGCGTGTTACTGGAAAGGTCATTTAGTCA 433
 86 A.nosocomialis_TG21145          AGGTTATTCGTGCGTTCCATTAGCGTGTTACTGGAAAGGTCATCTAGTCA 359
 87 A.nosocomialis_TG19596          AGGTTATTCGTGCGTTCCATTAGCGTGTTACTGGAAAGGTCATCTAGTCA 359
 88 A.nosocomialis_M2c_7            AGGTTATTCGTGCGTTCCATTAGCGTGTTACTGGAAAGGTCATCTGGTCA 445
 89 A.nosocomialis_NIPH2119         AGGTTATTCGTGCGTTCCATTAGCATGTTACTGGAAAGGTCATCTGGTCA 445
 90 A.nosocomialis_NIPH386          AGGTTATTCGTGCGTTCCATTAGCGTGTTACTGGAAAGGTCATCTGGTCA 359
 91 A.nosocomialis_Ab22222          AGGTTATTCGTGCGTTCCATTAGCGTGTTACTGGAAAGGTCATCTGGTCA 359
 92 A.genomosp.3.str.DSM21653       AGGTTACTCATGTGTTCCTTTAGCATGTTATTGGAAAGGTCACTTGGTGA 433
 93 A.genomosp.3str.DSM9306         AGGTTACTCATGTGTTCCTTTGGCATGTTACTGGAAAGGTCACTTGGTTA 433
 94 A.oleivorans_DR1                AGGCTACTCATGTGTTCCTTTAGCGTGTTATTGGAAAGGTCATTTAGTCA 445
 95 A.pittii_ANC4050                AGGTTACTCATGTGTTCCTTTAGCATGTTATTGGAAAGGTCACTTGGTTA 433
 96 A.pittii_ANC3678                AGGTTACTCATGTGTTCCTTTGGCATGTTACTGGAAAGGTCACTTGGTTA 433
 97 A.pittii_D499                   AGGTTACTCATGTGTTCCTTTAGCATGTTACTGGAAAGGTCACTTGGTTA 433
 98 A.pittii_CIP70.29               AGGTTACTCATGTGTTCCTTTAGCATGTTATTGGAAAGGTCACTTGGTGA 433
 99 A.pittii_TG6411                 AGGTTACTCATGTGTTCCTTTAGCATGTTACTGGAAAGGTCACTTGGTTA 433
100 A.pittii_ANC4052                AGGTTACTCATGTGTTCCTTTGGCATGTTACTGGAAAGGTCACTTGGTTA 433
101 A.junii_SH205                   AGGTTATTCATGTGTTCCTTTAGCCTGCTATTGGAAAGGTCACTTGGTTA 411
102 A.junii_NIPH182                 AGGTTATTCATGTGTTCCTTTAGCCTGCTATTGGAAAGGTCACTTGGTTA 411
103 A.junii_CIP64.5                 AGGTTATTCATGTGTTCCTTTAGCCTGCTATTGGAAAGGTCACTTGGTTA 411
104 A.junii_TG19608                 AGGTTATTCATGTGTTCCTTTAGCCTGCTATTGGAAAGGTCACTTGGTTA 411
105 A.junii_MTCC11364               AGGTTATTCATGTGTTCCTTTAGCCTGCTATTGGAAAGGTCACTTGGTTA 411
106 A.junii_CIP107470               AGGTTATTCATGTGTTCCTTTAGCCTGCTATTGGAAAGGTCACTTGGTTA 411
107 A.gyllenbergii_CIP110306        AGGCTATTCATGTGTACCTTTGGCATGTTATTGGAAAGGCCATTTGGTCA 411
108 A.gyllenbergii_MTCC11365        AGGCTATTCATGTGTACCTTTGGCATGTTATTGGAAAGGCCATTTGGTCA 411
109 A.beijerinckii_ANC3835          AGGTTATTCATGTGTTCCTCTGGCATGTTATTGGAAAGGTCCTTTGGTTA 411
110 A.beijerinckii_CIP110307        AGGTTATTCATGTGTTCCTCTGGCATGTTATTGGAAAGGTCCTTTGGTTA 411
111 A.brisouii_ANC4119              AGGTTACACTTGTGTACCTTTAGCATGTTACTGGAAAGGACATTTGGCGA 434
112 A.lwoffii_WJ10621               AGGTTATTCGTGTGTTCCACTTGTTGCTTATTGGAAAGGACCACGTGCGA 436
113 A.lwoffii_CIP70.31              AGGTTATTCCTGCGTGCCACTGGCCTGTTACTGGAAAGGCCCGCATGCCA 437
114 A.lwoffii_NIPH715               AGGTTATTCCTGCGTTCCACTGGCCTGCTACTGGAAAGGTCCACATGCCA 437
115 A.lwoffii_SH145                 AGGTTATTCCTGCGTTCCACTGGCCTGCTACTGGAAAGGTCCACATGCCA 437
116 A.lwoffii_TG19636               AGGTTATTCCTGCGTTCCACTGGCCTGCTACTGGAAAGGTCCACATGCCA 437
117 A.lwoffii_NCTC5866              AGGTTATTCCTGCGTTCCACTGGCCTGCTACTGGAAAGGTCCACATGCCA 436
118 A.lwoffii_NIPH478               AGGTTATTCCTGCGTACCACTGGCGTGTTACTGGAAAGGTCCACATGCCA 437
                                    *** **  * ** ** **  * *     ** ***** ** *     *  *
```

FIG. 7J

| SEQ ID NO: | | | |
|---|---|---|---|
| 66 | A.baumannii_AB307-0294 | AGCTTGAAATTGCACTCGTGAAAGGTAAACAACTTCACGATAAACGAGCG | 495 |
| 67 | A.baumannii_MRY10-0558 | AGCTTGAAATTGCACTCGTGAAAGGTAAACAACTTCACGATAAACGAGCA | 495 |
| 68 | A.baumannii_MDR-TJ | AGCTTGAAATTGCACTCGTGAAAGGTAAACAACTTCACGATAAACGAGCA | 495 |
| 69 | A.baumannii_D1279779 | AGCTTGAAATTGCACTCGTGAAAGGTAAACAACTTCACGATAAACGAGCA | 493 |
| 70 | A.baumannii_Naval-82 | AGCTTGAAATTGCACTCGTGAAAGGTAAACAACTTCACGATAAACGTGCG | 495 |
| 71 | A.baumannii_UMB002 | AGCTTGAAATTGCACTCGTGAAAGGTAAACAACTTCACGATAAACGAGCG | 495 |
| 72 | Acinetobacter_sp.ADP1 | AGCTCGAAATTGCACTGGTGAAAGGGAAACAGTTACATGATAAGCGTGCA | 495 |
| 73 | Acinetobacter_sp.RUH2624 | AGCTTGAAATTGCACTCGTGAAAGGTAAACAACTCCACGATAAACGTGCG | 495 |
| 74 | Acinetobacter_sp.SH024 | AACTTGAAATCGCGCTTGTGAAAGGTAAACAGCTTCACGACAAACGTGCG | 483 |
| 75 | A.calcoaceticus_PHEA-2B | AGCTTGAAATCGCGCTTGTGAAAGGTAAACAGCTTCACGACAAACGTGCG | 423 |
| 76 | A.calcoaceticus_PHEA-2 | AGCTTGAAATCGCGCTTGTGAAAGGTAAACAGCTTCACGACAAACGTGCG | 493 |
| 77 | A.calcoaceticus.anitratus_XM15 | AACTTGAAATCGCGCTTGTGAAAGGTAAACAGCTTCACGACAAACGTGCG | 483 |
| 78 | A.calcoaceticus_TG19585 | AACTTGAAATTGCGCTTGTGAAAGGTAAACAGCTTCACGACAAACGTGCA | 483 |
| 79 | A.calcoaceticus_RUH2202 | AACTTGAAATTGCACTTGTGAAAGGTAAACAACTTCACGACAAACGTGCA | 483 |
| 80 | A.calcoaceticus_ANC3811 | AACTAGAGATTGCACTTGTGAAGGGTAAACAGCTTCATGACAAACGTGCA | 483 |
| 81 | A.calcoaceticus_ANC3680 | AACTTGAAATTGCACTTGTGAAAGGTAAACAACTTCACGACAAACGTGCA | 423 |
| 82 | A.calcoaceticus_TG19593 | AACTTGAAATTGCGCTTGTGAAAGGTAAACAACTTCACGACAAACGTGCA | 483 |
| 83 | A.calcoaceticus_TG19588 | AACTTGAAATTGCGCTTGTGAAAGGTAAACAGCTTCACGACAAACGTGCA | 483 |
| 84 | A.calcoaceticus_DSM30006 | AACTTGAAATTGCGCTTGTGAAAGGTAAACAGCTTCACGACAAACGTGCA | 483 |
| 85 | A.calcoaceticus_NIPH_13 | AACTAGAAATTGCGCTTGTGAAGGGTAAACAACTTCATGACAAACGTGCA | 483 |
| 86 | A.nosocomialis_TG21145 | AGCTTGAAATTGCACTCGTGAAAGGTAAACAACTCCACGATAAACGTGCA | 409 |
| 87 | A.nosocomialis_TG19596 | AGCTTGAAATTGCACTCGTGAAAGGTAAACAACTCCACGATAAACGTGCA | 409 |
| 88 | A.nosocomialis_M2c_7 | AGCTTGAAATTGCACTCGTGAAAGGTAAACAACTCCACGATAAACGTGCG | 495 |
| 89 | A.nosocomialis_NIPH2119 | AGCTTGAAATTGCACTCGTGAAAGGTAAACAACTCCACGATAAACGTGCG | 495 |
| 90 | A.nosocomialis_NIPH386 | AGCTTGAAATTGCACTCGTGAAAGGTAAACAACTCCACGATAAACGTGCA | 409 |
| 91 | A.nosocomialis_Ab22222 | AGCTTGAAATTGCACTCGTGAAAGGTAAACAACTCCACGATAAACGTGCA | 409 |
| 92 | A.genomosp.3.str.DSM21653 | AGCTTGAAATCGCGCTTGTGAAAGGTAAACAGCTTCACGACAAACGTGCG | 483 |
| 93 | A.genomosp.3str.DSM9306 | AACTTGAAATCGCGCTTGTGAAAGGTAAACAGCTTCACGACAAACGTGCG | 483 |
| 94 | A.oleivorans_DR1 | AACTGGAGATTGCACTTGTGAAGGGTAAACAGCTTCATGACAAACGTGCA | 495 |
| 95 | A.pittii_ANC4050 | AACTTGAAATTGCTCTGGTGAAAGGTAAACAGCTTCATGACAAACGTGCG | 483 |
| 96 | A.pittii_ANC3678 | AACTTGAAATCGCGCTTGTGAAAGGTAAACAACTTCACGACAAACGTGCG | 483 |
| 97 | A.pittii_D499 | AACTTGAAATCGCGCTTGTGAAAGGTAAACAGCTTCACGACAAACGTGCG | 483 |
| 98 | A.pittii_CIP70.29 | AGCTTGAAATCGCGCTTGTGAAAGGTAAACAGCTTCACGACAAACGTGCG | 483 |
| 99 | A.pittii_TG6411 | AACTTGAAATCGCGCTTGTGAAAGGTAAACAACTTCACGACAAACGTGCG | 483 |
| 100 | A.pittii_ANC4052 | AACTTGAAATTGCCCTTGTGAAAGGTAAGCAGCTTCATGACAAACGTGCG | 483 |
| 101 | A.junii_SH205 | AGCTCGAAATTGCGTTGGTCAAAGGTAAGCAATTACATGACAAACGTGCT | 461 |
| 102 | A.junii_NIPH182 | AGCTCGAAATTGCGTTGGTCAAAGGTAAGCAATTACATGACAAACGTGCT | 461 |
| 103 | A.junii_CIP64.5 | AGCTCGAAATTGCGTTGGTCAAAGGTAAGCAATTACATGACAAACGTGCT | 461 |
| 104 | A.junii_TG19608 | AGCTCGAAATTGCGTTGGTCAAAGGTAAGCAATTACATGACAAACGTGCT | 461 |
| 105 | A.junii_MTCC11364 | AGCTCGAAATTGCGTTGGTCAAAGGTAAGCAATTACATGACAAACGTGCT | 461 |
| 106 | A.junii_CIP107470 | AGCTCGAAATTGCGTTGGTCAAAGGTAAGCAATTACATGACAAACGTGCT | 461 |
| 107 | A.gyllenbergii_CIP110306 | AACTTGAAATTGCACTGGTGAAAGGTAAGCAATTACATGACAAGCGTGCC | 461 |
| 108 | A.gyllenbergii_MTCC11365 | AACTTGAAATTGCACTGGTGAAAGGTAAGCAATTACATGACAAGCGTGCC | 461 |
| 109 | A.beijerinckii_ANC3835 | AACTAGAAATTGCCATGGTTAAAGGTAAACAGTTACACGATAAACGTGCA | 461 |
| 110 | A.beijerinckii_CIP110307 | AACTAGAAATTGCCATGGTTAAAGGTAAACAGTTACACGATAAACGTGCA | 461 |
| 111 | A.brisouii_ANC4119 | AACTGGAAATTGCGCTGGTAAAAGGTAAGCAACTCCATGATAAACGCGCT | 484 |
| 112 | A.lwoffii_WJ10621 | AATTAGAAATCGCTTTAGTGAAAGGCAAACAGCTGCATGACAAACGTGCC | 486 |
| 113 | A.lwoffii_CIP70.31 | AGCTGGAAATTGCACTGGTCAAAGGTAAGCAGCTTCATGACAAACGTGCC | 487 |
| 114 | A.lwoffii_NIPH715 | AGCTGGAAATTGCTCTGGTGAAAGGTAAGCAGCTTCATGACAAACGTGCC | 487 |
| 115 | A.lwoffii_SH145 | AGCTGGAAATTGCTCTGGTGAAAGGTAAGCAGCTTCATGACAAACGTGCC | 487 |
| 116 | A.lwoffii_TG19636 | AGCTGGAAATTGCTCTGGTCAAAGGTAAGCAGCTCCATGACAAACGTGCC | 487 |
| 117 | A.lwoffii_NCTC5866 | AGCTGGAAATTGCTCTGGTCAAAGGTAAGCAGCTTCATGACAAACGTGCC | 486 |
| 118 | A.lwoffii_NIPH478 | AACTGGAAATTGCCTTGGTGAAAGGTAAGCAACTCCATGACAAACGTGCC | 487 |
| | | *  * ** ** **  * ** ** ** ** **  * ** ** ** ** ** | |

FIG. 7K

```
SEQ ID NO:
 66 A.baumannii_AB307-0294           ACTGAAAAAGAACGTGACTGGCAACGTGATAAAGCACGTATATTTCATAA 545
 67 A.baumannii_MRY10-0558           ACTGAAAAAGAACGTGACTGGCAACGTGATAAAGCACGTATATTTCATAA 545
 68 A.baumannii_MDR-TJ               ACTGAAAAAGAACGTGACTGGCAACGTGATAAAGCACGTATATTTCATAA 545
 69 A.baumannii_D1279779             ACTGAAAAAGAACGTGACTGGCAACGTGATAAAGCACGTATATTTCATAA 543
 70 A.baumannii_Naval-82             ACTGAAAAAGAACGTGACTGGCAACGTGATAAAGCACGTATATTTCATAA 545
 71 A.baumannii_UMB002               ACTGAAAAAGAACGTGACTGGCAACGTGATAAAGCACGTATATTTCATAA 545
 72 Acinetobacter_sp.ADP1            ACCGAAAAAGATCGTGACTGGCAACGTGACAAAGCACGGATTATGCATAA 545
 73 Acinetobacter_sp.RUH2624         ACTGAAAAAGAACGTGACTGGCAACGTGATAAAGCCCGTATATTTCATAA 545
 74 Acinetobacter_sp.SH024           ACTGAAAAAGATCGCGATTGGCAGCGTGATAAAGCTCGTATATTTCATAA 533
 75 A.calcoaceticus_PHEA-2B          ACTGAAAAAGATCGCGATTGGCAGCGTGATAAAGCTCGTATATTTCATAA 473
 76 A.calcoaceticus_PHEA-2           ACTGAAAAAGATCGCGATTGGCAGCGTGATAAAGCTCGTATATTTCATAA 543
 77 A.calcoaceticus.anitratus_XM15   ACTGAAAAAGATCGCGATTGGCAGCGTGATAAAGCTCGTATATTTCATAA 533
 78 A.calcoaceticus_TG19585          ACTGAAAAAGACCGCGACTGGCAGCGTGATAAAGCTCGTATATTTCATAA 533
 79 A.calcoaceticus_RUH2202          ACTGAAAAAGACCGTGACTGGCAACGTGATAAAGCTCGTATATTTCATAA 533
 80 A.calcoaceticus_ANC3811          ACTGAAAAAGACCGTGACTGGCAACGTGATAAAGCTCGTATATTTCATAA 533
 81 A.calcoaceticus_ANC3680          ACCGAAAAAGACCGTGACTGGCAACGTGATAAAGCTCGTATATTTCATAA 473
 82 A.calcoaceticus_TG19593          ACTGAAAAAGACCGTGACTGGCAACGTGATAAAGCTCGTATATTTCATAA 533
 83 A.calcoaceticus_TG19588          ACTGAAAAAGACCGTGACTGGCAACGTGATAAAGCTCGTATATTTCATAA 533
 84 A.calcoaceticus_DSM30006         ACTGAAAAAGACCGTGACTGGCAACGTGATAAAGCTCGTATATTTCATAA 533
 85 A.calcoaceticus_NIPH_13          ACTGAAAAAGACCGTGACTGGCAACGTGATAAAGCTCGTATATTTCATAA 533
 86 A.nosocomialis_TG21145           ACTGAAAAAGAACGTGACTGGCAACGTGATAAAGCTCGTATATTTCATAA 459
 87 A.nosocomialis_TG19596           ACTGAAAAAGAACGTGACTGGCAACGTGATAAAGCTCGTATATTTCATAA 459
 88 A.nosocomialis_M2c_7             ACTGAAAAAGAACGTGACTGGCAACGTGATAAAGCCCGTATATTTCATAA 545
 89 A.nosocomialis_NIPH2119          ACTGAAAAAGAACGTGACTGGCAACGTGATAAAGCCCGTATATTTCATAA 545
 90 A.nosocomialis_NIPH386           ACTGAAAAAGAACGTGACTGGCAACGTGATAAAGCCCGTATATTTCATAA 459
 91 A.nosocomialis_Ab22222           ACTGAAAAAGAACGTGACTGGCAACGTGATAAAGCCCGTATATTTCATAA 459
 92 A.genomosp.3.str.DSM21653        ACTGAAAAAGATCGCGATTGGCAGCGTGATAAAGCTCGTATATTTCATAA 533
 93 A.genomosp.3str.DSM9306          ACTGAAAAAGATCGCGATTGGCAGCGTGATAAAGCTCGTATATTTCATAA 533
 94 A.oleivorans_DR1                 ACCGAAAAAGACCGTGACTGGCAACGTGATAAAGCTCGTATATTTCATAA 545
 95 A.pittii_ANC4050                 ACTGAAAAAGATCGCGATTGGCAACGTGATAAAGCTCGTATATTTCATAA 533
 96 A.pittii_ANC3678                 ACTGAAAAAGATCGCGATTGGCAGCGTGATAAAGCTCGTATATTTCATAA 533
 97 A.pittii_D499                    ACTGAAAAAGATCGCGATTGGCAGCGTGATAAAGCTCGTATATTTCATAA 533
 98 A.pittii_CIP70.29                ACTGAAAAAGATCGCGATTGGCAGCGTGATAAAGCTCGTATATTTCATAA 533
 99 A.pittii_TG6411                  ACTGAAAAAGATCGCGATTGGCAGCGTGATAAAGCTCGTATATTTCATAA 533
100 A.pittii_ANC4052                 ACTGAAAAAGATCGCGATTGGCAGCGTGATAAAGCTCGTATATTTCATAA 533
101 A.junii_SH205                    ACGGAAAAAGACCGTGATTGGCAGCGTGATAAAGCACGTATGTTGCATAA 511
102 A.junii_NIPH182                  ACGGAAAAAGACCGTGATTGGCAGCGTGATAAAGCACGTATGTTGCATAA 511
103 A.junii_CIP64.5                  ACGGAAAAAGACCGTGATTGGCAGCGTGATAAAGCACGTATGTTGCATAA 511
104 A.junii_TG19608                  ACGGAAAAAGACCGTGATTGGCAGCGTGATAAAGCACGTATGTTGCATAA 511
105 A.junii_MTCC11364                ACGGAAAAAGACCGTGATTGGCAGCGTGATAAAGCACGTATGTTGCATAA 511
106 A.junii_CIP107470                ACGGAAAAAGACCGTGATTGGCAGCGTGATAAAGCACGTATGTTGCATAA 511
107 A.gyllenbergii_CIP110306         ACTGAAAAAGACCGTGACTGGCAACGTGATAAATCTCGTCTGCTGCATAA 511
108 A.gyllenbergii_MTCC11365         ACTGAAAAAGACCGTGACTGGCAACGTGATAAATCTCGTCTGCTGCATAA 511
109 A.beijerinckii_ANC3835           ACTGAAAAAGATCGTGACTGGCAACGAGATAAATCACGTATGTTGCATAA 511
110 A.beijerinckii_CIP110307         ACTGAAAAAGATCGTGACTGGCAACGAGATAAATCACGTATGTTGCATAA 511
111 A.brisouii_ANC4119               ACTGAAAAAGACCGCGACTGGCAACGTGATAAAGCCCGTATTTTTCA--- 531
112 A.lwoffii_WJ10621                ACGGAAAAAGACCGTGACTGGCAACGTGATAAAGCCCGTATTATGCATAA 536
113 A.lwoffii_CIP70.31               ACCGAGAAAGACCGTGACTGGCAACGTGATAAGGCGCGAATTTTCCATAA 537
114 A.lwoffii_NIPH715                ACCGAAAAAGACCGTGACTGGCAACGTGATAAGGCGCGAATTTTCCATAA 537
115 A.lwoffii_SH145                  ACCGAAAAAGACCGTGACTGGCAACGTGATAAGGCGCGAATTTTCCATAA 537
116 A.lwoffii_TG19636                ACCGAAAAAGACCGTGACTGGCAACGTGATAAAGCACGAATTTTCCATAA 537
117 A.lwoffii_NCTC5866               ACCGAAAAAGACCGTGACTGGCAACGTGATAAAGCGCGAATTTTCCATAA 536
118 A.lwoffii_NIPH478                ACCGAAAAAGACCGTGACTGGCAACGTGATAAAGCGCGAATTTTCCATAA 537
                                     ** ** ***** ** ** ***** ** ** **  * **  *  * **
```

FIG. 7L

| SEQ ID NO: | | | |
|---|---|---|---|
| 66 | A.baumannii_AB307-0294 | GTAATAGACTAAAA-AGCCTCTTT-ATAGAGGCTTTTTTATTT------- | 586 |
| 67 | A.baumannii_MRY10-0558 | GTAATAGACTAAAA-AGCCTCTTT-ATAGAGGCTTTTTTATTT------- | 586 |
| 68 | A.baumannii_MDR-TJ | GTAATAGACTAAAA-AGCCTCTTT-ATAGAGGCTTTTTTATTT------- | 586 |
| 69 | A.baumannii_D1279779 | GTAATAGACTAAAA-AGCCTCTTT-ATAGAGGCTTTTTTATTT------- | 584 |
| 70 | A.baumannii_Naval-82 | GTAATAGACTAAAA-AGCCTCTTT-ATAGAGGCTTTTTTATTT------- | 586 |
| 71 | A.baumannii_UMB002 | GTAATAGACTAAAA-AGCCTCTTT-ATAGAGGCTTTTTTATTT------- | 586 |
| 72 | Acinetobacter_sp.ADP1 | GTAATTTATACAAAAAGCCTTTAC---TAAGGCTTTTTGTTTG------A | 586 |
| 73 | Acinetobacter_sp.RUH2624 | ATAATAGACTAAAA-AGCCTCTAT-AAAGAGGCTTTTTTATTT------- | 586 |
| 74 | Acinetobacter_sp.SH024 | GTAATTAAATAAAA-AGCCTCTTT-TTAGAGGCTTTTT--TAT------- | 572 |
| 75 | A.calcoaceticus_PHEA-2B | GTAA---------------------------------------------- | 477 |
| 76 | A.calcoaceticus_PHEA-2 | GTAATTAAATAAAA-AGCCTCTTT-TTAGAGGCTTTTTTATATCGCGGAA | 591 |
| 77 | A.calcoaceticus.anitratus_XM15 | GTAATTAAATAAAA-AGCCTCTTT-TTAGAGGCTTTTT--TAT------- | 572 |
| 78 | A.calcoaceticus_TG19585 | ATAATTTAATAAAAAAGCCTCTTT-TTAGAGGCTTTTT-ATATTTTTGAC | 581 |
| 79 | A.calcoaceticus_RUH2202 | GTAATA-------------------------------------------- | 539 |
| 80 | A.calcoaceticus_ANC3811 | GTAATAAAATAAA--AGCCTCTTT-TCAGAGGCTTTTTTA---------- | 570 |
| 81 | A.calcoaceticus_ANC3680 | GTAA---------------------------------------------- | 477 |
| 82 | A.calcoaceticus_TG19593 | GTAATA-------------------------------------------- | 539 |
| 83 | A.calcoaceticus_TG19588 | GTAATA-------------------------------------------- | 539 |
| 84 | A.calcoaceticus_DSM30006 | GTAATA-------------------------------------------- | 539 |
| 85 | A.calcoaceticus_NIPH_13 | GTAATA-------------------------------------------- | 539 |
| 86 | A.nosocomialis_TG21145 | ATAATA-------------------------------------------- | 465 |
| 87 | A.nosocomialis_TG19596 | ATAATA-------------------------------------------- | 465 |
| 88 | A.nosocomialis_M2c_7 | ATAATAGACTAAAA-AGCCTCTAT-AAAGAGGCTTTTTTATTT------- | 586 |
| 89 | A.nosocomialis_NIPH2119 | ATAATAGACTAAAA-AGCCTCTAT-AAAGAGGCTTTTTTATTT------- | 586 |
| 90 | A.nosocomialis_NIPH386 | ATAATAGACTAAAA-AGCCTCTAT-AAAGAGGCTTTTTTATTT------- | 500 |
| 91 | A.nosocomialis_Ab22222 | ATAATAGACTAAAA-AGCCTCTAT-AAAGAGGCTTTTTTATTT------- | 500 |
| 92 | A.genomosp.3.str.DSM21653 | GTAATTAAATAAAA-AGCCTCTTT-TTAGAGGCTTTTTTAT--------- | 572 |
| 93 | A.genomosp.3str.DSM9306 | GTAATTAAATAAAA-AGCCTCTTT-TTAGAGGCTTTTTA-TATCGCGGAA | 580 |
| 94 | A.oleivorans_DR1 | GTAATAAAACAAA--AGCCTCTTT-TCAGAGGCTTTTTTACGTCGTGAAG | 592 |
| 95 | A.pittii_ANC4050 | GTAATTAAATAAAA-AGCCTCTTTCTTAGAGGCTTTTTTACATCGTAAAG | 582 |
| 96 | A.pittii_ANC3678 | GTAATTAAATAAAA-AGCCTCTTT-TTAGAGGCTTTTT--TAT------- | 572 |
| 97 | A.pittii_D499 | GTAATTAAATAAAA-AGCCTCTTT-TTAGAGGCTTTTT--TAT------- | 572 |
| 98 | A.pittii_CIP70.29 | GTAATTAAATAAAA-AGCCTCTTT-TTAGAGGCTTTTTTAT--------- | 572 |
| 99 | A.pittii_TG6411 | GTAATTAAATAACA-AGCCTCTTT-TTAGAGGCTTTTT--TAT------- | 572 |
| 100 | A.pittii_ANC4052 | GTAATA-------------------------------------------- | 539 |
| 101 | A.junii_SH205 | ATAATA-------------------------------------------- | 517 |
| 102 | A.junii_NIPH182 | ATAATA-------------------------------------------- | 517 |
| 103 | A.junii_CIP64.5 | ATAATA-------------------------------------------- | 517 |
| 104 | A.junii_TG19608 | ATAATA-------------------------------------------- | 517 |
| 105 | A.junii_MTCC11364 | ATAATA-------------------------------------------- | 517 |
| 106 | A.junii_CIP107470 | ATAATA-------------------------------------------- | 517 |
| 107 | A.gyllenbergii_CIP110306 | GTAATAAAAAAACC------TCCAATTGGAGGTTTTTTTAT--------- | 546 |
| 108 | A.gyllenbergii_MTCC11365 | GTAATAAAAAAACC------TCCAATTGGAGGTTTTTTTAT--------- | 546 |
| 109 | A.beijerinckii_ANC3835 | ATAATA-------------------------------------------- | 517 |
| 110 | A.beijerinckii_CIP110307 | ATAATA-------------------------------------------- | 517 |
| 111 | A.brisouii_ANC4119 | -------------------------------------------------- | |
| 112 | A.lwoffii_WJ10621 | ATAATAAAAAA------CCTCCCATGTGGAGGTTTTTTATTATC------ | 574 |
| 113 | A.lwoffii_CIP70.31 | ATAATGGA----------------------------TTAAAA-------- | 551 |
| 114 | A.lwoffii_NIPH715 | ATAATGGA----------------------------TTAAAA-------- | 551 |
| 115 | A.lwoffii_SH145 | ATAATGGA----------------------------TTAAAA-------- | 551 |
| 116 | A.lwoffii_TG19636 | ATAATGGA----------------------------TTAAAAA------- | 552 |
| 117 | A.lwoffii_NCTC5866 | ATAATGGA----------------------------TTAAAA-------- | 550 |
| 118 | A.lwoffii_NIPH478 | ATAATGGA----------------------------TTAAAA-------- | 551 |

FIG. 7M

```
SEQ ID NO:
 66  A.baumannii_AB307-0294          TCCACTAATTTAATCTATATAAAAGCCCAGCAA-- 619
 67  A.baumannii_MRY10-0558          TTCACTAATTTAATCTATATAAAAGCCCAGCAA-- 619
 68  A.baumannii_MDR-TJ              TTCACTAATTTAATCTATATAAAAGCCCAGCAA-- 619
 69  A.baumannii_D1279779            TTCACTAATTTAATCTATATAAAAGCCCAGCAATA 619
 70  A.baumannii_Naval-82            TTCACTAATTTAATCTATATAAAAGCCCAGCAA-- 619
 71  A.baumannii_UMB002              TTCACTAATTTAATCTATATAAAAGCCCAGCAA-- 619
 72  Acinetobacter_sp.ADP1           TTGTTTAATGCAAACGGTAAAGTAACCCACCGA-- 619
 73  Acinetobacter_sp.RUH2624        TTTACTAATTTAATCTATATAAAAGTCCAGCAA-- 619
 74  Acinetobacter_sp.SH024          -----------------------------------
 75  A.calcoaceticus_PHEA-2B         -----------------------------------
 76  A.calcoaceticus_PHEA-2          TTTATTAATTTAATCTATATAAGAGTCC------- 619
 77  A.calcoaceticus.anitratus_XM15  -----------------------------------
 78  A.calcoaceticus_TG19585         TTTATTAATTTAATCTATATAAAAGCCCAGCAA-- 614
 79  A.calcoaceticus_RUH2202         -----------------------------------
 80  A.calcoaceticus_ANC3811         -----------------------------------
 81  A.calcoaceticus_ANC3680         -----------------------------------
 82  A.calcoaceticus_TG19593         -----------------------------------
 83  A.calcoaceticus_TG19588         -----------------------------------
 84  A.calcoaceticus_DSM30006        -----------------------------------
 85  A.calcoaceticus_NIPH_13         -----------------------------------
 86  A.nosocomialis_TG21145          -----------------------------------
 87  A.nosocomialis_TG19596          -----------------------------------
 88  A.nosocomialis_M2c_7            TTTACTAATTTAATCTATATAAAAGTCCAGCAA-- 619
 89  A.nosocomialis_NIPH2119         TTTACTAATTTAATCTATATAAAAGTCCAGCAA-- 619
 90  A.nosocomialis_NIPH386          TTTACTAATTTAATCTATATAAAAGTCCAGCAA-- 533
 91  A.nosocomialis_Ab22222          TTTACTAATTTAATCTATATAAAAGTCCAGCAA-- 533
 92  A.genomosp.3.str.DSM21653       -----------------------------------
 93  A.genomosp.3str.DSM9306         TTTATTAATTTAATCTATATAAGAGTCCAGCAA-- 613
 94  A.oleivorans_DR1                TTCATTAGTTTAATCTGTATAAAAGTC-------- 619
 95  A.pittii_ANC4050                TTTATTAATTTAATCTATATAAAAGACCAGCAA-- 615
 96  A.pittii_ANC3678                -----------------------------------
 97  A.pittii_D499                   -----------------------------------
 98  A.pittii_CIP70.29               -----------------------------------
 99  A.pittii_TG6411                 -----------------------------------
100  A.pittii_ANC4052                -----------------------------------
101  A.junii_SH205                   -----------------------------------
102  A.junii_NIPH182                 -----------------------------------
103  A.junii_CIP64.5                 -----------------------------------
104  A.junii_TG19608                 -----------------------------------
105  A.junii_MTCC11364               -----------------------------------
106  A.junii_CIP107470               -----------------------------------
107  A.gyllenbergii_CIP110306        -----------------------------------
108  A.gyllenbergii_MTCC11365        -----------------------------------
109  A.beijerinckii_ANC3835          -----------------------------------
110  A.beijerinckii_CIP110307        -----------------------------------
111  A.brisouii_ANC4119              -----------------------------------
112  A.lwoffii_WJ10621               -----------------------------------
113  A.lwoffii_CIP70.31              -----------------------------------
114  A.lwoffii_NIPH715               -----------------------------------
115  A.lwoffii_SH145                 -----------------------------------
116  A.lwoffii_TG19636               -----------------------------------
117  A.lwoffii_NCTC5866              -----------------------------------
118  A.lwoffii_NIPH478               -----------------------------------
```

Amplification Curves

FIG. 10A

| SEQ ID NO: | | | |
|---|---|---|---|
| 119 | Listeria_grayiDSM20601Contig17 | -TGCCAAAAGGTGAAGGAAAATTAATTGCGCAAAATAAAAAAGCCAGACA | 49 |
| 120 | Listeria_monocytogenes_EGD-e | ATGCCAAAAGGTGATGGTAAGCTAGTCGCGCAAAATAAAAAAGCGCGCCA | 50 |
| 121 | Listeria_monocytogenesSLCC2479 | ATGCCAAAAGGTGATGGTAAGCTAGTCGCGCAAAATAAAAAAGCGCGCCA | 50 |
| 122 | Listeria_monocytogenes | ATGCCAAAAGGTGATGGTAAGCTAGTCGCGCAAAATAAAAAAGCGCGCCA | 50 |
| 123 | Listeria_innocuaClip11262 | ATGCCAAAAGGTGATGGTAAACTAGTCGCGCAAAATAAAAAAGCGCGCCA | 50 |
| 124 | Listeria_welshimeriserovar6b | ATGCCAAAAGGTGATGGTAAACTAGTCGCGCAAAATAAAAAAGCGCGCCA | 50 |
| 125 | Listeria_ivanoviisubsp.londoni | ATGCCAAAAGGTGATGGTAAGCTAGTCGCGCAAAATAAAAAAGCGCGCCA | 50 |
| 126 | Listeria_seeligeriserovar | ATGCCAAAAGGTGATGGTAAGCTAGTCGCGCAAAATAAAAAAGCGCGCCA | 50 |
| | | ************* ** ** ** * ***************** * ** | |

| SEQ ID NO: | | | |
|---|---|---|---|
| 119 | Listeria_grayiDSM20601Contig17 | TGATTTTGCAATCGAAGAAACTTTTGAAGCCGGCATTGTCTTGCAAGGAA | 99 |
| 120 | Listeria_monocytogenes_EGD-e | CGATTACGCAATTGAAGAAACTTTTGAGGCTGGCATTGTCCTGCAAGGTA | 100 |
| 121 | Listeria_monocytogenesSLCC2479 | CGATTACGCAATTGAAGAAACTTTTGAGGCTGGCATTGTCCTGCAAGGTA | 100 |
| 122 | Listeria_monocytogenes | CGATTACGCAATTGAAGAAACTTTTGAGGCTGGCATTGTCCTGCAAGGTA | 100 |
| 123 | Listeria_innocuaClip11262 | CGATTACGCAATTGAAGAAACTTTTGAGGCTGGCATTGTCCTGCAAGGTA | 100 |
| 124 | Listeria_welshimeriserovar6b | CGATTACGCAATTGAAGAAACTTTTGAAGCTGGCATTGTCCTGCAAGGCA | 100 |
| 125 | Listeria_ivanoviisubsp.londoni | CGATTACGCAATTGAAGAAACTTTTGAGGCTGGCATTGTCCTGCAAGGTA | 100 |
| 126 | Listeria_seeligeriserovar | CGATTACGCAATTGAAGAAACTTTTGAGGCTGGCATTGTCCTGCAAGGTA | 100 |
| | | **** ***** ************** ** ********* ******* * | |

| SEQ ID NO: | | | |
|---|---|---|---|
| 119 | Listeria_grayiDSM20601Contig17 | CAGAGATCAAATCCGTTCCGTAATGCACCGAGTGAACTTAAAGGATTCTTAC | 149 |
| 120 | Listeria_monocytogenes_EGD-e | CTGAAATTAAATCCGTAAGAAACGCACGGGTAAACTTAAAGATTCCTAT | 150 |
| 121 | Listeria_monocytogenesSLCC2479 | CTGAAATTAAATCCGTAAGAAATGCACGGGTAAACTTAAAGATTCCTAT | 150 |
| 122 | Listeria_monocytogenes | CTGAAATTAAATCCGTAAGAAATGCACGGGTAAACTTAAAGATTCCTAT | 150 |
| 123 | Listeria_innocuaClip11262 | CTGAAATCAAATCCGTCAGAAACGCACGGGTAAACTTAAAGATTCCTAT | 150 |
| 124 | Listeria_welshimeriserovar6b | CCGAAATTAAATCCGTTAGAAACGCACGGGTAAACTTAAAGATTCCTAT | 150 |
| 125 | Listeria_ivanoviisubsp.londoni | CTGAAATTAAATCCGTTAGAAATGCACGGGTAAACTTAAAGATTCCTAT | 150 |
| 126 | Listeria_seeligeriserovar | CTGAAATTAAATCCGTTAGAAATGCACGGGTAAACTTAAAGATTCCTAT | 150 |
| | | * ** ** ******** * ** ***** ** ******** ***** ** | |

| SEQ ID NO: | | | |
|---|---|---|---|
| 119 | Listeria_grayiDSM20601Contig17 | GCCCGCATCGAACGCGGAGAAATTTTTTTACACAACATGCATATCAGCCC | 199 |
| 120 | Listeria_monocytogenes_EGD-e | GCACGTATCGACAAAGGGGAAATTTTCTTACACAATATGCATATTAGTCC | 200 |
| 121 | Listeria_monocytogenesSLCC2479 | GCACGTATCGACAAAGGGGAAATTTTCTTACACAATATGCATATTAGTCC | 200 |
| 122 | Listeria_monocytogenes | GCACGTATCGACAAAGGGGAAATTTTCTTACACAATATGCATATTAGTCC | 200 |
| 123 | Listeria_innocuaClip11262 | GCACGTATCGACAAAGGGGAAATTTTCTTACACAATATGCACATTAGTCC | 200 |
| 124 | Listeria_welshimeriserovar6b | GCACGTATCGACAAAGGGGAAATTTTCTTACACAATATGCATATTAGCCC | 200 |
| 125 | Listeria_ivanoviisubsp.londoni | GCACGTATTGATAAAGGGGAAATTTTTTTACACAATATGCACATTAGCCC | 200 |
| 126 | Listeria_seeligeriserovar | GCACGTATTGATAAAGGGGAAATTTCTTACACAATATGCACATTAGCCC | 200 |
| | | ** ** ** ** ** ******** ******** ***** ** ** ** | |

FIG. 10A(contd.)

```
SEQ ID
NO:
 119 Listeria_grayiDSM20601Contig17   TTACGACCAAGGGAATAGATTCAATCATGACCCACTTCGAACTCGTAAAT 249
 120 Listeria_monocytogenes_EGD-e     TTATGAACAAGGGAACCGCTACAATCATGATCCACTAAGAACGCGCAAGT 250
 121 Listeria_monocytogenesSLCC2479   TTATGAACAAGGGAACCGCTACAATCATGATCCACTAAGAACGCGCAAGT 250
 122 Listeria_monocytogenes           TTATGAACAAGGGAACCGCTACAATCATGATCCACTAAGAACGCGCAAGT 250
 123 Listeria_innocuaClip11262        ATATGAACAAGGGAACCGCTACAATCATGATCCACTAAGAACGCGCAAGT 250
 124 Listeria_welshimeriserovar6b     TTATGAACAAGGGAACCGCTACAATCATGATCCACTAAGAACGCGCAAAC 250
 125 Listeria_ivanoviisubsp.londoni   ATACGAACAAGGGAACCGCTACAACCACGACCCACTACGAACGCGCAAGT 250
 126 Listeria_seeligeriserovar        ATACGAACAAGGAAACCGTTACAATCACGACCCACTAAGAACACGCAAAT 250
                                       ** ** ***** **  * * *** ** ** *****  **** ** **
SEQ ID
NO:
 119 Listeria_grayiDSM20601Contig17   TGTTATTGCACAAAAAACAAATCAGCCGTCTGATTGGCGAAACAAAAGAA 299
 120 Listeria_monocytogenes_EGD-e     TGCTCTTACATAAGAAGCAAATCAGCCGTTTAATTGGAGAAACGAAAGAG 300
 121 Listeria_monocytogenesSLCC2479   TGCTCTTACATAAGAAGCAAATCAGCCGTTTAATTGGAGAAACGAAAGAG 300
 122 Listeria_monocytogenes           TGCTCTTACATAAGAAGCAAATCAGCCGTTTAATTGGAGAAACGAAAGAG 300
 123 Listeria_innocuaClip11262        TGCTCTTACATAAGAAGCAAATCAGCCGTTTAATTGGAGAAACGAAAGAG 300
 124 Listeria_welshimeriserovar6b     TGCTTTTACATAAGAAGCAAATCAGCCGTTTAATTGGCGAAACGAAAGAA 300
 125 Listeria_ivanoviisubsp.londoni   TGCTACTTCATAAAAAACAAATTAGCCGTTTAATTGGAGAAACAAAAGAG 300
 126 Listeria_seeligeriserovar        TACTTCTTCATAAAAAACAAATCAGTCGTTTAATTGGAGAAACAAAAGAG 300
                                      *  *  * ** ** ** ***** ** *** * ***** ***** *****
```

```
SEQ ID
NO:
 119 Listeria_grayiDSM20601Contig17   GCTGGCTATTCGATCGTCCCCCTAAAGCTCTATATCAAAGATGGATTTGC 349
 120 Listeria_monocytogenes_EGD-e     TCCGGTTATTCGATTGTTCCACTAAAAATGTATATTAAAGATGGCTACGC 350
 121 Listeria_monocytogenesSLCC2479   TCCGGTTATTCGATTGTTCCACTAAAAATGTATATTAAAGATGGCTACGC 350
 122 Listeria_monocytogenes           TCCGGTTATTCGATTGTTCCACTAAAAATGTATATTAAAGATGGCTACGC 350
 123 Listeria_innocuaClip11262        TCCGGTTATTCGATTGTTCCACTAAAAATGTATATTAAAGATGGCTACGC 350
 124 Listeria_welshimeriserovar6b     TCTGGTTATTCGATTGTTCCGCTTAAAATGTATATTAAAGATGGATACGC 350
 125 Listeria_ivanoviisubsp.londoni   TCTGGTTATTCGATTGTTCCGCTAAAAATGTATATTAAAGATGGCTACGC 350
 126 Listeria_seeligeriserovar        TCCGGTTATTCCATCGTCCCGCTAAAAATGTATATTAAAGATGGTTACGC 350
                                       * ** ***** ** ** ** ** **  * ***** ******** *  **
SEQ ID
NO:
 119 Listeria_grayiDSM20601Contig17   AAAAGTCTTGATCGGTGTAGCTAAAGGGAAGAAAAAATATGACAAACGCG 399
 120 Listeria_monocytogenes_EGD-e     AAAAGTACTTATCGGTGTAGCTCGAGGTAAAAAGAAATACGATAAACGCC 400
 121 Listeria_monocytogenesSLCC2479   AAAAGTACTTATCGGTGTAGCTCGAGGTAAAAAGAAATACGATAAACGCC 400
 122 Listeria_monocytogenes           AAAAGTACTTATCGGTGTAGCTCGAGGTAAAAAGAAATACGATAAACGCC 400
 123 Listeria_innocuaClip11262        AAAAGTACTCATCGGTGTAGCTCGAGGTAAAAAGAAATACGATAAACGCC 400
 124 Listeria_welshimeriserovar6b     AAAAGTACTCATCGGTGTAGCTAGAGGTAAAAAGAAATACGATAAACGCC 400
 125 Listeria_ivanoviisubsp.londoni   AAAAGTCTTAATTGGAGTAGCTAGAGGTAAAAAGAAATACGATAAGCGTC 400
 126 Listeria_seeligeriserovar        AAAAGTATTGATCGGTGTAGCTAGAGGTAAAAAGAAATATGATAAACGCC 400
                                      ******   * ** ** ******  *** ** ** ***** ** ** **
```

```
SEQ ID
NO:
 119 Listeria_grayiDSM20601Contig17   AAGATTTGAAACGCAAAGAAGCAAAACGTGATATTGAACGAGCGTTTAAA 449
 120 Listeria_monocytogenes_EGD-e     AAGACTTAAAACAAAAAGAAGCAAAACGTGATATCGAACGCGCTTTTAAA 450
 121 Listeria_monocytogenesSLCC2479   AAGACTTAAAACAAAAAGAAGCAAAACGTGATATCGAACGCGCTTTTAAA 450
 122 Listeria_monocytogenes           AAGACTTAAAACAAAAAGAAGCAAAACGTGATATCGAACGCGCTTTTAAA 450
 123 Listeria_innocuaClip11262        AAGACTTAAAACAAAAAGAAGCAAAACGTGATATTGAACGCGCCTTTAAA 450
 124 Listeria_welshimeriserovar6b     AAGATTTGAAACAAAAAGAAGCAAAACGTGATATTGAACGTGCATTTAAA 450
 125 Listeria_ivanoviisubsp.londoni   AAGATTTAAAACAAAAAGAAGCAAAACGTGATATTGAGCGTGCTTTCAAA 450
 126 Listeria_seeligeriserovar        AAGACTTAAAACAAAAAGAAGCAAAACGTGATATTGAGCGTGCTTTCAAA 450
                                      **** ** ****  ******************** ** ** ** ** ***
SEQ ID
NO:
 119 Listeria_grayiDSM20601Contig17   GAAAGACAACGATAA 464
 120 Listeria_monocytogenes_EGD-e     GAGCGCCAACAATAA 465
 121 Listeria_monocytogenesSLCC2479   GAGCGCCAACAATAA 465
 122 Listeria_monocytogenes           GAGCGCCAACAATAA 465
 123 Listeria_innocuaClip11262        GAGCGCCAACAATAA 465
 124 Listeria_welshimeriserovar6b     GAACGCCAACAATAA 465
 125 Listeria_ivanoviisubsp.londoni   GAACGCCAACAATA- 464
 126 Listeria_seeligeriserovar        GAACGCCAACAATAA 464
```

```
SEQ ID NO:
 127 Mycoplasma_pneumoniaeM129-B7  ATGCGAGTACTTGTCAACAATCCCAGAGCGCAATATGACTATTACCTTTT 50
 128 Mycoplasma_pneumoniaeM29      ATGCGAGTACTTGTCAACAATCCCAGAGCGCAATATGACTATTACCTTTT 50
 129 _Mycoplasma_pneumoniae309     ATGCGAGTACTTGTCAACAATCCCAGAGCGCAATATGACTATTACCTTTT 50
 130 Mycoplasma_pneumoniaeFH       ATGCGAGTACTTGTCAACAATCCCAGAGCGCAATATGACTATTACCTTTT 50
 131 Mycoplasma_pneumoniaeM129     ATGCGAGTACTTGTCAACAATCCCAGAGCGCAATATGACTATTACCTTTT 50
                                   **************************************************

SEQ ID NO:
 127 Mycoplasma_pneumoniaeM129-B7  AACGGGTTATTGTGCTGGCTTAGTCTTAAAAGGTAGTGAAGTCAAATCGC 100
 128 Mycoplasma_pneumoniaeM29      AACGGGTTATTGTGCTGGCTTAGTCTTAAAAGGTAGTGAAGTCAAATCGC 100
 129 _Mycoplasma_pneumoniae309     AACGGGTTATTGTGCTGGCTTAGTCTTAAAAGGTAGTGAAGTCAAATCGC 100
 130 Mycoplasma_pneumoniaeFH       AACGGGTTATTGTGCTGGCTTAGTCTTAAAAGGTAGTGAAGTCAAATCGC 100
 131 Mycoplasma_pneumoniaeM129     AACGGGTTATTGTGCTGGCTTAGTCTTAAAAGGTAGTGAAGTCAAATCGC 100
                                   **************************************************

SEQ ID NO:
 127 Mycoplasma_pneumoniaeM129-B7  TAGCTTTAGGGCAAGGTAGCTTAAAGGAAGCCTATGTTTTTATTGACAAG 150
 128 Mycoplasma_pneumoniaeM29      TAGCTTTAGGGCAAGGTAGCTTAAAGGAAGCCTATGTTTTTATTGACAAG 150
 129 _Mycoplasma_pneumoniae309     TAGCTTTAGGGCAAGGTAGCTTAAAGGAAGCCTATGTTTTTATTGACAAG 150
 130 Mycoplasma_pneumoniaeFH       TAGCTTTAGGGCAAGGTAGCTTAAAGGAAGCCTATGTTTTTATTGACAAG 150
 131 Mycoplasma_pneumoniaeM129     TAGCTTTAGGGCAAGGTAGCTTAAAGGAAGCCTATGTTTTTATTGACAAG 150
                                   **************************************************
```

FIG. 13(contd.)

```
SEQ ID NO:                                                                         Mpneu_F1
 127 Mycoplasma_pneumoniaeM129-B7 CACGAGGTCTATATTAAAGATTTTAGCATTTCGCCCTATGCCTTTTCAGG 200
 128 Mycoplasma_pneumoniaeM29     CACGAGGTCTATATTAAAGATTTTAGCATTTCGCCCTATGCCTTTTCAGG 200
 129 _Mycoplasma_pneumoniae309    CACGAGGTCTATATTAAAGATTTTAGCATTTCGCCCTATGCCTTTTCAGG 200
 130 Mycoplasma_pneumoniaeFH      CACGAGGTCTATATTAAAGATTTTAGCATTTCGCCCTATGCCTTTTCAGG 200
 131 Mycoplasma_pneumoniaeM129    CACGAGGTCTATATTAAAGATTTTAGCATTTCGCCCTATGCCTTTTCAGG 200
                                  **************************************************

SEQ ID NO:                                               Mpneu_P1
 127 Mycoplasma_pneumoniaeM129-B7 CGAGTTCAACCACCCCTTCAAACGGGTGAAAAAGCTCCTTTTAAACCGGA 250
 128 Mycoplasma_pneumoniaeM29     CGAGTTCAACCACCCCTTCAAACGGGTGAAAAAGCTCCTTTTAAACCGGA 250
 129 _Mycoplasma_pneumoniae309    CGAGTTCAACCACCCCTTCAAACGGGTGAAAAAGCTCCTTTTAAACCGGA 250
 130 Mycoplasma_pneumoniaeFH      CGAGTTCAACCACCCCTTCAAACGGGTGAAAAAGCTCCTTTTAAACCGGA 250
 131 Mycoplasma_pneumoniaeM129    CGAGTTCAACCACCCCTTCAAACGGGTGAAAAAGCTCCTTTTAAACCGGA 250
                                  **************************************************

SEQ ID NO:                                                                          Mpneu_R1
 127 Mycoplasma_pneumoniaeM129-B7 ATGAGATTAAACAAATTACGGCACGCCAAAGCAAGAAGGACTTTCCATT 300
 128 Mycoplasma_pneumoniaeM29     ATGAGATTAAACAAATTACGGCACGCCAAAGCAAGAAGGACTTTCCATT 300
 129 _Mycoplasma_pneumoniae309    ATGAGATTAAACAAATTACGGCACGCCAAAGCAAGAAGGACTTTCCATT 300
 130 Mycoplasma_pneumoniaeFH      ATGAGATTAAACAAATTACGGCACGCCAAAGCAAGAAGGACTTTCCATT 300
 131 Mycoplasma_pneumoniaeM129    ATGAGATTAAACAAATTACGGCACGCCAAAGCAAGAAGGACTTTCCATT 300
                                  **************************************************
```

FIG. 13(contd.)

```
SEQ ID NO:
 127 Mycoplasma_pneumoniaeM129-B7 ATTCCACTTAAAGTGTTCTTTAAAAA-TGGCAAAATTAAAATGGAAATCT 349
 128 Mycoplasma_pneumoniaeM29     ATTCCACTTAAAGTGTTCTTTAAAAA-TGGCAAAATTAAAATGGAAATCT 349
 129 _Mycoplasma_pneumoniae309    ATTCCACTTAAAGTGTTCTTTAAAAA-TGGCAAAATTAAAATGGAAATCT 349
 130 Mycoplasma_pneumoniaeFH      ATTCCACTTAAAGTGTTCTTTAAAAAATGGCAAAATTAAAATGGAAATCT 350
 131 Mycoplasma_pneumoniaeM129    ATTCCACTTAAAGTGTTCTTTAAAAA-TGGCAAAATTAAAATGGAAATCT 349
                                  ************************** ***********************

SEQ ID NO:
 127 Mycoplasma_pneumoniaeM129-B7 GGTTGGCCAAACCTAAGAAAAAATTTGATAAACGTGAAGCCATCAAAAGT 399
 128 Mycoplasma_pneumoniaeM29     GGTTGGCCAAACCTAAGAAAAAATTTGATAAACGTGAAGCCATCAAAAGT 399
 129 _Mycoplasma_pneumoniae309    GGTTGGCCAAACCTAAGAAAAAATTTGATAAACGTGAAGCCATCAAAAGT 399
 130 Mycoplasma_pneumoniaeFH      GGTTGGCCAAACCTAAGAAAAAATTTGATAAACGTGAAGCCATCAAAAGT 400
 131 Mycoplasma_pneumoniaeM129    GGTTGGCCAAACCTAAGAAAAAATTTGATAAACGTGAAGCCATCAAAAGT 399
                                  **************************************************

SEQ ID NO:
 127 Mycoplasma_pneumoniaeM129-B7 AAAACGATCCAGCGCGAATTGCGCCAACAATATGGATCGCCA 441
 128 Mycoplasma_pneumoniaeM29     AAAACGATCCAGCGCGAATTGCGCCAACAATATGGATCGCCA 441
 129 _Mycoplasma_pneumoniae309    AAAACGATCCAGCGCGAATTGCGCCAACAATATGGATCGCCA 441
 130 Mycoplasma_pneumoniaeFH      AAAACGATCCAGCGCGAATTGCGCCAACAATATGGATCGCCA 442
 131 Mycoplasma_pneumoniaeM129    AAAACGATCCAGCGCGAATTGCGCCAACAATATGGATCGCCA 441
                                  ******************************************
```

FIG. 16A

```
SEQ ID NO:
140 Mycobacterium_avium_paratuberc GTGGCCAAGGGTTCCGGCCGGGCCAAAGCGGCGGGCGGCAAAGGTGGCAG 50
141 Mycobacterium_avium            GTGGCCAAGGGTTCCGGCCGGGCCAAAGCGGCGGGCGGCAAAGGTGGCAG 50
139 Mycobacterium_intracellulare   GTGGCCAAGGGATCCGGCCGGGCCAAGGCGGCGGGCGGCAAAGGCGGCAG 50
137 Mycobacterium_lepraestrainTN   GTGGCCA-GAAACCC--TCG------------------------TGGCGG 23
132 Mycobacterium_tuberculosis     GTGTCCAAG---TC--GTCGCG----------------------TGGCGG 23
133 Mycobacterium_bovis            GTGTCCAAG---TC--GTCGCG----------------------TGGCGG 23
134 MycobacteriumbovisBCGstr.ATCC3 GTGTCCAAG---TC--GTCGCG----------------------TGGCGG 23
135 Mycobacterium_canettii         GTGTCCAAG---TC--GTCGCG----------------------TGGCGG 23
136 Mycobacterium_africanumGM04118 GTGTCCAAG---TC--GTCGCG----------------------TGGCGG 23
138 Mycobacterium.smegmatis        GTGACCAAGAAGAGC-GCCTC-----------------------CAGCAA 26
142 Mycobacterium_abscessus_strain ATGAGTAAGAA-----ACCGGC----------------------CGACGG 23
                                    **   * *         *                            *

SEQ ID NO:
140 Mycobacterium_avium_paratuberc CAAACAGATCATTGCCACCAATCGCAAAGCGCGGCACAACTATTCGATCA 100
141 Mycobacterium_avium            CAAACAGATCATTGCCACCAATCGCAAAGCGCGGCACAACTATTCGATCA 100
139 Mycobacterium_intracellulare   CAAACAAGTTGTGGCCACCAATCGCAAAGCGCGGCATAACTATTCGATCA 100
137 Mycobacterium_lepraestrainTN   CAAGCAGATTGTGGCCACCAATCGCAAGGCTCGGCACGATTACGCAATCA 73
132 Mycobacterium_tuberculosis     CCGGCAGATCGTTGCCAGCAATCGCAAAGCCCGGCACAACTATTCGATCA 73
133 Mycobacterium_bovis            CCGGCAGATCGTTGCCAGCAATCGCAAAGCCCGGCACAACTATTCGATCA 73
134 MycobacteriumbovisBCGstr.ATCC3 CCGGCAGATCGTTGCCAGCAATCGCAAAGCCCGGCACAACTATTCGATCA 73
135 Mycobacterium_canettii         CCGGCAGATCGTTGCCAGCAATCGCAAAGCCCGGCACAACTATTCGATCA 73
136 Mycobacterium_africanumGM04118 CCGGCAGATCGTTGCCAGCAATCGCAAAGCCCGGCACAACTATTCGATCA 73
138 Mycobacterium.smegmatis        CAACAAGGTGGTCGCCACCAACCGCAAGGCGCGACACAACTACACGATCC 76
142 Mycobacterium_abscessus_strain ACGAAAAGTCATCGCGACCAATCGCAAGGCACGACACAACTATTCGATCA 73
                                        *  *  * ** * *** ***** ** ** **  * **  * ***
```

FIG. 16A(contd.)

```
SEQ ID NO:
140 Mycobacterium_avium_paratuberc TCGAAACGTACGAGGCCGGGGTGGCGTTGCAAGGAACCGAGGTCAAAAGC 150
141 Mycobacterium_avium            TCGAAACGTACGAGGCCGGGGTGGCGTTGCAAGGAACCGAGGTCAAAAGC 150
139 Mycobacterium_intracellulare   TCGAATCGTTCGAGGCCGGGGTCGCGCTGCAAGGCACCGAGGTCAAAAGC 150
137 Mycobacterium_lepraestrainTN   TTGAATTGTTTGAGGCTGGGGTGGCGTTGCTTGGCACCGAGGTGAAAAGT 123
132 Mycobacterium_tuberculosis     TCGAGGTGTTCGAGGCCGGGGTTGCGCTGCAAGGCACGGAGGTGAAGAGC 123
133 Mycobacterium_bovis            TCGAGGTGTTCGAGGCCGGGGTTGCGCTGCAAGGCACGGAGGTGAAGAGC 123
134 MycobacteriumbovisBCGstr.ATCC3 TCGAGGTGTTCGAGGCCGGGGTTGCGCTGCAAGGCACGGAGGTGAAGAGC 123
135 Mycobacterium_canettii         TCGAGGTGTTCGAGGCCGGGGTTGCGCTGCAAGGCACGGAGGTGAAGAGC 123
136 Mycobacterium_africanumGM04118 TCGAGGTGTTCGAGGCCGGGGTTGCGCTGCAAGGCACGGAGGTGAAGAGC 123
138 Mycobacterium.smegmatis        TCGACACCTACGAGGCCGGGATCGTGTTGATGGGCACGGAGGTCAAGAGC 126
142 Mycobacterium_abscessus_strain TCGATGTGTATGAGGCCGGGGTGCAGTTGGTGGGCACCGAGGTCAAGACA 123
                                   * **    *  ***** *** *   * **   ** ** ***** ** *

SEQ ID NO:
140 Mycobacterium_avium_paratuberc CTGCGGGAGGGCCAAGCGTCGTTAGCTGACGCGTTCGCAACGATCGACGA 200
141 Mycobacterium_avium            CTGCGGGAGGGCCAAGCGTCGTTAGCTGACGCGTTCGCAACGATCGACGA 200
139 Mycobacterium_intracellulare   CTGCGCGAGGGCCAAGCTTCGTTAGCTGACGCCTTCGCAACGATCGACGA 200
137 Mycobacterium_lepraestrainTN   CTGCGGGAGGGGCATGCGTCGCTGGCCGACGCGTTCGCAACCGTCGACAG 173
132 Mycobacterium_tuberculosis     CTGCGGGAAGGGCAGGCGTCGCTGGCCGATTCGTTCGCCACCATCGACGA 173
133 Mycobacterium_bovis            CTGCGGGAAGGGCAGGCGTCGCTGGCCGATTCGTTCGCCACCATCGACGA 173
134 MycobacteriumbovisBCGstr.ATCC3 CTGCGGGAAGGGCAGGCGTCGCTGGCCGATTCGTTCGCCACCATCGACGA 173
135 Mycobacterium_canettii         CTGCGGGAAGGGCAGGCGTCGCTGGCCGATTCGTTCGCCACCATCGACGA 173
136 Mycobacterium_africanumGM04118 CTGCGGGAAGGGCAGGCGTCGCTGGCCGATTCGTTCGCCACCATCGACGA 173
138 Mycobacterium.smegmatis        CTGCGCGAAGGTCAGGCCTCGCTGGCCGACGCGTTCGCCACGGTCGACGA 176
142 Mycobacterium_abscessus_strain CTGCGCGAGGGCAAGGCATCGCTGGTCGATGCCTTCGCCACCGTCGATGA 173
                                   ***** ** **  * ** *** * *  **  * ***** **  ****
```

```
SEQ ID NO:
140 Mycobacterium_avium_paratuberc CGGTGAAGTCTGGTTGCGCAACTTGTACATCCCGGAGTATCAACACGGTA 250
141 Mycobacterium_avium            CGGTGAAGTCTGGTTGCGCAACTTGTACATCCCGGAGTATCAACACGGTA 250
139 Mycobacterium_intracellulare   CGGCGAAGTGTGGTTGCGCAACTTGTACATTGCGGAGTACCAGCACGGTA 250
137 Mycobacterium_lepraestrainTN   CGGTGAAGTGTGGTTGCGAAACATGCACATCCCGGAGTATCAGCATGGTA 223
132 Mycobacterium_tuberculosis     CGGCGAAGTGTGGCTGCGCAACGCGCACATCCCGGAATACCGGCACGGCA 223
133 Mycobacterium_bovis            CGGCGAAGTGTGGCTGCGCAACGCGCACATCCCGGAATACCGGCACGGCA 223
134 MycobacteriumbovisBCGstr.ATCC3 CGGCGAAGTGTGGCTGCGCAACGCGCACATCCCGGAATACCGGCACGGCA 223
135 Mycobacterium_canettii         CGGCGAAGTGTGGCTGCGCAACGCGCACATCCCGGAATACCGGCACGGCA 223
136 Mycobacterium_africanumGM04118 CGGCGAAGTGTGGCTGCGCAACGCGCACATCCCGGAATACCGGCACGGCA 223
138 Mycobacterium.smegmatis        CGGCGAGATCTGGCTGCGCAACGTCCACATCGCCGAATATCACCACGGCA 226
142 Mycobacterium_abscessus_strain CGGCGAGGTGTGGTTGCGCGGCGTGCATATCCCGCAATACGACCACGGCA 223
                                   *** **  * *** ****   *    * **  *  * **    ** ** *

SEQ ID NO:
140 Mycobacterium_avium_paratuberc GCTGGACCAATCACGACCCACGCCGGAACCGAAAGTTGTTGTTACATAGG 300
141 Mycobacterium_avium            GCTGGACCAATCACGACCCACGCCGGAACCGAAAGTTGTTGTTACATAGG 300
139 Mycobacterium_intracellulare   GCTGGACCAATCATGACCCCCGGCGCAACCGAAAGTTGTTGTTACATCGG 300
137 Mycobacterium_lepraestrainTN   GCTGGACCAATCACGATCCTCGCCGTAACCGCAAGCTGCTGCTGCACCGC 273
132 Mycobacterium_tuberculosis     GCTGGACCAACCACGAGCCGCGACGCAACCGCAAACTGCTGTTGCATCGC 273
133 Mycobacterium_bovis            GCTGGACCAACCACGAGCCGCGACGCAACCGCAAACTGCTGTTGCATCGC 273
134 MycobacteriumbovisBCGstr.ATCC3 GCTGGACCAACCACGAGCCGCGACGCAACCGCAAACTGCTGTTGCATCGC 273
135 Mycobacterium_canettii         GCTGGACCAACCACGAGCCGCGACGCAACCGCAAACTGCTGTTGCATCGC 273
136 Mycobacterium_africanumGM04118 GCTGGACCAACCACGAGCCGCGACGCAACCGCAAACTGCTGTTGCATCGC 273
138 Mycobacterium.smegmatis        CCTGGACCAACCACGCGCCGCGGCGCAACCGCAAACTGCTGCTGCACCGC 276
142 Mycobacterium_abscessus_strain CCTGGACCAATCACGCTCCGCTGCGGAACCGGAAACTGTTGTTGCACAGG 273
                                    ********* ** *  ** *  ** ***** **  ** ** * **  *
```

```
SEQ ID NO:
140 Mycobacterium_avium_paratuberc CAACAAATCGACAGACTGGTCGGCAAGATCCGGGATGGTAACCTCGCCTT 350
141 Mycobacterium_avium            CAACAAATCGACAGACTGGTCGGCAAGATCCGGGATGGTAACCTCGCCTT 350
139 Mycobacterium_intracellulare   CAACAAATCGACAGGCTGGTCGGCAAGATTCGAGATGGTAACCTCGCCTT 350
137 Mycobacterium_lepraestrainTN   CGCCAGATCGACACCCTGGTTGGCAAGATCCGTGACGGCAACCTCGCGCT 323
132 Mycobacterium_tuberculosis     CGCCAGATCGACACCTTGGTCGGCAAGATCCGCGAAGGCAACTTCGCCCT 323
133 Mycobacterium_bovis            CGCCAGATCGACACCTTGGTCGGCAAGATCCGCGAAGGCAACTTCGCCCT 323
134 MycobacteriumbovisBCGstr.ATCC3 CGCCAGATCGACACCTTGGTCGGCAAGATCCGCGAAGGCAACTTCGCCCT 323
135 Mycobacterium_canettii         CGCCAGATCGACACCTTGGTCGGCAAGATCCGCGAAGGCAACTTCGCCCT 323
136 Mycobacterium_africanumGM04118 CGCCAGATCGACACCTTGGTCGGCAAGATCCGCGAAGGCAACTTCGCCCT 323
138 Mycobacterium.smegmatis        AAGCAGATCGACAACCTCATCGGCAAGATCCGCGACGGCAACCTCACGCT 326
142 Mycobacterium_abscessus_strain GCGCAGATCGACATGCTGGTCGGCAAGACCCGCGACGGCAATCTGACCCT 323
                                      ** *******   *  * *******  ** ** ** **  *  *  *

SEQ ID NO:
140 Mycobacterium_avium_paratuberc GATGCCGCTGTCGCTGTACTTCTCCGAGGGCAAAGTGAAGGTAGAGCTCG 400
141 Mycobacterium_avium            GATGCCGCTGTCGCTGTACTTCTCCGAGGGCAAAGTGAAGGTAGAGCTCG 400
139 Mycobacterium_intracellulare   GATGCCGCTGTCTCTGTATTTCTCCGAGGGCAAGGTCAAGGTCGAACTGG 400
137 Mycobacterium_lepraestrainTN   AGTGCCGTTATCGTTGTATTTTGCCGAGGGCAAGGTCAAGGTCGAGCTTG 373
132 Mycobacterium_tuberculosis     GGTGCCGTTGTCGCTGTATTTCGCCGAAGGCAAGGTCAAGGTTGAGCTTG 373
133 Mycobacterium_bovis            GGTGCCGTTGTCGCTGTATTTCGCCGAAGGCAAGGTCAAGGTTGAGCTTG 373
134 MycobacteriumbovisBCGstr.ATCC3 GGTGCCGTTGTCGCTGTATTTCGCCGAAGGCAAGGTCAAGGTTGAGCTTG 373
135 Mycobacterium_canettii         GGTGCCGTTGTCGCTGTATTTCGCCGAAGGCAAGGTCAAGGTTGAGCTTG 373
136 Mycobacterium_africanumGM04118 GGTGCCGTTGTCGCTGTATTTCGCCGAAGGCAAGGTCAAGGTTGAGCTTG 373
138 Mycobacterium.smegmatis        GGTGCCGCTGTCGATCTACTTCACCGACGGCAAGGTCAAGGTCGAGTTGG 376
142 Mycobacterium_abscessus_strain GGTACCGCTGTCGCTGTACTTCCTGGACGGCAAGGTCAAGGTGGAGTTGG 373
                                     * *** * **  * ** **    ** ***** ** ***** **  * *
```

FIG. 16B(contd.)

```
SEQ ID NO:
140 Mycobacterium_avium_paratuberc CTCTCGCGCGGCAAGAAGGCTTACGACAAACGCCAGGACCTGGCCCAG 450
141 Mycobacterium_avium            CTCTCGCGCGGCAAGAAGGCTTACGACAAACGCCAGGACCTGGCCCAG 450
139 Mycobacterium_intracellulare   CCCTTGCGCGCGGCAAAAGGGCTTACGACAAACGCCAGGACATGGCCCAG 450
137 Mycobacterium_lepraestrainTN   CGCTGGCGCGCGGCAAGAAACTGCACGACAAGCGCCAGGACATGGCGCGT 423
132 Mycobacterium_tuberculosis     CGCTGGCCCGAGGCAAGCAAGCCCGCGACAAACGCCAGGACATGGCCCGT 423
133 Mycobacterium_bovis            CGCTGGCCCGAGGCAAGCAAGCCCGCGACAAACGCCAGGACATGGCCCGT 423
134 MycobacteriumbovisBCGstr.ATCC3 CGCTGGCCCGAGGCAAGCAAGCCCGCGACAAACGCCAGGACATGGCCCGT 423
135 Mycobacterium_canettii         CGCTGGCCCGAGGCAAGCAAGCCCGCGACAAACGCCAGGACATGGCCCGT 423
136 Mycobacterium_africanumGM04118 CGCTGGCCCGAGGCAAGCAAGCCCGCGACAAACGCCAGGACATGGCCCGT 423
138 Mycobacterium.smegmatis        CGCTCGCCCGCGGCAAGCAGGCCCACGACAAGCGCCAGGACCTCGCCCGT 426
142 Mycobacterium_abscessus_strain CGCTGGCGCGGGGTAAGCAGGCTCACGACAAGCGTCAGGACATCGCCAAA 423
                                   * ** ** ** ** **         ****** ** ****** * **

SEQ ID NO:
140 Mycobacterium_avium_paratuberc CGCGACGCACAGCGCGAAGTCGTTCGTCAACTGGGACGCCGAACAAAGGG 500
141 Mycobacterium_avium            CGCGACGCACAGCGCGAAGTCGTTCGTCAACTGGGACGCCGAACAAAGGG 500
139 Mycobacterium_intracellulare   CGCGACGCACAGCGCGAAGTGGTCCGTGAACTAGGGCGCCGAGCGAAGGG 500
137 Mycobacterium_lepraestrainTN   CGCGATGCTCAGCGCGAAGTAATCCGTGAACTCGGTCGCCGTGCCAAGGG 473
132 Mycobacterium_tuberculosis     CGTGATGCCCAGCGTGAAGTGCTCCGCGAGTTGGGTCGGCGCGCTAAGGG 473
133 Mycobacterium_bovis            CGTGATGCCCAGCGTGAAGTGCTCCGCGAGTTGGGTCGGCGCGCTAAGGG 473
134 MycobacteriumbovisBCGstr.ATCC3 CGTGATGCCCAGCGTGAAGTGCTCCGCGAGTTGGGTCGGCGCGCTAAGGG 473
135 Mycobacterium_canettii         CGTGATGCCCAGCGTGAAGTGCTCCGCGAGTTGGGTCGGCGCGCTAAGGG 473
136 Mycobacterium_africanumGM04118 CGTGATGCCCAGCGTGAAGTGCTCCGCGAGTTGGGTCGGCGCGCTAAGGG 473
138 Mycobacterium.smegmatis        CGAGACGCTCAACGCGAGGTGATCCGCGAGCTGGGCCGCCGGGCCAAGGG 476
142 Mycobacterium_abscessus_strain CGGGACGCTTCGCGTGAGATCACCCGTGAGCTGGGACGCCGCGCCAAAGG 473
                                   ** ** **    ** **  *    **  *  * ** ** **  * ** **
```

```
SEQ ID NO:
140 Mycobacterium_avium_paratuberc        GATGATCTGA 510
141 Mycobacterium_avium                   GATGATCTGA 510
139 Mycobacterium_intracellulare          CATGACCTGA 510
137 Mycobacterium_lepraestrainTN          CATGCTCTGA 483
132 Mycobacterium_tuberculosis            CATGACCTGA 483
133 Mycobacterium_bovis                   CATGACCTGA 483
134 MycobacteriumbovisBCGstr.ATCC3        CATGACCTGA 483
135 Mycobacterium_canettii                CATGACCTGA 483
136 Mycobacterium_africanumGM04118        CATGACCTGA 483
138 Mycobacterium.smegmatis               CAAGATCTGA 486
142 Mycobacterium_abscessus_strain        CATG---TGA 480
                                           * *   ***
```

```
SEQ ID NO:
 169 H.influenzaeRdKW20              ATGACAAAGAAAAAAGTAAAACCCAATTCAAATACTATCGCACTAAATAA 50
 170 H.influenzaeF3031               ATGACAAAGAAAAAAGTAAAACCCAATTCAAATACTATCGCACTAAATAA 50
 171 H.influenzae86-028NP            ATGACAAAGAAAAAAGTAAAACCCAATTCAAATACTATCGCACTGAATAA 50
 172 H.influenzaeKR494               ATGACAAAGAAAAAAGTAAAACCCAATTCAAATACTATCGCACTGAATAA 50
 173 H.influenzae10810               ATGACAAAGAAAAAAGTAAAACCCAATTCAAATACTATCGCACTAAATAA 50
 174 H.influenzaeF3047               ATGACAAAGAAAAAAGTAAAACCCAATTCAAATACTATCGCACTGAATAA 50
 175 H.influenzaePittGG              ATGACAAAGAAAAAAGTAAAACCCAATTCAAATACTATCGCACTGAATAA 50
 176 H.influenzaeR2846               ATGACAAAGAAAAAAGTAAAACCCAATTCAAATACTATCGCACTGAATAA 50
 177 H.influenzaePittEE              ATGACAAAGAAAAAAGTAAAACCCAATTCAAATACTATCGCACTGAATAA 50
 178 H.influenzaeR2866               ATGACAAAGAAAAAAGTAAAACCCAATTCAAATACTATCGCACTGAATAA 50
 179 H.haemolyticusHK386             ATGACAAAGAAAAAAGTAAAACCAGGATCAAACACTATCGCACTGAATAA 50
 180 H.haemolyticusM21639            ATGACAAAGAAAAAAGTAAAACCAGGATCAAATACTATCGCACTGAATAA 50
 181 H.haemolyticusM21621            ATGACAAAGAAAAAAGTAAAACCAGAATCAAATACTATTGCACTGAATAA 50
 182 H.haemolyticusM21127            ATGACAAAGAAAAAAGTAAAACCAGGATCAAACACTATCGCACTGAATAA 50
 183 H.haemolyticusM19501            ATGACAAAGAAAAAAGTAAAACCAGGATCAAATACTATCGCACTGAATAA 50
 184 H.haemolyticusM19107            ATGACAAAGAAAAA-GTAAAACCAGGATCAAATACTATCGCACTGAATAA 49
 185 Haemophilus_parainfluenzae_HK2  ATGACCAAGAAAAAAGTCAAAGTCGGCTCCAGCACCATTGCGTTAAATAA 50
 186 Haemophilus_parainfluenzae_T3T  ATGACCAAGAAGAAAGTCAAAGTCGGCTCCAATACCATTGCGTTAAATAA 50
 187 H.somnus2336                    ATGACAAAGAAAAAAGCAAAGGTAGCATCTAATACGATTGCCTTAAATAA 50
 188 H.somnus129PT                   ATGACAAAGAAAAAAGCAAAGGTAGCATCTAATACGATTGCCTTAAATAA 50
 189 H.ducreyi35000HP                ---------------------------TCAAACACGATTGCACTCAACAA 23
 190 Haemophilus_pittmaniae_HK_85    ATGACCAAGAAAAAAGCTAAAGTTGGCGCAAACACCATCGCATTAAACAA 50
 191 Haemophilus_sputorum_HK_2154    ATGGCAAA---AAAACCTAAAGTTGCTTCAAATACTATTGCGCTAAATAA 47
 192 H.parasuis_SH0165               ATGAGTAA---AAAACCAAAAGTAGCTTCAAACACGATTGCCTTAAATAA 47
 193 H.parasuis_ZJ0906               ATGAGTAA---AAAACCAAAAGTAGCTTCAAATACGATTGCCTTAAATAA 47
                                                                * *  ** ** **  * ** **
```

FIG. 17A(contd.)

```
SEQ ID NO:
  169 H.influenzaeRdKW20                ACGTGCAAGACACGATTATTTTATTGAAGATGAAATTGAAGCAGGTCTTG 100
  170 H.influenzaeF3031                 ACGTGCAAGACACGATTATTTTATTGAAGATGAAATTGAAGCAGGTCTTG 100
  171 H.influenzae86-028NP              ACGTGCAAGACACGATTATTTTATTGAAGATGAAATTGAAGCAGGTCTTG 100
  172 H.influenzaeKR494                 ACGTGCAAGACACGATTATTTTATTGAAGATGAAATTGAAGCAGGTCTTG 100
  173 H.influenzae10810                 ACGTGCAAGACACGATTATTTTATTGAAGATGAAATTGAATCAGGTCTTG 100
  174 H.influenzaeF3047                 ACGTGCAAGACACGATTATTTTATTGAAGATGAAATTGAAGCCGGTCTTG 100
  175 H.influenzaePittGG                ACGTGCAAGACACGATTATTTTATTGAAGATGAAATTGAAGCAGGTCTTG 100
  176 H.influenzaeR2846                 ACGTGCAAGACACGATTATTTTATTGAAGATGAAATTGAAGCAGGTCTTG 100
  177 H.influenzaePittEE                ACGTGCAAGACACGATTATTTTATTGAAGATGAAATTGAAGCAGGTCTTG 100
  178 H.influenzaeR2866                 ACGTGCAAGACACGATTATTTTATTGAAGATGAAATTGAAGCAGGTCTTG 100
  179 H.haemolyticusHK386               ACGTGCGAGACATGATTATTTTATAGAAGATGAAATTGAAGCGGGTCTTG 100
  180 H.haemolyticusM21639              ACGTGCGAAACATGATTATTTTATAGAAGATGAAATTGAAGCAGGTCTTG 100
  181 H.haemolyticusM21621              ACGTGCTAGACATGACTATTTTATAGAAGATGAAATTGAAGCGGGTCTTG 100
  182 H.haemolyticusM21127              ACGTGCGAGACATGATTATTTTATAGAAGATGAAATTGAAGCGGGTCTTG 100
  183 H.haemolyticusM19501              ACGTGCGAGACATGATTATTTTATAGAAGATGAAATTGAAGCAGGTCTTG 100
  184 H.haemolyticusM19107              ACGTGCGAGACATGATTATTTTATAGAAGATGAAATTGAAGCAGGTCTTG 99
  185 Haemophilus_parainfluenzae_HK2    ACGAGCCAGACACGAATATTTTATTGAAGATGAAATTGAAGCCGGCCTTG 100
  186 Haemophilus_parainfluenzae_T3T    ACGAGCTCGACACGAATATTTTATTGAAGATGAAATTGAAGCCGGTCTTG 100
  187 H.somnus2336                      ACGAGCAAGACACGATTATTTTATTGAAGATGAAATCGAAGCCGGTCTTT 100
  188 H.somnus129PT                     ACGAGCAAGACACGATTATTTTATTGAAGATGAAATCGAAGCCGGTCTTT 100
  189 H.ducreyi35000HP                  ACGAGCCCGCCACGAATATTTTATTGAAGATGAAATTGAAGCAGGTTTAG 73
  190 Haemophilus_pittmaniae_HK_85      ACGCGCGCGCCACGATTATTTTATTGAAGACGAAGTTGAAGCCGGTTTGG 100
  191 Haemophilus_sputorum_HK_2154      ACGCGCACGACATGAATATTTTATTGAAGAAGAAATTGAAGCCGGCTTAG 97
  192 H.parasuis_SH0165                 ACGTGCCAGACACGAATATTTTATCGAAGAAGAAATCGAAGCTGGTCTAG 97
  193 H.parasuis_ZJ0906                 ACGTGCCAGACACGAATATTTTATCGAAGAAGAAATCGAAGCTGGTCTAG 97
                                        *** **     ** ** ******** ***** *** * *** * **  *
```

```
SEQ ID NO:
  169 H.influenzaeRdKW20             AATTACAAGGCTGGGAAGTCAAATCTATGCGCGCAGGCAAGGCAAATATT 150
  170 H.influenzaeF3031              AATTACAAGGCTGGGAAGTCAAATCTATGCGCGCAGGCAAGGCAAATATT 150
  171 H.influenzae86-028NP           AATTACAAGGCTGGGAAGTCAAATCTATGCGCGCAGGCAAGGCAAATATT 150
  172 H.influenzaeKR494              AATTACAAGGCTGGGAAGTCAAATCTATGCGCGCAGGCAAGGCAAATATT 150
  173 H.influenzae10810              AATTACAAGGCTGGGAAGTCAAATCTATGCGCGCAGGCAAGGCAAATATT 150
  174 H.influenzaeF3047              AATTACAAGGCTGGGAAGTCAAATCTATGCGCGCAGGCAAGGCAAATATT 150
  175 H.influenzaePittGG             AATTACAAGGCTGGGAAGTCAAATCTATACGCGCAGGCAAGGCAAATATT 150
  176 H.influenzaeR2846              AATTACAAGGCTGGGAAGTTAAATCTATGCGCGCAGGCAAGGCAAATATT 150
  177 H.influenzaePittEE             AATTACAAGGCTGGGAAGTTAAATCTATGCGCGCAGGCAAGGCAAATATT 150
  178 H.influenzaeR2866              AATTACAAGGCTGGGAAGTCAAATCTATGCGCGCAGGCAAGGCAAATATT 150
  179 H.haemolyticusHK386            AATTACAAGGCTGGGAAGTCAAATCAATGCGCGCAGGCAAGGCAAACATT 150
  180 H.haemolyticusM21639           AACTACAAGGCTGGGAAGTCAAATCAATGCGCGCAGGCAAGGCAAACATT 150
  181 H.haemolyticusM21621           AATTACAAGGCTGGGAAGTCAAAGCAATGCGCGCAGGCAAGGCAAACATT 150
  182 H.haemolyticusM21127           AATTACAAGGCTGGGAAGTCAAATCAATGCGCGCAGGCAAGGCAAACATT 150
  183 H.haemolyticusM19501           AACTACAAGGCTGGGAAGTTAAATCAATGCGCGCAGGCAAGGCAAACATT 150
  184 H.haemolyticusM19107           AACTACAAGGCTGGGAAGTCAAATCAATGCGCGCAGGCAAGGCAAACATT 149
  185 Haemophilus_parainfluenzae_HK2 AATTACAAGGTTGGGAAGTGAAATCAATGCGCGCGGGTAAAGCCAATATC 150
  186 Haemophilus_parainfluenzae_T3T AATTACAAGGTTGGGAAGTGAAATCAATGCGCGCAGGTAAAGCCAATATC 150
  187 H.somnus2336                   CTTTGCAAGGCTGGGAAGTTAAATCGATGCGTGCAGGTAAAGCGAGTATT 150
  188 H.somnus129PT                  CTTTGCAAGGCTGGGAAGTTAAATCGATGCGTGCAGGTAAGGCGAGTATT 150
  189 H.ducreyi35000HP               CATTGCAAGGCTGGGAAGTTAAATCTTTACGCGCAGGTAAAGCAAATATC 123
  190 Haemophilus_pittmaniae_HK_85   AGTTGCAAGGTTGGGAAGTAAAATCCATGCGCGCTGGTAAAGCTAATATC 150
  191 Haemophilus_sputorum_HK_2154   AACTCCAAGGTTGGGAAGTGAAATCTCTGCGCGCCGGTAAAGCTAATATT 147
  192 H.parasuis_SH0165              AATTACAAGGCTGGGAAGTCAAATCCCTGCGAGCAGGCAAAGCCAATATC 147
  193 H.parasuis_ZJ0906              AATTACAAGGCTGGGAAGTCAAATCCCTGCGAGCAGGTAAAGCCAATATC 147
                                        * ***** ******** *** *  * ** ** ** ** ** *  **
```

```
SEQ ID NO:
169 H.influenzaeRdKW20              AGTGATAGTTATGTTATTTTTAAAAATGGCGAAGCCTTTTTATTCGGCGC 200
170 H.influenzaeF3031               AGTGATAGTTATGTTATTTTTAAAAATGGCGAAGCCTTTTTATTCGGCGC 200
171 H.influenzae86-028NP            AGTGATAGTTATGTTATTTTTAAAAATGGCGAAGCCTTTTTATTCGGCGC 200
172 H.influenzaeKR494               AGTGATAGTTATGTTATTTTTAAAAATGGCGAAGCCTTTTTATTCGGCGC 200
173 H.influenzae10810               AGTGATAGTTATGTTATTTTTAAAAATGGCGAAGCCTTTTTATTCGGCGC 200
174 H.influenzaeF3047               AGTGATAGTTATGTTATTTTTAAAAATGGCGAAGCCTTTTTATTCGGCGC 200
175 H.influenzaePittGG              AGTGATAGTTATGTTATTTTTAAAAATGGCGAAGCCTTTTTATTCGGCGC 200
176 H.influenzaeR2846               AGTGATAGTTATGTTATTTTTAAAAATGGCGAAGCCTTTTTATTCGGTGC 200
177 H.influenzaePittEE              AGTGATAGTTATGTTATTTTTAAAAATGGCGAAGCCTTTTTATTCGGTGC 200
178 H.influenzaeR2866               AGTGATAGTTATGTTATTTTTAAAAATGGCGAAGCCTTTTTATTCGGGGC 200
179 H.haemolyticusHK386             AGTGATAGTTATGTCATTTTTAAAAATGGCGAAGCCTTTTTATTCGGCGC 200
180 H.haemolyticusM21639            AGTGATAGTTATGTCATTTTCAAAAATGGCGAAGCCTTTTTATTCGGTGC 200
181 H.haemolyticusM21621            AGTGATAGTTATGTCATTTTTAAAAATGGCGAAGCCTTTTTATTCGGGGC 200
182 H.haemolyticusM21127            AGTGATAGTTATGTCATTTTTAAAAATGGCGAAGCCTTTTTATTCGGGGC 200
183 H.haemolyticusM19501            AGTGATAGTTATGTCATTTTTAAAAATGGCGAAGCCTTTTTATTCGGTGC 200
184 H.haemolyticusM19107            AGTGATAGTTATGTCATTTTCAAAAATGGCGAAGCCTTTTTATTCGGCGC 199
185 Haemophilus_parainfluenzae_HK2  AGCGACAGCTATATCATTTTTAAAAACGGTGAAGCTTATTTATTTGGTGC 200
186 Haemophilus_parainfluenzae_T3T  AGCGACAGCTATATCATTTTTAAAAACGGGGAAGCCTATTTATTTGGTGC 200
187 H.somnus2336                    GGCGATAGTTATATTATTTTTAAGCATGGCGAGGCATATTTATTTGGTGC 200
188 H.somnus129PT                   GGCGATAGTTATATTATTTTTAAGCATGGTGAGGCATATTTATTTGGTGC 200
189 H.ducreyi35000HP                GGTGATAGCTATGTTACTTTTCGTCATGGTGAAGCCTTTTTATTTGGCGC 173
190 Haemophilus_pittmaniae_HK_85    AGCGACAGTTACATTATTTTCAAAAATGGCGAGGCTTATTTATTTGGCGC 200
191 Haemophilus_sputorum_HK_2154    GGGGATAGCTATGTTACCTTTAGAAACGGCGAAGCCTTTTTATTCGGTGC 197
192 H.parasuis_SH0165               GGCGATAGCTATGTCACTTTCCGTAATGGCGAAGCCTTTTTATTCGGTGG 197
193 H.parasuis_ZJ0906               GGTGATAGTTATGTGACATTTCGCAACGGCGAAGCCTTTTTATTCGGTGG 197
                                     * ** ** **  * *  **     * ** ** ** * ****** ** *
```

FIG. 17B(contd.)

```
SEQ ID NO:                                                                            H. inf smpB F1
  169 H.influenzaeRdKW20                 AAGCATTCAGCCATTAAATGTTGCATCAACGCATATTGTTTGTGATCCAA 250
  170 H.influenzaeF3031                  AAGCATTCAGCCATTAAATGTTGCATCAACGCATATTGTTTGTGATCCAA 250
  171 H.influenzae86-028NP               AAGCATTCAGCCATTAAATGTTGCATCAACGCATATTGTTTGTGATCCAA 250
  172 H.influenzaeKR494                  AAGCATTCAGCCATTAAATGTTGCATCAACGCATATTGTTTGTGATCCAA 250
  173 H.influenzae10810                  AAGCATTCAGCCATTAAATGTTGCATCAACGCATATTGTTTGTGATCCAA 250
  174 H.influenzaeF3047                  AAGCATTCAGCCATTAAATGTTGCATCAACGCATATTGTTTGTGATCCAA 250
  175 H.influenzaePittGG                 AAGCATTCAGCCATTAAATGTTGCATCAACGCATATTGTTTGTGATCCAA 250
  176 H.influenzaeR2846                  AAGCATTCAGCCATTAAATGTTGCATCAACGCATATTGTTTGTGATCCAA 250
  177 H.influenzaePittEE                 AAGCATTCAGCCATTAAATGTTGCATCAACGCATATTGTTTGTGATCCAA 250
  178 H.influenzaeR2866                  AAGCATTCAGCCATTAAATGTCGCATCAACGCATATTGTTTGTGATCCAA 250
  179 H.haemolyticusHK386                AAGCATTCAGCCATTAAATGTTGCATCAACGCATATTATTTGTGATCCAA 250
  180 H.haemolyticusM21639               AAGCATTCAGCCATTAAATGTTGCATCAACGCATATTGTTTGTGATCCAA 250
  181 H.haemolyticusM21621               AAGCATTCAGCCATTAAATGTTGCATCAACGCATATTGTTTGTGATCCAA 250
  182 H.haemolyticusM21127               AAGCATTCAGCCATTAAATGTTGCATCAACACATATTGTTTGTGATCCAA 250
  183 H.haemolyticusM19501               AAGCATTCAGCCATTAAATGTAGCATCAACGCATATTGTTTGTGATCCAA 250
  184 H.haemolyticusM19107               AAGCATTCAGCCATTAAATGTTGCATCAACGCACATTGTTTGTGATCCAA 249
  185 Haemophilus_parainfluenzae_HK2     AACCATTCAACCATTAAGCTTGGCTTCTACCCACGTGGTTTGCGATCCGA 250
  186 Haemophilus_parainfluenzae_T3T     GACCATTCAACCATTAAGCTTGGCTTCTACTCACGTGGTTTGCGATCCGA 250
  187 H.somnus2336                       AACCATTCAGCCGTTAAGTGTTGCTTCAACGCATATTGTTTGCGATCCCA 250
  188 H.somnus129PT                      AACCATTCAGCCGTTAAGTGTTGCTTCAACGCATATTGTTTGCGATCCCA 250
  189 H.ducreyi35000HP                   TACAATTACCCCATTAAATATCGCTTCTACTCATATTGTTGCAGATCCAA 223
  190 Haemophilus_pittmaniae_HK_85       GACCATTCAGCCTTTATCTCTAGCATCCACCCATGTGGTTTGCGATCCGA 250
  191 Haemophilus_sputorum_HK_2154       AACCATTACCCCGCTGAATATCGCGTCAACACATATCGTTGCCGACCCAA 247
  192 H.parasuis_SH0165                  CACTATTACCCCGTTAAATGTCGCTTCTACCCATATTGTGTGCGACCCAA 247
  193 H.parasuis_ZJ0906                  CACTATTACCCCGTTAAATGTCGCTTCTACCCATATTGTGTGCGATCCAA 247
                                          *  ***   **  *     * ** ** ** **   *   *    ** ** *
```

```
SEQ ID NO:
  169 H.influenzaeRdKW20                  CTCGCACTCGTAAGTTATTGTTAAATAAACGCGAATTAGCATCCCTATTT 300
  170 H.influenzaeF3031                   CTCGCACTCGTAAGTTATTGTTAAATAAACGCGAATTAGCATCCCTATTT 300
  171 H.influenzae86-028NP                CTCGCACTCGTAAGTTATTGTTAAATAAACGCGAATTAGCATCCCTATTT 300
  172 H.influenzaeKR494                   CTCGCACTCGTAAGTTATTGTTAAATAAACGCGAATTAGCATCCCTATTT 300
  173 H.influenzae10810                   CTCGCACTCGTAAGTTATTGTTAAATAAACGCGAATTAGCATCCCTATTT 300
  174 H.influenzaeF3047                   CTCGCACTCGTAAGTTATTGTTAAATAAACGCGAATTAGCATCCCTATTT 300
  175 H.influenzaePittGG                  CTCGCACTCGTAAGTTATTGTTAAATAAACGCGAATTAGCATCCCTATTT 300
  176 H.influenzaeR2846                   CTCGCACTCGTAAGTTATTGTTAAATAAACGCGAATTAGCATCCCTATTT 300
  177 H.influenzaePittEE                  CTCGCACTCGTAAGTTATTGTTAAATAAACGCGAATTAGCATCCCTATTT 300
  178 H.influenzaeR2866                   CTCGCACTCGTAAGTTATTGTTAAATAAACGCGAATTAACATCCCTATTT 300
  179 H.haemolyticusHK386                 CTCGCACTCGTAAGTTATTATTAAATAAACGCGAATTAGCATCCCTATTT 300
  180 H.haemolyticusM21639                CTCGCACTCGTAAGTTATTATTAAATAAACGCGAATTAGCATCCCTATTT 300
  181 H.haemolyticusM21621                CTCGCACTCGTAAGTTATTATTAAATAAACGCGAATTAGCATCCCTATTT 300
  182 H.haemolyticusM21127                CTCGCACTCGTAAGTTATTATTAAATAAACGCGAATTAGCATCCCTATTT 300
  183 H.haemolyticusM19501                CTCGCACTCGTAAGTTATTATTAAATAAACGTGAATTAGAATCCCTATTT 300
  184 H.haemolyticusM19107                CTCGCACTCGTAAGTTATTATTAAATAAACGTGAACTAGCATCCCTATTT 299
  185 Haemophilus_parainfluenzae_HK2      CTCGCACACGTAAGCTTTTATTGAATAAACGTGAACTGGATAATCTTTTC 300
  186 Haemophilus_parainfluenzae_T3T      CGCGTACACGTAAGCTTTTATTGAATAAACGTGAACTGGATAATCTTTTC 300
  187 H.somnus2336                        CAAGAACACGTAAACTTTTATTAAACCAGAAAGAGTTGGCTTCATTATTT 300
  188 H.somnus129PT                       CAAGAACACGTAAACTTTTATTAAACCAGAAAGAGTTGGCTTCATTATTT 300
  189 H.ducreyi35000HP                    CACGTACTCGTAAGCTACTATTAAATCAAAGAGAATTAGACTCATTATTT 273
  190 Haemophilus_pittmaniae_HK_85        CCCGCACCCGTAAACTGTTACTCAATAAACGCGAACTGGATAATCTTTTT 300
  191 Haemophilus_sputorum_HK_2154        CTAGAACCAGAAAATTATTACTCAATAAACGAGAACTCGATTCACTCTTT 297
  192 H.parasuis_SH0165                   CCCGTACCCGTAAATTATTGTTAAATAAGCGTGAGTTAGACACGCTTTAT 297
  193 H.parasuis_ZJ0906                   CCCGTACCCGTAAGTTATTGTTAAATAAGCGTGAGTTAGACACGCTTTAT 297
                                          *  * **  * **  *  *  * **  *   **  *        * *
```

```
SEQ ID NO:                                                       H. inf smpB P1
 169 H.influenzaeRdKW20                  GGTAAAGCAAACCGAGACGGTTTTACCATAGTTGCACTTTCTCTTTATTG 350
 170 H.influenzaeF3031                   GGTAAAGCAAACCGAGACGGTTTTACCATAGTTGCACTTTCTCTTTACTG 350
 171 H.influenzae86-028NP                GGCAAAGCAAACCGAGACGGTTTTACCATAGTTGCACTTTCTCTTTACTG 350
 172 H.influenzaeKR494                   GGCAAAGCAAACCGAGACGGTTTTACCATAGTTGCACTTTCTCTTTACTG 350
 173 H.influenzae10810                   GGCAAAGCAAACCGAGACGGTTTTACCATAGTTGCACTTTCTCTTTACTG 350
 174 H.influenzaeF3047                   GGCAAAGCAAACCGAGACGGTTTTACCATAGTTGCACTTTCTCTTTACTG 350
 175 H.influenzaePittGG                  GGCAAAGCAAACCGAGACGGTTTTACCATAGTTGCACTTTCTCTTTACTG 350
 176 H.influenzaeR2846                   GGCAAAGCAAACCGAGACGGTTTTACCATAGTTGCACTTTCTCTTTACTG 350
 177 H.influenzaePittEE                  GGCAAAGCAAACCGAGACGGTTTTACCATAGTTGCACTTTCTCTTTACTG 350
 178 H.influenzaeR2866                   GGCAAAGCAAACCGAGACGGTTTTACCATAGTTGCACTTTCTCTTTACTG 350
 179 H.haemolyticusHK386                 GGCAAAGCAAACCGAGACGGTTTTACCATCGT GCGCTTTCTCTTTATTG 350
 180 H.haemolyticusM21639                GGCAAAGCAAACCGAGACGGTTTTACCATCGT GCGCTTTCTCTTTATTG 350
 181 H.haemolyticusM21621                GGCAAAGCAAACCGAGACGGTTTTACCATCGT GCGCTTTCTCTTTATTG 350
 182 H.haemolyticusM21127                GGCAAAGCAAACCGAGACGGTTTTACCATCGT GCGCTTTCTCTTTATTG 350
 183 H.haemolyticusM19501                GGCAAAGCAAACCGAGACGGTTTTACCATCGT GCGCTTTCTCTTTACTG 350
 184 H.haemolyticusM19107                GGCAAAGCAAACCGAGACGGTTTTACCATCGT GCGCTTTCTCTTTACTG 349
 185 Haemophilus_parainfluenzae_HK2      GGTAAATCAAGCCGTGATGGTTTTACCATTGTTGCCCTTTCTCTTTATTG 350
 186 Haemophilus_parainfluenzae_T3T      GGTAAATCAAGCCGTGATGGTTTTACCATTGTTGCCCTTTCTCTTTATTG 350
 187 H.somnus2336                        GGTAAAGCAAATCGAGATGGTTTCACTATTGTTGCACTTTCATTATATTG 350
 188 H.somnus129PT                       GGTAAAGCAAATCGAGATGGTTTCACTATTGTTGCACTTTCATTATATTG 350
 189 H.ducreyi35000HP                    GGTAAAGTAAATCGAGATGGAATCACTGTGGTGGCACTTTCGCTTTATTG 323
 190 Haemophilus_pittmaniae_HK_85        GGTAAATCAGCACGTGATGGTTTTACCATCGTAGCGCTTTCCCTTTATTG 350
 191 Haemophilus_sputorum_HK_2154        GGTAAAGTGAACCGAGATGGAATCACTGTTGTTGCCCTTTCCCTTTATTG 347
 192 H.parasuis_SH0165                   GGTAAAGTCAGCCGTGATGGCTTTACCGTTGTCGCCCTGTCGCTCTACTG 347
 193 H.parasuis_ZJ0906                   GGTAAAGTCAGCCGTGATGGCTTTACCGTTGTCGCTCTGTCGCTTTACTG 347
                                         ** ***      ** ** **  * **  * ** ** ** **  * ** **
```

FIG. 17C(contd.)

```
                                                     H. inf smpB R1
SEQ ID NO:
  169 H.influenzaeRdKW20                  GAAAAGTGCGTGGGCAAAAGTCAAAATCGGTTTAGCCAAAGGTAAAAAAC 400
  170 H.influenzaeF3031                   GAAAAGTGCGTGGGCAAAAGTCAAAATCGGTTTAGCCAAAGGTAAAAAAC 400
  171 H.influenzae86-028NP                GAAAAGTGCGTGGGCAAAAGTCAAAATCGGTTTAGCCAAAGGTAAAAAAC 400
  172 H.influenzaeKR494                   GAAAAGTGCGTGGGCAAAAGTCAAAATTGGTTTAGCCAAAGGTAAAAAAC 400
  173 H.influenzae10810                   GAAAAGTGCGTGGGCAAAAGTCAAAATTGGTTTAGCCAAAGGTAAAAAAC 400
  174 H.influenzaeF3047                   GAAAAGTGCGTGGGCAAAAGTCAAAATCGGTTTAGCCAAAGGTAAAAAAC 400
  175 H.influenzaePittGG                  GAAAAGTGCGTGGGCAAAAGTCAAAATTGGTTTAGCCAAAGGTAAAAAAC 400
  176 H.influenzaeR2846                   GAAAAGTGCGTGGGCAAAAGTCAAAATTGGTTTAGCCAAAGGTAAAAAAC 400
  177 H.influenzaePittEE                  GAAAAGTGCGTGGGCAAAAGTCAAAATTGGTTTAGCCAAAGGTAAAAAAC 400
  178 H.influenzaeR2866                   GAAAAGTGCGTGGGCAAAAGTCAAAATTGGTTTAGCCAAAGGTAAAAAAC 400
  179 H.haemolyticusHK386                 GAAAAGTGCATGGGCAAAAGTCAAGATTGGTTTAGCCAAAGGTAAAAAAC 400
  180 H.haemolyticusM21639                GAAAAGTGCATGGGCAAAAGTCAAAATTGGTTTAGCCAAAGGTAAAAAAC 400
  181 H.haemolyticusM21621                GAAAAGTGCATGGGCAAAAGTCAAAATTGGTTTAGCCAAAGGTAAAAAAC 400
  182 H.haemolyticusM21127                GAAAAGTGCATGGGCAAAAGTCAAAATTGGTTTAGCCAAAGGTAAAAAAC 400
  183 H.haemolyticusM19501                GAAAAGTGCATGGGCAAAAGTCAAAATTGGTTTAGCCAAAGGTAAAAAAC 400
  184 H.haemolyticusM19107                GAAAAGTGCATGGGCAAAAGTCAAAATTGGTTTAGCTAAAGGTAAAAAAC 399
  185 Haemophilus_parainfluenzae_HK2      GAAAGGTCCTTGGGCAAAGATCAAAATCGGTCTTGCGAAAGGTAAAAAAC 400
  186 Haemophilus_parainfluenzae_T3T      GAAAGGCCCTTGGGCAAAGATCAAAATCGGCCTTGCGAAAGGTAAAAAAC 400
  187 H.somnus2336                        GAAAGGTCCTTGGGCAAAGGTGAAAATAGGTTTAGCAAAAGGGAAAAAAT 400
  188 H.somnus129PT                       GAAAGGTCCTTGGGCAAAGGTGAAAATAGGTTTAGCAAAAGGGAAAAAAT 400
  189 H.ducreyi35000HP                    GAAAAATGCTTGGGCGAAAGTCAAGATAGGGCTAGCGAAAGGCAAAAAAC 373
  190 Haemophilus_pittmaniae_HK_85        GAAAGGCGCCTGGGCAAAAATTAAAATCGGTTTGGCGAAGGGTAAGAAAC 400
  191 Haemophilus_sputorum_HK_2154        GAAAGCCGCTTGGGCAAAAGTGAAAATTGGTGTGGCAAAAGGCAAAAAAT 397
  192 H.parasuis_SH0165                   GAAAAATGCGTGGGCGAAGGTCAAAATCGGCTTGGCGAAAGGGAAAAAAT 397
  193 H.parasuis_ZJ0906                   GAAAAATGCGTGGGCGAAAGTCAAAATCGGCTTGGCGAAAGGGAAAAAAT 397
                                          ****    * ***** **  * ** ** **  * ** ** ** ** ***
```

```
SEQ ID NO:
169 H.influenzaeRdKW20              AACAGGATAAACGTGATGATATTAAAGAACGTGAATGGAAAGTAACAAAA 450
170 H.influenzaeF3031               AACAGGATAAACGTGATGATATTAAAGAACGTGAATGGAAAGTAACAAAA 450
171 H.influenzae86-028NP            AACAGGATAAACGTGATGATATTAAAGAACGTGAATGGAAAGTAACAAAA 450
172 H.influenzaeKR494               AACAGGATAAACGTGATGATATTAAAGAACGTGAATGGAAAGTAACAAAA 450
173 H.influenzae10810               AACAGGATAAACGTGATGATATTAAAGAACGTGAATGGAAAGTAACAAAA 450
174 H.influenzaeF3047               AGCAGGATAAACGTGATGATATTAAAGAACGTGAATGGAAAGTAACAAAA 450
175 H.influenzaePittGG              AACAGGATAAACGTGATGATATTAAAGAACGTGAATGGAAAGTAACAAAA 450
176 H.influenzaeR2846               AACAGGATAAACGTGATGATATTAAAGAACGTGAATGGAAAGTAACAAAA 450
177 H.influenzaePittEE              AACAGGATAAACGTGATGATATTAAAGAACGTGAATGGAAAGTAACAAAA 450
178 H.influenzaeR2866               AACAGGATAAACGTGATGATATTAAAGAACGTGAATGGAAAGTAACAAAA 450
179 H.haemolyticusHK386             AACATGATAAACGCGATGATATTAAAGAGCGTGAATGGAAAGTAACAAAA 450
180 H.haemolyticusM21639            AACATGATAAACGCGATGATATTAAAGAGCGTGAATGGAAAGTAACAAAA 450
181 H.haemolyticusM21621            AACATGATAAACGCGATGATATTAAAGAGCGTGAATGGAAAGTAACAAAA 450
182 H.haemolyticusM21127            AACATGATAAACGCGATGATATTAAAGAGCGTGAATGGAAAGTAACAAAA 450
183 H.haemolyticusM19501            AACATGATAAACGCGATGATATTAAAGAGCGTGAATGGAAAGTAACAAAA 450
184 H.haemolyticusM19107            AACATGATAAACGCGATGATATCAAAGAGCGTGAATGGAAAGTAACAAAA 449
185 Haemophilus_parainfluenzae_HK2  AACATGATAAACGTGATGATATTAAAGAGCGTGAATGGAAAGTGGCAAAA 450
186 Haemophilus_parainfluenzae_T3T  AACATGATAAACGTGATGATATTAAAGAGCGTGAATGGAAAGTGGCGAAA 450
187 H.somnus2336                    TACATGATAAGCGTGAAGATATTAAAGATCGTGAATGGAAAGTAACGAAA 450
188 H.somnus129PT                   TACATGATAAGCGTGAAGATATTAAAGATCGTGAATGGAAAGTAACGAAA 450
189 H.ducreyi35000HP                TTCACGATAAACGTGAAGATATTAAAGATCGTGAATGGCACGTTACTAAG 423
190 Haemophilus_pittmaniae_HK_85    AACATGACAAACGCGAAGACATCAAAGAACGCGAATGGAAGTTGGATAAA 450
191 Haemophilus_sputorum_HK_2154    TACACGATAAACGTGAAGATATTAAAGACCGCGAATGGCAAGTTGCTAAA 447
192 H.parasuis_SH0165               TGCACGATAAACGTGAAGATATTAAAGACCGTGAGTGGCAAGTTGCTAAA 447
193 H.parasuis_ZJ0906               TGCACGATAAGCGTGAAGATATTAAAGACCGTGAGTGGCAAGTTGCTAAA 447
                                      ** ** ** ** ** ** ** ***** ** ** *** *  *    **
```

```
SEQ ID NO:
   169 H.influenzaeRdKW20                GATCGCATTATGAAAAATGCACATCGAAGATCTTAA 486
   170 H.influenzaeF3031                 GATCGCATTATGAAAAATGCACATCGAAGATCTTAA 486
   171 H.influenzae86-028NP              GATCGCATTATGAAAAATGCACATCGAAGATCTTAA 486
   172 H.influenzaeKR494                 GATCGCATTATGAAAAATGCACATCGAAGATCTTAA 486
   173 H.influenzae10810                 GATCGCATTATGAAAAATGCACATCGAAGATCTTAA 486
   174 H.influenzaeF3047                 GATCGCATTATGAAAAATGCACATCGAAGATCTTAA 486
   175 H.influenzaePittGG                GATCGCATTATGAAAAATGCACATCGAAGATCTTAA 486
   176 H.influenzaeR2846                 GATCGCATTATGAAAAATGCACATCGAAGATCTTAA 486
   177 H.influenzaePittEE                GATCGCATTATGAAAAATGCACATCGAAGATCTTAA 486
   178 H.influenzaeR2866                 GATCGCATTATGAAAAATGCACATCGAAGATCTTAA 486
   179 H.haemolyticusHK386               GATCGCATTATGAAAAATGCACATCGAGGAT----- 481
   180 H.haemolyticusM21639              GATCGCATTATGAAAAATGCACATCGAGGAT----- 481
   181 H.haemolyticusM21621              GATCGCATTATGAAAAATGCACATCGAGGAT----- 481
   182 H.haemolyticusM21127              GATCGCATTATGAAAAATGCACATCGAGGAT----- 481
   183 H.haemolyticusM19501              GATCGCATTATGAAAAATTCACATCGAGGAT----- 481
   184 H.haemolyticusM19107              GATCGCATTATGAAAAATGCACATCGAGGAT----- 480
   185 Haemophilus_parainfluenzae_HK2    GAGCGTATTATGAAAAATGCGCATCGTGGATAA--- 483
   186 Haemophilus_parainfluenzae_T3T    GAGCGTATTATGAAAAACGCGCACCG---------- 476
   187 H.somnus2336                      GATCGCATTATGAAAAATGCACAGCGA--------- 477
   188 H.somnus129PT                     GATCGCATTATGAAAAATGCACAGCGA--------- 477
   189 H.ducreyi35000HP                  CAACGCATTATGAAAAATGC---------------- 443
   190 Haemophilus_pittmaniae_HK_85      CAACGAATTATGAAAAATGCCAATCGCGGCTAA--- 483
   191 Haemophilus_sputorum_HK_2154      CAACGTATTATGAAAAACGCGAACCGTGGTTAA--- 480
   192 H.parasuis_SH0165                 CAGCGGATTATGAAGAATGCGAA---TAGGTAG--- 477
   193 H.parasuis_ZJ0906                 CAGCGGATTATGAAGAATGCGAA---TAGGTAG--- 477
                                          * ** ******** **  *
```

FIG. 18A

| SEQ ID NO: | | | |
|---|---|---|---|
| 143 | L.pneumophilaATCC43290 | GGGGGCGACCTGGCTTCGACGTGGGTTGCAAAACCGGAAGTGCATGCCGA | 50 |
| 144 | L.pneumophila_ThunderBay | GGGGGCGACCTGGCTTCGACGTGGGTTGCAAAACCGGAAGTGCATGCCGA | 50 |
| 145 | L.pneumophila_HL06041035 | GGGGGCGACCTGGCTTCGACGTGGGTTGCAAAACCGGAAGTGCATGCCGA | 50 |
| 146 | L.pneumophila_str.Philadelphia | GGGGGCGACCTGGCTTCGACGTGGGTTGCAAAACCGGAAGTGCATGCCGA | 50 |
| 147 | >L.pneumophila_Lens | GGGGGCGACCTGGCTTCGACGTGGGTTGCAAAACCGGAAGTGCATGCCGA | 50 |
| 148 | L.pneumophila_Paris | GGGGGCGACCTGGCTTCGACGTGGGTTGCAAAACCGGAAGTGCATGCCGA | 50 |
| 149 | L.pneumophila_Corby | GGGGGCGACCTGGCTTCGACGTGGGTTGCAAAACCGGAAGTGCATGCCGA | 50 |
| 150 | L.pneumophila_2300/99Alcoy | GGGGGCGACCTGGCTTCGACGTGGGTTGCAAAACCGGAAGTGCATGCCGA | 50 |
| 151 | L.pneumophila_Lorraine | GGGGGCGACCTGGCTTCGACGTGGGTTGCAAAACCGGAAGTGCATGCCGA | 50 |
| 152 | L.longbeachaeD-4968 | GGGGGCGACCTGGCTTCGACGTGGGTTGCAAAACCAGAGGTGCATGCCGA | 50 |
| 153 | L.longbeachaeNSW150 | GGGGGCGACCTGGCTTCGACGTGGGTTGCAAAACCAGAGGTGCATGCCGA | 50 |
| 154 | L.fallonii_LLAP-10 | GGGGGCGACCTGGCTTCGACGTGGGTTGCAAAACCGGAAGTGCATGCCGA | 50 |
| 155 | L.hackeliae_LHA | GGGGGCGACCTGGCTTCGACGTGGGTTGCGAAACCTGAAGTGCATGCCGA | 50 |
| 156 | L.oakridgensis_ATCC33761 | GGGGGCGACCTGGCTTCGACGTGGGTTGCGAAACCTGAAGTGCATGCCGA | 50 |
| 157 | L.micdadei_LMI | GGGGGCGACCTGGCTTCGACGTGGGTTGCGAAACCTGAGGTGCATGCCGA | 50 |
| 158 | L.sainthelensi_ATCC35248 | GGGGGCGACCTGGCTTCGACGTGGGTTGCAAAACCAGAGGTGCATGCCGA | 50 |
| 159 | L.wadsworthiiDSM21896 | GGGGGCGACCTGGTTTCGACGTGGGTTGCAAAACCAGAGGTGCATGCCGA | 50 |
| 160 | L.cherrii_DSM19213 | GGGGGCGACCTGGCTTCGACGTGGGTTGCAAAACCAGAGGTGCATGCCGA | 50 |
| 161 | L.moravicaDSM19234 | GGGGGCGACCTGGCTTCGACGTGGGTTGCAAAACCAGAGGTGCATGCCGA | 50 |
| 162 | L.norrlandica | GGGGGCGACCTGGCTTCGACGTGGGTTGCAAAACCGGAAGTGCATGCCGA | 50 |
| 163 | L.shakespeareiDSM23087 | GGGGGCGACCTGGCTTCGACGTGGGTTGCGAAACCGGAAGTGCATGCCGA | 50 |
| 164 | L.drancourtiiLLAP12 | GGGGGCGACCTGGCTTCGACGGGGGTTGCAAAACCAGAGGTGCATGCCGA | 50 |
| 165 | L.lansingensis_DSM19556 | GGGGGCGACCTGGCTTCGACGTGGGTTGCGAAACCTGATGTGCATGCCGA | 50 |
| 166 | L.fairfieldensis_ATCC_49588 | GGGGGCGACCTGGCTTCGACGCGGGTTGCGAAACCTGAGGGGCATGCCGA | 50 |
| 167 | L.massiliensis_PRJEB110 | GGGGGCGACCTGGCTTCGACGTGGGTTGCGAAACCTGATGTGCATGCCGA | 50 |
| 168 | L.geestianaDSM21217 | GGGGGCGACCTGGCTTCGACGTGGGTTGCGAAACCTGATGTGCATGCCGA | 50 |
| | | ************* ******* ******* ***** ** * ********* | |

| SEQ ID NO: | | Leg ssrA F1 | |
|---|---|---|---|
| 143 | L.pneumophilaATCC43290 | GAAGGAGATCTCTCGTAAATAAGACTCAATT-AAATATAAATGCAAACGA | 99 |
| 144 | L.pneumophila_ThunderBay | GAAGGAGATCTCTCGTAAATAAGACTCAATT-AAATATAAATGCAAACGA | 99 |
| 145 | L.pneumophila_HL06041035 | GAAGGAGATCTCTCGTAAATAAGACTCAATT-AAATATAAATGCAAACGA | 99 |
| 146 | L.pneumophila_str.Philadelphia | GAAGGAGATCTCTCGTAAATAAGACTCAATT-AAATATAAATGCAAACGA | 99 |
| 147 | >L.pneumophila_Lens | GAAGGAGATCTCTCGTAAATAAGACTCAATT-AAATATAAATGCAAACGA | 99 |
| 148 | L.pneumophila_Paris | GAAGGAGATCTCTCGTAAATAAGACTCAATT-AAATATAAATGCAAACGA | 99 |
| 149 | L.pneumophila_Corby | GAAGGAGATCTCTCGTAAATAAGACTCAATT-AAATATAAATGCAAACGA | 99 |
| 150 | L.pneumophila_2300/99Alcoy | GAAGGAGATCTCTCGTAAATAAGACTCAATT-AAATATAAATGCAAACGA | 99 |
| 151 | L.pneumophila_Lorraine | GAAGGAGATCTCTCGTAAATAAGACTCAATT-AAATATAAATGCAAACGA | 99 |
| 152 | L.longbeachaeD-4968 | GAATGAGGACTCTCGTAAATCAGACTCAACT-AAATATAAATGCAAACGA | 99 |
| 153 | L.longbeachaeNSW150 | GAATGAGGACTCTCGTAAATCAGACTCAACT-AAATATAAATGCAAACGA | 99 |
| 154 | L.fallonii_LLAP-10 | GAATGAGAACTCTCGTAAATCAGACTCACT--AAATATAAATGCAAACGA | 98 |
| 155 | L.hackeliae_LHA | GAATGAGACGTCTCGTAAATCAGACTCACT--AAATATAAATGCAAACGA | 98 |
| 156 | L.oakridgensis_ATCC33761 | GAATGAGATCTCTCGTAAATAAGGCTCACT--AAATATAAATGCAAATGA | 98 |
| 157 | L.micdadei_LMI | GAATGAGATCTCTCGTAAATAAGACTCACT--AAATATAAATGCAAACGA | 98 |
| 158 | L.sainthelensi_ATCC35248 | GAATGAGGACTCTCGTAAATCAGACTCAACT-AAATATAAATGCAAACGA | 99 |
| 159 | L.wadsworthiiDSM21896 | GATTGAGAACTCTCGTAAATCAGACTCAACTTAAATATAAATGCAAACGA | 100 |
| 160 | L.cherrii_DSM19213 | GAATGAGAACTCTCGTAAATCAGACTCAACT-AAATATAAATGCAAACGA | 99 |
| 161 | L.moravicaDSM19234 | GAATGAGAACTCTCGTAAATCAGACTCAACT-AAATATAAACGCAAACGA | 99 |
| 162 | L.norrlandica | GAATGAGATCTCTCGTAAATAAGACTCAATT-AAATATAAATGCAAACGA | 99 |
| 163 | L.shakespeareiDSM23087 | GAATGAGAACTCTCGTAAATCAGACTCAAA--AAATATAAATGCAAACGA | 98 |
| 164 | L.drancourtiiLLAP12 | GAATGAGATCTCTCGTAAATCAGGCTCAAT--AAATATAAATGCAAACAA | 98 |
| 165 | L.lansingensis_DSM19556 | GAAAGAGTACTCTCGTAAATCAGTCTCACT--AAATATAAATGCAAACGA | 98 |
| 166 | L.fairfieldensis_ATCC_49588 | GAATGAGAACTCTCGTAAATCAGACTCACT--AAATATAAATGCAAACGA | 98 |
| 167 | L.massiliensis_PRJEB110 | GATTGAGACTTCTCGTTAATCAGACTCACT--AAACATAAATGCAAACGA | 98 |
| 168 | L.geestianaDSM21217 | GGATGAGAACTCTCGTAAAACGGGCTCGAT--AAATATAAATGCAAACGA | 98 |
| | | * *** ****** ** * *** *** ***** ***** * | |

| SEQ ID NO: | | | |
|---|---|---|---|
| 143 | L.pneumophilaATCC43290 | TGAAAACTTTGCTGG------------TGGGGA---AG---CTATCGCT- | 130 |
| 144 | L.pneumophila_ThunderBay | TGAAAACTTTGCTGG------------TGGGGA---AG---CTATCGCT- | 130 |
| 145 | L.pneumophila_HL06041035 | TGAAAACTTTGCTGG------------TGGGGA---AG---CTATCGCT- | 130 |
| 146 | L.pneumophila_str.Philadelphia | TGAAAACTTTGCTGG------------TGGGGA---AG---CTATCGCT- | 130 |
| 147 | >L.pneumophila_Lens | TGAAAACTTTGCTGG------------TGGGGA---AG---CTATCGCT- | 130 |
| 148 | L.pneumophila_Paris | TGAAAACTTTGCTGG------------TGGGGA---AG---CTATCGCT- | 130 |
| 149 | L.pneumophila_Corby | TGAAAACTTTGCTGG------------TGGGGA---AG---CTATCGCT- | 130 |
| 150 | L.pneumophila_2300/99Alcoy | TGAAAACTTTGCTGG------------TGGGGA---AG---CTATCGCT- | 130 |
| 151 | L.pneumophila_Lorraine | TGAAAACTTTGCTGG------------TGGGGA---AG---CTATCGCT- | 130 |
| 152 | L.longbeachaeD-4968 | TGAAAACTTTGCTGG------------TGGGGA---AG---CTATTGCT- | 130 |
| 153 | L.longbeachaeNSW150 | TGAAAACTTTGCTGG------------TGGGGA---AG---CTATTGCT- | 130 |
| 154 | L.fallonii_LLAP-10 | AGAAAACTTCGATGGCGTAGCTAATCTTGAAGG---AG----TAGCGCAA | 141 |
| 155 | L.hackeliae_LHA | TGAAAACTTTGCAGG------------TG---A---AG---CTATCGCT- | 126 |
| 156 | L.oakridgensis_ATCC33761 | TGAAAACTTTGCTGG------------TGTTGAGGGAGAAGCTATCGCT- | 135 |
| 157 | L.micdadei_LMI | TGAAAACTTTGCTGG------------TGGAGA---AGGCGCTATCGCT- | 132 |
| 158 | L.sainthelensi_ATCC35248 | TGAAAACTTTGCTGG------------TGGGGA---AG---CTATTGCT- | 130 |
| 159 | L.wadsworthiiDSM21896 | TGAAAACTTTGCTGG------------TGGAGA---AG---CTATCGCT- | 131 |
| 160 | L.cherrii_DSM19213 | TGAAAACTTTGCTGG------------TGGGGA---AG---CTATCGCT- | 130 |
| 161 | L.moravicaDSM19234 | TGAAAACTTTGCTGG------------TGGAGA---AG---CTATCGCT- | 130 |
| 162 | L.norrlandica | TGAAAACTTTGCTGG------------TGGTGA---AG---CTATCGCT- | 130 |
| 163 | L.shakespeareiDSM23087 | TGCAAACTTCGCTGATAACG------TTGATGG---AG---CAATTGCT- | 135 |
| 164 | L.drancourtiiLLAP12 | TGCAAACTTTGATGATGTTTC---TTTTGACGG---GG---CTATTGCA- | 138 |
| 165 | L.lansingensis_DSM19556 | TGAAAACTTTGCTGG------------TGGTGA---AG---CTGTCGCT- | 129 |
| 166 | L.fairfieldensis_ATCC_49588 | TGAAAACTTTGCAGG------------TG---A---AG---CTATCGCT- | 126 |
| 167 | L.massiliensis_PRJEB110 | TGAAAACTTTGCAGA------------TGGAGA---AG---CTATCGCT- | 129 |
| 168 | L.geestianaDSM21217 | TGAAATGTTCGCTGG---------------AGA---AG---CTGTAGCT- | 126 |
| | | * ** ** * * * ** | |

```
SEQ ID
NO:
143 L.pneumophilaATCC43290          ---GCCTAATAAGCACT-TTAG------TTAAACCA------TCACTGTG 164
144 L.pneumophila_ThunderBay        ---GCCTAATAAGCACT-TTAG------TTAAACCA------TCACTGTG 164
145 L.pneumophila_HL06041035        ---GCCTAATAAGCACT-TTAG------TTAAACCA------TCACTGTG 164
146 L.pneumophila_str.Philadelphia  ---GCCTAATAAGCACT-TTAG------TTAAACCA------TCACTGTG 164
147 >L.pneumophila_Lens             ---GCCTAATAAGCACT-TTAG------TTAAACCA------TCACTGTG 164
148 L.pneumophila_Paris             ---GCCTAATAAGCACT-TTAG------TTAAACCA------TCACTGTG 164
149 L.pneumophila_Corby             ---GCCTAATAAGCACT-TTAG------TTAAACCA------TCACTGTG 164
150 L.pneumophila_2300/99Alcoy      ---GCCTAATAAGCACT-TTAG------TTAAACCA------TCACTGTG 164
151 L.pneumophila_Lorraine          ---GCCTAATAAGCACT-TTAG------TTAAACCA------TCACTGTG 164
152 L.longbeachaeD-4968             ---GCCTAATAAGCACT-TTAG------ATAAACCA------TCACTGTG 164
153 L.longbeachaeNSW150             ---GCCTAATAAGCACT-TTAG------ATAAACCA------TCACTGTG 164
154 L.fallonii_LLAP-10              GCTGCTTAAT---CTTTTTTAG------TTAAACCA------TAAC-GTG 175
155 L.hackeliae_LHA                 ---GCGTAA---GCTTTGATAG------TGTAACCG-------CACCGTG 157
156 L.oakridgensis_ATCC33761        ---GCGTAA---GCATTGATGG------TTTTACCAAAAACATCACTGTG 173
157 L.micdadei_LMI                  ---GCGTAA---GCATTGATAGA-AACTTTTCCCCA--------ATCGTG 167
158 L.sainthelensi_ATCC35248        ---GCCTAATAAGCACT-TTAG------TTAAACCA------TCACTGTG 164
159 L.wadsworthiiDSM21896           ---GCCTAATAAGCACT-TTAG------TTGAACCA------TCACTGTG 165
160 L.cherrii_DSM19213              ---GCCTAATAAGCACT-TTAG------TTAAACCA------TCACTGTG 164
161 L.moravicaDSM19234              ---GCCTAATAAGCACT-TTAG------TTGAACCA------TCACTGTG 164
162 L.norrlandica                   ---GCCTAATAAGCACGATTAG------ATAAACCC------CAATCGTG 165
163 L.shakespeareiDSM23087          ---GCTTAAT---CAA---TAG------TTAAAA-G------CAAC-GTG 162
164 L.drancourtiiLLAP12             ---GCTTAAT---CAGATTAAA------CTAATC---------GAC-GTG 166
165 L.lansingensis_DSM19556         ---GCGTAA---GCTTTGATAGTCAACT----ACCG--------ATAGTG 161
166 L.fairfieldensis_ATCC_49588     ---GCTTAA---GCTTTGATAG------TTTAACCG-------CACCGTG 157
167 L.massiliensis_PRJEB110         ---GCGTAA---GCTTTGATAGG---TTTTTCGTCG-------CACCGTG 163
168 L.geestianaDSM21217             ---GCGTAA---GCAACTGCGG--------TGACCGAAG----CACAGTG 158
                                       ** ***   *                               *  ***
```

| SEQ ID NO: | | | |
|---|---|---|---|
| 143 | L.pneumophilaATCC43290 | TACTGGCCAATAAACCCAGTATCCCGTTCGACCGAGCCCGCTTATCGGTA | 214 |
| 144 | L.pneumophila_ThunderBay | TACTGGCCAATAAACCCAGTATCCCGTTCGACCGAGCCCGCTTATCGGTA | 214 |
| 145 | L.pneumophila_HL06041035 | TACTGGCCAATAAACCCAGTATCCCGTTCGACCGAGCCCGCTTATCGGTA | 214 |
| 146 | L.pneumophila_str.Philadelphia | TACTGGCCAATAAACCCAGTATCCCGTTCGACCGAGCCCGCTTATCGGTA | 214 |
| 147 | >L.pneumophila_Lens | TACTGGCCAATAAACCCAGTATCCCGTTCGACCGAGCCCGCTTATCGGTA | 214 |
| 148 | L.pneumophila_Paris | TACTGGCCAATAAACCCAGTATCCCGTTCGACCGAGCCCGCTTATCGGTA | 214 |
| 149 | L.pneumophila_Corby | TACTGGCCAATAAACCCAGTATCCCGTTCGACCGAGCCCGCTTATCGGTA | 214 |
| 150 | L.pneumophila_2300/99Alcoy | TACTGGCCAATAAACCCAGTATCCCGTTCGACCGAGCCCGCTTATCGGTA | 214 |
| 151 | L.pneumophila_Lorraine | TACTGGCCAATAAACCCAGTATCCCGTTCGACCGAGCCCGCTTATCGGTA | 214 |
| 152 | L.longbeachaeD-4968 | TACTGGCCAATAAACCCAGTATCCCGTTCGACCGAGCCCGCTTATCGGTA | 214 |
| 153 | L.longbeachaeNSW150 | TACTGGCCAATAAACCCAGTATCCCGTTCGACCGAGCCCGCTTATCGGTA | 214 |
| 154 | L.fallonii_LLAP-10 | TACTGGCTT-TAACCCCAGTGCCCCGTT-GACCGAGCTCGCTTATCGGTA | 223 |
| 155 | L.hackeliae_LHA | CGCTG--CTATATAACCAGCGCCCCGTT-GACCGAGCTCGCTTATCGGTA | 204 |
| 156 | L.oakridgensis_ATCC33761 | CGCTG--CCA-AAAACCAGCGCCCCGTT-GACCGAGCTCGCTTGTCGGTA | 219 |
| 157 | L.micdadei_LMI | CGCTG--CCA-AAAACCAGCGCCCCGTT-GACCGAGCTCGCTTACCGGTA | 213 |
| 158 | L.sainthelensi_ATCC35248 | TACTGGCCAATAAACCCAGTATCCCGTTCGACCGAGCCCGCTTATCGGTA | 214 |
| 159 | L.wadsworthiiDSM21896 | TACTGGCCAATAAACCCAGTATCCCGTTCGACCGAGCCCGCTTATCGGTA | 215 |
| 160 | L.cherrii_DSM19213 | TACTGGCCAATAAACCCAGTATCCCGTTCGACCGAGCCCGCTTATCGGTA | 214 |
| 161 | L.moravicaDSM19234 | TACTGGCCAATAAACCCAGTATCCCGTTCGACCGAGCCCGCTTATCGGTA | 214 |
| 162 | L.norrlandica | TACTGGCCAA-AAACCCAGTATCCCGTT-GACCGAGCTCGCTTATCGGTA | 213 |
| 163 | L.shakespeareiDSM23087 | TACTGGCCT-AAACCCCGGTGCCCCGTT-GACCGAGCTCGCTTATTGGTA | 210 |
| 164 | L.drancourtiiLLAP12 | TACTGGCCT-TAACCCCAGTGCCCCGTT-GACCGAGCTCGCTTATTGGTA | 214 |
| 165 | L.lansingensis_DSM19556 | CGCTG--CCATAAAACCAGCGCCCCGTT-GACCGAGCTCGCTTATCGGTA | 208 |
| 166 | L.fairfieldensis_ATCC_49588 | CGCTG--CCATAAAACCAGCGCCCCGTT-GACCGAGCTTGCTTATCGGTA | 204 |
| 167 | L.massiliensis_PRJEB110 | TGCTG--CTATAAAACCAGCACCCCGTT-GACCGAGCTTGCTTATCGGTA | 210 |
| 168 | L.geestianaDSM21217 | CGCTG--CCAAAAACCCAGCGCCCCGTT-GACCGGGCTTGCTTGCCGGTA | 205 |
| | | *** * ** * ****** ***** ** **** **** | |

Leg ssrA P3

| SEQ ID NO: | | | |
|---|---|---|---|
| 143 | L.pneumophilaATCC43290 | TCGAATCAACGGTCATAAGAGATAAGCTAGCGTCCTAATCTATCCCGGGT | 264 |
| 144 | L.pneumophila_ThunderBay | TCGAATCAACGGTCATAAGAGATAAGCTAGCGTCCTAATCTATCCCGGGT | 264 |
| 145 | L.pneumophila_HL06041035 | TCGAATCAACGGTCATAAGAGATAAGCTAGCGTCCTAATCTATCCCGGGT | 264 |
| 146 | L.pneumophila_str.Philadelphia | TCGAATCAACGGTCATAAGAGATAAGCTAGCGTCCTAATCTATCCCGGGT | 264 |
| 147 | >L.pneumophila_Lens | TCGAATCAACGGTCATAAGAGATAAGCTAGCGTCCTAATCTATCCCGGGT | 264 |
| 148 | L.pneumophila_Paris | TCGAATCAACGGTCATAAGAGATAAGCTAGCGTCCTAATCTATCCCGGGT | 264 |
| 149 | L.pneumophila_Corby | TCGAATCAACGGTCATAAGAGATAAGCTAGCGTCCTAATCTATCCCGGGT | 264 |
| 150 | L.pneumophila_2300/99Alcoy | TCGAATCAACGGTCATAAGAGATAAGCTAGCGTCCTAATCTATCCCGGGT | 264 |
| 151 | L.pneumophila_Lorraine | TCGAATCAACGGTCATAAGAGATAAGCTAGTGTCCTAATCTATCCCGGGT | 264 |
| 152 | L.longbeachaeD-4968 | TCGAATCAACGGTCATAAGAGATAAGCTAGCGTCCTAATCCATCCCGTAT | 264 |
| 153 | L.longbeachaeNSW150 | TCGAATCAACGGTCATAAGAGATAAGCTAGCGTCCTAATCCATCCCGTAT | 264 |
| 154 | L.fallonii_LLAP-10 | TCGAATCAACGGTCATAGAAGATAAGCTAGTGTCCTAATCTATCCCGGGT | 273 |
| 155 | L.hackeliae_LHA | TCGAATCAACGGTCATAGAAGATAAGCTCGCATCTTAACCCGTCCCGAGT | 254 |
| 156 | L.oakridgensis_ATCC33761 | TCGAATCAACGGTCATAGAAGATAAGCTAGTCTTTTGATTTGTCCCGCAT | 269 |
| 157 | L.micdadei_LMI | TCGAATCAACGGTCATAAGAGATAAGCTCGCAACTTGGTTAGTCCCGCAT | 263 |
| 158 | L.sainthelensi_ATCC35248 | TCGAATCAACGGTCATAAGAGATAAGCTAGCGTCCTAATCCATCCCGTAT | 264 |
| 159 | L.wadsworthiiDSM21896 | TCGAATCAACGGTCATAAGAGATAAGCTAGCGTCCTAATCCATCCCGTAT | 265 |
| 160 | L.cherrii_DSM19213 | TCGAATCAACGGTCATAAGAGATAAGCTAGTGTCTTAATCCATCCCGTAT | 264 |
| 161 | L.moravicaDSM19234 | TCGAATCAACGGTCATAAGAGATAAGCTAGTGTCTTAATCCATCCCGAAT | 264 |
| 162 | L.norrlandica | TCGAATCAACGGTCATAGAAGATAAGCTAGTACTTTAATCTATCCTGGGT | 263 |
| 163 | L.shakespeareiDSM23087 | TCGAATCAACGGTCATAGAAGATAAGCTAGCTTCTTAATGAATCCCGAGT | 260 |
| 164 | L.drancourtiiLLAP12 | TCGAATCAACGGTCATAGAAGATAAGCTAGTGTTTTAATTTATCCCGGAT | 264 |
| 165 | L.lansingensis_DSM19556 | TCGAATCAACGGTCATAAGAGATAAGCTCGCATCTTGGTTCGTCCCGCAC | 258 |
| 166 | L.fairfieldensis_ATCC_49588 | TCGAATCAACGGTCATAGAAGATAAGCTCGCATTTTGGTACGTCCCGCAT | 254 |
| 167 | L.massiliensis_PRJEB110 | TCGAATCAACGGTCATAGAAGATAAGCTCGCAGCTTGATATTTCCCGTAT | 260 |
| 168 | L.geestianaDSM21217 | CCGAATCAACGGTCATAGAAGACAAGCTGGTATCCTGGTGTATCCCGCGC | 255 |
| | | **************** *** ***** * * *** * | |

| SEQ ID NO: | | | |
|---|---|---|---|
| 143 | L.pneumophilaATCC43290 | TATGGCGCGAAACTCAGGGAATCGCTGTGTATCATCCTGCCCGTCGGAGG | 314 |
| 144 | L.pneumophila_ThunderBay | TATGGCGCGAAACTCAGGGAATCGCTGTGTATCATCCTGCCCGTCGGAGG | 314 |
| 145 | L.pneumophila_HL06041035 | TATGGCGCGAAACTCAGGGAATCGCTGTGTATCATCCTGCCCGTCGGAGG | 314 |
| 146 | L.pneumophila_str.Philadelphia | TATGGCGCGAAACTCAGGGAATCGCTGTGTATCATCCTGCCCGTCGGAGG | 314 |
| 147 | >L.pneumophila_Lens | TATGGCGCGAAACTCAGGGAATCGCTGTGTATCATCCTGCCCGTCGGAGG | 314 |
| 148 | L.pneumophila_Paris | TATGGCGCGAAACTCAGGGAATCGCTGTGTATCATCCTGCCCGTCGGAGG | 314 |
| 149 | L.pneumophila_Corby | TATGGCGCGAAATTCAGGGAATCGCTGTGTATCATCCTGCCCGTCGGAGG | 314 |
| 150 | L.pneumophila_2300/99Alcoy | TATGGCGCGAAATTCAGGGAATCGCTGTGTATCATCCTGCCCGTCGGAGG | 314 |
| 151 | L.pneumophila_Lorraine | TATGGCGCAAAACTAAGGGAATCGCTGTGTATCATCCTGCCTGTCGGAGG | 314 |
| 152 | L.longbeachaeD-4968 | TAAGGCGCGAAACTCAGGGAATCGCTGTGTAGTATCCTGCCCGTCGGAGA | 314 |
| 153 | L.longbeachaeNSW150 | TAAGGCGCGAAACTCAGGGAATCGCTGTGTAGTATCCTGCCCGTCGGAGA | 314 |
| 154 | L.fallonii_LLAP-10 | TACGATGCGAAACTCAGGGAGTAGCTGTGTACCATCCTGCCTGTCGGAGA | 323 |
| 155 | L.hackeliae_LHA | TAAGCTGTTAAATTAAGGGAATCGCCGTGTTCAATCCTGCCCGTCGGAGG | 304 |
| 156 | L.oakridgensis_ATCC33761 | CAAAGGGCGAAATTCAGGGAATCGCCGTGTATCATCCTGCCAGTCGGAGG | 319 |
| 157 | L.micdadei_LMI | CAAGTTGTTAAATCCAGGGAATCGCCGTAAACCATCCTGCCTGTCGGAGG | 313 |
| 158 | L.sainthelensi_ATCC35248 | TAAGGCGCGAAACTTAGGGAATCGCTGTGTAGTATCCTGCCCGTCGGAGA | 314 |
| 159 | L.wadsworthiiDSM21896 | TAAGGCGCGAAATTCAGGGAATCGCTGTGTAGTATCCTGCCCGTCGGAGA | 315 |
| 160 | L.cherrii_DSM19213 | TAAGATGCGAAATTCAGGGAATCGCTGTGTAGTATCCTGCCCGTCGGAGA | 314 |
| 161 | L.moravicaDSM19234 | TAAGGCGCGAAATTCAGGGAATCGCTGTGTAGTATCCTGCCTGTCGGAGA | 314 |
| 162 | L.norrlandica | TATGGTGCGAAATTTAGGGAATCGCTGTGTATCATCCTGCCCGTCGGAGG | 313 |
| 163 | L.shakespeareiDSM23087 | TAAGACGCGAAATTCAGGGAATCGCTGTGTACCATCCTGCCCGTCGGAGT | 310 |
| 164 | L.drancourtiiLLAP12 | TAAAATGCGAAACTCAGGGAATCGCTGTGTACCATCCTGCCTGTCGGAGA | 314 |
| 165 | L.lansingensis_DSM19556 | CAAGATGTTAAATCAAGGGAATCGCCGTGTCCCATCCTGCCTGTCGGAGA | 308 |
| 166 | L.fairfieldensis_ATCC_49588 | CAAAATGTTAAATTAAGGGAATCGCCGTGTACTATCCTGCCTGTCGGAGA | 304 |
| 167 | L.massiliensis_PRJEB110 | CAAGATGTTAAATCCAGGGAATCGCCGCGAACCATCCTGCCTGTCGGAGG | 310 |
| 168 | L.geestianaDSM21217 | CAGTATACAAGACTCAGGGAATCGCTGCCGACCATCCTGCCTGTCGGAGG | 305 |
| | | * * * ***** * ** * ******** ******* | |

| SEQ ID NO: | | Leg ssrA R1 | |
|---|---|---|---|
| 143 | L.pneumophilaATCC43290 | AGCCACAGTTAAATTCAAAAGACAAGGCTATGCATGTAGAGCTAAAGGCA | 364 |
| 144 | L.pneumophila_ThunderBay | AGCCACAGTTAAATTCAAAAGACAAGGCTATGCATGTAGAGCTAAAGGCA | 364 |
| 145 | L.pneumophila_HL06041035 | AGCCACAGTTAAATTCAAAAGACAAGGCTATGCATGTAGAGCTAAAGGCA | 364 |
| 146 | L.pneumophila_str.Philadelphia | AGCCACAGTTAAATTCAAAAGACAAGGCTATGCATGTAGAGCTAAAGGCA | 364 |
| 147 | >L.pneumophila_Lens | AGCCACAGTTAAATTCAAAAGACAAGGCTATGCATGTAGAGCTAAAGGCA | 364 |
| 148 | L.pneumophila_Paris | AGCCACAGTTAAATTCAAAAGACAAGGCTATGCATGTAGAGCTAAAGGCA | 364 |
| 149 | L.pneumophila_Corby | AGCCACAGTTAAATTCAAAAGACAAGGCTATGCATGTAGAGCTAAAGGCA | 364 |
| 150 | L.pneumophila_2300/99Alcoy | AGCCACAGTTAAATTCAAAAGACAAGGCTATGCATGTAGAGCTAAAGGCA | 364 |
| 151 | L.pneumophila_Lorraine | AGCCACAGTTAAATTCAAAAGACAAGGCTATGCATGTAGAGCTAAAGGCA | 364 |
| 152 | L.longbeachaeD-4968 | ATGCACAGTTAAAT-CAAAAGACAAGGCTACGCATGTAGAGCTGAAGGCA | 363 |
| 153 | L.longbeachaeNSW150 | ATGCACAGTTAAAT-CAAAAGACAAGGCTACGCATGTAGAGCTGAAGGCA | 363 |
| 154 | L.fallonii_LLAP-10 | GTCCACAGTTAAAT-CAAATGACAAGGCTACGCATGTAGAGCTGAAGGCA | 372 |
| 155 | L.hackeliae_LHA | GACCACGGTTAAC-TTAAAAGACAAGGCTACGCATGTAGAGCTGATGGCA | 353 |
| 156 | L.oakridgensis_ATCC33761 | GTCCACGGTCAGAAT-AATAGACCAGGCTAAGCATGTAGAGCTGATGGCA | 368 |
| 157 | L.micdadei_LMI | GGCTACGGTTAAC-TTAATAGACAAGGCTAAGCATGTAGAACTGATGGCA | 362 |
| 158 | L.sainthelensi_ATCC35248 | ATGCACAGTTAAAT-CAAAAGACACGGCTACGCATGTAGAGCTGAAGGCA | 363 |
| 159 | L.wadsworthiiDSM21896 | ATGCACAGTTAAAT-CAAAAGACACGGCTACGCATGTAGAGCTGAAGGCA | 364 |
| 160 | L.cherrii_DSM19213 | ATGCACAGTTAAAT-CAAAAGACACGGCTACGCATGTAGAGCTGAAGGCA | 363 |
| 161 | L.moravicaDSM19234 | ATGCACAGTTAAAT-TAAAAGACAAGGCTACGCATGTAGAGCTGAAGGCA | 363 |
| 162 | L.norrlandica | AGCCACAGTTAAATTTAATAGACAAGGCTAAGCATGTAGAGCTAAAGGCA | 363 |
| 163 | L.shakespeareiDSM23087 | GTCCACAGTTAAAC-CAAAAGACAAGGCTACGCATGTAGAGCTAAAGGCA | 359 |
| 164 | L.drancourtiiLLAP12 | GTCCACAGTTAAAT-CAAATGACAAGGCTACGCATGTAGAACTGAAGGCA | 363 |
| 165 | L.lansingensis_DSM19556 | GGCCACGGTTAAC-TAAAAAGACAAGGCTAAGCATGTAGATCTGACGGCA | 357 |
| 166 | L.fairfieldensis_ATCC_49588 | GTCCACGGTTAACATAAATAGACAAGGCTACGCATGTAGAACTGACGGCA | 354 |
| 167 | L.massiliensis_PRJEB110 | GGACTCGGTTAAT-TGAATAGACAAGGCTACGCATGTAGAGCTGACGGCA | 359 |
| 168 | L.geestianaDSM21217 | GGAAGCAGTTAAAA-CAAATGACAAGGCTAAGCATGTAGATCTGACGGCA | 354 |
| | | * ** *     **  ***  ***** ********* ** * **** | |

| SEQ ID NO: | | | |
|---|---|---|---|
| 143 | L.pneumophilaATCC43290 | GACGACTTGCGGACGCGGGTTCGATTCCCGCCGCCTCCACCA | 406 |
| 144 | L.pneumophila_ThunderBay | GACGACTTGCGGACGCGGGTTCGATTCCCGCCGCCTCCACCA | 406 |
| 145 | L.pneumophila_HL06041035 | GACGACTTGCGGACGCGGGTTCGATTCCCGCCGCCTCCACCA | 406 |
| 146 | L.pneumophila_str.Philadelphia | GACGACTTGCGGACGCGGGTTCGATTCCCGCCGCCTCCACCA | 406 |
| 147 | >L.pneumophila_Lens | GACGACTTGCGGACGCGGGTTCGATTCCCGCCGCCTCCACCA | 406 |
| 148 | L.pneumophila_Paris | GACGACTTGCGGACGCGGGTTCGATTCCCGCCGCCTCCACCA | 406 |
| 149 | L.pneumophila_Corby | GACGACTTGCGGACGCGGGTTCGATTCCCGCCGCCTCCACCA | 406 |
| 150 | L.pneumophila_2300/99Alcoy | GACGACTTGCGGACGCGGGTTCGATTCCCGCCGCCTCCACCA | 406 |
| 151 | L.pneumophila_Lorraine | GACGACTTGCGGACGCGGGTTCGATTCCCGCCGCCTCCACCA | 406 |
| 152 | L.longbeachaeD-4968 | GACGATTTGCGGACGCGGGTTCGATTCCCGCCGCCTCCACCA | 405 |
| 153 | L.longbeachaeNSW150 | GACGATTTGCGGACGCGGGTTCGATTCCCGCCGCCTCCACCA | 405 |
| 154 | L.fallonii_LLAP-10 | GACGATTTGCGGACGCGGGTTCGATTCCCGCCGCCTCCACCA | 414 |
| 155 | L.hackeliae_LHA | GACGATTTGCGGACGCGGGTTCGATTCCCGCCGCCTCCACCA | 395 |
| 156 | L.oakridgensis_ATCC33761 | GACGATTTGCGGACGCGGGTTCGATTCCCGCCGCCTCCACCA | 410 |
| 157 | L.micdadei_LMI | GACGATTTGCGGACGCGGGTTCAATTCCCGCCGCCTCCACCA | 404 |
| 158 | L.sainthelensi_ATCC35248 | GACGATTTGCGGACGCGGGTTCGATTCCCGCCGCCTCCACCA | 405 |
| 159 | L.wadsworthiiDSM21896 | GACGACTTGCGGACGCGGGTTCGATTCCCGCCGCCTCCACCA | 406 |
| 160 | L.cherrii_DSM19213 | GACGATTTGCGGACGCGGGTTCGATTCCCGCCGCCTCCACCA | 405 |
| 161 | L.moravicaDSM19234 | GACGATTTGCGGACGCGGGTTCGATTCCCGCCGCCTCCACCA | 405 |
| 162 | L.norrlandica | GACGACTTGCGGACGCGG-TTCGATTCCCGCCGCCTCCACCA | 404 |
| 163 | L.shakespeareiDSM23087 | GACGATTTGCGGACGCGGGTTCGATTCCCGCCGCCTCCACCA | 401 |
| 164 | L.drancourtiiLLAP12 | GACGATCTGCGGACGCGGGTTCGATTCCCGCCGCCTCCACCA | 405 |
| 165 | L.lansingensis_DSM19556 | GACGATTTGCGGACGCGGGTTCGATTCCCGCCGCCTCCACCA | 399 |
| 166 | L.fairfieldensis_ATCC_49588 | GACGATTTGCGGACGCGGGTTCGATTCCCGCCGCCTCCACCA | 396 |
| 167 | L.massiliensis_PRJEB110 | GACGATTTGCGGACGCGGGTTCAATTCCCGCCGCCTCCACCA | 401 |
| 168 | L.geestianaDSM21217 | GACGATTTGCGGACGCGGGTTCGATTCCCGCCGCCTCCACCA | 396 |
| | | ***** *********** *** ****************** | |

Amplification Curves

SEQUENCE LISTING

```
<160> NUMBER OF SEQ ID NOS: 193

<210> SEQ ID NO 1
<211> LENGTH: 486
<212> TYPE: DNA
<213> ORGANISM: Haemophilus influenzae

<400> SEQUENCE: 1

atgacaaaga aaaaagtaaa acccaattca aatactatcg cactaaataa acgtgcaaga     60

cacgattatt ttattgaaga tgaaattgaa gcaggtcttg aattacaagg ctgggaagtc    120

aaatctatgc gcgcaggcaa ggcaaatatt agtgatagtt atgttatttt taaaaatggc    180

gaagcctttt tattcggcgc aagcattcag ccattaaatg ttgcatcaac gcatattgtt    240

tgtgatccaa ctcgcactcg taagttattg ttaaataaac gcgaattagc atccctattt    300

ggtaaagcaa accgagacgg ttttaccata gttgcacttt ctctttattg gaaaagtgcg    360

tgggcaaaag tcaaaatcgg tttagccaaa ggtaaaaaac aacaggataa acgtgatgat    420

attaaagaac gtgaatggaa agtaacaaaa gatcgcatta tgaaaaatgc acatcgaaga    480

tcttaa                                                               486


<210> SEQ ID NO 2
<211> LENGTH: 161
<212> TYPE: PRT
<213> ORGANISM: Haemophilus influenzae

<400> SEQUENCE: 2

Met Thr Lys Lys Lys Val Lys Pro Asn Ser Asn Thr Ile Ala Leu Asn
1               5                   10                  15

Lys Arg Ala Arg His Asp Tyr Phe Ile Glu Asp Glu Ile Glu Ala Gly
            20                  25                  30
```

-continued

```
Leu Glu Leu Gln Gly Trp Glu Val Lys Ser Met Arg Ala Gly Lys Ala
        35                  40                  45

Asn Ile Ser Asp Ser Tyr Val Ile Phe Lys Asn Gly Glu Ala Phe Leu
    50                  55                  60

Phe Gly Ala Ser Ile Gln Pro Leu Asn Val Ala Ser Thr His Ile Val
65                  70                  75                  80

Cys Asp Pro Thr Arg Thr Arg Lys Leu Leu Leu Asn Lys Arg Glu Leu
                85                  90                  95

Ala Ser Leu Phe Gly Lys Ala Asn Arg Asp Gly Phe Thr Ile Val Ala
            100                 105                 110

Leu Ser Leu Tyr Trp Lys Ser Ala Trp Ala Lys Val Lys Ile Gly Leu
        115                 120                 125

Ala Lys Gly Lys Lys Gln Gln Asp Lys Arg Asp Asp Ile Lys Glu Arg
    130                 135                 140

Glu Trp Lys Val Thr Lys Asp Arg Ile Met Lys Asn Ala His Arg Arg
145                 150                 155                 160

Ser


<210> SEQ ID NO 3
<211> LENGTH: 20
<212> TYPE: DNA
<213> ORGANISM: Artificial Sequence
<220> FEATURE:
<223> OTHER INFORMATION: H. influenzae smpB F1

<400> SEQUENCE: 3

attaaatgty gcatcaacgc                                                  20


<210> SEQ ID NO 4
<211> LENGTH: 17
<212> TYPE: DNA
<213> ORGANISM: Artificial Sequence
<220> FEATURE:
<223> OTHER INFORMATION: H. influenzae smpB R1

<400> SEQUENCE: 4

gacttttgcc cacgcac                                                     17


<210> SEQ ID NO 5
<211> LENGTH: 27
<212> TYPE: DNA
<213> ORGANISM: Artificial Sequence
<220> FEATURE:
<223> OTHER INFORMATION: H. influenzae smpB P1

<400> SEQUENCE: 5

acgrttttac catagttgca ctttctc                                          27


<210> SEQ ID NO 6
<211> LENGTH: 21
<212> TYPE: DNA
<213> ORGANISM: Artificial Sequence
<220> FEATURE:
<223> OTHER INFORMATION: MTC FwP

<400> SEQUENCE: 6

caaggcacgg aggtgaagag c                                                21


<210> SEQ ID NO 7
<211> LENGTH: 17
<212> TYPE: DNA
<213> ORGANISM: Artificial Sequence
```

<220> FEATURE:
<223> OTHER INFORMATION: Bacillus subtilis F1

<400> SEQUENCE: 7
aacgtagcat tagctgc 17

<210> SEQ ID NO 8
<211> LENGTH: 17
<212> TYPE: DNA
<213> ORGANISM: Artificial Sequence
<220> FEATURE:
<223> OTHER INFORMATION: Bacillus subtilis R1

<400> SEQUENCE: 8
ctcatcttct tgcctgc 17

<210> SEQ ID NO 9
<211> LENGTH: 21
<212> TYPE: DNA
<213> ORGANISM: Artificial Sequence
<220> FEATURE:
<223> OTHER INFORMATION: Bacillus subtilis P1

<400> SEQUENCE: 9
cacatccaag taggctacgc t 21

<210> SEQ ID NO 10
<211> LENGTH: 22
<212> TYPE: DNA
<213> ORGANISM: Artificial Sequence
<220> FEATURE:
<223> OTHER INFORMATION: LegPneuF1

<400> SEQUENCE: 10
cacgtgataa tmaaatacgg tg 22

<210> SEQ ID NO 11
<211> LENGTH: 21
<212> TYPE: DNA
<213> ORGANISM: Artificial Sequence
<220> FEATURE:
<223> OTHER INFORMATION: MTC RvP

<400> SEQUENCE: 11
ctcgtggttg gtccagctgc c 21

<210> SEQ ID NO 12
<211> LENGTH: 19
<212> TYPE: DNA
<213> ORGANISM: Artificial Sequence
<220> FEATURE:
<223> OTHER INFORMATION: LegPneuR1

<400> SEQUENCE: 12
ttcatcaaya gcttgcgyg 19

<210> SEQ ID NO 13
<211> LENGTH: 28
<212> TYPE: DNA
<213> ORGANISM: Artificial Sequence
<220> FEATURE:
<223> OTHER INFORMATION: MTC_P

<400> SEQUENCE: 13
caggcgtcgc tggccgattc gttcgcca 28

-continued

<210> SEQ ID NO 14
<211> LENGTH: 26
<212> TYPE: DNA
<213> ORGANISM: Artificial Sequence
<220> FEATURE:
<223> OTHER INFORMATION: LegPneuP3

<400> SEQUENCE: 14
cygcatccac tcattttatt cctgat 26

<210> SEQ ID NO 15
<211> LENGTH: 20
<212> TYPE: DNA
<213> ORGANISM: Artificial Sequence
<220> FEATURE:
<223> OTHER INFORMATION: A.baum smpB F1

<400> SEQUENCE: 15
tggcatgtct ttactaggct 20

<210> SEQ ID NO 16
<211> LENGTH: 22
<212> TYPE: DNA
<213> ORGANISM: Artificial Sequence
<220> FEATURE:
<223> OTHER INFORMATION: A.baum smpB R1

<400> SEQUENCE: 16
gcacaatatg tgtagatgca ga 22

<210> SEQ ID NO 17
<211> LENGTH: 23
<212> TYPE: DNA
<213> ORGANISM: Artificial Sequence
<220> FEATURE:
<223> OTHER INFORMATION: A.baum smpB P

<400> SEQUENCE: 17
tggtgctcag attcaaccac tcc 23

<210> SEQ ID NO 18
<211> LENGTH: 17
<212> TYPE: DNA
<213> ORGANISM: Artificial Sequence
<220> FEATURE:
<223> OTHER INFORMATION: L.gra smpB F1

<400> SEQUENCE: 18
cggcattgtc ttgcaag 17

<210> SEQ ID NO 19
<211> LENGTH: 20
<212> TYPE: DNA
<213> ORGANISM: Artificial Sequence
<220> FEATURE:
<223> OTHER INFORMATION: L.gra smpB R1

<400> SEQUENCE: 19
gctgatatgc atgttgtgta 20

<210> SEQ ID NO 20
<211> LENGTH: 22
<212> TYPE: DNA
<213> ORGANISM: Artificial Sequence
<220> FEATURE:
<223> OTHER INFORMATION: L.gra smpB PHEX2

<400> SEQUENCE: 20
agttcactcg tgcattacga ac 22

<210> SEQ ID NO 21
<211> LENGTH: 19
<212> TYPE: DNA
<213> ORGANISM: Artificial Sequence
<220> FEATURE:
<223> OTHER INFORMATION: Mpneu_F1

<400> SEQUENCE: 21
ttagcatttc gccctatgc 19

<210> SEQ ID NO 22
<211> LENGTH: 19
<212> TYPE: DNA
<213> ORGANISM: Artificial Sequence
<220> FEATURE:
<223> OTHER INFORMATION: Mpneu_R1

<400> SEQUENCE: 22
agtccttctt gcttttggc 19

<210> SEQ ID NO 23
<211> LENGTH: 20
<212> TYPE: DNA
<213> ORGANISM: Artificial Sequence
<220> FEATURE:
<223> OTHER INFORMATION: Mpneu_P1

<400> SEQUENCE: 23
ccaccccttc aaacgggtga 20

<210> SEQ ID NO 24
<211> LENGTH: 19
<212> TYPE: DNA
<213> ORGANISM: Artificial Sequence
<220> FEATURE:
<223> OTHER INFORMATION: M. av_avp FwP

<400> SEQUENCE: 24
cgttgcaagg aaccgaggt 19

<210> SEQ ID NO 25
<211> LENGTH: 21
<212> TYPE: DNA
<213> ORGANISM: Artificial Sequence
<220> FEATURE:
<223> OTHER INFORMATION: M. av_avp RvP

<400> SEQUENCE: 25
gtcgtgattg gtccagctac c 21

<210> SEQ ID NO 26
<211> LENGTH: 24
<212> TYPE: DNA
<213> ORGANISM: Artificial Sequence
<220> FEATURE:
<223> OTHER INFORMATION: M. av_avp P

<400> SEQUENCE: 26
caagcgtcgt tagctgacgc gttc 24

<210> SEQ ID NO 27

<211> LENGTH: 19
<212> TYPE: DNA
<213> ORGANISM: Artificial Sequence
<220> FEATURE:
<223> OTHER INFORMATION: M. int FwP

<400> SEQUENCE: 27
gctgcaaggc accgaggtc 19

<210> SEQ ID NO 28
<211> LENGTH: 21
<212> TYPE: DNA
<213> ORGANISM: Artificial Sequence
<220> FEATURE:
<223> OTHER INFORMATION: M. int RvP

<400> SEQUENCE: 28
gtcatgattg gtccagctac c 21

<210> SEQ ID NO 29
<211> LENGTH: 24
<212> TYPE: DNA
<213> ORGANISM: Artificial Sequence
<220> FEATURE:
<223> OTHER INFORMATION: M. int P

<400> SEQUENCE: 29
caagcttcgt tagctgacgc cttc 24

<210> SEQ ID NO 30
<211> LENGTH: 18
<212> TYPE: DNA
<213> ORGANISM: Artificial Sequence
<220> FEATURE:
<223> OTHER INFORMATION: LgensmpB_F

<400> SEQUENCE: 30
gatcaatacg aagcaggc 18

<210> SEQ ID NO 31
<211> LENGTH: 20
<212> TYPE: DNA
<213> ORGANISM: Artificial Sequence
<220> FEATURE:
<223> OTHER INFORMATION: LgensmpB_R

<400> SEQUENCE: 31
gccattctct gtctttgatc 20

<210> SEQ ID NO 32
<211> LENGTH: 21
<212> TYPE: DNA
<213> ORGANISM: Artificial Sequence
<220> FEATURE:
<223> OTHER INFORMATION: Leg ssrA F1

<400> SEQUENCE: 32
ygcaaayraw gmaawsttyg m 21

<210> SEQ ID NO 33
<211> LENGTH: 21
<212> TYPE: DNA
<213> ORGANISM: Artificial Sequence
<220> FEATURE:
<223> OTHER INFORMATION: Leg ssrA R1

<400> SEQUENCE: 33
ctctgccdty aghtctacat g 21

<210> SEQ ID NO 34
<211> LENGTH: 25
<212> TYPE: DNA
<213> ORGANISM: Artificial Sequence
<220> FEATURE:
<223> OTHER INFORMATION: Leg ssrA P3

<400> SEQUENCE: 34
yggtaycgaa tcaacggtca tarra 25

<210> SEQ ID NO 35
<211> LENGTH: 19
<212> TYPE: DNA
<213> ORGANISM: Artificial Sequence
<220> FEATURE:
<223> OTHER INFORMATION: SIAC F2

<400> SEQUENCE: 35
atgccagtca gcataagga 19

<210> SEQ ID NO 36
<211> LENGTH: 21
<212> TYPE: DNA
<213> ORGANISM: Artificial Sequence
<220> FEATURE:
<223> OTHER INFORMATION: SIAC R2

<400> SEQUENCE: 36
cagacctctg gtaggatgta c 21

<210> SEQ ID NO 37
<211> LENGTH: 20
<212> TYPE: DNA
<213> ORGANISM: Artificial Sequence
<220> FEATURE:
<223> OTHER INFORMATION: H. influenzae smpB F1

<400> SEQUENCE: 37
attaaatgtt gcatcaacgc 20

<210> SEQ ID NO 38
<211> LENGTH: 19
<212> TYPE: DNA
<213> ORGANISM: Artificial Sequence
<220> FEATURE:
<223> OTHER INFORMATION: LegPneuR1

<400> SEQUENCE: 38
ttcatcaata gcttgcgyg 19

<210> SEQ ID NO 39
<211> LENGTH: 25
<212> TYPE: DNA
<213> ORGANISM: Artificial Sequence
<220> FEATURE:
<223> OTHER INFORMATION: Leg ssrA P3

<400> SEQUENCE: 39
yggtatcgaa tcaacggtca tarra 25

<210> SEQ ID NO 40
<211> LENGTH: 21
<212> TYPE: DNA

<213> ORGANISM: Artificial Sequence
<220> FEATURE:
<223> OTHER INFORMATION: Leg ssrA F1

<400> SEQUENCE: 40
tgcaaacgat gaaaactttg c 21

<210> SEQ ID NO 41
<211> LENGTH: 21
<212> TYPE: DNA
<213> ORGANISM: Artificial Sequence
<220> FEATURE:
<223> OTHER INFORMATION: Leg ssrA R1

<400> SEQUENCE: 41
ctctgccttt agctctacat g 21

<210> SEQ ID NO 42
<211> LENGTH: 20
<212> TYPE: DNA
<213> ORGANISM: Artificial Sequence
<220> FEATURE:
<223> OTHER INFORMATION: SIAC P1

<400> SEQUENCE: 42
tcggcactac cgacacgaac 20

<210> SEQ ID NO 43
<211> LENGTH: 500
<212> TYPE: DNA
<213> ORGANISM: Artificial Sequence
<220> FEATURE:
<223> OTHER INFORMATION: SIAC

<400> SEQUENCE: 43
acctctaagt aagtgagcgg tcgtgacatt atccctgatt ttctcactac tattagtact 60
cacggcgcaa ttccaccaca gccttgtctc gccagaatgc cagtcagcat aaggaagagc 120
tcaaggcagg tcaactcgca ctgtgagggt cacatgggcg ttcggcacta ccgacacgaa 180
cctcagttag cgtacatcct accagaggtc tgtggccccg tggtcaaaag tgcgggtttc 240
gtatttgctg ctcgtcagta ctttcagaat catgacctgc acggcaaaga gacgcttatt 300
atggagctcg acatggcaat aacgcgacga atctacgtca cgacgagaat agtgtaaacg 360
aagctgctga cggcggaagc gtcaaagggg tctgtgaatt gttattcgcg aaaaacatcc 420
gtccccgtgg gggatagtca ccgacgccgt tttatagaag cctaggggaa caggttggtt 480
taactagctt aagaaagtaa 500

<210> SEQ ID NO 44
<211> LENGTH: 471
<212> TYPE: DNA
<213> ORGANISM: Legionella pneumophila

<400> SEQUENCE: 44
atgactacca aaaaacaacc agattccacc atagccttga atagaaaagc tggttttgat 60
tattttattg aagatcaata cgaagcaggc ctggttttgg agggctggga agtaaaaagt 120
ctgcgtgctg ggaaaatcaa tttgtcggat tcacacgtga taatcaaata cggtgaggca 180
ttcctattgg gcgcccaaat acagcctctt cccaccgcat ccactcattt tattcctgat 240
ccggtcagga cgcgcaagct attgatgaat aaaaaagaat taaaccatct cattggaagt 300
gttgaaaggc aaggctatac catagtccct ctttctttgt attggaaaaa aaataaaatt 360
aaaataaaaa ttgctctggc caaaggaaaa aaagagcatg acaaaagaga cacgatcaaa 420
gacagagaat ggcaaagaga tcgttcaaga ataatgaaaa agaacacttg a 471

<210> SEQ ID NO 45
<211> LENGTH: 471
<212> TYPE: DNA
<213> ORGANISM: Legionella pneumophila

<400> SEQUENCE: 45
atgactacca aaaaacaacc agattccacc atagccttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagccgctt cccaccgcat ccactcattt tattcctgat 240
ccgatcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc caaaggaaaa aaagagcatg acaaaagaga cacgatcaaa 420
gacagagaat ggcaaaggga tcgttcaaga ataatgaaaa agaacacttg a 471

<210> SEQ ID NO 46
<211> LENGTH: 398
<212> TYPE: DNA
<213> ORGANISM: Legionella pneumophila

<400> SEQUENCE: 46
atgactacca aaaaacaacc agattccacc atagccttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagcctctt cccaccgcat ccactcattt tattcctgat 240
ccgatcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc taaaggaaaa aaagagca 398

<210> SEQ ID NO 47
<211> LENGTH: 471
<212> TYPE: DNA
<213> ORGANISM: Legionella pneumophila

<400> SEQUENCE: 47
atgactacca aaaaacaacc agattccacc atagctttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagcctctt ccaaccgcat ccactcattt tattcctgat 240
ccggtcagga cgcgcaagct attgatgaat aaaaaagaat taaaccatct cattggaagt 300
gttgaaaggc aaggctatac catagtccct ctttctttgt attggaaaaa aaataaaatt 360
aaaataaaaa ttgctctggc caaaggaaaa aaagagcatg acaaaagaga cacgatcaaa 420
gacagagaat ggcaaagaga tcgttcaaga ataatgaaaa agaacacttg a 471

<210> SEQ ID NO 48
<211> LENGTH: 471
<212> TYPE: DNA

<213> ORGANISM: Legionella pneumophila

<400> SEQUENCE: 48
atgactacca aaaaacaacc agattccacc atagccttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagccgctt cccaccgcat ccactcattt tattcctgat 240
ccgatcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc caaaggaaaa aaagagcatg acaaaagaga cacgatcaaa 420
gacagagaat ggcaaaggga tcgttcaaga ataatgaaaa agaacacttg a 471

<210> SEQ ID NO 49
<211> LENGTH: 471
<212> TYPE: DNA
<213> ORGANISM: Legionella pneumophila

<400> SEQUENCE: 49
atgactacca aaaaacaacc agattccacc atagccttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagcctctt cccaccgcat ccactcattt tattcctgat 240
ccgatcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc taaaggaaaa aaagagcatg acaaaagaga cacgatcaaa 420
gacagagaat ggcaaaggga tcgttcaaga ataatgaaaa agaacacttg a 471

<210> SEQ ID NO 50
<211> LENGTH: 471
<212> TYPE: DNA
<213> ORGANISM: Legionella pneumophila

<400> SEQUENCE: 50
atgactacca aaaaacaacc agattcaacc atagctttga atagaaaagc tggttttgat 60
tactttattg aagatcaata cgaagcaggc ctggttttgg aaggctggga agtaaaaagt 120
ctgcgtgctg gaaaaatcaa tttgtcggat tcacacgtga taatcaaata cggtgaggca 180
ttcctattgg gcgcccaaat acagcctctt cccaccgcat ccactcattt tattcctgat 240
ccggtcagga cgcgcaagct attgatgaat aaaaaagaat taaaccatct cataggaagt 300
gttgaaaggc aaggctatac catagtccct ctttctttgt attggaaaaa aaataaaatt 360
aaaataaaaa ttgctctggc caaaggaaaa aaagagcatg acaaaagaga cacgatcaaa 420
gacagagaat ggcaaaggga tcgttcaaga ataatgaaaa agaacacttg a 471

<210> SEQ ID NO 51
<211> LENGTH: 471
<212> TYPE: DNA
<213> ORGANISM: Legionella pneumophila

<400> SEQUENCE: 51
atgactacca aaaaacaacc agattccacc atagccttga atagaaaagc tggttttgat 60
tactttattg aagatcaata cgaagcaggc ctggttttgg aaggctggga agtaaaaagt 120

```
ctgcgtgctg gaaaaatcaa tttgtcggat tcacacgtga taatcaaata cggtgaggca    180

ttcctattgg gcgcccaaat acagcctctt cccaccgcat ccactcattt tattcctgat    240

ccgctgagga cgcgcaagct attgatgaat aaaagagaat taaaccatct cataggaagt    300

gttgaaaggc aaggctatac catagtccct ctttctttgt attggaaaaa aaataaaatt    360

aaaataaaaa ttgctctggc caaaggaaaa aaagagcatg acaaaagaga cacgatcaaa    420

gacagagaat ggcaaaggga tcgttcaaga ataatgaaaa agaacacttg a             471
```

<210> SEQ ID NO 52
<211> LENGTH: 471
<212> TYPE: DNA
<213> ORGANISM: Legionella pneumophila

<400> SEQUENCE: 52

```
atgactacca aaaaacaacc agattccacc atagccttga atagaaaagc tggttttgat     60

tactttattg aagatcaata cgaagcaggc ctggttttgg aaggctggga agtaaaaagt    120

ctgcgtgctg gaaaaatcaa tttgtcggat tcacacgtga taatcaaata cggtgaggca    180

ttcctattgg gcgcccaaat acagcctctt cccaccgcat ccactcattt tattcctgat    240

ccgatcagga cgcgcaagct attgatgaat aaaaaagaat taaaccatct cataggaagt    300

gttgaaaggc aaggctatac catagtccct ctttctttgt attggaaaaa aaataaaatt    360

aaaataaaaa ttgctctggc taaaggaaaa aaagagcatg acaaaagaga cacgatcaaa    420

gacagagaat ggcaaaggga tcgttcaaga ataatgaaaa agaacacttg a             471
```

<210> SEQ ID NO 53
<211> LENGTH: 471
<212> TYPE: DNA
<213> ORGANISM: Legionella pneumophila

<400> SEQUENCE: 53

```
atgactacca aaaaacaacc agattccacc atagccttga atagaaaagc tggttttgat     60

tactttattg aagatcaata cgaagcaggc ctggttttgg aaggctggga agtaaaaagt    120

ctgcgtgctg gaaaaatcaa tttgtcggat tcacacgtga taatcaaata cggtgaggca    180

ttcctattgg gcgcccaaat acagcctctt cccaccgcat ccactcattt tattcctgat    240

ccgatcagga cgcgcaagct attgatgaat aaaaaagaat taaaccatct cataggaagt    300

gttgaaaggc aaggctatac catagtccct ctttctttgt attggaaaaa aaataaaatt    360

aaaataaaaa ttgctctggc taaaggaaaa aaagagcatg acaaaagaga cacgatcaaa    420

gacagagaat ggcaaaggga tcgttcaaga ataatgaaaa agaacacttg a             471
```

<210> SEQ ID NO 54
<211> LENGTH: 361
<212> TYPE: DNA
<213> ORGANISM: Legionella pneumophila

<400> SEQUENCE: 54

```
gatcaatacg aagcaggcct ggttttggag ggctgggaag taaaaagtct gcgtgctggg     60

aaaatcaatt tgtcggattc acacgtgata atcaaatacg gtgaggcatt cctattgggc    120

gcccaaatac agcctcttcc caccgcatcc actcatttta ttcctgatcc ggtcaggacg    180

cgcaagctat tgatgaataa aaaagaatta aaccatctca ttggaagtgt tgaaaggcaa    240

ggctatacca tagtccctct ttctttgtat tggaaaaaaa ataaaattaa aataaaaatt    300
```

-continued

```
gctctggcca aaggaaaaaa agagcatgac aaaagagaca cgatcaaaga cagagaatgg    360

c                                                                    361


<210> SEQ ID NO 55
<211> LENGTH: 361
<212> TYPE: DNA
<213> ORGANISM: Legionella pneumophila

<400> SEQUENCE: 55

gatcaatacg aagcaggcct ggttttggaa ggctgggaag taaaaagtct gcgtgctgga     60

aaaatcaatt tgtcggattc acacgtgata atcaaatacg gtgaggcatt cctattgggc    120

gcccaaatac agccgcttcc caccgcatcc actcatttta ttcctgatcc gatcaggacg    180

cgcaagctat tgatgaataa aaaagaatta aaccatctca taggaagtgt tgaaaggcaa    240

ggctatacca tagtccctct ttctttgtat tggaaaaaaa ataaaattaa aataaaaatt    300

gctctggcca aaggaaaaaa agagcatgac aaaagagaca cgatcaaaga cagagaatgg    360

c                                                                    361


<210> SEQ ID NO 56
<211> LENGTH: 361
<212> TYPE: DNA
<213> ORGANISM: Legionella pneumophila

<400> SEQUENCE: 56

gatcaatacg aagcaggcct ggttttggaa ggctgggaag taaaaagtct gcgtgctgga     60

aaaatcaatt tgtcggattc acacgtgata atcaaatacg gtgaggcatt cctattgggc    120

gcccaaatac agcctcttcc caccgcatcc actcatttta ttcctgatcc ggtcaggacg    180

cgcaagctat tgatgaataa aaaagaatta aaccatctca ttggaagtgt tgaaaggcaa    240

ggctatacca tagtccctct ttctttgtat tggaaaaaaa ataaaattaa aataaaaatt    300

gctctggcca aaggaaaaaa agagcatgac aaaagagaca cgatcaaaga cagagaatgg    360

c                                                                    361


<210> SEQ ID NO 57
<211> LENGTH: 361
<212> TYPE: DNA
<213> ORGANISM: Legionella pneumophila

<400> SEQUENCE: 57

gatcaatacg aagcaggcct ggttttggaa ggctgggaag taaaaagtct gcgtgctgga     60

aaaatcaatt tgtcggattc acacgtgata atcaaatacg gtgaggcatt cctattgggc    120

gcccaaatac agcctcttcc caccgcatcc actcatttta ttcctgatcc gatcaggacg    180

cgcaagctat tgatgaataa aaaagaatta aaccatctca taggaagtgt tgaaaggcaa    240

ggctatacca tagtccctct ttctttgtat tggaaaaaaa ataaaattaa aataaaaatt    300

gctctggcta aaggaaaaaa agagcatgac aaaagagaca cgatcaaaga cagagaatgg    360

c                                                                    361


<210> SEQ ID NO 58
<211> LENGTH: 361
<212> TYPE: DNA
<213> ORGANISM: Legionella pneumophila

<400> SEQUENCE: 58

gatcaatacg aagcaggctt ggttttggaa ggctgggaag taaaaagtct gcgggcagga     60
```

aaaatcaatt tgtcagatgc acacgtgata atcaaatacg gtgaggcatt cctgttagga 120
gctcaaatac agcctcttcc tactgcatcc actcatttta ttcctgatcc ggtcaggaca 180
cgcaagctat tgatgaataa aaaagaatta aaccatctca tcggaagtgt tgaaagacaa 240
ggctatacca tagtgcctct ttctttgtat tggaaaaaga ataaaattaa aataaaaatc 300
gctctggcta aaggaaaaaa agagcatgac aaaagagaca cgatcaaaga cagagaatgg 360
c 361

<210> SEQ ID NO 59
<211> LENGTH: 361
<212> TYPE: DNA
<213> ORGANISM: Legionella pneumophila

<400> SEQUENCE: 59
gatcaatacg aagcaggctt ggttttggaa ggctgggaag taaaaagtct gcgtgcagga 60
aaaatcaatt tgtcggatgc acacgtgata ataaaatacg gtgaggcatt cctgttagga 120
gcccaaatac agcctcttcc tactgcatcc actcatttta ttcctgatcc agtcaggaca 180
cgcaagctgt tgatgaataa aaaagaatta aaccatctta tcggaagtgt tgaaagacaa 240
ggctatacca tagttcctct ttctttgtat tggaaaaaga ataaaattaa aataaaaatc 300
gcactggcca aaggaaagaa agagcatgac aaaagagaca cgatcaaaga cagagaatgg 360
c 361

<210> SEQ ID NO 60
<211> LENGTH: 361
<212> TYPE: DNA
<213> ORGANISM: Legionella pneumophila

<400> SEQUENCE: 60
gatcaatacg aagcaggcct ggttttggaa ggctgggaag taaaaagtct gcgtgctggg 60
aaaatcaatt tgtcggattc acacgtgata atcaaatacg gtgaagcatt cctattgggc 120
gcccaaatac agcctcttcc caccgcatcc actcatttta ttcctgatcc ggtcaggacg 180
cgcaagctat tgatgaataa aaaagaatta aaccatctca ttggaagtgt tgaaaggcaa 240
ggctatacca tagtccctct ttctttgtat tggaaaaaaa ataaaattaa aataaaaatt 300
gctctggcca aaggaaaaaa agagcatgac aaaagagaca cgatcaaaga cagagaatgg 360
c 361

<210> SEQ ID NO 61
<211> LENGTH: 361
<212> TYPE: DNA
<213> ORGANISM: Legionella pneumophila

<400> SEQUENCE: 61
gatcaatacg aagcaggcct ggttttggaa ggctgggaag taaaaagtct gcgtgctgga 60
aaaatcaatt tgtcggattc acacgtgata atcaaatacg gtgaggcatt cctattgggc 120
gcccaaatac agcctcttcc caccgcatcc actcatttta ttcctgatcc gatcaggacg 180
cgcaagctat tgatgaataa aaaagaatta aaccatctca taggaagtgt tgaaaggcaa 240
ggctatacca tagtccctct ttctttgtat tggaaaaaaa ataaaattaa aataaaaatt 300
gctctggcta aaggaaaaaa agagcatgac aaaagagaca cgatcaaaga cagagaatgg 360
c 361

<210> SEQ ID NO 62
<211> LENGTH: 361
<212> TYPE: DNA
<213> ORGANISM: Legionella pneumophila

<400> SEQUENCE: 62
gatcaatacg aagcaggcct ggttttggaa ggctgggaag taaaaagtct gcgtgctgga 60
aaaatcaatt tgtcggattc acacgtgata atcaaatacg gtgaggcatt cctattgggc 120
gcccaaatac agcctcttcc caccgcatcc actcatttta ttcctgatcc gctgaggacg 180
cgcaagctat tgatgaataa aagagaatta aaccatctca taggaagtgt tgaaaggcaa 240
ggctatacca tagtccctct ttctttgtat tggaaaaaaa ataaaattaa aataaaaatt 300
gctctggcca aaggaaaaaa agagcatgac aaaagagaca cgatcaaaga cagagaatgg 360
c 361

<210> SEQ ID NO 63
<211> LENGTH: 361
<212> TYPE: DNA
<213> ORGANISM: Legionella pneumophila

<400> SEQUENCE: 63
gatcaatacg aagcaggcct ggttttggaa ggctgggaag taaaaagtct gcgtgctgga 60
aaaatcaatt tgtcggattc acacgtgata atcaaatacg gtgaggcatt cctattgggc 120
gcccaaatac agcctcttcc caccgcatcc actcatttta ttcctgatcc gctgaggacg 180
cgcaagctat tgatgaataa aagagaatta aaccatctca taggaagtgt tgaaaggcaa 240
ggctatacca tagtccctct ttctttgtat tggaaaaaaa ataaaattaa aataaaaatt 300
gctctggcca aaggaaaaaa agagcatgac aaaagagaca cgatcaaaga cagagaatgg 360
c 361

<210> SEQ ID NO 64
<211> LENGTH: 361
<212> TYPE: DNA
<213> ORGANISM: Legionella pneumophila

<400> SEQUENCE: 64
gatcaatacg aagcaggcct ggttttggaa ggctgggaag taaaaagtct gcgtgctgga 60
aaaatcaatt tgtcggattc acacgtgata atcaaatacg gtgaggcatt cctattgggc 120
gcccaaatac agcctcttcc caccgcatcc actcatttta ttcctgatcc gctgaggacg 180
cgcaagctat tgatgaataa aagagaatta aaccatctca taggaagtgt tgaaaggcaa 240
ggctatacca tagtccctct ttctttgtat tggaaaaaaa ataaaattaa aataaaaatt 300
gctctggcca aaggaaaaaa agagcatgac aaaagagaca cgatcaaaga cagagaatgg 360
c 361

<210> SEQ ID NO 65
<211> LENGTH: 361
<212> TYPE: DNA
<213> ORGANISM: Legionella pneumophila

<400> SEQUENCE: 65
gatcaatacg aagcaggcct ggttttggaa ggctgggaag taaaaagtct gcgtgctgga 60
aaaatcaatt tgtcggattc acacgtgata atcaaatacg gtgaggcatt cctattgggc 120
gcccaaatac agcctcttcc caccgcatcc actcatttta ttcctgatcc ggtcaggacg 180

```
cgcaagctat tgatgaataa aaaagaatta aaccatctca taggaagtgt tgaaaggcaa    240
ggctatacca tagtccctct ttctttgtat tggaaaaaaa ataaaattaa aataaaaatt    300
gctctggcca aaggaaaaaa agagcatgac aaaagagaca cgatcaaaga cagagaatgg    360
c                                                                    361
```

<210> SEQ ID NO 66
<211> LENGTH: 618
<212> TYPE: DNA
<213> ORGANISM: Acinetobacter baumannii

<400> SEQUENCE: 66

```
tgatatgtgg gaaaaaactt caccttggca tcagtttacg gcacaatagg gacaattgtg     60
gaagtttgaa ttatggcgaa agcaacagta gtaaagaaac ataatggcgg aaccatcgca    120
caaaacaaac gtgcccgtca tgattatttt atcgaagaaa aatttgaagc tggcatgtct    180
ttactaggct gggaagtaaa atctttacgt gccggtcgta tgagtttgac agaaagttat    240
gtcattttta aaaatggtga agcattctta tttggtgctc agattcaacc actcctttct    300
gcatctacac atattgtgcc ggaagctaca cgtacacgaa aattattatt atctcgtcgt    360
gaacttgaaa agcttatggg tgcggtgaac caaaaaggtt attcttgcgt tccattagca    420
tgttactgga aaggtcatct ggttaagctt gaaattgcac tcgtgaaagg taaacaactt    480
cacgataaac gagcgactga aaaagaacgt gactggcaac gtgataaagc acgtatattt    540
cataagtaat agactaaaaa gccctttata gaggcttttt tattttccac taatttaatc    600
tatataaaag cccagcaa                                                  618
```

<210> SEQ ID NO 67
<211> LENGTH: 619
<212> TYPE: DNA
<213> ORGANISM: Acinetobacter baumannii

<400> SEQUENCE: 67

```
tgatatgtgg gaaaaaactt caccttggca tcagtttacg gcacaatagg gacaattgtg     60
gaagtttgaa ttatggcgaa agcaacagta gtaaagaaac ataatggcgg aaccattgca    120
caaaacaaac gtgcccgtca tgattatttt atcgaagaaa aatttgaagc tggcatgtct    180
ttactaggct gggaagtaaa atctttacgt gccggtcgta tgagtttgac agaaagttat    240
gtcattttta aaaatggtga agcattctta tttggtgctc agattcaacc actcctttct    300
gcatctacac atattgtgcc ggaagctaca cgtacacgaa aattattatt atctcgtcgt    360
gaacttgaaa agcttatggg tgcagtgaac caaaaaggtt attcgtgcgt tccattagca    420
tgttactgga aaggtcatct ggttaagctt gaaattgcac tcgtgaaagg taaacaactt    480
cacgataaac gagcaactga aaaagaacgt gactggcaac gtgataaagc acgtatattt    540
cataagtaat agactaaaaa gcctctttat agaggctttt ttatttttca ctaatttaat    600
ctatataaaa gcccagcaa                                                 619
```

<210> SEQ ID NO 68
<211> LENGTH: 619
<212> TYPE: DNA
<213> ORGANISM: Acinetobacter baumannii

<400> SEQUENCE: 68

```
tgatatgtgg gaaaaaactt caccttggca tcagtttacg gcacaatagg gacaattgtg     60
```

-continued

```
gaagtttgaa ttatggcgaa agcaacagta gtaaagaaac ataatggcgg aaccattgca    120
caaaacaaac gtgcccgtca tgattatttt atcgaagaaa aatttgaagc tggcatgtct    180
ttactaggct gggaagtaaa atctttacgt gccggtcgta tgagtttgac agaaagttat    240
gtcattttta aaaatggtga agcattctta tttggtgctc agattcaacc actcctttct    300
gcatctacac atattgtgcc ggaagctaca cgtacacgaa aattattatt atctcgtcgt    360
gaacttgaaa agcttatggg tgcagtgaac caaaaaggtt attcgtgcgt tccattagca    420
tgttactgga aaggtcatct ggttaagctt gaaattgcac tcgtgaaagg taaacaactt    480
cacgataaac gagcaactga aaaagaacgt gactggcaac gtgataaagc acgtatattt    540
cataagtaat agactaaaaa gcctctttat agaggctttt ttatttttca ctaatttaat    600
ctatataaaa gcccagcaa                                                 619
```

<210> SEQ ID NO 69
<211> LENGTH: 619
<212> TYPE: DNA
<213> ORGANISM: Acinetobacter baumannii

<400> SEQUENCE: 69

```
atatgtggga aaaaacttca ccttggcatc agtttacggc acaataggga caattgtgga     60
agtttgaatt atggcgaaag caacagtagt aaagaaacat aatggcggaa ccattgcaca    120
aaacaaacgt gcccgtcatg attattttat cgaagaaaaa tttgaagctg gcatgtcttt    180
actaggctgg gaagtaaaat ctttacgtgc cggtcgtatg agtttgacag aaagttatgt    240
catttttaaa aatggtgaag cattcttatt tggtgctcag attcaaccac tcctttctgc    300
atctacacat attgtgccgg aagctacacg tacacgaaaa ttattattat ctcgtcgtga    360
acttgaaaag cttatgggtg cggtgaacca aaaaggttat tcgtgcgttc cattagcatg    420
ttactggaaa ggtcatctgg ttaagcttga aattgcactc gtgaaaggta aacaacttca    480
cgataaacga gcaactgaaa aagaacgtga ctggcaacgt gataaagcac gtatatttca    540
taagtaatag actaaaaagc ctctttatag aggctttttt atttttcact aatttaatct    600
atataaaagc ccagcaata                                                 619
```

<210> SEQ ID NO 70
<211> LENGTH: 619
<212> TYPE: DNA
<213> ORGANISM: Acinetobacter baumannii

<400> SEQUENCE: 70

```
tgatatgtgg gaaaaaactt caccttggca tcagtttacg gcacaatagg gacaattgtg     60
gaagtttgaa ttatggcgaa agcaacagta gtaaagaaac ataatggcgg aaccatcgca    120
caaaacaaac gtgcccgtca tgattatttt atcgaagaaa aatttgaagc tggcatgtct    180
ttactaggct gggaagtaaa atctttacgt gccggtcgta tgagtttgac agaaagttat    240
gtcattttta aaaatggtga agcattctta tttggtgctc agattcaacc actcctttct    300
gcatctacac atattgtgcc ggaagctaca cgtacacgaa aattattatt atctcgtcgt    360
gaacttgaaa agcttatggg tgcggtgaac caaaaaggtt attcgtgcgt tccattagca    420
tgttactgga aaggtcatct ggttaagctt gaaattgcac tcgtgaaagg taaacaactt    480
cacgataaac gtgcgactga aaaagaacgt gactggcaac gtgataaagc acgtatattt    540
cataagtaat agactaaaaa gcctctttat agaggctttt ttatttttca ctaatttaat    600
ctatataaaa gcccagcaa                                                 619
```

<210> SEQ ID NO 71
<211> LENGTH: 619
<212> TYPE: DNA
<213> ORGANISM: Acinetobacter baumannii

<400> SEQUENCE: 71
tgatatgtgg gaaaaaactt caccttggca tcagtttacg gcacaatagg gacaattgtg 60
gaagtttgaa ttatggcgaa agcaacagta gtaaagaaac ataatggcgg aaccatcgca 120
caaaacaaac gtgcccgtca tgattatttt atcgaagaaa aatttgaagc tggcatgtct 180
ttactaggct gggaagtaaa atctttacgt gccggtcgta tgagtttgac agaaagttat 240
gtcattttta aaaatggtga agcattctta tttggtgctc agattcaacc actcctttct 300
gcatctacac atattgtgcc ggaagctacg cgtacacgaa aattattatt atctcgtcgt 360
gaacttgaaa agcttatggg tgcggtgaac caaaaaggtt attcgtgcgt tccattagca 420
tgttactgga aaggtcatct ggttaagctt gaaattgcac tcgtgaaagg taaacaactt 480
cacgataaac gagcgactga aaaagaacgt gactggcaac gtgataaagc acgtatattt 540
cataagtaat agactaaaaa gcctctttat agaggctttt ttatttttca ctaatttaat 600
ctatataaaa gcccagcaa 619

<210> SEQ ID NO 72
<211> LENGTH: 619
<212> TYPE: DNA
<213> ORGANISM: Acinetobacter baumannii

<400> SEQUENCE: 72
cattaaaatg aaaaaacttc acctcggtcg ttgtttaagg cacaataagc ataactttgg 60
aattttaaga ttatgtcgaa agcagtagta gttaaaaaaa ataatggcgg taccattgcg 120
cagaataaac gcgcccgaca cgattatttt attgaagaaa aatttgaagc aggtatgtct 180
ttgcaaggct gggaagtaaa atccttgcgt gcaggtcgta tgagccttac cgaaagctat 240
atcatcttta aaaatggtga agcctaccta tttggtgctc aaattcaacc gttgcttacc 300
gcatcgagcc atgttgtgcc tgaagccaca cggacacgta aattactact gtcacgtcgt 360
gaaattggtc aactactagg tgctgtcaat cagaaaggtt attcgtgtgt acctttggca 420
tgttactgga aaggtcactt ggtcaagctc gaaattgcac tggtgaaagg gaaacagtta 480
catgataagc gtgcaaccga aaaagatcgt gactggcaac gtgacaaagc acggattatg 540
cataagtaat ttatacaaaa agcctttact aaggcttttt gtttgattgt ttaatgcaaa 600
cggtaaagta acccaccga 619

<210> SEQ ID NO 73
<211> LENGTH: 619
<212> TYPE: DNA
<213> ORGANISM: Acinetobacter baumannii

<400> SEQUENCE: 73
tgatatgtgg gaaaaaactt caccttggca tcagtttacg gcacaatagg ggcaattgtg 60
gaagtttgaa ttatggcgaa agcaacagta gtaaagaaac ataatggcgg aaccatcgca 120
caaaataaac gtgcccgtca tgattatttt atcgaagaaa aatttgaagc tggcatgtct 180
ttactcggct gggaagtaaa gtctttacgt gctggtcgta tgagtttgac agaaagttat 240
gtcattttta aaaacggtga agcattttta tttggtgcgc aaattcaacc gctcctttct 300

```
gcatctacac atatcgtgcc ggaagctaca cgtacacgta aattattatt atctcgtcgt    360

gaacttgaaa agcttatggg tgcagtgaac caaaaaggtt attcgtgcgt tccattagca    420

tgttactgga aaggtcatct ggtcaagctt gaaattgcac tcgtgaaagg taaacaactc    480

cacgataaac gtgcgactga aaaagaacgt gactggcaac gtgataaagc ccgtatattt    540

cataaataat agactaaaaa gcctctataa agaggctttt ttattttttta ctaatttaat    600

ctatataaaa gtccagcaa                                                 619
```

<210> SEQ ID NO 74
<211> LENGTH: 572
<212> TYPE: DNA
<213> ORGANISM: Acinetobacter baumannii

<400> SEQUENCE: 74

```
aaaaacttca ccttagcatc agtttacggc acaatagggg caattgtgga agtttgaatt     60

atggcgaaag caacagtagt gaaaaaacat aatggtggaa ccatcgcaca aaacaaacgt    120

gcccgccatg attattttat cgaagaaaaa tttgaagctg gtatgtcttt actcggctgg    180

gaagtaaagt ctttacgtgc tggtcgcatg agtttgacag aaagttatgt catttttaag    240

aatggtgaag cgtttttatt tggtgcacaa attcaaccgc tcctttcagc atctactcat    300

gtagtacctg aagctacacg tacacgtaaa ttattattat cacgccgaga actagaaaag    360

ctaacaggtt cagttaacca aaaaggttac tcatgtgttc ctttagcatg ttactggaaa    420

ggtcacttgg ttaaacttga aatcgcgctt gtgaaaggta aacagcttca cgacaaacgt    480

gcgactgaaa aagatcgcga ttggcagcgt gataaagctc gtatatttca taagtaatta    540

aataaaaagc ctctttttag aggctttttt at                                  572
```

<210> SEQ ID NO 75
<211> LENGTH: 477
<212> TYPE: DNA
<213> ORGANISM: Acinetobacter calcoaceticus

<400> SEQUENCE: 75

```
atggcgaaag caacagtagt aaagaaacat aatggcggaa ccatcgcaca aaataaacgt     60

gcccgtcatg attattttat cgaagaaaaa tttgaagctg gtatgtcttt actcggctgg    120

gaagtaaagt ctttacgtgc tggtcgcatg agtttgacag aaagttatgt catttttaag    180

aatggtgaag cgtttttatt tggtgcacaa attcaaccgc tcctttcggc atctactcat    240

gtagtacctg aagctacacg tacacgtaaa ttattattat cacgccgaga actagaaaag    300

ctaacgggtt cagtgaacca aaaaggttac tcatgtgttc ctttggcatg ttattggaaa    360

ggtcacttgg tgaagcttga aatcgcgctt gtgaaaggta aacagcttca cgacaaacgt    420

gcgactgaaa aagatcgcga ttggcagcgt gataaagctc gtatatttca taagtaa       477
```

<210> SEQ ID NO 76
<211> LENGTH: 619
<212> TYPE: DNA
<213> ORGANISM: Acinetobacter calcoaceticus

<400> SEQUENCE: 76

```
gacgtgcagg aaaaacttca ccttagcatc agtttacggc acaatagggg caattgtgga     60

agtttgaatt atggcgaaag caacagtagt aaagaaacat aatggcggaa ccatcgcaca    120

aaataaacgt gcccgtcatg attattttat cgaagaaaaa tttgaagctg gtatgtcttt    180

actcggctgg gaagtaaagt ctttacgtgc tggtcgcatg agtttgacag aaagttatgt    240
```

-continued

```
catttttaag aatggtgaag cgtttttatt tggtgcacaa attcaaccgc tcctttcggc    300

atctactcat gtagtacctg aagctacacg tacacgtaaa ttattattat cacgccgaga    360

actagaaaag ctaacgggtt cagtgaacca aaaaggttac tcatgtgttc ctttggcatg    420

ttattggaaa ggtcacttgg tgaagcttga aatcgcgctt gtgaaaggta aacagcttca    480

cgacaaacgt gcgactgaaa aagatcgcga ttggcagcgt gataaagctc gtatatttca    540

taagtaatta aataaaaagc ctctttttag aggctttttt atatcgcgga atttattaat    600

ttaatctata taagagtcc                                                 619
```

<210> SEQ ID NO 77
<211> LENGTH: 572
<212> TYPE: DNA
<213> ORGANISM: Acinetobacter calcoaceticus

<400> SEQUENCE: 77

```
aaaaacttca ccttagcatc agtttacggc acaatagggg caattgtgga agtttgaatt     60

atggcgaaag caacagtagt gaaaaaacat aatggtggaa ccatcgcaca aaacaaacgt    120

gcccgccatg attattttat cgaagaaaaa tttgaagctg gtatgtcttt actcggctgg    180

gaagtaaagt ctttacgtgc tggtcgcatg agtttgacag aaagttatgt catttttaag    240

aatggtgaag cgtttttatt tggtgcacaa attcaaccgc tcctttcagc atctactcat    300

gtagtacctg aagctacacg tacacgtaaa ttattattat cacgccgaga actagaaaag    360

ctaacaggtt cagttaacca aaaaggttac tcatgtgttc ctttagcatg ttactggaaa    420

ggtcacttgg ttaaacttga aatcgcgctt gtgaaaggta aacagcttca cgacaaacgt    480

gcgactgaaa aagatcgcga ttggcagcgt gataaagctc gtatatttca taagtaatta    540

aataaaaagc ctctttttag aggctttttt at                                  572
```

<210> SEQ ID NO 78
<211> LENGTH: 614
<212> TYPE: DNA
<213> ORGANISM: Acinetobacter calcoaceticus

<400> SEQUENCE: 78

```
aaaaacttca ccttagcatc agtttacggc acaataggca taattgtgga agtttgaatt     60

atggcgaaag caacagtagt aaagaaacat aatggcggaa caatcgcaca aaataaacgt    120

gcccgtcatg attattttat cgaagaaaaa tttgaagcgg gcatgtcact tcaaggttgg    180

gaagtaaaat ccttacgtgc tgggcgcatg actttgacgg aaagttatgt cattttcaag    240

aatggcgaag catttttact tggctcacaa attcagcctt tattatcggc ttcgacccat    300

gtggtacctg aagcaacacg cacccgtaag ttattgctct cccgacgtca gcttgaacac    360

ctaatgggtg cagttaacca aaaaggttac tcatgtgttc ctttggcgtg ttactggaaa    420

ggtcacttgg ttaaacttga aattgcgctt gtgaaaggta aacagcttca cgacaaacgt    480

gcaactgaaa aagaccgcga ctggcagcgt gataaagctc gtatatttca taaataattt    540

aataaaaaag cctcttttta gaggcttttt atatttttga ctttattaat ttaatctata    600

taaaagccca gcaa                                                      614
```

<210> SEQ ID NO 79
<211> LENGTH: 539
<212> TYPE: DNA
<213> ORGANISM: Acinetobacter calcoaceticus

<400> SEQUENCE: 79
aaaaacttca ccttagcatc agtttacggc acaataggca taattgtgga agtttgaatt 60
atggcgaaag caacagtagt aaagaaacat aatggcggaa caatcgcaca aaataaacgt 120
gcccgtcatg attattttat cgaagaaaaa tttgaagcag gcatgtcact tcaaggttgg 180
gaagtaaaat ccttacgtgc tgggcgtatg actttgacgg aaagttatgt cattttcaag 240
aatagcgaag catttttact tggttcacaa attcagcctt tattatcggc ttcgacccat 300
gtggtacctg aagcaacacg tacccgtaag ttattgctct cccgccgtca gcttgaacac 360
ctgatgggtg cagttaacca aaaaggttac tcgtgcgttc ctttggcgtg ttactggaaa 420
ggtcacttgg ttaaacttga aattgcactt gtgaaaggta aacaacttca cgacaaacgt 480
gcaactgaaa aagaccgtga ctggcaacgt gataaagctc gtatatttca taagtaata 539

<210> SEQ ID NO 80
<211> LENGTH: 570
<212> TYPE: DNA
<213> ORGANISM: Acinetobacter calcoaceticus

<400> SEQUENCE: 80
aaaaacttca ccttagcatc agtttacggc acaataggca taattgtgga agtttgaatt 60
atggcgaaag caacagtagt gaaaaaacac aatggcggaa caatcgcaca aaacaaacgt 120
gcccgtcatg attattttat cgaagaaaaa tttgaagcag gcatgtcact tcaaggttgg 180
gaagtaaaat ccttacgtgc tggacgtatg actttgactg aaagttatgt gattttcaaa 240
aatggcgaag catttttact tggctcacaa attcagcctt tattatcagc ttcgactcat 300
gttgtacctg aagcaacacg tacccgtaag ttattgctct cccgacgtca gcttgaacac 360
ctaatgggtg cagttaacca gaaaggttac tcatgcgttc ctttagcgtg ttactggaag 420
ggtcatttag tcaaactaga gattgcactt gtgaagggta aacagcttca tgacaaacgt 480
gcaactgaaa aagaccgtga ctggcaacgt gataaagctc gtatatttca taagtaataa 540
aataaaagcc tcttttcaga ggcttttta 570

<210> SEQ ID NO 81
<211> LENGTH: 477
<212> TYPE: DNA
<213> ORGANISM: Acinetobacter calcoaceticus

<400> SEQUENCE: 81
atggcgaaag caacagtagt gaaaaaacac aatggcggaa caatcgcaca aaataaacgt 60
gcccgtcatg attattttat tgaagaaaaa tttgaagctg gtatgtcact tcaaggttgg 120
gaagtaaaat ccttacgtgc tgggcgtatg actttgacgg aaagttatgt cattttcaag 180
aatagcgaag catttttact tggttcacaa attcagcctt tattatcggc ttcgacccat 240
gtggtacctg aagcaacacg tacccgtaag ttattactct ccagacgtca gcttgaacac 300
ctaatgggtg cagttaacca aaaaggttac tcatgcgttc ctttggcgtg ttactggaaa 360
ggtcatttag tcaaacttga aattgcactt gtgaaaggta aacaacttca cgacaaacgt 420
gcaaccgaaa aagaccgtga ctggcaacgt gataaagctc gtatatttca taagtaa 477

<210> SEQ ID NO 82
<211> LENGTH: 539
<212> TYPE: DNA
<213> ORGANISM: Acinetobacter calcoaceticus

<400> SEQUENCE: 82

-continued

```
aaaaacttca ccttagcatc agtttacggc acaataggca taattgtgga agtttgaatt     60
atggcgaaag caacagtagt gaaaaaacac aatggcggaa caatcgcaca aaataaacgt    120
gcccgtcatg attattttat cgaagaaaaa tttgaagcgg gtatgtcact tcaaggttgg    180
gaagtaaaat ccttacgcgc tgggcgcatg actttgacgg aaagttatgt cattttcaag    240
aatggcgaag catttttact tggctcacaa attcagcctt tattatcggc ttcgacccat    300
gtggtacctg aagcaacacg cacccgtaag ttattactct cccgacgtca gcttgaacac    360
ctaatgggtg cagttaacca aaaaggttac tcatgcgttc ctttggcgtg ttactggaaa    420
ggtcatttag tcaaacttga aattgcgctt gtgaaaggta aacaacttca cgacaaacgt    480
gcaactgaaa aagaccgtga ctggcaacgt gataaagctc gtatatttca taagtaata     539
```

<210> SEQ ID NO 83
<211> LENGTH: 539
<212> TYPE: DNA
<213> ORGANISM: Acinetobacter calcoaceticus

<400> SEQUENCE: 83

```
aaaaacttca ccttagcatc agtttacggc acaataggca taattgtgga agtttgaatt     60
atggcgaaag caacagtagt gaaaaaacac aatggcggaa caatcgcaca aaataaacgt    120
gcccgtcatg attattttat cgaagaaaaa tttgaagcgg gtatgtcact tcaaggttgg    180
gaagtaaaat ccttacgtgc tgggcgtatg actttgacgg aaagttatgt cattttcaag    240
aatggcgaag catttttact tggctcacaa attcagcctt tattatcggc ttcgacccat    300
gtggtacctg aagcaacacg cacccgtaag ttattgctct cccgacgtca gcttgaacac    360
ctaatgggcg cagttaacca aaaaggttac tcatgtgttc ctttggcgtg ttactggaaa    420
ggtcacttgg ttaaacttga aattgcgctt gtgaaaggta aacagcttca cgacaaacgt    480
gcaactgaaa aagaccgtga ctggcaacgt gataaagctc gtatatttca taagtaata     539
```

<210> SEQ ID NO 84
<211> LENGTH: 539
<212> TYPE: DNA
<213> ORGANISM: Acinetobacter calcoaceticus

<400> SEQUENCE: 84

```
aaaaacttca ccttagcatc agtttacggc acaataggca taattgtgga agtttgaatt     60
atggcgaaag caacagtagt gaaaaaacac aatggcggaa caatcgcaca aaataaacgt    120
gcccgtcatg attattttat cgaagaaaaa tttgaagcgg gtatgtcact tcaaggttgg    180
gaagtaaaat ccttacgtgc tgggcgtatg actttgacgg aaagttatgt cattttcaag    240
aatggcgaag catttttact tggctcacaa attcagcctt tattatcggc ttcgacccat    300
gtggtacctg aagcaacacg cacccgtaag ttattgctct cccgacgtca gcttgaacac    360
ctaatgggcg cagttaacca aaaaggttac tcatgtgttc ctttggcgtg ttactggaaa    420
ggtcacttgg ttaaacttga aattgcgctt gtgaaaggta aacagcttca cgacaaacgt    480
gcaactgaaa aagaccgtga ctggcaacgt gataaagctc gtatatttca taagtaata     539
```

<210> SEQ ID NO 85
<211> LENGTH: 539
<212> TYPE: DNA
<213> ORGANISM: Acinetobacter calcoaceticus

<400> SEQUENCE: 85

-continued

```
aaaaacttca ccttagcatc agtttacggc acaataggca taattgtgga agtttgaatt     60

atggcgaaag caacagtagt gaaaaaacac aatggcggaa caatcgcaca aaataaacgt    120

gcccgtcatg attattttat cgaagaaaaa tttgaagcgg gtatgtcact tcaaggttgg    180

gaagtaaaat ccttacgtgc tgggcgtatg actttgacgg aaagttatgt cattttcaag    240

aatggcgaag catttttact tggctcacaa attcagcctt tattatcggc ttcaactcat    300

gtggtacctg aagcaacacg cacccgtaag ttattgctct cccgacgtca gcttgaacac    360

ctaatgggtg cagttaacca aaaaggttac tcatgcgttc ctttggcgtg ttactggaaa    420

ggtcatttag tcaaactaga aattgcgctt gtgaagggta aacaacttca tgacaaacgt    480

gcaactgaaa aagaccgtga ctggcaacgt gataaagctc gtatatttca taagtaata     539
```

<210> SEQ ID NO 86
<211> LENGTH: 465
<212> TYPE: DNA
<213> ORGANISM: Acinetobacter nosocomialis

<400> SEQUENCE: 86

```
agttgtaaag aaacataatg gcggaaccat cgcacaaaat aaacgtgccc gtcatgatta     60

ttttatcgaa gaaaaatttg aagctggcat gtctttactc ggctgggaag taaagtcttt    120

acgtgctggt cgtatgagtt tgacagaaag ttatgtcatt tttaaaaacg gtgaagcatt    180

tttatttggt gcacaaattc aaccgctcct ttctgcatct acacatatcg tgccggaagc    240

tacacgtaca cgtaaattat tattatctcg tcgtgaactt gaaaagctta tgggtgcagt    300

gaaccaaaaa ggttattcgt gcgttccatt agcgtgttac tggaaaggtc atctagtcaa    360

gcttgaaatt gcactcgtga aaggtaaaca actccacgat aaacgtgcaa ctgaaaaaga    420

acgtgactgg caacgtgata aagctcgtat atttcataaa taata                    465
```

<210> SEQ ID NO 87
<211> LENGTH: 465
<212> TYPE: DNA
<213> ORGANISM: Acinetobacter nosocomialis

<400> SEQUENCE: 87

```
agttgtaaag aaacataatg gcggaaccat cgcacaaaat aaacgtgccc gtcatgatta     60

ttttatcgaa gaaaaatttg aagctggcat gtctttactc ggctgggaag taaagtcttt    120

acgtgctggt cgtatgagtt tgacagaaag ttatgtcatt tttaaaaacg gtgaagcatt    180

tttatttggt gcacaaattc aaccgctcct ttctgcatct acacatatcg tgccggaagc    240

tacacgtaca cgtaaattat tattatctcg tcgtgaactt gaaaagctta tgggtgcagt    300

gaaccaaaaa ggttattcgt gcgttccatt agcgtgttac tggaaaggtc atctagtcaa    360

gcttgaaatt gcactcgtga aaggtaaaca actccacgat aaacgtgcaa ctgaaaaaga    420

acgtgactgg caacgtgata aagctcgtat atttcataaa taata                    465
```

<210> SEQ ID NO 88
<211> LENGTH: 619
<212> TYPE: DNA
<213> ORGANISM: Acinetobacter nosocomialis

<400> SEQUENCE: 88

```
tgatatgtgg gaaaaaactt caccttggca tcagtttacg gcacaatagg gacaattgtg     60

gaagtttgaa ttatggcgaa agcaacagta gtaaagaaac ataatggcgg aaccatcgca    120

caaaataaac gtgcccgtca tgattatttt atcgaagaaa aatttgaagc tggcatgtct    180
```

```
ttactcggct gggaagtaaa gtctttacgt gctggtcgta tgagtttgac agaaagttat    240

gtcattttta aaaacggtga agcattttta tttggtgcac aaattcaacc gctcctttct    300

gcatctacac atatcgtgcc ggaagctaca cgtacacgta aattattatt atctcgtcgt    360

gaacttgaaa agcttatggg tgcagtgaac caaaaaggtt attcgtgcgt tccattagcg    420

tgttactgga aaggtcatct ggtcaagctt gaaattgcac tcgtgaaagg taaacaactc    480

cacgataaac gtgcgactga aaaagaacgt gactggcaac gtgataaagc ccgtatattt    540

cataaataat agactaaaaa gcctctataa agaggctttt ttattttttta ctaatttaat    600

ctatataaaa gtccagcaa                                                 619
```

<210> SEQ ID NO 89
<211> LENGTH: 619
<212> TYPE: DNA
<213> ORGANISM: Acinetobacter nosocomialis

<400> SEQUENCE: 89

```
tgatatgtgg gaaaaaactt caccttggca tcagtttacg gcacaatagg ggcaattgtg     60

gaagtttgaa ttatggcgaa agcaactgta gtaaagaaac ataatggcgg aaccatcgca    120

caaaataaac gtgcccgtca tgattatttt atcgaagaaa aatttgaagc tggcatgtct    180

ttactcggct gggaagtaaa gtctttacgt gctggtcgta tgagtttgac agaaagttat    240

gtcattttta aaaacggtga agcattttta tttggtgcac aaattcaacc gctcctttct    300

gcatctacac atatcgtgcc ggaagctaca cgtacacgta aattattatt atctcgtcgt    360

gaacttgaaa agcttatggg tgcagtgaac caaaaaggtt attcgtgcgt tccattagca    420

tgttactgga aaggtcatct ggtcaagctt gaaattgcac tcgtgaaagg taaacaactc    480

cacgataaac gtgcgactga aaaagaacgt gactggcaac gtgataaagc ccgtatattt    540

cataaataat agactaaaaa gcctctataa agaggctttt ttattttttta ctaatttaat    600

ctatataaaa gtccagcaa                                                 619
```

<210> SEQ ID NO 90
<211> LENGTH: 533
<212> TYPE: DNA
<213> ORGANISM: Acinetobacter nosocomialis

<400> SEQUENCE: 90

```
agttgtaaag aaacataatg gcggaaccat cgcacaaaat aagcgtgccc gtcatgatta     60

ttttatcgaa gaaaaatttg aagctggcat gtctttactc ggctgggaag taaagtcttt    120

acgtgccggt cgtatgagtt tgacagaaag ttatgtcatt tttaaaaacg gtgaagcatt    180

tttatttggt gcacaaattc aaccgcttct ttctgcatct acacatattg tgccggaggc    240

tacacgtaca cgtaaattat tattatctcg tcgtgaactt gaaaagctta tgggtgcagt    300

gaaccaaaaa ggttattcgt gcgttccatt agcgtgttac tggaaaggtc atctggtcaa    360

gcttgaaatt gcactcgtga aaggtaaaca actccacgat aaacgtgcaa ctgaaaaaga    420

acgtgactgg caacgtgata aagcccgtat atttcataaa taatagacta aaaagcctct    480

ataaagaggc ttttttattt tttactaatt taatctatat aaaagtccag caa           533
```

<210> SEQ ID NO 91
<211> LENGTH: 533
<212> TYPE: DNA
<213> ORGANISM: Acinetobacter nosocomialis

<400> SEQUENCE: 91
agttgtaaag aaacataatg gcggaaccat cgcacaaaat aagcgtgccc gtcatgatta 60
ttttatcgaa gaaaaatttg aagctggcat gtctttactc ggctgggaag taaagtcttt 120
acgtgccggt cgtatgagtt tgacagaaag ttatgtcatt tttaaaaacg gtgaagcatt 180
tttatttggt gcacaaattc aaccgcttct ttctgcatct acacatattg tgccggaggc 240
tacacgtaca cgtaaattat tattatctcg tcgtgaactt gaaaagctta tgggtgcagt 300
gaaccaaaaa ggttattcgt gcgttccatt agcgtgttac tggaaaggtc atctggtcaa 360
gcttgaaatt gcactcgtga aaggtaaaca actccacgat aaacgtgcaa ctgaaaaaga 420
acgtgactgg caacgtgata aagcccgtat atttcataaa taatagacta aaaagcctct 480
ataaagaggc ttttttattt tttactaatt taatctatat aaaagtccag caa 533

<210> SEQ ID NO 92
<211> LENGTH: 572
<212> TYPE: DNA
<213> ORGANISM: Acinetobacter genomosp.

<400> SEQUENCE: 92
aaaaacttca ccttagcatc agtttacggc acaatagggg caattgtgga agtttgaatt 60
atggcgaaag caacagtagt aaagaaacat aatggcggaa ccatcgcaca aaataaacgt 120
gcccgtcatg attattttat cgaagaaaaa tttgaagctg gtatgtcttt actcggctgg 180
gaagtaaagt ctttacgtgc tggtcgcatg agtttgacag aaagttatgt catttttaag 240
aatggtgaag cgtttttatt tggtgcacaa attcaaccgc tcctttcggc atctactcat 300
gtagtacctg aagctacacg tacacgtaaa ttattattat cacgccgaga actagaaaag 360
ctaacgggtt cagttaacca aaaaggttac tcatgtgttc ctttagcatg ttattggaaa 420
ggtcacttgg tgaagcttga aatcgcgctt gtgaaaggta aacagcttca cgacaaacgt 480
gcgactgaaa aagatcgcga ttggcagcgt gataaagctc gtatatttca taagtaatta 540
aataaaaagc ctctttttag aggctttttt at 572

<210> SEQ ID NO 93
<211> LENGTH: 613
<212> TYPE: DNA
<213> ORGANISM: Acinetobacter genomosp.

<400> SEQUENCE: 93
aaaaacttca ccttagcatc agtttacggc acaataggca taattgtgga agtttgaatt 60
atggcgaaag caacagtagt aaagaaacat aatggcggaa ccatcgcaca aaacaaacgt 120
gcccgccatg attattttat cgaagaaaaa tttgaagctg gtatgtcttt actcggttgg 180
gaagtaaagt ctttacgtgc tggtcgcatg agtttgacag aaagttatgt catttttaag 240
aatggtgaag cgtttttatt tggtgcacaa attcaaccgc tcctttcagc atctactcat 300
gtagtacctg aagctacacg tacacgtaaa ttattattat cgcgccgaga actagaaaag 360
ctaacaggtt cagttaacca aaaaggttac tcatgtgttc ctttggcatg ttactggaaa 420
ggtcacttgg ttaaacttga aatcgcgctt gtgaaaggta aacagcttca cgacaaacgt 480
gcgactgaaa aagatcgcga ttggcagcgt gataaagctc gtatatttca taagtaatta 540
aataaaaagc ctctttttag aggcttttta tatcgcggaa tttattaatt taatctatat 600
aagagtccag caa 613

-continued

<210> SEQ ID NO 94
<211> LENGTH: 619
<212> TYPE: DNA
<213> ORGANISM: Acinetobacter oleivorans

<400> SEQUENCE: 94
ttcatgtgca ggaaaaactt caccttagca tcagtttacg gcacaatagg cataattgtg 60
gaagtttgaa ttatggcgaa agcaacagta gtaaagaaac ataatggcgg aacaatcgca 120
caaaataagc gtgcccgtca tgattatttt atcgaagaaa aatttgaagc aggcatgtca 180
cttcaaggtt gggaagtaaa atccttacgt gctgggcgta tgactttgac ggaaagttat 240
gtcattttca aaaatggcga agcatttttta cttggttcac aaattcagcc tttattatcg 300
gcttcgaccc atgttgtacc tgaggcaaca cgtacccgta aactattgct ctcccgacgt 360
cagcttgaac atctaatggg tgcagttaac cagaaaggct actcatgtgt tcctttagcg 420
tgttattgga aaggtcattt agtcaaactg gagattgcac ttgtgaaggg taaacagctt 480
catgacaaac gtgcaaccga aaaagaccgt gactggcaac gtgataaagc tcgtatattt 540
cataagtaat aaaacaaaag cctcttttca gaggcttttt tacgtcgtga agttcattag 600
tttaatctgt ataaaagtc 619

<210> SEQ ID NO 95
<211> LENGTH: 615
<212> TYPE: DNA
<213> ORGANISM: Acinetobacter pittii

<400> SEQUENCE: 95
aaaaacttca ccttagcatc agtttacggc acaatagagg caattgtgga agtttgaatt 60
atggcgaaag caacagtagt aaagaaacat aatggcggaa ccatcgcaca aaataaacgt 120
gcccgtcatg attattttat cgaagaaaaa tttgaagctg gtatgtcttt actcggctgg 180
gaagtaaagt ctttacgtgc tggtcgcatg agtttgacag aaagttatgt catttttaag 240
aatggtgaag cgtttttatt tggtgcacaa attcaaccgc tcctttcggc gtctactcat 300
gtagtacctg aagctacacg tacacgtaaa ttattattat cacgccgaga actagaaaag 360
ctaacaggtt cagtgaacca aaaaggttac tcatgtgttc ctttagcatg ttattggaaa 420
ggtcacttgg ttaaacttga aattgctctg gtgaaaggta aacagcttca tgacaaacgt 480
gcgactgaaa aagatcgcga ttggcaacgt gataaagctc gtatatttca taagtaatta 540
aataaaaagc ctctttctta gaggcttttt tacatcgtaa agtttattaa tttaatctat 600
ataaaagacc agcaa 615

<210> SEQ ID NO 96
<211> LENGTH: 572
<212> TYPE: DNA
<213> ORGANISM: Acinetobacter pittii

<400> SEQUENCE: 96
aaaaacttca ccttagcatc agtttacggc acaatagggg caattgtgga agtttgaatt 60
atggcgaaag cgacagtagt gaaaaaacat aatggcggaa ccatcgcaca aaacaaacgt 120
gcccgccatg attattttat cgaagaaaaa tttgaagctg gtatgtcttt actaggctgg 180
gaagtaaagt ctttacgtgc tggtcggatg agcttgacag aaagttatgt catttttaag 240
aatggtgaag cgtttttatt tggtgcacaa attcaaccgc tcctttcagc atctactcat 300
gtagtacctg aagctacacg tacacgtaaa ttattattat cacgccgaga actagaaaag 360
ctaacaggtt cagttaacca aaaaggttac tcatgtgttc ctttggcatg ttactggaaa 420
ggtcacttgg ttaaacttga aatcgcgctt gtgaaaggta aacaacttca cgacaaacgt 480
gcgactgaaa aagatcgcga ttggcagcgt gataaagctc gtatatttca taagtaatta 540
aataaaaagc ctctttttag aggctttttt at 572

<210> SEQ ID NO 97
<211> LENGTH: 572
<212> TYPE: DNA
<213> ORGANISM: Acinetobacter pittii

<400> SEQUENCE: 97
aaaaacttca ccttagcatc agtttacggc acaatagggg caattgtgga agtttgaatt 60
atggcgaaag caacagtagt gaaaaaacat aatggtggaa ccatcgcaca aaacaaacgt 120
gcccgccatg attattttat cgaagaaaaa tttgaagctg gtatgtcttt actcggctgg 180
gaagtaaagt ctttacgtgc tggtcgcatg agtttgacag aaagttatgt catttttaag 240
aatggtgaag cgtttttatt tggtgcacaa attcaaccgc tcctttcagc atctactcat 300
gtagtacctg aagctacacg tacacgtaaa ttattattat cacgccgaga actagaaaag 360
ctaacaggtt cagttaacca aaaaggttac tcatgtgttc ctttagcatg ttactggaaa 420
ggtcacttgg ttaaacttga aatcgcgctt gtgaaaggta aacagcttca cgacaaacgt 480
gcgactgaaa aagatcgcga ttggcagcgt gataaagctc gtatatttca taagtaatta 540
aataaaaagc ctctttttag aggctttttt at 572

<210> SEQ ID NO 98
<211> LENGTH: 572
<212> TYPE: DNA
<213> ORGANISM: Acinetobacter pittii

<400> SEQUENCE: 98
aaaaacttca ccttagcatc agtttacggc acaatagggg caattgtgga agtttgaatt 60
atggcgaaag caacagtagt aaagaaacat aatggcggaa ccatcgcaca aaataaacgt 120
gcccgtcatg attattttat cgaagaaaaa tttgaagctg gtatgtcttt actcggctgg 180
gaagtaaagt ctttacgtgc tggtcgcatg agtttgacag aaagttatgt catttttaag 240
aatggtgaag cgtttttatt tggtgcacaa attcaaccgc tcctttcggc atctactcat 300
gtagtacctg aagctacacg tacacgtaaa ttattattat cacgccgaga actagaaaag 360
ctaacgggtt cagttaacca aaaaggttac tcatgtgttc ctttagcatg ttattggaaa 420
ggtcacttgg tgaagcttga aatcgcgctt gtgaaaggta aacagcttca cgacaaacgt 480
gcgactgaaa aagatcgcga ttggcagcgt gataaagctc gtatatttca taagtaatta 540
aataaaaagc ctctttttag aggctttttt at 572

<210> SEQ ID NO 99
<211> LENGTH: 572
<212> TYPE: DNA
<213> ORGANISM: Acinetobacter pittii

<400> SEQUENCE: 99
aaaaacttca ccttagcatc agtttacggc acaatagggg caattgtgga agtttgaatt 60
atggcgaaag cgacagtagt gaaaaaacat aatggcggaa ccatcgcaca aaacaaacgt 120
gcccgccatg attattttat cgaagaaaaa tttgaagctg gtatgtcttt actcggctgg 180
gaagtaaagt ctttacgtgc tggtcggatg agcttgacag aaagttatgt catttttaag 240
aatggtgaag cgtttttatt tggtgcacaa attcaaccgc tcctttcagc atctactcat 300
gtagtacctg aagctacacg tacacgtaaa ttattattat cacgccgaga actagaaaag 360
ctaacaggtt cagttaacca aaaaggttac tcatgtgttc ctttagcatg ttactggaaa 420
ggtcacttgg ttaaacttga aatcgcgctt gtgaaaggta aacaacttca cgacaaacgt 480
gcgactgaaa aagatcgcga ttggcagcgt gataaagctc gtatatttca taagtaatta 540
aataacaagc ctctttttag aggctttttt at 572

<210> SEQ ID NO 100
<211> LENGTH: 539
<212> TYPE: DNA
<213> ORGANISM: Acinetobacter pittii

<400> SEQUENCE: 100
aaaaacttca ccttagcatc agtttacggc acaatagggg caattgtgga agtttgaatt 60
atggcgaaag caacagtagt aaagaaacat aatggcggaa ccatcgcaca aaacaaacgt 120
gcccgccatg attattttat cgaagaaaaa tttgaagctg gtatgtcttt actcggctgg 180
gaagtaaagt ctttacgtgc tggtcgcatg agtttgacag aaagttatgt catttttaag 240
aatggtgaag cgtttttatt tggtgcacaa attcaaccgc tcctttctgc ctctactcat 300
gtagtacctg aagctacacg tacacgtaaa ttattattat cacgccgaga actagaaaag 360
ttaacaggtt cagttaacca aaaaggttac tcatgtgttc ctttggcatg ttactggaaa 420
ggtcacttgg ttaaacttga aattgccctt gtgaaaggta agcagcttca tgacaaacgt 480
gcgactgaaa aagatcgcga ttggcagcgt gataaagctc gtatatttca taagtaata 539

<210> SEQ ID NO 101
<211> LENGTH: 517
<212> TYPE: DNA
<213> ORGANISM: Acinetobacter junii

<400> SEQUENCE: 101
tttacggcac aatagatgca attgtggaag tttgaattat ggcgcaagca acagttgtaa 60
aaaaacataa tggtggcacg attgctcaaa ataaaagagc gcgtcacgat tactttatcg 120
aagaaaaatt tgaagcaggc atgtcacttc agggttggga agtaaaatcc ttacgtgctg 180
gacgtatgac cttgtctgaa agttatgtca tttttaaaaa tggtgaagcc tttttatttg 240
gttcacagat tcagccttta ttgtctgcat caacccatgt cgtacctgaa tcgacacgta 300
cacgaaagtt attattatct cgtcgtgaac tagaaaagtt actaggtgct gtgaaccaaa 360
aaggttattc atgtgttcct ttagcctgct attggaaagg tcacttggtt aagctcgaaa 420
ttgcgttggt caaaggtaag caattacatg acaaacgtgc tacggaaaaa gaccgtgatt 480
ggcagcgtga taaagcacgt atgttgcata aataata 517

<210> SEQ ID NO 102
<211> LENGTH: 517
<212> TYPE: DNA
<213> ORGANISM: Acinetobacter junii

<400> SEQUENCE: 102
tttacggcac aatagatgca attgtggaag tttgaattat ggcgcaagca acagttgtaa 60
aaaaacataa tggtggcacg attgctcaaa ataaaagagc gcgtcacgat tattttatcg 120
aagaaaaatt tgaagcaggc atgtcacttc agggttggga agtaaaatcc ttacgcgctg 180

```
gacgtatgac cttgtctgaa agttatgtca tttttaaaaa tggtgaagcc tttttatttg    240

gttcacagat tcagccttta ttgtctgcat caacccatgt cgtacctgaa tcaacacgta    300

cacgaaagtt attattatct cgtcgtgaac tagaaaagtt actaggcgca gtgaaccaaa    360

aaggttattc atgtgttcct ttagcctgct attggaaagg tcacttggtt aagctcgaaa    420

ttgcgttggt caaaggtaag caattacatg acaaacgtgc tacggaaaaa gaccgtgatt    480

ggcagcgtga taaagcacgt atgttgcata aataata                              517
```

```
<210> SEQ ID NO 103
<211> LENGTH: 517
<212> TYPE: DNA
<213> ORGANISM: Acinetobacter junii

<400> SEQUENCE: 103

tttacggcac aatagatgca attgtggaag tttgaattat ggcgcaagca acagttgtaa     60

aaaaacataa tggtggcacg attgctcaga ataaaagagc gcgtcacgat tactttatcg    120

aagaaaaatt tgaagcaggc atgtcacttc agggttggga agtaaaatcc ttacgtgctg    180

gacgtatgac attgtctgaa agttatgtca tttttaaaaa tggtgaagcc tttttatttg    240

gttcacagat tcagccttta ttgtctgcat caacccatgt cgtacctgaa tcgacacgta    300

cacgaaagtt attattatct cgtcgtgaac tagaaaagtt actaggcgca gtgaaccaaa    360

aaggttattc atgtgttcct ttagcctgct attggaaagg tcacttggtt aagctcgaaa    420

ttgcgttggt caaaggtaag caattacatg acaaacgtgc tacggaaaaa gaccgtgatt    480

ggcagcgtga taaagcacgt atgttgcata aataata                              517
```

```
<210> SEQ ID NO 104
<211> LENGTH: 517
<212> TYPE: DNA
<213> ORGANISM: Acinetobacter junii

<400> SEQUENCE: 104

tttacggcac aatagatgca attgtggaag tttgaattat ggcgcaagca acagttgtaa     60

aaaaacataa tggtggcacg attgctcaga ataaaagagc gcgtcacgat tactttatcg    120

aagaaaaatt tgaagcaggc atgtcacttc agggttggga agtaaaatcc ttacgtgctg    180

gacgtatgac attgtctgaa agttatgtca tttttaaaaa tggtgaagcc tttttatttg    240

gttcacagat tcagccttta ttgtctgcat caacccatgt cgtacctgaa tcgacacgta    300

cacgaaagtt attattatct cgtcgtgaac tagaaaagtt actaggcgca gtgaaccaaa    360

aaggttattc atgtgttcct ttagcctgct attggaaagg tcacttggtt aagctcgaaa    420

ttgcgttggt caaaggtaag caattacatg acaaacgtgc tacggaaaaa gaccgtgatt    480

ggcagcgtga taaagcacgt atgttgcata aataata                              517
```

```
<210> SEQ ID NO 105
<211> LENGTH: 517
<212> TYPE: DNA
<213> ORGANISM: Acinetobacter junii

<400> SEQUENCE: 105

tttacggcac aatagatgca attgtggaag tttgaattat ggcgcaagca acagttgtaa     60

aaaaacataa tggtggcacg attgctcaga ataaaagagc gcgtcacgat tactttatcg    120

aagaaaaatt tgaagcaggc atgtcacttc agggttggga agtaaaatcc ttacgtgctg    180

gacggatgac tttgtctgaa agttatgtca tttttaaaaa tggtgaagcc tttttatttg    240
```

gttcacagat tcagccttta ttgtctgcat caacccatgt cgtacctgaa tcaacacgta 300
cacgaaagtt attattatct cgtcgcgaac tagaaaagtt actaggcgca gtgaaccaaa 360
aaggttattc atgtgttcct ttagcctgct attggaaagg tcacttggtt aagctcgaaa 420
ttgcgttggt caaaggtaag caattacatg acaaacgtgc tacggaaaaa gaccgtgatt 480
ggcagcgtga taaagcacgt atgttgcata aataata 517

<210> SEQ ID NO 106
<211> LENGTH: 517
<212> TYPE: DNA
<213> ORGANISM: Acinetobacter junii

<400> SEQUENCE: 106
tttacggcac aatagatgca attgtggaag tttgaattat ggcgcaagca acagttgtaa 60
aaaaacataa tggtggcacg attgctcaga ataaaagagc gcgtcacgat tactttatcg 120
aagaaaaatt tgaagcaggc atgtcacttc agggttggga agtaaaatcc ttacgtgctg 180
gacggatgac tttgtctgaa agttatgtca tttttaaaaa tggtgaagcc tttttatttg 240
gttcacagat tcagccttta ttgtctgcat caacccatgt cgtacctgaa tcaacacgta 300
cacgaaagtt attattatct cgtcgcgaac tagaaaagtt actaggcgca gtgaaccaaa 360
aaggttattc atgtgttcct ttagcctgct attggaaagg tcacttggtt aagctcgaaa 420
ttgcgttggt caaaggtaag caattacatg acaaacgtgc tacggaaaaa gaccgtgatt 480
ggcagcgtga taaagcacgt atgttgcata aataata 517

<210> SEQ ID NO 107
<211> LENGTH: 546
<212> TYPE: DNA
<213> ORGANISM: Acinetobacter gyllenbergii

<400> SEQUENCE: 107
tttacggcac aatagagcca attgtggaag tttaaattat ggcgcaagca acagttgtaa 60
aaaaacataa tggtggcacg attgctcaaa ataaaagagc gcgccacgat tactttatcg 120
aagaaaaatt tgaagcaggc atgtccctac aaggttggga agtaaaatcc ctacgtgctg 180
ggcgtatgag cttgactgaa agttatgtca tttttaaaaa tggtgaagct tttttattgg 240
gctcacaaat tcagcccttg ttgtctgcct caactcatgt ggttccagaa gcaacacgta 300
cgcgtaaatt actgctctct cgtcgtgagc tagaaaagct tttgggtgca gtgaatcaaa 360
aaggctattc atgtgtacct ttggcatgtt attggaaagg ccatttggtc aaacttgaaa 420
ttgcactggt gaaaggtaag caattacatg acaagcgtgc cactgaaaaa gaccgtgact 480
ggcaacgtga taaatctcgt ctgctgcata agtaataaaa aaacctccaa ttggaggttt 540
ttttat 546

<210> SEQ ID NO 108
<211> LENGTH: 546
<212> TYPE: DNA
<213> ORGANISM: Acinetobacter gyllenbergii

<400> SEQUENCE: 108
tttacggcac aatagagcca attgtggaag tttaaattat ggcgcaagca acagttgtaa 60
aaaaacataa tggtggcacg attgctcaaa ataaaagagc gcgccacgat tactttatcg 120
aagaaaaatt tgaagcaggc atgtccctac aaggttggga agtaaaatcc ctacgtgctg 180
ggcgtatgag cttgactgaa agttatgtca tttttaaaaa tggtgaagct tttttattgg 240
gctcacaaat tcagcccttg ttgtctgcct caactcatgt ggttccagaa gcaacacgta 300
cgcgtaaatt actgctctct cgtcgtgagc tagaaaagct tttgggtgca gtgaatcaaa 360
aaggctattc atgtgtacct ttggcatgtt attggaaagg ccatttggtc aaacttgaaa 420
ttgcactggt gaaaggtaag caattacatg acaagcgtgc cactgaaaaa gaccgtgact 480
ggcaacgtga taaatctcgt ctgctgcata agtaataaaa aaacctccaa ttggaggttt 540
ttttat 546

<210> SEQ ID NO 109
<211> LENGTH: 517
<212> TYPE: DNA
<213> ORGANISM: Acinetobacter beijerinckii

<400> SEQUENCE: 109
tttacggcac aataggcata attgtggaag tttgaattat ggcgaaagca actgtagtta 60
aaaaaaataa tggtggaacg attgctcaaa acaaaagagc gcgtcacgat tactttattg 120
aagaaaaaat tgaagctggt atgtctttac aaggctggga agtgaaatca cttcgtgccg 180
gtcgtatgac tctgactgaa agctatgtca tttttaaaaa tggtgaagca tttttactgg 240
gttcacaaat tcagccttta ttgtcagcat caagtcatgt ggttcctgag gcaactcgta 300
cacgtaagtt actactttct cgccgtgaga tagatagact aatgggcgca gtgaatcaga 360
aaggttattc atgtgttcct ctggcatgtt attggaaagg tcctttggtt aaactagaaa 420
ttgccatggt taaaggtaaa cagttacacg ataaacgtgc aactgaaaaa gatcgtgact 480
ggcaacgaga taaatcacgt atgttgcata aataata 517

<210> SEQ ID NO 110
<211> LENGTH: 517
<212> TYPE: DNA
<213> ORGANISM: Acinetobacter beijerinckii

<400> SEQUENCE: 110
tttacggcac aataggcata attgtggaag tttgaattat ggcgaaagca actgtagtta 60
aaaaaaataa tggtggaacg attgctcaaa acaaaagagc gcgtcacgat tactttattg 120
aagaaaaaat tgaagctggt atgtctttac aaggctggga agtgaagtca cttcgtgccg 180
gtcgtatgac gctgactgaa agctatgtca tttttaaaaa tggtgaagca tttttactgg 240
gttcacaaat tcagccttta ttatcagcat caagtcatgt ggttcctgag gcaactcgta 300
cacgtaagtt actactttct cgccgtgaga tagatagact aatgggcgca gtgaatcaga 360
aaggttattc atgtgttcct ctggcatgtt attggaaagg tcctttggtt aaactagaaa 420
ttgccatggt taaaggtaaa cagttacacg ataaacgtgc aactgaaaaa gatcgtgact 480
ggcaacgaga taaatcacgt atgttgcata aataata 517

<210> SEQ ID NO 111
<211> LENGTH: 531
<212> TYPE: DNA
<213> ORGANISM: Acinetobacter brisouii

<400> SEQUENCE: 111
aaaagcttca ccttgggaaa agtttgcggc acaatagata cagttttgga atgatttaat 60
tatggcgaaa gcaactgtag tcaagaaaaa taatggcgga actattgcac aaaataagcg 120
tgcccgtcat gattatttta tcgaagaaaa atttgaagcg ggtctttccc tacagggttg 180

```
ggaagtcaaa tccttgcgtg ctgggcgtat gagtctggtt gagagctata ttatttttaa    240

aaataatgaa gcgtttttat ttggcgcaca gattcagcca ctcttgtctg cctcaactca    300

tgtcgtaccc gaagccactc gcactcgcaa actattactg tcacgccgtg aactggaaca    360

gctcacaggc gcagtaaatc aaaaaggtta cacttgtgta cctttagcat gttactggaa    420

aggacatttg gcgaaactgg aaattgcgct ggtaaaaggt aagcaactcc atgataaacg    480

cgctactgaa aaagaccgcg actggcaacg tgataaagcc cgtatttttc a             531
```

<210> SEQ ID NO 112
<211> LENGTH: 574
<212> TYPE: DNA
<213> ORGANISM: Acinetobacter lwoffii

<400> SEQUENCE: 112

```
gaaaaaactt caccttaacc atgctttaag gcacaatagg tacattgttg gaagtaattg     60

attatggcga aagcaactgt agttaaaaaa aataccagcg ggacgattgc acagaataaa    120

cgtgcacgtc acgactattt tattgaagaa aaatttgaag ctggcctgtc actgcaaggc    180

tgggaagtga aatcattacg tgcaggtcgt atgacgctgt ctgagagtta tatcaccttt    240

aaaaatggtg aagctttcct gttcggtgct caaattcagc ctttactcag tgcatctacg    300

cacattgttc ctgaagcgac ccgtacccgt aagttactgt tgaaccgtcg tgaactggat    360

aagctactcg gcgcagtgaa tcaaaaaggt tattcgtgtg ttccacttgt tgcttattgg    420

aaaggaccac gtgcgaaatt agaaatcgct ttagtgaaag gcaaacagct gcatgacaaa    480

cgtgccacgg aaaaagaccg tgactggcaa cgtgataaag cccgtattat gcataaataa    540

taaaaaacct cccatgtgga ggttttttat tatc                                574
```

<210> SEQ ID NO 113
<211> LENGTH: 551
<212> TYPE: DNA
<213> ORGANISM: Acinetobacter lwoffii

<400> SEQUENCE: 113

```
aaaaaacttc accttatttc tagttgcggt acaatagcag cacgtttgga agtatcagat     60

tatggcgaaa gcatctattg tagtaaaaaa aaataatggc ggtaccattg cactgaataa    120

acgtgcccgc cacgattatt ttattgaaga gaaatttgaa gcggggctgt cattaaaggg    180

ctgggaagtc aaatcaatgc gtgccggtcg tatgaccatt gtagaaagct atattacctt    240

taaaaatggt gaagctttcc tgtttggtgc gcaagttcag cctttgctga gtgcttcaac    300

acacgtggtg cctgaagcga cccgtacccg aaaactgttg ttgaatcgcc gtgaaattga    360

aaagctgatg ggcgcgatta accagaaagg ttattcctgc gtgccactgg cctgttactg    420

gaaaggcccg catgccaagc tggaaattgc actggtcaaa ggtaagcagc ttcatgacaa    480

acgtgccacc gagaaagacc gtgactggca acgtgataag gcgcgaattt tccataaata    540

atggattaaa a                                                         551
```

<210> SEQ ID NO 114
<211> LENGTH: 551
<212> TYPE: DNA
<213> ORGANISM: Acinetobacter lwoffii

<400> SEQUENCE: 114

```
aaaaaacttc accttatttc tagttgcggt acaatagcag cacgtttgga agtatcagat     60
```

tatggcgaaa gcatctattg tagtaaaaaa aaataatggc ggtaccattg cactgaataa 120
acgtgcccgc cacgattatt ttattgaaga gaaatttgaa gcggggcttt cattaaaagg 180
ctgggaagtc aaatcaatgc gtgctggtcg catgaccatc gtagaaagtt atattacctt 240
taaaaatggt gaagcgttct tgtttggtgc acaggttcag cccttgttaa gtgcttcgac 300
ccatgtggtg cctgaagcaa cccgtacccg caaactgttg ctgaatcgcc gtgaaattga 360
aaagttgatg ggtgcgatta accagaaagg ttattcctgc gttccactgg cctgctactg 420
gaaaggtcca catgccaagc tggaaattgc tctggtgaaa ggtaagcagc ttcatgacaa 480
acgtgccacc gaaaaagacc gtgactggca acgtgataag gcgcgaattt tccataaata 540
atggattaaa a 551

<210> SEQ ID NO 115
<211> LENGTH: 551
<212> TYPE: DNA
<213> ORGANISM: Acinetobacter lwoffii

<400> SEQUENCE: 115
aaaaaacttc accttatttc tagttgcggt acaatagcag cacgtttgga agtatcagat 60
tatggcgaaa gcatctattg tagtaaaaaa aaataatggc ggtaccattg cactgaataa 120
acgtgcccgc cacgattatt ttattgaaga gaaatttgaa gcggggcttt cattaaaagg 180
ctgggaagtc aaatcaatgc gtgctggtcg catgaccatc gtagaaagtt atattacctt 240
taaaaatggt gaagcgttct tgtttggtgc acaggttcag cccttgttaa gtgcttcgac 300
ccatgtggtg cctgaagcaa cccgtacccg caaactgttg ctgaatcgcc gtgaaattga 360
aaagttgatg ggtgcgatta accagaaagg ttattcctgc gttccactgg cctgctactg 420
gaaaggtcca catgccaagc tggaaattgc tctggtgaaa ggtaagcagc ttcatgacaa 480
acgtgccacc gaaaaagacc gtgactggca acgtgataag gcgcgaattt tccataaata 540
atggattaaa a 551

<210> SEQ ID NO 116
<211> LENGTH: 552
<212> TYPE: DNA
<213> ORGANISM: Acinetobacter lwoffii

<400> SEQUENCE: 116
aaaaaacttc accttatttc tagttgcggt acaatagcag cacgtttgga agtatcagat 60
tatggcgaaa gcatctattg tagtaaaaaa aaataatggc ggtaccattg cactgaataa 120
acgtgcccgc cacgattatt ttattgaaga gaaatttgaa gcggggcttt cattaaaagg 180
ctgggaagtc aaatcaatgc gcgctggtcg catgaccatt gtagaaagtt atattacctt 240
taaaaatggt gaagcgttct tgtttggtgc acaggttcag cccttgttaa gtgcttcgac 300
ccatgtggtg cctgaagcaa cccgtacccg caaactgttg ctgaatcgcc gtgaaattga 360
aaagttgatg ggtgcgatta accagaaagg ttattcctgc gttccactgg cctgctactg 420
gaaaggtcca catgccaagc tggaaattgc tctggtcaaa ggtaagcagc tccatgacaa 480
acgtgccacc gaaaaagacc gtgactggca acgtgataaa gcacgaattt tccataaata 540
atggattaaa aa 552

<210> SEQ ID NO 117
<211> LENGTH: 550
<212> TYPE: DNA
<213> ORGANISM: Acinetobacter lwoffii

<400> SEQUENCE: 117
aaaaaacttc accttatttc tagttgcggt acaatagcag cacgtttgga agtatcagat 60
tatggcgaaa gcatctattg tagtaaaaaa aataatggcg gtaccattgc actgaataaa 120
cgtgcccgcc acgattattt tattgaagag aaatttgaag cggggctttc attaaaaggc 180
tgggaagtca aatcaatgcg cgctggtcgc atgaccattg tagaaagtta tattaccttt 240
aaaaatggtg aagcgttctt gtttggtgca caggttcagc ccttgttaag tgcttcgacc 300
catgtggtgc ctgaagcaac ccgtacccgc aaactgttgc tgaatcgccg tgaaattgaa 360
aagttgatgg gtgcgattaa ccagaaaggt tattcctgcg ttccactggc ctgctactgg 420
aaaggtccac atgccaagct ggaaattgct ctggtcaaag gtaagcagct tcatgacaaa 480
cgtgccaccg aaaaagaccg tgactggcaa cgtgataaag cgcgaatttt ccataaataa 540
tggattaaaa 550

<210> SEQ ID NO 118
<211> LENGTH: 551
<212> TYPE: DNA
<213> ORGANISM: Acinetobacter lwoffii

<400> SEQUENCE: 118
aaaaaacttc accttatttc tagttgcggt acaatagcag cacgtttgga agtatcagat 60
tatggcgaaa gcatctattg tagtaaaaaa aaataatggc ggtaccattg cactgaataa 120
acgtgcccgc cacgattatt ttattgaaga gaaatttgaa gcggggcttt cattaaaagg 180
ttgggaagtc aaatcaatgc gtgctggtcg catgaccatc gtagaaagtt atattacctt 240
taaaaatggt gaagcgttct tgtttggtgc acaggttcag cccttgttaa gcgcttcgac 300
ccatgtggtg cctgaagcaa cccgtactcg caagctgttg ctgaatcgcc gtgaaattga 360
aaagctgatg ggtgcgatta accagaaagg ttattcctgc gtaccactgg cgtgttactg 420
gaaaggtcca catgccaaac tggaaattgc cttggtgaaa ggtaagcaac tccatgacaa 480
acgtgccacc gaaaaagacc gtgactggca acgtgataaa gcgcgaattt tccataaata 540
atggattaaa a 551

<210> SEQ ID NO 119
<211> LENGTH: 464
<212> TYPE: DNA
<213> ORGANISM: Listeria grayi

<400> SEQUENCE: 119
tgccaaaagg tgaaggaaaa ttaattgcgc aaaataaaaa agccagacat gattttgcaa 60
tcgaagaaac ttttgaagcc ggcattgtct tgcaaggaac agagatcaaa tccgttcgta 120
atgcacgagt gaacttaaag gattcttacg cccgcatcga acgcggagaa attttttttac 180 acaacatgca tatcagccct tacgaccaag ggaatagatt caatcatgac ccacttcgaa 240
ctcgtaaatt gttattgcac aaaaaacaaa tcagccgtct gattggcgaa acaaaagaag 300
ctggctattc gatcgtcccc ctaaagctct atatcaaaga tggatttgca aaagtcttga 360
tcggtgtagc taaagggaag aaaaaatatg acaaacgcga agatttgaaa cgcaaagaag 420
caaaacgtga tattgaacga gcgtttaaag aaagacaacg ataa 464

<210> SEQ ID NO 120
<211> LENGTH: 465
<212> TYPE: DNA

<213> ORGANISM: Listeria monocytogenes

<400> SEQUENCE: 120
atgccaaaag gtgatggtaa gctagtcgcg caaaataaaa aagcgcgcca cgattacgca 60
attgaagaaa cttttgaggc tggcattgtc ctgcaaggta ctgaaattaa atccgtaaga 120
aacgcacggg taaacttaaa agattcctat gcacgtatcg acaaagggga aattttctta 180
cacaatatgc atattagtcc ttatgaacaa gggaaccgct acaatcatga tccactaaga 240
acgcgcaagt tgctcttaca taagaagcaa atcagccgtt taattggaga aacgaaagag 300
tccggttatt cgattgttcc actaaaaatg tatattaaag atggctacgc aaaagtactt 360
atcggtgtag ctcgaggtaa aaagaaatac gataaacgcc aagacttaaa acaaaaagaa 420
gcaaaacgtg atatcgaacg cgcttttaaa gagcgccaac aataa 465

<210> SEQ ID NO 121
<211> LENGTH: 465
<212> TYPE: DNA
<213> ORGANISM: Listeria monocytogenes

<400> SEQUENCE: 121
atgccaaaag gtgatggtaa gctagtcgcg caaaataaaa aagcgcgcca cgattacgca 60
attgaagaaa cttttgaggc tggcattgtc ctgcaaggta ctgaaattaa atccgtaaga 120
aatgcacggg taaacttaaa agattcctat gcacgtatcg acaaagggga aattttctta 180
cacaatatgc atattagtcc ttatgaacaa gggaaccgct acaatcatga tccactaaga 240
acgcgcaagt tgctcttaca taagaagcaa atcagccgtt taattggaga aacgaaagag 300
tccggttatt cgattgttcc actaaaaatg tatattaaag atggctacgc aaaagtactt 360
atcggtgtag ctcgaggtaa aaagaaatac gataaacgcc aagacttaaa acaaaaagaa 420
gcaaaacgtg atatcgaacg cgcttttaaa gagcgccaac aataa 465

<210> SEQ ID NO 122
<211> LENGTH: 465
<212> TYPE: DNA
<213> ORGANISM: Listeria monocytogenes

<400> SEQUENCE: 122
atgccaaaag gtgatggtaa gctagtcgcg caaaataaaa aagcgcgcca cgattacgca 60
attgaagaaa cttttgaggc tggcattgtc ctgcaaggta ctgaaattaa atccgtaaga 120
aatgcacggg taaacttaaa agattcctat gcacgtatcg acaaagggga aattttctta 180
cacaatatgc atattagtcc ttatgaacaa gggaaccgct acaatcatga tccactaaga 240
acgcgcaagt tgctcttaca taagaagcaa atcagccgtt taattggaga aacgaaagag 300
tccggttatt cgattgttcc actaaaaatg tatattaaag atggctacgc aaaagtactt 360
atcggtgtag ctcgaggtaa aaagaaatac gataaacgcc aagacttaaa acaaaaagaa 420
gcaaaacgtg atatcgaacg cgcttttaaa gagcgccaac aataa 465

<210> SEQ ID NO 123
<211> LENGTH: 465
<212> TYPE: DNA
<213> ORGANISM: Listeria innocua

<400> SEQUENCE: 123
atgccaaaag gtgatggtaa actagtcgcg caaaataaaa aagcgcgcca cgattacgca 60
attgaagaaa cttttgaggc tggcattgtc ctgcaaggta ctgaaatcaa atccgtcaga 120
aacgcacggg taaacttaaa agattcctat gcacgtatcg acaaagggga aattttctta 180
cacaatatgc acattagtcc atatgaacaa gggaaccgct acaatcatga tccactaaga 240
acgcgcaagt tgctcttaca taagaagcaa atcagccgtt taattggaga aacgaaagag 300
tccggttatt cgattgttcc actaaaaatg tatattaaag atggctacgc aaaagtactc 360
atcggtgtag ctcgaggtaa aaagaaatac gataaacgcc aagacttaaa acaaaaagaa 420
gcaaaacgtg atattgaacg cgcctttaaa gagcgccaac aataa 465

<210> SEQ ID NO 124
<211> LENGTH: 465
<212> TYPE: DNA
<213> ORGANISM: Listeria welshimeri

<400> SEQUENCE: 124
atgccaaaag gtgatggtaa actagtcgcg caaaataaaa aagcgcgcca cgattacgca 60
attgaagaaa cttttgaagc tggcattgtc ctgcaaggca ccgaaattaa atccgttaga 120
aacgcacggg taaacttaaa agattcctat gcacgtatcg acaaagggga aattttctta 180
cacaatatgc atattagccc ttatgaacaa gggaaccgct acaatcatga tccactaaga 240
acgcgcaaac tgcttttaca taagaagcaa atcagccgtt taattggcga aacgaaagaa 300
tctggttatt cgattgttcc gcttaaaatg tatattaaag atggatacgc aaaagtactc 360
atcggtgtag ctagaggtaa aaagaaatac gataaacgcc aagatttgaa acaaaaagaa 420
gcaaaacgtg atattgaacg tgcatttaaa gaacgccaac aataa 465

<210> SEQ ID NO 125
<211> LENGTH: 464
<212> TYPE: DNA
<213> ORGANISM: Listeria ivanovii

<400> SEQUENCE: 125
atgccaaaag gtgatggtaa gctagtcgcg caaaataaaa aagcgcgcca cgattacgca 60
attgaagaaa cttttgaggc tggcattgtc ctgcaaggta ctgaaattaa atccgttaga 120
aatgcacggg taaacttaaa agattcctat gcacgtattg ataaagggga aatttttta 180 cacaatatgc acattagccc atacgaacaa gggaaccgct acaaccacga cccactacga 240
acgcgcaagt tgctacttca taaaaaacaa attagccgtt taattggaga aacaaaagag 300
tctggttatt cgattgttcc gctaaaaatg tatattaaag atggctacgc aaaagtctta 360
attggagtag ctagaggtaa aaagaaatac gataagcgtc aagatttaaa acaaaaagaa 420
gcaaaacgtg atattgagcg tgctttcaaa gaacgccaac aata 464

<210> SEQ ID NO 126
<211> LENGTH: 465
<212> TYPE: DNA
<213> ORGANISM: Listeria seeligeri

<400> SEQUENCE: 126
atgccaaaag gtgatggtaa gctagtcgcg caaaataaaa aagcgcgcca cgattacgca 60
attgaagaaa cttttgaggc tggcattgtc ctgcaaggta ctgaaattaa atccgttaga 120
aatgcacggg taaacttaaa agattcctat gcacgtattg ataaagggga aattttctta 180
cacaatatgc acattagccc atacgaacaa ggaaaccgtt acaatcacga cccactaaga 240
acacgcaaat tacttcttca taaaaaacaa atcagtcgtt taattggaga aacaaaagag 300

```
tccggttatt ccatcgtccc gctaaaaatg tatattaaag atggttacgc aaaagtattg      360

atcggtgtag ctagaggtaa aaagaaatat gataaacgcc aagacttaaa acaaaaagaa      420

gcaaaacgtg atattgagcg tgctttcaaa gaacgccaac aataa                     465

<210> SEQ ID NO 127
<211> LENGTH: 441
<212> TYPE: DNA
<213> ORGANISM: Mycoplasma pneumoniae

<400> SEQUENCE: 127

atgcgagtac ttgtcaacaa tcccagagcg caatatgact attacctttt aacgggttat       60

tgtgctggct tagtcttaaa aggtagtgaa gtcaaatcgc tagctttagg gcaaggtagc      120

ttaaaggaag cctatgtttt tattgacaag cacgaggtct atattaaaga ttttagcatt      180

tcgccctatg ccttttcagg cgagttcaac caccccttca aacgggtgaa aaagctcctt      240

ttaaaccgga atgagattaa acaaattacg gcacgccaaa agcaagaagg actttccatt      300

attccactta aagtgttctt taaaaatggc aaaattaaaa tggaaatctg gttggccaaa      360

cctaagaaaa aatttgataa acgtgaagcc atcaaaagta aaacgatcca gcgcgaattg      420

cgccaacaat atggatcgcc a                                              441

<210> SEQ ID NO 128
<211> LENGTH: 441
<212> TYPE: DNA
<213> ORGANISM: Mycoplasma pneumoniae

<400> SEQUENCE: 128

atgcgagtac ttgtcaacaa tcccagagcg caatatgact attacctttt aacgggttat       60

tgtgctggct tagtcttaaa aggtagtgaa gtcaaatcgc tagctttagg gcaaggtagc      120

ttaaaggaag cctatgtttt tattgacaag cacgaggtct atattaaaga ttttagcatt      180

tcgccctatg ccttttcagg cgagttcaac caccccttca aacgggtgaa aaagctcctt      240

ttaaaccgga atgagattaa acaaattacg gcacgccaaa agcaagaagg actttccatt      300

attccactta aagtgttctt taaaaatggc aaaattaaaa tggaaatctg gttggccaaa      360

cctaagaaaa aatttgataa acgtgaagcc atcaaaagta aaacgatcca gcgcgaattg      420

cgccaacaat atggatcgcc a                                              441

<210> SEQ ID NO 129
<211> LENGTH: 441
<212> TYPE: DNA
<213> ORGANISM: Mycoplasma pneumoniae

<400> SEQUENCE: 129

atgcgagtac ttgtcaacaa tcccagagcg caatatgact attacctttt aacgggttat       60

tgtgctggct tagtcttaaa aggtagtgaa gtcaaatcgc tagctttagg gcaaggtagc      120

ttaaaggaag cctatgtttt tattgacaag cacgaggtct atattaaaga ttttagcatt      180

tcgccctatg ccttttcagg cgagttcaac caccccttca aacgggtgaa aaagctcctt      240

ttaaaccgga atgagattaa acaaattacg gcacgccaaa agcaagaagg actttccatt      300

attccactta aagtgttctt taaaaatggc aaaattaaaa tggaaatctg gttggccaaa      360

cctaagaaaa aatttgataa acgtgaagcc atcaaaagta aaacgatcca gcgcgaattg      420

cgccaacaat atggatcgcc a                                              441
```

<210> SEQ ID NO 130
<211> LENGTH: 441
<212> TYPE: DNA
<213> ORGANISM: Mycoplasma pneumoniae

<400> SEQUENCE: 130
atgcgagtac ttgtcaacaa tcccagagcg caatatgact attacctttt aacgggttat 60
tgtgctggct tagtcttaaa aggtagtgaa gtcaaatcgc tagctttagg gcaaggtagc 120
ttaaaggaag cctatgtttt tattgacaag cacgaggtct atattaaaga ttttagcatt 180
tcgccctatg ccttttcagg cgagttcaac caccccttca aacgggtgaa aaagctcctt 240
ttaaaccgga atgagattaa acaaattacg gcacgccaaa agcaagaagg actttccatt 300
attccactta aagtgttctt taaaaatggc aaaattaaaa tggaaatctg gttggccaaa 360
cctaagaaaa aatttgataa acgtgaagcc atcaaaagta aaacgatcca gcgcgaattg 420
cgccaacaat atggatcgcc a 441

<210> SEQ ID NO 131
<211> LENGTH: 442
<212> TYPE: DNA
<213> ORGANISM: Mycoplasma pneumoniae

<400> SEQUENCE: 131
atgcgagtac ttgtcaacaa tcccagagcg caatatgact attacctttt aacgggttat 60
tgtgctggct tagtcttaaa aggtagtgaa gtcaaatcgc tagctttagg gcaaggtagc 120
ttaaaggaag cctatgtttt tattgacaag cacgaggtct atattaaaga ttttagcatt 180
tcgccctatg ccttttcagg cgagttcaac caccccttca aacgggtgaa aaagctcctt 240
ttaaaccgga atgagattaa acaaattacg gcacgccaaa agcaagaagg actttccatt 300
attccactta aagtgttctt taaaaaatgg caaaattaaa atggaaatct ggttggccaa 360
acctaagaaa aaatttgata aacgtgaagc catcaaaagt aaaacgatcc agcgcgaatt 420
gcgccaacaa tatggatcgc ca 442

<210> SEQ ID NO 132
<211> LENGTH: 483
<212> TYPE: DNA
<213> ORGANISM: Mycobacterium tuberculosis

<400> SEQUENCE: 132
gtgtccaagt cgtcgcgtgg cggccggcag atcgttgcca gcaatcgcaa agcccggcac 60
aactattcga tcatcgaggt gttcgaggcc ggggttgcgc tgcaaggcac ggaggtgaag 120
agcctgcggg aagggcaggc gtcgctggcc gattcgttcg ccaccatcga cgacggcgaa 180
gtgtggctgc gcaacgcgca catcccggaa taccggcacg gcagctggac caaccacgag 240
ccgcgacgca accgcaaact gctgttgcat cgccgccaga tcgacacctt ggtcggcaag 300
atccgcgaag gcaacttcgc cctggtgccg ttgtcgctgt atttcgccga aggcaaggtc 360
aaggttgagc ttgcgctggc ccgaggcaag caagcccgcg acaaacgcca ggacatggcc 420
cgtcgtgatg cccagcgtga agtgctccgc gagttgggtc ggcgcgctaa gggcatgacc 480
tga 483

<210> SEQ ID NO 133
<211> LENGTH: 483
<212> TYPE: DNA
<213> ORGANISM: Mycobacterium bovis

<400> SEQUENCE: 133
gtgtccaagt cgtcgcgtgg cggccggcag atcgttgcca gcaatcgcaa agcccggcac 60
aactattcga tcatcgaggt gttcgaggcc ggggttgcgc tgcaaggcac ggaggtgaag 120
agcctgcggg aagggcaggc gtcgctggcc gattcgttcg ccaccatcga cgacggcgaa 180
gtgtggctgc gcaacgcgca catcccggaa taccggcacg gcagctggac caaccacgag 240
ccgcgacgca accgcaaact gctgttgcat cgccgccaga tcgacacctt ggtcggcaag 300
atccgcgaag gcaacttcgc cctggtgccg ttgtcgctgt atttcgccga aggcaaggtc 360
aaggttgagc ttgcgctggc ccgaggcaag caagcccgcg acaaacgcca ggacatggcc 420
cgtcgtgatg cccagcgtga agtgctccgc gagttgggtc ggcgcgctaa gggcatgacc 480
tga 483

<210> SEQ ID NO 134
<211> LENGTH: 483
<212> TYPE: DNA
<213> ORGANISM: Mycobacterium bovis

<400> SEQUENCE: 134
gtgtccaagt cgtcgcgtgg cggccggcag atcgttgcca gcaatcgcaa agcccggcac 60
aactattcga tcatcgaggt gttcgaggcc ggggttgcgc tgcaaggcac ggaggtgaag 120
agcctgcggg aagggcaggc gtcgctggcc gattcgttcg ccaccatcga cgacggcgaa 180
gtgtggctgc gcaacgcgca catcccggaa taccggcacg gcagctggac caaccacgag 240
ccgcgacgca accgcaaact gctgttgcat cgccgccaga tcgacacctt ggtcggcaag 300
atccgcgaag gcaacttcgc cctggtgccg ttgtcgctgt atttcgccga aggcaaggtc 360
aaggttgagc ttgcgctggc ccgaggcaag caagcccgcg acaaacgcca ggacatggcc 420
cgtcgtgatg cccagcgtga agtgctccgc gagttgggtc ggcgcgctaa gggcatgacc 480
tga 483

<210> SEQ ID NO 135
<211> LENGTH: 483
<212> TYPE: DNA
<213> ORGANISM: Mycobacterium canettii

<400> SEQUENCE: 135
gtgtccaagt cgtcgcgtgg cggccggcag atcgttgcca gcaatcgcaa agcccggcac 60
aactattcga tcatcgaggt gttcgaggcc ggggttgcgc tgcaaggcac ggaggtgaag 120
agcctgcggg aagggcaggc gtcgctggcc gattcgttcg ccaccatcga cgacggcgaa 180
gtgtggctgc gcaacgcgca catcccggaa taccggcacg gcagctggac caaccacgag 240
ccgcgacgca accgcaaact gctgttgcat cgccgccaga tcgacacctt ggtcggcaag 300
atccgcgaag gcaacttcgc cctggtgccg ttgtcgctgt atttcgccga aggcaaggtc 360
aaggttgagc ttgcgctggc ccgaggcaag caagcccgcg acaaacgcca ggacatggcc 420
cgtcgtgatg cccagcgtga agtgctccgc gagttgggtc ggcgcgctaa gggcatgacc 480
tga 483

<210> SEQ ID NO 136
<211> LENGTH: 483
<212> TYPE: DNA
<213> ORGANISM: Mycobacterium africanum

<400> SEQUENCE: 136
gtgtccaagt cgtcgcgtgg cggccggcag atcgttgcca gcaatcgcaa agcccggcac 60
aactattcga tcatcgaggt gttcgaggcc ggggttgcgc tgcaaggcac ggaggtgaag 120
agcctgcggg aagggcaggc gtcgctggcc gattcgttcg ccaccatcga cgacggcgaa 180
gtgtggctgc gcaacgcgca catcccggaa taccggcacg gcagctggac caaccacgag 240
ccgcgacgca accgcaaact gctgttgcat cgccgccaga tcgacacctt ggtcggcaag 300
atccgcgaag gcaacttcgc cctggtgccg ttgtcgctgt atttcgccga aggcaaggtc 360
aaggttgagc ttgcgctggc ccgaggcaag caagcccgcg acaaacgcca ggacatggcc 420
cgtcgtgatg cccagcgtga agtgctccgc gagttgggtc ggcgcgctaa gggcatgacc 480
tga 483

<210> SEQ ID NO 137
<211> LENGTH: 483
<212> TYPE: DNA
<213> ORGANISM: Mycobacterium lepraestrain

<400> SEQUENCE: 137
gtggccagaa accctcgtgg cggcaagcag attgtggcca ccaatcgcaa ggctcggcac 60
gattacgcaa tcattgaatt gtttgaggct ggggtggcgt tgcttggcac cgaggtgaaa 120
agtctgcggg aggggcatgc gtcgctggcc gacgcgttcg caaccgtcga cagcggtgaa 180
gtgtggttgc gaaacatgca catcccggag tatcagcatg gtagctggac caatcacgat 240
cctcgccgta accgcaagct gctgctgcac cgccgccaga tcgacaccct ggttggcaag 300
atccgtgacg gcaacctcgc gctagtgccg ttatcgttgt attttgccga gggcaaggtc 360
aaggtcgagc ttgcgctggc gcgcggcaag aaactgcacg acaagcgcca ggacatggcg 420
cgtcgcgatg ctcagcgcga agtaatccgt gaactcggtc gccgtgccaa gggcatgctc 480
tga 483

<210> SEQ ID NO 138
<211> LENGTH: 486
<212> TYPE: DNA
<213> ORGANISM: Mycobacterium smegmatis

<400> SEQUENCE: 138
gtgaccaaga agagcgcctc cagcaacaac aaggtggtcg ccaccaaccg caaggcgcga 60
cacaactaca cgatcctcga cacctacgag gccgggatcg tgttgatggg cacggaggtc 120
aagagcctgc gcgaaggtca ggcctcgctg gccgacgcgt tcgccacggt cgacgacggc 180
gagatctggc tgcgcaacgt ccacatcgcc gaatatcacc acggcacctg gaccaaccac 240
gcgccgcggc gcaaccgcaa actgctgctg caccgcaagc agatcgacaa cctcatcggc 300
aagatccgcg acggcaacct cacgctggtg ccgctgtcga tctacttcac cgacggcaag 360
gtcaaggtcg agttggcgct cgcccgcggc aagcaggccc acgacaagcg ccaggacctc 420
gcccgtcgag acgctcaacg cgaggtgatc cgcgagctgg gccgccgggc caagggcaag 480
atctga 486

<210> SEQ ID NO 139
<211> LENGTH: 510
<212> TYPE: DNA
<213> ORGANISM: Mycobacterium intracellulare

<400> SEQUENCE: 139

-continued

```
gtggccaagg gatccggccg ggccaaggcg gcgggcggca aaggcggcag caaacaagtt     60

gtggccacca atcgcaaagc gcggcataac tattcgatca tcgaatcgtt cgaggccggg    120

gtcgcgctgc aaggcaccga ggtcaaaagc ctgcgcgagg gccaagcttc gttagctgac    180

gccttcgcaa cgatcgacga cggcgaagtg tggttgcgca acttgtacat tgcggagtac    240

cagcacggta gctggaccaa tcatgacccc cggcgcaacc gaaagttgtt gttacatcgg    300

caacaaatcg acaggctggt cggcaagatt cgagatggta acctcgcctt gatgccgctg    360

tctctgtatt tctccgaggg caaggtcaag gtcgaactgg cccttgcgcg cggcaaaagg    420

gcttacgaca aacgccagga catggcccag cgcgacgcac agcgcgaagt ggtccgtgaa    480

ctagggcgcc gagcgaaggg catgacctga                                      510
```

<210> SEQ ID NO 140
<211> LENGTH: 510
<212> TYPE: DNA
<213> ORGANISM: Mycobacterium avium

<400> SEQUENCE: 140

```
gtggccaagg gttccggccg ggccaaagcg gcgggcggca aaggtggcag caaacagatc     60

attgccacca atcgcaaagc gcggcacaac tattcgatca tcgaaacgta cgaggccggg    120

gtggcgttgc aaggaaccga ggtcaaaagc ctgcgggagg gccaagcgtc gttagctgac    180

gcgttcgcaa cgatcgacga cggtgaagtc tggttgcgca acttgtacat cccggagtat    240

caacacggta gctggaccaa tcacgaccca cgccggaacc gaaagttgtt gttacatagg    300

caacaaatcg acagactggt cggcaagatc cgggatggta acctcgcctt gatgccgctg    360

tcgctgtact tctccgaggg caaagtgaag gtagagctcg ctctcgcgcg cggcaagaag    420

gcttacgaca aacgccagga cctggcccag cgcgacgcac agcgcgaagt cgttcgtcaa    480

ctgggacgcc gaacaaaggg gatgatctga                                      510
```

<210> SEQ ID NO 141
<211> LENGTH: 510
<212> TYPE: DNA
<213> ORGANISM: Mycobacterium avium

<400> SEQUENCE: 141

```
gtggccaagg gttccggccg ggccaaagcg gcgggcggca aaggtggcag caaacagatc     60

attgccacca atcgcaaagc gcggcacaac tattcgatca tcgaaacgta cgaggccggg    120

gtggcgttgc aaggaaccga ggtcaaaagc ctgcgggagg gccaagcgtc gttagctgac    180

gcgttcgcaa cgatcgacga cggtgaagtc tggttgcgca acttgtacat cccggagtat    240

caacacggta gctggaccaa tcacgaccca cgccggaacc gaaagttgtt gttacatagg    300

caacaaatcg acagactggt cggcaagatc cgggatggta acctcgcctt gatgccgctg    360

tcgctgtact tctccgaggg caaagtgaag gtagagctcg ctctcgcgcg cggcaagaag    420

gcttacgaca aacgccagga cctggcccag cgcgacgcac agcgcgaagt cgttcgtcaa    480

ctgggacgcc gaacaaaggg gatgatctga                                      510
```

<210> SEQ ID NO 142
<211> LENGTH: 480
<212> TYPE: DNA
<213> ORGANISM: Mycobacterium abscessus

<400> SEQUENCE: 142

```
atgagtaaga aaccggccga cggacgaaaa gtcatcgcga ccaatcgcaa ggcacgacac     60
```

aactattcga tcatcgatgt gtatgaggcc ggggtgcagt tggtgggcac cgaggtcaag 120
acactgcgcg agggcaaggc atcgctggtc gatgccttcg ccaccgtcga tgacggcgag 180
gtgtggttgc gcggcgtgca tatcccgcaa tacgaccacg gcacctggac caatcacgct 240
ccgctgcgga accggaaact gttgttgcac agggcgcaga tcgacatgct ggtcggcaag 300
acccgcgacg gcaatctgac cctggtaccg ctgtcgctgt acttcctgga cggcaaggtc 360
aaggtggagt tggcgctggc gcggggtaag caggctcacg acaagcgtca ggacatcgcc 420
aaacgggacg cttcgcgtga gatcacccgt gagctgggac gccgcgccaa aggcatgtga 480

<210> SEQ ID NO 143
<211> LENGTH: 406
<212> TYPE: DNA
<213> ORGANISM: Legionella pneumophila

<400> SEQUENCE: 143
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 144
<211> LENGTH: 406
<212> TYPE: DNA
<213> ORGANISM: Legionella pneumophila

<400> SEQUENCE: 144
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 145
<211> LENGTH: 406
<212> TYPE: DNA
<213> ORGANISM: Legionella pneumophila

<400> SEQUENCE: 145
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 146
<211> LENGTH: 406
<212> TYPE: DNA
<213> ORGANISM: Legionella pneumophila

<400> SEQUENCE: 146
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 147
<211> LENGTH: 406
<212> TYPE: DNA
<213> ORGANISM: Legionella pneumophila

<400> SEQUENCE: 147
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 148
<211> LENGTH: 406
<212> TYPE: DNA
<213> ORGANISM: Legionella pneumophila

<400> SEQUENCE: 148
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaactca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 149
<211> LENGTH: 406
<212> TYPE: DNA
<213> ORGANISM: Legionella pneumophila

<400> SEQUENCE: 149
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaattca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 150
<211> LENGTH: 406
<212> TYPE: DNA
<213> ORGANISM: Legionella pneumophila

<400> SEQUENCE: 150
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatctatccc gggttatggc gcgaaattca gggaatcgct gtgtatcatc 300
ctgcccgtcg gaggagccac agttaaattc aaaagacaag gctatgcatg tagagctaaa 360
ggcagaggac ttgcggacgc gggttcgatt cccgccgcct ccacca 406

<210> SEQ ID NO 151
<211> LENGTH: 406
<212> TYPE: DNA
<213> ORGANISM: Legionella pneumophila

<400> SEQUENCE: 151
gggggcgacc tggcttcgac gtgggttgca aaaccggaag tgcatgccga gaaggagatc 60
tctcgtaaat aagactcaat taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagtgtcct aatctatccc gggttatggc gcaaaactaa gggaatcgct gtgtatcatc 300
ctgcctgtcg gaggagccac agttaaattc aaaagacaag gctatgcatg tagagctaaa 360
ggcagaggac ttgcggacgc gggttcgatt cccgccgcct ccacca 406

<210> SEQ ID NO 152
<211> LENGTH: 405
<212> TYPE: DNA
<213> ORGANISM: Legionella longbeachae

<400> SEQUENCE: 152
gggggcgacc tggcttcgac gtgggttgca aaaccagagg tgcatgccga gaatgaggac 60
tctcgtaaat cagactcaac taaatataaa tgcaaacgat gaaaactttg ctggtgggga 120
agctattgct gcctaataag cactttagat aaaccatcac tgtgtactgg ccaataaacc 180
cagtatcccg ttcgaccgag cccgcttatc ggtatcgaat caacggtcat aagagataag 240
ctagcgtcct aatccatccc gtattaaggc gcgaaactca gggaatcgct gtgtagtatc 300
ctgcccgtcg gagaatgcac agttaaatca aaagacaagg ctacgcatgt agagctgaag 360
gcagaggatt tgcggacgcg ggttcgattc ccgccgcctc cacca 405

<210> SEQ ID NO 153

-continued

<211> LENGTH: 405
<212> TYPE: DNA
<213> ORGANISM: Legionella longbeachae

<400> SEQUENCE: 153
gggggcgacc tggcttcgac gtgggttgca aaaccagagg tgcatgccga gaatgaggac 60
tctcgtaaat cagactcaac taaatataaa tgcaaacgat gaaaactttg ctggtgggga 120
agctattgct gcctaataag cactttagat aaaccatcac tgtgtactgg ccaataaacc 180
cagtatcccg ttcgaccgag cccgcttatc ggtatcgaat caacggtcat aagagataag 240
ctagcgtcct aatccatccc gtattaaggc gcgaaactca gggaatcgct gtgtagtatc 300
ctgcccgtcg gagaatgcac agttaaatca aaagacaagg ctacgcatgt agagctgaag 360
gcagaggatt tgcggacgcg ggttcgattc ccgccgcctc cacca 405

<210> SEQ ID NO 154
<211> LENGTH: 414
<212> TYPE: DNA
<213> ORGANISM: Legionella fallonii

<400> SEQUENCE: 154
gggggcgacc tggcttcgac gtgggttgca aaaccggaag tgcatgccga gaatgagaac 60
tctcgtaaat cagactcact aaatataaat gcaaacgaag aaaacttcga tggcgtagct 120
aatcttgaag gagtagcgca agctgcttaa tcttttttag ttaaaccata acgtgtactg 180
gctttaaccc cagtgccccg ttgaccgagc tcgcttatcg gtatcgaatc aacggtcata 240
gaagataagc tagtgtccta atctatcccg ggttacgatg cgaaactcag ggagtagctg 300
tgtaccatcc tgcctgtcgg agagtccaca gttaaatcaa atgacaaggc tacgcatgta 360
gagctgaagg cagaggattt gcggacgcgg gttcgattcc cgccgcctcc acca 414

<210> SEQ ID NO 155
<211> LENGTH: 395
<212> TYPE: DNA
<213> ORGANISM: Legionella hackeliae

<400> SEQUENCE: 155
gggggcgacc tggcttcgac gtgggttgcg aaacctgaag tgcatgccga gaatgagacg 60
tctcgtaaat cagactcact aaatataaat gcaaacgatg aaaactttgc aggtgaagct 120
atcgctgcgt aagctttgat agtgtaaccg caccgtgcgc tgctatataa ccagcgcccc 180
gttgaccgag ctcgcttatc ggtatcgaat caacggtcat agaagataag ctcgcatctt 240
aacccgtccc gagttaagct gttaaattaa gggaatcgcc gtgttcaatc ctgcccgtcg 300
gagggaccac ggttaactta aaagacaagg ctacgcatgt agagctgatg gcagaggatt 360
tgcggacgcg ggttcgattc ccgccgcctc cacca 395

<210> SEQ ID NO 156
<211> LENGTH: 410
<212> TYPE: DNA
<213> ORGANISM: Legionella oakridgensis

<400> SEQUENCE: 156
gggggcgacc tggcttcgac gtgggttgcg aaacctgaag tgcatgccga gaatgagatc 60
tctcgtaaat aaggctcact aaatataaat gcaaatgatg aaaactttgc tggtgttgag 120
ggagaagcta tcgctgcgta agcattgatg gttttaccaa aaacatcact gtgcgctgcc 180
aaaaaccagc gccccgttga ccgagctcgc ttgtcggtat cgaatcaacg gtcatagaag 240
ataagctagt cttttgattt gtcccgcatc aaagggcgaa attcagggaa tcgccgtgta 300
tcatcctgcc agtcggaggg tccacggtca gaataataga ccaggctaag catgtagagc 360
tgatggcaga ggatttgcgg acgcgggttc gattcccgcc gcctccacca 410

<210> SEQ ID NO 157
<211> LENGTH: 404
<212> TYPE: DNA
<213> ORGANISM: Legionella micdadei

<400> SEQUENCE: 157
gggggcgacc tggcttcgac gtgggttgcg aaacctgagg tgcatgccga gaatgagatc 60
tctcgtaaat aagactcact aaatataaat gcaaacgatg aaaactttgc tggtggagaa 120
ggcgctatcg ctgcgtaagc attgatagaa acttttcccc aatcgtgcgc tgccaaaaac 180
cagcgccccg ttgaccgagc tcgcttaccg gtatcgaatc aacggtcata agagataagc 240
tcgcaacttg gttagtcccg catcaagttg ttaaatccag ggaatcgccg taaaccatcc 300
tgcctgtcgg aggggctacg gttaacttaa tagacaaggc taagcatgta gaactgatgg 360
cagaggattt gcggacgcgg gttcaattcc cgccgcctcc acca 404

<210> SEQ ID NO 158
<211> LENGTH: 405
<212> TYPE: DNA
<213> ORGANISM: Legionella sainthelensi

<400> SEQUENCE: 158
gggggcgacc tggcttcgac gtgggttgca aaaccagagg tgcatgccga gaatgaggac 60
tctcgtaaat cagactcaac taaatataaa tgcaaacgat gaaaactttg ctggtgggga 120
agctattgct gcctaataag cactttagtt aaaccatcac tgtgtactgg ccaataaacc 180
cagtatcccg ttcgaccgag cccgcttatc ggtatcgaat caacggtcat aagagataag 240
ctagcgtcct aatccatccc gtattaaggc gcgaaactta gggaatcgct gtgtagtatc 300
ctgcccgtcg gagaatgcac agttaaatca aaagacacgg ctacgcatgt agagctgaag 360
gcagaggatt tgcggacgcg ggttcgattc ccgccgcctc cacca 405

<210> SEQ ID NO 159
<211> LENGTH: 406
<212> TYPE: DNA
<213> ORGANISM: Legionella wadsworthii

<400> SEQUENCE: 159
gggggcgacc tggtttcgac gtgggttgca aaaccagagg tgcatgccga gattgagaac 60
tctcgtaaat cagactcaac ttaaatataa atgcaaacga tgaaaacttt gctggtggag 120
aagctatcgc tgcctaataa gcactttagt tgaaccatca ctgtgtactg gccaataaac 180
ccagtatccc gttcgaccga gcccgcttat cggtatcgaa tcaacggtca taagagataa 240
gctagcgtcc taatccatcc cgtattaagg cgcgaaattc agggaatcgc tgtgtagtat 300
cctgcccgtc ggagaatgca cagttaaatc aaaagacacg gctacgcatg tagagctgaa 360
ggcagaggac ttgcggacgc gggttcgatt cccgccgcct ccacca 406

<210> SEQ ID NO 160
<211> LENGTH: 405
<212> TYPE: DNA
<213> ORGANISM: Legionella cherrii

<400> SEQUENCE: 160
gggggcgacc tggcttcgac gtgggttgca aaaccagagg tgcatgccga gaatgagaac 60
tctcgtaaat cagactcaac taaatataaa tgcaaacgat gaaaactttg ctggtgggga 120
agctatcgct gcctaataag cactttagtt aaaccatcac tgtgtactgg ccaataaacc 180
cagtatcccg ttcgaccgag cccgcttatc ggtatcgaat caacggtcat aagagataag 240
ctagtgtctt aatccatccc gtattaagat gcgaaattca gggaatcgct gtgtagtatc 300
ctgcccgtcg gagaatgcac agttaaatca aaagacacgg ctacgcatgt agagctgaag 360
gcagaggatt tgcggacgcg ggttcgattc ccgccgcctc cacca 405

<210> SEQ ID NO 161
<211> LENGTH: 405
<212> TYPE: DNA
<213> ORGANISM: Legionella moravica

<400> SEQUENCE: 161
gggggcgacc tggcttcgac gtgggttgca aaaccagagg tgcatgccga gaatgagaac 60
tctcgtaaat cagactcaac taaatataaa cgcaaacgat gaaaactttg ctggtggaga 120
agctatcgct gcctaataag cactttagtt gaaccatcac tgtgtactgg ccaataaacc 180
cagtatcccg ttcgaccgag cccgcttatc ggtatcgaat caacggtcat aagagataag 240
ctagtgtctt aatccatccc gaattaaggc gcgaaattca gggaatcgct gtgtagtatc 300
ctgcctgtcg gagaatgcac agttaaatta aaagacaagg ctacgcatgt agagctgaag 360
gcagaggatt tgcggacgcg ggttcgattc ccgccgcctc cacca 405

<210> SEQ ID NO 162
<211> LENGTH: 404
<212> TYPE: DNA
<213> ORGANISM: Legionella norrlandica

<400> SEQUENCE: 162
gggggcgacc tggcttcgac gtgggttgca aaaccggaag tgcatgccga gaatgagatc 60
tctcgtaaat aagactcaat taaatataaa tgcaaacgat gaaaactttg ctggtggtga 120
agctatcgct gcctaataag cacgattaga taaaccccaa tcgtgtactg gccaaaaacc 180
cagtatcccg ttgaccgagc tcgcttatcg gtatcgaatc aacggtcata gaagataagc 240
tagtacttta atctatcctg ggttatggtg cgaaatttag ggaatcgctg tgtatcatcc 300
tgcccgtcgg aggagccaca gttaaattta atagacaagg ctaagcatgt agagctaaag 360
gcagaggact tgcggacgcg gttcgattcc cgccgcctcc acca 404

<210> SEQ ID NO 163
<211> LENGTH: 401
<212> TYPE: DNA
<213> ORGANISM: Legionella shakespearei

<400> SEQUENCE: 163
gggggcgacc tggcttcgac gtgggttgcg aaaccggaag tgcatgccga gaatgagaac 60
tctcgtaaat cagactcaaa aaatataaat gcaaacgatg caaacttcgc tgataacgtt 120
gatggagcaa ttgctgctta atcaatagtt aaaagcaacg tgtactggcc taaaccccgg 180
tgccccgttg accgagctcg cttattggta tcgaatcaac ggtcatagaa gataagctag 240
cttcttaatg aatcccgagt taagacgcga aattcaggga atcgctgtgt accatcctgc 300
ccgtcggagt gtccacagtt aaaccaaaag acaaggctac gcatgtagag ctaaaggcag 360

-continued aggatttgcg gacgcgggtt cgattcccgc cgcctccacc a 401

<210> SEQ ID NO 164
<211> LENGTH: 405
<212> TYPE: DNA
<213> ORGANISM: Legionella drancourtii

<400> SEQUENCE: 164
gggggcgacc tggcttcgac gggggttgca aaaccagagg tgcatgccga gaatgagatc 60
tctcgtaaat caggctcaat aaatataaat gcaaacaatg caaactttga tgatgtttct 120
tttgacgggg ctattgcagc ttaatcagat taaactaatc gacgtgtact ggccttaacc 180
ccagtgcccc gttgaccgag ctcgcttatt ggtatcgaat caacggtcat agaagataag 240
ctagtgtttt aatttatccc ggattaaaat gcgaaactca gggaatcgct gtgtaccatc 300
ctgcctgtcg gagagtccac agttaaatca aatgacaagg ctacgcatgt agaactgaag 360
gcagaggatc tgcggacgcg ggttcgattc ccgccgcctc cacca 405

<210> SEQ ID NO 165
<211> LENGTH: 399
<212> TYPE: DNA
<213> ORGANISM: Legionella lansingensis

<400> SEQUENCE: 165
gggggcgacc tggcttcgac gtgggttgcg aaacctgatg tgcatgccga gaaagagtac 60
tctcgtaaat cagtctcact aaatataaat gcaaacgatg aaaactttgc tggtggtgaa 120
gctgtcgctg cgtaagcttt gatagtcaac taccgatagt gcgctgccat aaaaccagcg 180
ccccgttgac cgagctcgct tatcggtatc gaatcaacgg tcataagaga taagctcgca 240
tcttggttcg tcccgcacca agatgttaaa tcaagggaat cgccgtgtcc catcctgcct 300
gtcggagagg ccacggttaa ctaaaaagac aaggctaagc atgtagatct gacggcagag 360
gatttgcgga cgcgggttcg attcccgccg cctccacca 399

<210> SEQ ID NO 166
<211> LENGTH: 396
<212> TYPE: DNA
<213> ORGANISM: Legionella fairfieldensis

<400> SEQUENCE: 166
gggggcgacc tggcttcgac gcgggttgcg aaacctgagg ggcatgccga gaatgagaac 60
tctcgtaaat cagactcact aaatataaat gcaaacgatg aaaactttgc aggtgaagct 120
atcgctgctt aagctttgat agtttaaccg caccgtgcgc tgccataaaa ccagcgcccc 180
gttgaccgag cttgcttatc ggtatcgaat caacggtcat agaagataag ctcgcatttt 240
ggtacgtccc gcatcaaaat gttaaattaa gggaatcgcc gtgtactatc ctgcctgtcg 300
gagagtccac ggttaacata aatagacaag gctacgcatg tagaactgac ggcagaggat 360
ttgcggacgc gggttcgatt cccgccgcct ccacca 396

<210> SEQ ID NO 167
<211> LENGTH: 401
<212> TYPE: DNA
<213> ORGANISM: Legionella massiliensis

<400> SEQUENCE: 167
gggggcgacc tggcttcgac gtgggttgcg aaacctgatg tgcatgccga gattgagact 60

```
tctcgttaat cagactcact aaacataaat gcaaacgatg aaaactttgc agatggagaa    120

gctatcgctg cgtaagcttt gataggtttt tcgtcgcacc gtgtgctgct ataaaaccag    180

caccccgttg accgagcttg cttatcggta tcgaatcaac ggtcatagaa gataagctcg    240

cagcttgata tttcccgtat caagatgtta aatccaggga atcgccgcga accatcctgc    300

ctgtcggagg ggactcggtt aattgaatag acaaggctac gcatgtagag ctgacggcag    360

aggatttgcg gacgcgggtt caattcccgc cgcctccacc a                        401
```

<210> SEQ ID NO 168
<211> LENGTH: 396
<212> TYPE: DNA
<213> ORGANISM: Legionella geestiana

<400> SEQUENCE: 168

```
gggggcgacc tggcttcgac gtgggttgcg aaacctgatg tgcatgccga ggatgagaac     60

tctcgtaaaa cgggctcgat aaatataaat gcaaacgatg aaatgttcgc tggagaagct    120

gtagctgcgt aagcaactgc ggtgaccgaa gcacagtgcg ctgccaaaaa cccagcgccc    180

cgttgaccgg gcttgcttgc cggtaccgaa tcaacggtca tagaagacaa gctggtatcc    240

tggtgtatcc cgcgccagta tacaagactc agggaatcgc tgccgaccat cctgcctgtc    300

ggaggggaag cagttaaaac aaatgacaag gctaagcatg tagatctgac ggcagaggat    360

ttgcggacgc gggttcgatt cccgccgcct ccacca                              396
```

<210> SEQ ID NO 169
<211> LENGTH: 486
<212> TYPE: DNA
<213> ORGANISM: Haemophilus influenzae

<400> SEQUENCE: 169

```
atgacaaaga aaaaagtaaa acccaattca aatactatcg cactaaataa acgtgcaaga     60

cacgattatt ttattgaaga tgaaattgaa gcaggtcttg aattacaagg ctgggaagtc    120

aaatctatgc gcgcaggcaa ggcaaatatt agtgatagtt atgttatttt taaaaatggc    180

gaagcctttt tattcggcgc aagcattcag ccattaaatg ttgcatcaac gcatattgtt    240

tgtgatccaa ctcgcactcg taagttattg ttaaataaac gcgaattagc atccctattt    300

ggtaaagcaa accgagacgg ttttaccata gttgcacttt ctctttattg gaaaagtgcg    360

tgggcaaaag tcaaaatcgg tttagccaaa ggtaaaaaac aacaggataa acgtgatgat    420

attaaagaac gtgaatggaa agtaacaaaa gatcgcatta tgaaaaatgc acatcgaaga    480

tcttaa                                                               486
```

<210> SEQ ID NO 170
<211> LENGTH: 486
<212> TYPE: DNA
<213> ORGANISM: Haemophilus influenzae

<400> SEQUENCE: 170

```
atgacaaaga aaaaagtaaa acccaattca aatactatcg cactaaataa acgtgcaaga     60

cacgattatt ttattgaaga tgaaattgaa gcaggtcttg aattacaagg ctgggaagtc    120

aaatctatgc gcgcaggcaa ggcaaatatt agtgatagtt atgttatttt taaaaatggc    180

gaagcctttt tattcggcgc aagcattcag ccattaaatg ttgcatcaac gcatattgtt    240

tgtgatccaa ctcgcactcg taagttattg ttaaataaac gcgaattagc atccctattt    300

ggtaaagcaa accgagacgg ttttaccata gttgcacttt ctctttactg gaaaagtgcg    360
```

tgggcaaaag tcaaaatcgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 171
<211> LENGTH: 486
<212> TYPE: DNA
<213> ORGANISM: Haemophilus influenzae

<400> SEQUENCE: 171
atgacaaaga aaaaagtaaa acccaattca aatactatcg cactgaataa acgtgcaaga 60
cacgattatt ttattgaaga tgaaattgaa gcaggtcttg aattacaagg ctgggaagtc 120
aaatctatgc gcgcaggcaa ggcaaatatt agtgatagtt atgttatttt taaaaatggc 180
gaagcctttt tattcggcgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaatcgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 172
<211> LENGTH: 486
<212> TYPE: DNA
<213> ORGANISM: Haemophilus influenzae

<400> SEQUENCE: 172
atgacaaaga aaaaagtaaa acccaattca aatactatcg cactgaataa acgtgcaaga 60
cacgattatt ttattgaaga tgaaattgaa gcaggtcttg aattacaagg ctgggaagtc 120
aaatctatgc gcgcaggcaa ggcaaatatt agtgatagtt atgttatttt taaaaatggc 180
gaagcctttt tattcggcgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 173
<211> LENGTH: 486
<212> TYPE: DNA
<213> ORGANISM: Haemophilus influenzae

<400> SEQUENCE: 173
atgacaaaga aaaaagtaaa acccaattca aatactatcg cactaaataa acgtgcaaga 60
cacgattatt ttattgaaga tgaaattgaa tcaggtcttg aattacaagg ctgggaagtc 120
aaatctatgc gcgcaggcaa ggcaaatatt agtgatagtt atgttatttt taaaaatggc 180
gaagcctttt tattcggcgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 174
<211> LENGTH: 486
<212> TYPE: DNA
<213> ORGANISM: Haemophilus influenzae

<400> SEQUENCE: 174
atgacaaaga aaaaagtaaa acccaattca aatactatcg cactgaataa acgtgcaaga 60
cacgattatt ttattgaaga tgaaattgaa gccggtcttg aattacaagg ctgggaagtc 120
aaatctatgc gcgcaggcaa ggcaaatatt agtgatagtt atgttatttt taaaaatggc 180
gaagcctttt tattcggcgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaatcgg tttagccaaa ggtaaaaaac agcaggataa acgtgatgat 420
attaaagaac gtgaatggaa agtaacaaaa gatcgcatta tgaaaaatgc acatcgaaga 480
tcttaa 486

<210> SEQ ID NO 175
<211> LENGTH: 486
<212> TYPE: DNA
<213> ORGANISM: Haemophilus influenzae

<400> SEQUENCE: 175
atgacaaaga aaaaagtaaa acccaattca aatactatcg cactgaataa acgtgcaaga 60
cacgattatt ttattgaaga tgaaattgaa gcaggtcttg aattacaagg ctgggaagtc 120
aaatctatac gcgcaggcaa ggcaaatatt agtgatagtt atgttatttt taaaaatggc 180
gaagcctttt tattcggcgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 176
<211> LENGTH: 486
<212> TYPE: DNA
<213> ORGANISM: Haemophilus influenzae

<400> SEQUENCE: 176
atgacaaaga aaaaagtaaa acccaattca aatactatcg cactgaataa acgtgcaaga 60
cacgattatt ttattgaaga tgaaattgaa gcaggtcttg aattacaagg ctgggaagtt 120
aaatctatgc gcgcaggcaa ggcaaatatt agtgatagtt atgttatttt taaaaatggc 180
gaagcctttt tattcggtgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 177
<211> LENGTH: 486
<212> TYPE: DNA
<213> ORGANISM: Haemophilus influenzae

<400> SEQUENCE: 177
atgacaaaga aaaaagtaaa acccaattca aatactatcg cactgaataa acgtgcaaga 60
cacgattatt ttattgaaga tgaaattgaa gcaggtcttg aattacaagg ctgggaagtt 120
aaatctatgc gcgcaggcaa ggcaaatatt agtgatagtt atgttatttt taaaaatggc 180
gaagcctttt tattcggtgc aagcattcag ccattaaatg ttgcatcaac gcatattgtt 240
tgtgatccaa ctcgcactcg taagttattg ttaaataaac gcgaattagc atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 178
<211> LENGTH: 486
<212> TYPE: DNA
<213> ORGANISM: Haemophilus influenzae

<400> SEQUENCE: 178
atgacaaaga aaaaagtaaa acccaattca aatactatcg cactgaataa acgtgcaaga 60
cacgattatt ttattgaaga tgaaattgaa gcaggtcttg aattacaagg ctgggaagtc 120
aaatctatgc gcgcaggcaa ggcaaatatt agtgatagtt atgttatttt taaaaatggc 180
gaagcctttt tattcggggc aagcattcag ccattaaatg tcgcatcaac gcatattgtt 240
tgtgatccaa ctcgcactcg taagttattg ttaaataaac gcgaattaac atccctattt 300
ggcaaagcaa accgagacgg ttttaccata gttgcacttt ctctttactg gaaaagtgcg 360
tgggcaaaag tcaaaattgg tttagccaaa ggtaaaaaac aacaggataa acgtgatgat 420
attaaagaac gtgaatggaa agtaacaaaa gatcgcatta tgaaaaatgc acatcgaaga 480
tcttaa 486

<210> SEQ ID NO 179
<211> LENGTH: 481
<212> TYPE: DNA
<213> ORGANISM: Haemophilus haemolyticus

<400> SEQUENCE: 179
atgacaaaga aaaaagtaaa accaggatca aacactatcg cactgaataa acgtgcgaga 60
catgattatt ttatagaaga tgaaattgaa gcgggtcttg aattacaagg ctgggaagtc 120
aaatcaatgc gcgcaggcaa ggcaaacatt agtgatagtt atgtcatttt taaaaatggc 180
gaagcctttt tattcggcgc aagcattcag ccattaaatg ttgcatcaac gcatattatt 240
tgtgatccaa ctcgcactcg taagttatta ttaaataaac gcgaattagc atccctattt 300
ggcaaagcaa accgagacgg ttttaccatc gtagcgcttt ctctttattg gaaaagtgca 360
tgggcaaaag tcaagattgg tttagccaaa ggtaaaaaac aacatgataa acgcgatgat 420
attaaagagc gtgaatggaa agtaacaaaa gatcgcatta tgaaaaatgc acatcgagga 480
t 481

<210> SEQ ID NO 180
<211> LENGTH: 481
<212> TYPE: DNA
<213> ORGANISM: Haemophilus haemolyticus

<400> SEQUENCE: 180
atgacaaaga aaaaagtaaa accaggatca aatactatcg cactgaataa acgtgcgaaa 60
catgattatt ttatagaaga tgaaattgaa gcaggtcttg aactacaagg ctgggaagtc 120
aaatcaatgc gcgcaggcaa ggcaaacatt agtgatagtt atgtcatttt caaaaatggc 180
gaagcctttt tattcggtgc aagcattcag ccattaaatg ttgcatcaac gcatattgtt 240
tgtgatccaa ctcgcactcg taagttatta ttaaataaac gcgaattagc atccctattt 300
ggcaaagcaa accgagacgg ttttaccatc gtagcgcttt ctctttattg gaaaagtgca 360
tgggcaaaag tcaaaattgg tttagccaaa ggtaaaaaac aacatgataa acgcgatgat 420
attaaagagc gtgaatggaa agtaacaaaa gatcgcatta tgaaaaatgc acatcgagga 480
t 481

<210> SEQ ID NO 181
<211> LENGTH: 481
<212> TYPE: DNA
<213> ORGANISM: Haemophilus haemolyticus

<400> SEQUENCE: 181
atgacaaaga aaaaagtaaa accagaatca aatactattg cactgaataa acgtgctaga 60
catgactatt ttatagaaga tgaaattgaa gcgggtcttg aattacaagg ctgggaagtc 120
aaagcaatgc gcgcaggcaa ggcaaacatt agtgatagtt atgtcatttt taaaaatggc 180
gaagcctttt tattcggggc aagcattcag ccattaaatg ttgcatcaac gcatattgtt 240
tgtgatccaa ctcgcactcg taagttatta ttaaataaac gcgaattagc atccctattt 300
ggcaaagcaa accgagacgg ttttaccatc gtagcgcttt ctctttattg gaaaagtgca 360
tgggcaaaag tcaaaattgg tttagccaaa ggtaaaaaac aacatgataa acgcgatgat 420
attaaagagc gtgaatggaa agtaacaaaa gatcgcatta tgaaaaatgc acatcgagga 480
t 481

<210> SEQ ID NO 182
<211> LENGTH: 481
<212> TYPE: DNA
<213> ORGANISM: Haemophilus haemolyticus

<400> SEQUENCE: 182
atgacaaaga aaaaagtaaa accaggatca aacactatcg cactgaataa acgtgcgaga 60
catgattatt ttatagaaga tgaaattgaa gcgggtcttg aattacaagg ctgggaagtc 120
aaatcaatgc gcgcaggcaa ggcaaacatt agtgatagtt atgtcatttt taaaaatggc 180
gaagcctttt tattcggggc aagcattcag ccattaaatg ttgcatcaac acatattgtt 240
tgtgatccaa ctcgcactcg taagttatta ttaaataaac gcgaattagc atccctattt 300
ggcaaagcaa accgagacgg ttttaccatc gtagcgcttt ctctttattg gaaaagtgca 360
tgggcaaaag tcaaaattgg tttagccaaa ggtaaaaaac aacatgataa acgcgatgat 420
attaaagagc gtgaatggaa agtaacaaaa gatcgcatta tgaaaaatgc acatcgagga 480
t 481

<210> SEQ ID NO 183
<211> LENGTH: 481
<212> TYPE: DNA
<213> ORGANISM: Haemophilus haemolyticus

<400> SEQUENCE: 183
atgacaaaga aaaaagtaaa accaggatca aatactatcg cactgaataa acgtgcgaga 60
catgattatt ttatagaaga tgaaattgaa gcaggtcttg aactacaagg ctgggaagtt 120
aaatcaatgc gcgcaggcaa ggcaaacatt agtgatagtt atgtcatttt taaaaatggc 180
gaagcctttt tattcggtgc aagcattcag ccattaaatg tagcatcaac gcatattgtt 240
tgtgatccaa ctcgcactcg taagttatta ttaaataaac gtgaattaga atccctattt 300
ggcaaagcaa accgagacgg ttttaccatc gtagcgcttt ctctttactg gaaaagtgca 360
tgggcaaaag tcaaaattgg tttagccaaa ggtaaaaaac aacatgataa acgcgatgat 420
attaaagagc gtgaatggaa agtaacaaaa gatcgcatta tgaaaaattc acatcgagga 480
t 481

<210> SEQ ID NO 184
<211> LENGTH: 480
<212> TYPE: DNA
<213> ORGANISM: Haemophilus haemolyticus

<400> SEQUENCE: 184
atgacaaaga aaaagtaaaa ccaggatcaa atactatcgc actgaataaa cgtgcgagac 60
atgattattt tatagaagat gaaattgaag caggtcttga actacaaggc tgggaagtca 120
aatcaatgcg cgcaggcaag gcaaacatta gtgatagtta tgtcattttc aaaaatggcg 180
aagccttttt attcggcgca agcattcagc cattaaatgt tgcatcaacg cacattgttt 240
gtgatccaac tcgcactcgt aagttattat taaataaacg tgaactagca tccctatttg 300
gcaaagcaaa ccgagacggt tttaccatcg tagcgctttc tctttactgg aaaagtgcat 360
gggcaaaagt caaaattggt ttagctaaag gtaaaaaaca acatgataaa cgcgatgata 420
tcaaagagcg tgaatggaaa gtaacaaaag atcgcattat gaaaaatgca catcgaggat 480

<210> SEQ ID NO 185
<211> LENGTH: 483
<212> TYPE: DNA
<213> ORGANISM: Haemophilus parainfluenzae

<400> SEQUENCE: 185
atgaccaaga aaaaagtcaa agtcggctcc agcaccattg cgttaaataa acgagccaga 60
cacgaatatt ttattgaaga tgaaattgaa gccggccttg aattacaagg ttgggaagtg 120
aaatcaatgc gcgcgggtaa agccaatatc agcgacagct atatcatttt taaaaacggt 180
gaagcttatt tatttggtgc aaccattcaa ccattaagct tggcttctac ccacgtggtt 240
tgcgatccga ctcgcacacg taagctttta ttgaataaac gtgaactgga taatcttttc 300
ggtaaatcaa gccgtgatgg ttttaccatt gttgcccttt ctctttattg gaaaggtcct 360
tgggcaaaga tcaaaatcgg tcttgcgaaa ggtaaaaaac aacatgataa acgtgatgat 420
attaaagagc gtgaatggaa agtggcaaaa gagcgtatta tgaaaaatgc gcatcgtgga 480
taa 483

<210> SEQ ID NO 186
<211> LENGTH: 476
<212> TYPE: DNA
<213> ORGANISM: Haemophilus parainfluenzae

<400> SEQUENCE: 186
atgaccaaga agaaagtcaa agtcggctcc aataccattg cgttaaataa acgagctcga 60
cacgaatatt ttattgaaga tgaaattgaa gccggtcttg aattacaagg ttgggaagtg 120
aaatcaatgc gcgcaggtaa agccaatatc agcgacagct atatcatttt taaaaacggg 180
gaagcctatt tatttggtgc gaccattcaa ccattaagct tggcttctac tcacgtggtt 240
tgcgatccga cgcgtacacg taagctttta ttgaataaac gtgaactgga taatcttttc 300
ggtaaatcaa gccgtgatgg ttttaccatt gttgcccttt ctctttattg gaaaggccct 360
tgggcaaaga tcaaaatcgg ccttgcgaaa ggtaaaaaac aacatgataa acgtgatgat 420
attaaagagc gtgaatggaa agtggcgaaa gagcgtatta tgaaaaacgc gcaccg 476

<210> SEQ ID NO 187
<211> LENGTH: 477
<212> TYPE: DNA
<213> ORGANISM: Haemophilus somnus

<400> SEQUENCE: 187
atgacaaaga aaaaagcaaa ggtagcatct aatacgattg ccttaaataa acgagcaaga 60
cacgattatt ttattgaaga tgaaatcgaa gccggtcttt ctttgcaagg ctgggaagtt 120
aaatcgatgc gtgcaggtaa agcgagtatt ggcgatagtt atattatttt taagcatggc 180
gaggcatatt tatttggtgc aaccattcag ccgttaagtg ttgcttcaac gcatattgtt 240
tgcgatccca caagaacacg taaactttta ttaaaccaga aagagttggc ttcattattt 300
ggtaaagcaa atcgagatgg tttcactatt gttgcacttt cattatattg gaaaggtcct 360
tgggcaaagg tgaaaatagg tttagcaaaa gggaaaaaat tacatgataa gcgtgaagat 420
attaaagatc gtgaatggaa agtaacgaaa gatcgcatta tgaaaaatgc acagcga 477

<210> SEQ ID NO 188
<211> LENGTH: 477
<212> TYPE: DNA
<213> ORGANISM: Haemophilus somnus

<400> SEQUENCE: 188
atgacaaaga aaaaagcaaa ggtagcatct aatacgattg ccttaaataa acgagcaaga 60
cacgattatt ttattgaaga tgaaatcgaa gccggtcttt ctttgcaagg ctgggaagtt 120
aaatcgatgc gtgcaggtaa ggcgagtatt ggcgatagtt atattatttt taagcatggt 180
gaggcatatt tatttggtgc aaccattcag ccgttaagtg ttgcttcaac gcatattgtt 240
tgcgatccca caagaacacg taaactttta ttaaaccaga aagagttggc ttcattattt 300
ggtaaagcaa atcgagatgg tttcactatt gttgcacttt cattatattg gaaaggtcct 360
tgggcaaagg tgaaaatagg tttagcaaaa gggaaaaaat tacatgataa gcgtgaagat 420
attaaagatc gtgaatggaa agtaacgaaa gatcgcatta tgaaaaatgc acagcga 477

<210> SEQ ID NO 189
<211> LENGTH: 443
<212> TYPE: DNA
<213> ORGANISM: Haemophilus ducreyi

<400> SEQUENCE: 189

```
tcaaacacga ttgcactcaa caaacgagcc cgccacgaat attttattga agatgaaatt     60

gaagcaggtt tagcattgca aggctgggaa gttaaatctt tacgcgcagg taaagcaaat    120

atcggtgata gctatgttac ttttcgtcat ggtgaagcct ttttatttgg cgctacaatt    180

accccattaa atatggcttc tactcatatt gttgcagatc caacacgtac tcgtaagcta    240

ctattaaatc aaagagaatt agactcatta tttggtaaag taaatcgaga tggaatgact    300

gtggtggcac tttcgcttta ttggaaaaat gcttgggcga aagtcaagat agggctagcg    360

aaaggcaaaa aacttcacga taaacgtgaa gatattaaag atcgtgaatg gcacgttact    420

aagcaacgca ttatgaaaaa tgc                                            443
```

<210> SEQ ID NO 190
<211> LENGTH: 483
<212> TYPE: DNA
<213> ORGANISM: Haemophilus pittmaniae

<400> SEQUENCE: 190

```
atgaccaaga aaaaagctaa agttggcgca aacaccatcg cattaaacaa acgcgcgcgc     60

cacgattatt ttattgaaga cgaagttgaa gccggtttgg agttgcaagg ttgggaagta    120

aaatccatgc gcgctggtaa agctaatatc agcgacagtt acattatttt caaaaatggc    180

gaggcttatt tatttggcgc gaccattcag cctttatctc tagcatccac ccatgtggtt    240

tgcgatccga cccgcacccg taaactgtta ctcaataaac gcgaactgga taatcttttt    300

ggtaaatcag cacgtgatgg ttttaccatc gtagcgcttt ccctttattg gaaaggcgcc    360

tgggcaaaaa ttaaaatcgg tttggcgaag ggtaagaaac aacatgacaa acgcgaagac    420

atcaaagaac gcgaatggaa gttggataaa caacgaatta tgaaaaatgc caatcgcggc    480

taa                                                                  483
```

<210> SEQ ID NO 191
<211> LENGTH: 480
<212> TYPE: DNA
<213> ORGANISM: Haemophilus sputorum

<400> SEQUENCE: 191

```
atggcaaaaa aacctaaagt tgcttcaaat actattgcgc taaataaacg cgcacgacat     60

gaatatttta ttgaagaaga aattgaagcc ggcttagaac tccaaggttg ggaagtgaaa    120

tctctgcgcg ccggtaaagc taatattggg gatagctatg ttacctttag aaacggcgaa    180

gcctttttat tcggtgcaac cattaccccg ctgaatatgg cgtcaacaca tatcgttgcc    240

gacccaacta gaaccagaaa attattactc aataaacgag aactcgattc actctttggt    300

aaagtgaacc gagatggaat gactgttgtt gccctttccc tttattggaa agccgcttgg    360

gcaaaagtga aaattggtgt ggcaaaaggc aaaaaattac acgataaacg tgaagatatt    420

aaagaccgcg aatggcaagt tgctaaacaa cgtattatga aaaacgcgaa ccgtggttaa    480
```

<210> SEQ ID NO 192
<211> LENGTH: 477
<212> TYPE: DNA
<213> ORGANISM: Haemophilus parasuis

<400> SEQUENCE: 192

```
atgagtaaaa aaccaaaagt agcttcaaac acgattgcct taaataaacg tgccagacac     60

gaatatttta tcgaagaaga aatcgaagct ggtctagaat tacaaggctg ggaagtcaaa    120
```

-continued

```
tccctgcgag caggcaaagc caatatcggc gatagctatg tcactttccg taatggcgaa    180

gcctttttat tcggtggcac tattaccccg ttaaatgtcg cttctaccca tattgtgtgc    240

gacccaaccc gtacccgtaa attattgtta aataagcgtg agttagacac gctttatggt    300

aaagtcagcc gtgatgggtt taccgttgtc gccctgtcgc tctactggaa aaatgcgtgg    360

gcgaaggtca aaatcggctt ggcgaaaggg aaaaaattgc acgataaacg tgaagatatt    420

aaagaccgtg agtggcaagt tgctaaacag cggattatga agaatgcgaa taggtag       477


<210> SEQ ID NO 193
<211> LENGTH: 477
<212> TYPE: DNA
<213> ORGANISM: Haemophilus parasuis

<400> SEQUENCE: 193

atgagtaaaa aaccaaaagt agcttcaaat acgattgcct taaataaacg tgccagacac     60

gaatatttta tcgaagaaga aatcgaagct ggtctagaat tacaaggctg ggaagtcaaa    120

tccctgcgag caggtaaagc caatatcggt gatagttatg tgacatttcg caacggcgaa    180

gcctttttat tcggtggcac tattaccccg ttaaatgtcg cttctaccca tattgtgtgc    240

gatccaaccc gtacccgtaa gttattgtta aataagcgtg agttagacac gctttatggt    300

aaagtcagcc gtgatgggtt taccgttgtc gctctgtcgc tttactggaa aaatgcgtgg    360

gcgaaagtca aaatcggctt ggcgaaaggg aaaaaattgc acgataagcg tgaagatatt    420

aaagaccgtg agtggcaagt tgctaaacag cggattatga agaatgcgaa taggtag       477
```

DIAGNOSTIC METHOD FOR BACTERIAL ORGANISMS USING THE SMPB GENE

CROSS REFERENCE TO RELATED APPLICATIONS

This application is a U.S. National Stage of PCT/EP2016/061599, filed May 23, 2016, which claims the benefit of priority to Great Britain Patent Application No. 1508860.2, filed May 22, 2015, the disclosures of which are incorporated herein by reference in their entirety.

FIELD OF THE INVENTION

The present invention relates to methods for determining the presence or absence of a member of a group of bacterial organisms in a sample. More specifically, the invention relates to methods for determining the presence or absence of a member of a group of bacterial organisms by determining whether a target region of the smpB gene is present in a sample. Primers, probes and kits for use in these methods also form part of the invention, as does the use of an smpB gene target region to detect the presence or absence of a member of a group of bacterial organisms in a sample, in a range of clinical and non-clinical applications.

BACKGROUND TO THE INVENTION

Bacterial infections are a major cause of disease worldwide. A wide range of bacterial organisms are responsible for infection and there is a need for assays to detect and to identify bacterial organisms.

The need extends to detecting and identifying bacterial organisms in a clinical context (e.g. in a sample from a subject or patient) and also to detecting and identifying bacterial organisms in other samples, such as clinical products, food products (including drinking water) and environmental samples. Detecting and identifying bacterial organisms in a clinical context is useful for example to diagnose infection in a subject or patient, whereas identifying bacterial organisms in other samples is also useful to detect and identify bacterial organisms as a source of contamination and as potential causes of disease. The presence of undesirable bacteria in food has the potential to cause serious illness or even death as a consequence of its ingestion by the consumer. Likewise, bacterial contamination of clinical products (e.g. blood products) can have harmful consequences if infection is caused as a result of the use of such products. Further, there is the need to monitor the environment for bacterial contamination. This is of particular concerns in locations such as hospitals where there are people who are vulnerable to infection, or in recreational facilities such as swimming pools and lakes, which may be contaminated with high levels of bacteria.

Accordingly, there is a need for detecting and identifying bacterial contamination in numerous products that are consumed or used by humans, as well as in the environment and in detecting and identifying bacterial organisms causing infection in patients/subjects.

Traditional assays to detect and identify bacterial organisms commonly rely on microbiological culture methods and biochemical methods to identify the cause of microbial infections. Such methods are often time-consuming, requiring several days to culture the infectious agent before definitive identification can take place. Furthermore, such methods can have poor sensitivity. In a clinical setting this can not only lead to delays in providing treatment, but also cause the wrong treatment to be administered.

Nucleic acid based assays to detect and identify bacterial organisms are desirable as not only are they quick to carry out, but also they have the potential to afford a high level of specificity and sensitivity. Nucleic acid based assays to detect and identify bacterial organisms require suitable nucleic acid targets to be present in the bacterial organism of interest.

Accordingly, there is a need for the identification of novel molecular targets that can be used for rapid, selective and specific detection and identification of bacteria.

A number of nucleic acid targets have been identified for use in bacterial diagnostics assays including the ssrA [1], lepA [2] and 16sRNA genes [3]. Whilst these targets have been useful in the development of assays for certain bacterial organisms, there are limitations associated with these targets owing to the high degree of nucleotide sequence homology across the bacterial kingdom. In other instances, sequence heterogeneity can also pose a problem. For example, the use of 16S rRNA as a diagnostics target has been complicated by the fact that bacteria harbour multiple heterogeneous copies of this gene (ranging from 1-15). Sequence heterogeneity within single bacterial genomes can create a significant problem for diagnostic development. It can also lead to an overestimation of microbial populations present in samples [4,5].

It is an aim of the present invention to identify further nucleic acid targets that can be used in nucleic acid based assays to detect and identify bacterial organisms. Furthermore, the identification of further targets will facilitate the development of multi-target assays that can further increase specificity of assays. For reliable detection and identification of a bacterial organism, the target will preferably be highly specific. An assay is specific if there is low or no cross-reactivity with nucleic acids from other organisms, i.e., the assay does not generate false positive results, or does so with low frequency, and if most or all organisms of interest are identified, i.e. the assay does not generate false negative results or does so with low frequency. The former is defined with respect to "exclusivity" panels, and the latter with respect to "inclusivity" panels.

*Haemophilus influenza* is a Gram-negative, coccobacillary, facultatively anaerobic bacterium which frequently colonises the Upper Respiratory Tract (URT) and is a significant causative agent of Respiratory Tract Infections (RTI) and pneumonia worldwide. There is a requirement for the development of a rapid *H. influenzae* diagnostics assay which would allow for the implementation of infection control measures and also improve antimicrobial stewardship for patients. There is currently no single nucleic acid diagnostics target described in the literature that can unambiguously identify *H. influenzae*. Accordingly, there is a need for the identification of novel molecular targets that can be used for rapid and specific detection of *H. influenzae.*

Traditional culture and phenotypic based methodologies for the identification of *H. influenzae* are slow and in many cases cannot differentiate *H. influenzae* from the closely related *H. haemolyticus* or other *Haemophilus* species [6, 7, 8]. In recent years a number of novel molecular based approaches have been described for the detection of *H. influenzae* including MALDI-TOF mass spectrometry and nucleic acid based diagnostics assays [9, 10, 11, 12]. As mass spectrometers are still relatively expensive and require specialist training they are not available in all diagnostic and clinical laboratories. More importantly, the requirement for bacterial culture prior to analysis by MALDI-TOF MS takes a minimum of one day, often longer. Furthermore, false negative reporting of results can occur if antimicrobial therapy has been administered prior to collection of the clinical samples. Several real-time PCR (RT-PCR) diagnostic assays have been described for *H. influenzae*. These include those that target the fucK, hpdA, bexA, ompP2, P6 genes, respectively [8,12,13,14]. However many of these diagnostics assays lack specificity which can pose challenges for the clinical laboratory. For instance, it has previously been demonstrated that the fucose operon can be deleted in some strains of *H. influenzae* which can result in the reporting of false negative results when using the fucK assay [71]. hpdA and ompP2, been found to cross react with other *Haemophilus* species resulting in the reporting of false positive results [8,13].

*Legionella* spp., the causative agent of Legionnaires' disease are responsible for outbreaks of both hospital acquired and community acquired pneumonia [15]. In healthcare settings, there is an increasing proportion of immunologically compromised patients leading to added potential for infection of patients by such opportunistic pathogenic microorganisms. The most common microorganism associated with Legionnaires disease is *Legionella pneumophila*. Currently, routine testing for *L. pneumophila* is performed using traditional microbiological based techniques. This method is limited by the fastidious nature and long incubation periods required by *Legionella* spp. and also by the presence of viable but nonculturable Legionellae. Accordingly, there is a need for the identification of novel molecular targets that can be used for rapid and specific detection of *L. pneumophila*.

In particular, multiplex assays that are able to detect *Legionella* at the genus and species and levels are desirable. It is possible to find multiple species of *Legionella* in a sample so it is useful to determine whether a *Legionella* species is present. The most clinically relevant species in the context of human disease is *Legionella pneumophila* (which accounts for ~90-95% of infections) so it is important to specifically identify this microorganism. Accordingly, there is a need for the identification of novel molecular targets that can be used for rapid and specific detection of *L. pneumophila*, which can be used alone or in combination with other targets for detection of *Legionella* at a genus level.

*A. baumannii* are a Gram-negative, strictly aerobic, non-fermenting, bacteria. Its natural reservoir has not yet been determined however it has been found in the environment in soil and water [16, 17]. In recent years *A. baumannii* has emerged as one of the most important pathogens in healthcare institutions. *A. baumannii* has an ability to survive for long periods of time in the healthcare environment in areas such as hospital equipment, rooms curtains, pillows, furniture and sinks leading to an increased risk transmission of Health Care Associated Infections (HCAI's). It is a common cause of pneumonia (Including Ventilator associated pneumonia), wound and soft tissue infections, sepsis, urinary tract infections and meningitis.

Accordingly, there is a need for the identification of novel molecular targets that can be used for rapid and specific detection of *A. baumannii*.

The genus *Listeria* are ubiquitous in nature, having been isolated from soil, plants, and feces of humans and animals. *Listeria monocytogenes* is the most clinically relevant human pathogen in this genus, however other member of the genus have been implicated in human disease including *Listeria grayi*. Specific identification of this microorganism is important clinically due to decreased sensitivity to ampicillin. Accordingly, there is a need for the identification of novel molecular targets that can be used for rapid and specific detection of *L. grayi*.

*Mycoplasma* is a genus of bacteria that lack a cell wall around their cell membrane and as such these microorganisms are unaffected by many common antibiotics such as penicillin or other beta-lactam antibiotics that target cell wall synthesis [18]. They represent the smallest self-replicating organisms capable of cell-free existence, both in cellular dimensions (1-2 mm long and 0.1-0.2 mm wide) and genome size [19]. There are currently more than 200 *Mycoplasma* species of which the commonly studied is *Mycoplasma pneumoniae*. M pneumonia is a common cause of lower respiratory tract infections and has been implicated important causes of atypical bacterial Community Acquired Pneumonia [19,20]. Traditional diagnosis of M pneumonia relies on culture based techniques which are slow to perform (days to weeks) [21]. As such there is a need to develop rapid nucleic acid based approaches to specifically identify M pneumonia to ensure appropriate antimicrobial therapy for patients.

Non Tuberculosis *Mycobacteria* (NTM) are ubiquitous in the environment and are commonly isolated from soil and water [22,23]. Historically, NTM were considered non virulent to healthy individuals, however it is now accepted that NTM are emerging as a major cause of infection in certain patient groups particularly those suffering from cystic fibrosis, chronic obstructive pulmonary disease, are HIV positive, transplant patients and other immunosuppressive conditions [24,25,26,27,28]. Published reports suggest that in many countries in Europe, the US and Canada the rates of NTM disease are increasing [29,30,31,32,33,34]. Unlike Tuberculosis, NTM disease is rarely if ever transmitted from patient to patient. The exact routes of transmission are not currently known, however owing to the environmental reservoirs of these microorganisms, disease is believed to be acquired from environmental exposures [22, 23]. In healthcare facilities, water and water distribution have been identified as reservoirs for colonisation with NTM [35,36]. Water and water distribution systems within healthcare facilities can act as a vector for transmission of infection through bathing/showering, inhalation and contact with medical devices [35,36,37,38,39].

In a recent study, 91 different NTM were isolated from 20182 patients in 30 countries across six continents. Of these NTM, *Mycobacterium avium* complex (which includes *M. avium, M. avium intracellulare* and *M. avium* paratuberculosis) bacteria predominated in most countries, followed by *M. gordonae* and *M. xenopi* [40].

To ensure patient safety, there is a growing need to rapidly detect, identify and quantify NTM associated with contamination of water and water distribution systems. Traditionally identification of NTM relies on microbiological culture based techniques and biochemical tests. These tests are slow to perform based on the slow growing nature of some NTM (up to six weeks), are labour intensive and often yield unreliable results Tuberculosis (TB) is the leading cause of death worldwide from an infectious agent [41], with the WHO estimating that one third of the global population are infected with TB. In a global report from the WHO (2009), it was estimated that there were 9.27 million cases of TB in 2007, with 2 million associated deaths. TB in mammals is caused by members of the *Mycobacterium tuberculosis* Complex (MTC). The eight closely related species in the complex have a wide range of natural hosts including humans hosts (*M. tuberculosis M. africanum M. canetti*), bovine hosts (*M. bovis*), caprine hosts (*M. caprae*), rodent hosts (*M. microti*) and pinniped hosts (*M. pinnipedii*) along with the attenuated *M. bovis* strain BCG (*Bacillus* Calmette-Guérin), the commonly used vaccine strain. While there are a number of natural hosts, each member of the MTC has been implicated in human infection [42,43].

Traditionally, diagnosis of TB relies on culture techniques and a battery of biochemical tests which are time consuming, labour intensive and often yield insensitive results [44]. Nucleic Acid Diagnostics (NAD) in particular real-time PCR techniques exist, but the identification of additional target regions to determine the presence or absence of a member of the MTC is desirable.

The inventors have identified smpB as a useful gene for the provision of nucleic acid target regions, which can be used in a range of methods to determine the presence or absence of a member of a group of bacterial organisms in a sample. The approach has been validated in assays to determine the presence or absence of a member of a number of different groups of bacterial organisms.

SUMMARY OF THE INVENTION

The invention provides a method for determining the presence or absence of a member of a group of bacterial organisms in a sample, wherein the method comprises determining whether a target region of the smpB gene is present in said sample.

The smpB gene or regions contained within this gene have not previously been used as a target region for determining the presence or absence of a bacterial organism in a sample. The inventors have surprisingly found that this gene is particularly suited to this purpose, at least because it is found in all bacterial species, and because of the regions of sequence variation and conservation that are present in the gene.

smpB is an RNA-binding protein that is an essential component of the bacterial ssrA quality control system that is conserved throughout the bacterial kingdom [45]. The smpB gene, which codes for the RNA binding protein small protein B (smpB), has been identified in all bacterial species to date [46]. It is considered an essential component of quality control in bacteria as it facilitates the binding of tmRNA to stalled ribosomes which in turn allows for removal of incomplete polypeptides from the cell [45,47]. As smpB is considered essential for the correct functioning of tmRNA in a bacterial cell, the smpB gene is considered to be amongst a core set of genes necessary to sustain bacterial viability [48]. smpB has not previously been proposed as a target for use in bacterial detection or identification, nor have probes or primers specific to this gene been used in methods of determining the presence or absence of a bacterial organism in a sample.

The smpB gene is particularly suitable for this purpose in view of the fact that it is present in all known bacterial species. It also contains significant sequence variability, which allows target regions to be identified which allow differentiation of the subspecies, species or genus (or group thereof) concerned from other subspecies, species or genera (or groups thereof), but, on the other hand, have sufficient sequence conservation between the members of each of these groups to allow the detection of all organisms of interest.

The inventors have surprisingly found that the smpB gene, which is only 460 bp in length, has sufficient sequence heterogeneity amongst the various members of the bacterial kingdom to allow the development of assays that are based on this gene and which can be used to determine the presence or absence of members of groups of bacterial organisms in a sample. For example, *H. influenzae*, can be detected without detecting other related *Haemophilus* species such as *H. haemolyticus*, all tested strains of *Legionella pneuomophila* can be detected in a single diagnostic assay based on smpB, *Acinetobacter baumannii* can be detected in an assay based on smpB, without detecting other *Acinetobacter* species, *Listeria grayi* can be detected in an assay based on smpB without detecting other *Listeria* species, all tested strains of *Mycoplasma pneuomoniae* can be detected, and various *Mycobacterium* species such as *M. avium* and *M. intracellularae* (or groups thereof such as the MTC or NTM) can be detected without detecting other *Mycobacterium* species (or without detecting other species that are not within that group).

In general terms, the inventors have surprisingly found that there is sufficient variation in regions of this gene between different groups of bacterial organisms, whilst at the same time there is sufficient sequence conservation within the members of groups of bacterial organisms so that the regions containing sequence conservation within the members of the groups of bacterial organisms can be used as target regions in methods to determine the presence or absence of a bacterial organism within that group. In such methods, determining the presence or absence of that target region will provide information about whether the bacterial organism containing that target region is present. Where there is sufficient variation in a region of this gene between a group of bacterial organisms of interest and bacterial organisms that are not members of this group, and at the same time there is sufficient sequence conservation in the region of the gene within the group of bacterial organisms of interest, specificity is provided.

By way of example it has been shown by the inventors that there is sufficient variation in regions of this gene between a group which is a species, as compared to bacterial organisms that are not within this group, yet sufficient sequence conservation within members of the group (e.g. subspecies, strains and/or serotypes of the same species), to be able to determine the presence or absence of a specific species using the relevant region of the gene as a target (e.g. *H. influenzae, Legionella pneuomophila, Acinetobacter baumannii, Listeria grayi, Mycoplasma pneuomoniae, M. avium, M. intracellulare*). In a further example, there is sufficient variation in regions of this gene between a group of multiple bacterial species, compared to species not within this group, yet sufficient sequence conservation within the species that are members of the group to determine the presence or absence of a member of the group using the relevant region of the gene as a target (e.g. where the group is the *Mycobacterium Tuberculosis* Complex (MTC) or Nontuberculosis *Mycobacteria* (NTM)).

These regions of sequence variation and conservation between groups of bacterial organisms provides specificity in these assays (with respect to inclusivity i.e. the ability to detect most or all members of the group and exclusivity, i.e. excluding or not detecting bacterial organisms that are not members of the group). A group of bacterial organisms may be a single subspecies, species or genus, or a plurality of these (e.g. 2, 3, 4, 5, 6, 7, 8, 9, 10, 11, 12, 13, 14, 15, e.g. 2-10, 3-7, 4-6).

The methods of the invention are particularly suited to nucleic acid amplification (e.g. PCR) assays, such as real-time PCR assays. Multiplex assays are of particular interest. In general in a multiplex assay at least one control (such as an internal amplification control (IAC)) is used, and optionally multiple target regions are amplified. Multiplex assays may use one or a plurality of more, e.g. two or more of the target regions identified herein, alone or in combination with one or a plurality of target regions from one or a plurality of other genes. Advances in real-time PCR such as the availability of multiple fluorophores, along with the development of non-fluorescent quenchers has facilitated multiplexing, allowing for the simultaneous detection and discrimination of multiple targets, along with internal controls, in one reaction.

The use of an smpB gene target region to determine the presence or absence of a member of a group of bacterial organisms in a sample is also provided.

Probes and primers and kits (e.g. diagnostic kits) containing such probes and/or primers, e.g. for use in the methods of the invention are also provided.

BRIEF DESCRIPTION OF DRAWINGS

FIG. 2A-2E: Multiple sequence alignment of publicly available *Legionella pneumophila* smpB gene sequences FIG. 3A-3H: Multiple sequence alignment of sequences generated for a number of culture collection strains using sequencing primers LgensmpB_F and LgensmpB.

FIG. 4A-4J: Multiple sequence alignment of publically available *Legionella pneumophila* smpB gene sequences and partial smpB gene sequences generated using sequencing primers LgensmpB_F and LgensmpB.

FIG. 7A-7M: Multiple sequence alignment of publically available *Acinetobacter* species

FIG. 10A-10E: Multiple sequence alignment of *Listeria* species smpB nucleotide sequence

FIG. 13A-C: Multiple sequence alignment of publicly available smpB *Mycoplasma pneumoniae* sequences.

FIG. 16A-16F: Multiple sequence alignment of publicly available smpB *Mycobacterium* sequences.

FIG. 17A-17J: Multiple sequence alignment of publicly available smpB *Haemophilus* sequences.

FIG. 18A-18I: Multiple sequence alignment of publicly available ssrA *Legionella* sequences.

DETAILED DESCRIPTION OF THE INVENTION

Assay Components

Target Region and Target Sequences

Figure 1:
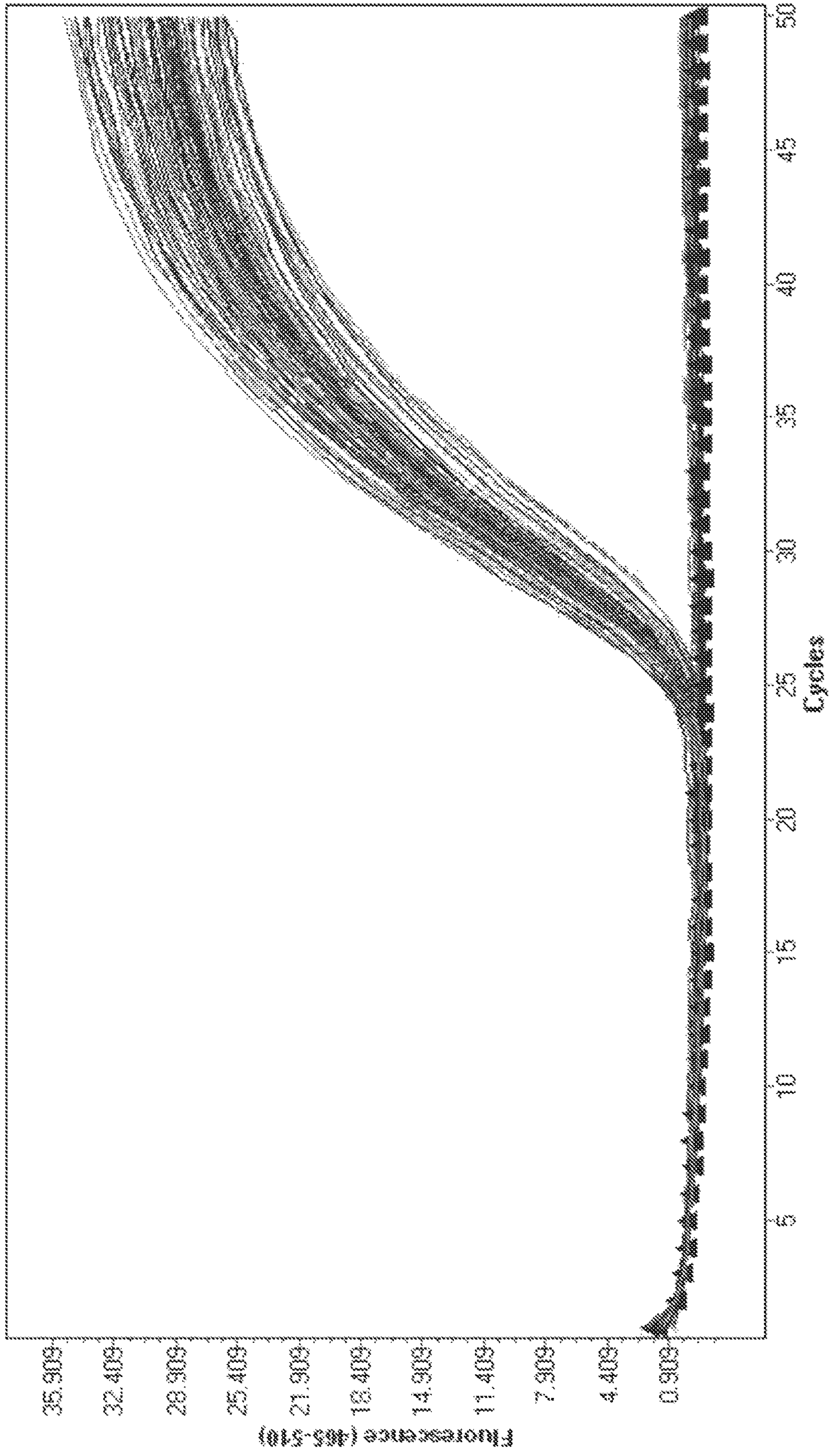
FIG. 1A-1B: Real-time amplification curves. The amplification curves generated in each of the analysis channels for the *Haemophilus influenzae* duplex assay (smpB and IAC).

The target region is a region of a gene that is amplified and detected to determine the presence or absence of a member of a group of bacterial organisms. The target region can therefore be specific to the group of bacterial organisms of interest.

The smpB gene, which provides the target region in this invention, is present in all bacterial species. Its sequence is particularly useful for identifying target regions that can be used to determine the presence or absence of a member of a group of bacterial organisms because of the level of sequence variation that is present in this gene between different bacterial organisms. This sequence variation allows the members of the group of bacterial organisms of interest to be distinguished from other bacterial organisms (e.g. those that are not members of the group of bacterial organisms of interest).

An appropriate target region for determining the presence or absence of a member of a group of bacterial organisms of interest can be selected based on the amount of sequence variation and identity that is present between the versions of the smpB gene that are found in different bacterial organisms. For example, sequences of the smpB gene from members of the group of bacterial organisms of interest can be aligned, e.g. to identify regions of similarity or identity within the members of the group of bacterial organisms of interest. The sequences may also be compared (e.g. by alignment) to sequences of the smpB gene from bacterial organisms which are not members of the group of bacterial organisms of interest (e.g. to identify regions of variation between the smpB gene sequence of those bacterial organisms that are in the group of interest and those that are not, and/or to confirm that a region of similarity or identity in the smpB gene sequence between members of a group of interest is absent in the bacterial genome of bacterial organisms that are not in the group of interest). The selection of a target region may thus be made by carrying out an in silico alignment of bacterial smpB sequences from a group of interest and/or with sequences (e.g. smpB sequences) from bacterial organisms that are not members of the group to identify regions of variation between the members of the group of bacterial organisms of interest and bacterial organisms that are not within the group, and regions of similarity or identity within the members of the group of bacterial organisms of interest. Appropriate ways to align multiple sequences include Clustal Omega (see the internet at www.ebi.ac.uk/Tools/msa/clustalo/) and ClustalW (see the internet at www.ebi.ac.uk/Tools/msa/clustalw2/).

Regions that contain sequences that have high levels of identity or similarity within the members of the group of bacterial organisms of interest can be used as target regions to determine the presence or absence of a member of the group of those bacterial organisms that share that target region. Assays that detect such target regions can therefore be used to determine whether that target region is present in a sample. In turn this provides information about the bacterial organism(s) that is present in the sample, i.e. whether a member of a group of bacteria organisms of interest is present in the sample.

The target region is in general amplified and detected by primers and probes in the methods of the invention, e.g. specifically amplified and detected by primers and probes. In the examples provided, the target region is the region that is amplified and detected using the exemplified primers and probes. In most cases, the target region comprises three sequences that in combination are specific to the group of bacterial organisms to be detected. These three sequences correspond to (i.e. are, or are the reverse complement of) the two primer binding sites and to the probe binding site. In some cases the target region comprises two sequences that in combination are specific to the group of bacterial organisms to be detected. This may be where one of the primer binding sites and the probe sequence in combination are specific to the group of bacterial organisms to be detected, or where the two primer sequences in combination are specific to the group of bacterial organisms to be detected. In other cases the target region comprises one sequence that is specific to the group of bacterial organisms to be detected, which may be a primer or probe binding site.

The target region thus contains one or more (e.g. 1, 2, 3, 4 or 5, but in general 3) nucleotide sequences that, alone or in combination, are specific to the group of bacterial organisms to be detected. These sequences are referred to as target sequences. The target sequence may be e.g. 10-50, 15-40, 16-35, 17-30, 18-25 nucleotides in length. The target sequence may be a sequence that is present in one or more members of the group (e.g. all members of the group), or may be a consensus sequence that is generated from comparing the sequences in multiple members (e.g. all members) of the group. In such a case a plurality of probes or primers may be used for each target sequence (e.g. 2, 3, 4, 5, 6 primers or probes), or a single probe or primer may be used (e.g. which is able to perform its function in amplification and detection despite the presence of one or more mismatches within the sequence). In general, where the target sequence is a consensus sequence, sequence variation is present only at up to 5, 4, 3, 2, or 1 nucleotide position.

The target sequences are in general used to design the primers and/or probes that are used to detect the target region. As well as being selected on the basis of the criteria mentioned above, the target sequences may be selected on the basis that they allow the design of suitable probe and/or primer sequences (alone or in combination). Criteria for the design of primers and probes are well known in the art, and include achieving a suitable length, melting temperature with the target, suitable G-C content.

Because the target sequences, alone or in combination, are specific to the group of bacterial organisms to be detected, the target region is specific to the group of bacterial organisms to be detected. Where there are more than one target sequences in the target region they may be contiguous or overlapping (e.g. by up to 10, 9, 8, 7, 6, 5, 4, 3 2 or 1 nucleotide) or they may be separated by sequences which may or which may not be specific to the group of bacterial organisms of interest (e.g. separated by one or more sequences of 1-150, 10-100, 20-90, 30-80, 40-70, 50-60 nucleotides).

The group of bacterial organisms may be a single genus, species (or subspecies) or may contain multiple genera, species (or subspecies). Preferably the target region is present in the members of the group of bacterial organisms of interest and not present in other bacterial organisms. By way of example a target region that contains one or more nucleic acid sequences that are highly conserved across a genus, species (or subspecies) of the bacterial organism of interest can be used to identify the specific genus, species (or subspecies) across which the sequence is conserved. The conservation may be across a genus, e.g. conserved across all bacterial species in a genus, in which case it can be used to identify a bacterial organism of that genus. Such a target region is particularly useful where it is not present in other bacterial genera. The conservation may be across a species, e.g. conserved across all bacterial subspecies or across all bacterial serogroups within a species, in which case it can be used to identify a bacterial organism of that species (e.g. all bacterial subspecies or all bacterial serogroups within that species). Such a target region is particularly useful where it is not present in other bacterial species. A target region that is conserved within a particular subspecies (or group thereof) can likewise be used to identify the presence of a particular bacterial subspecies (or group thereof) in a sample.

Determining whether a target region of the smpB gene is present in said sample may therefore provide information about the presence or absence of a member of a group of bacterial organisms (e.g. one or more genus, species (or subspecies)). The target region is in general present in one genus, species (or subspecies) and absent in others, but in some cases may be present in multiple (e.g. 2, 3, 4 or 5) genera, species (or subspecies), and absent in others, in which case determining whether the target region of the smpB is present in the sample will provide information about whether one of these multiple genera, species (or subspecies) is present.

The inventors have identified target regions for a number of different groups of bacterial organisms, and these are set out in more detail below. Target regions for other bacterial organisms (which can be used to provide information about whether a given genus, species, subspecies is present in a sample) can similarly be identified by obtaining and aligning multiple smpB sequences within the group that is to be the subject of the assay and identifying conserved regions within the group that is to be the subject of the assay, and appropriate target sequences. The target region is preferably not shared by bacterial organisms that are not within the group that is to be the subject of the assay.

The methods can therefore also alternatively be described as methods of identifying a member of a group of bacterial organisms.

The methods of the invention comprise determining whether a target region of the smpB gene is present in a sample. The invention also provides use of a target region of the smpB to determine the presence or absence of a bacterial organism in a sample.

In one embodiment, the target region is at least 20, 30, 40, 50, 60, 70, 80, 90, 100, 120, 140, 160, 180, 200, 250, 300, 350, or 400 nucleotides in length (e.g. nucleotides of the smpB gene), e.g. 15-200, 20-190, 30-180, 40-170, 50-160, 50-150, 70-140 nucleotides (e.g. nucleotides of the smpB gene).

In general, to carry out the method of the invention, a nucleic amplification method is performed to generate multiple copies of the target region. Primers which amplify the target region may be used. The amplification may amplify the target region in members of that group and in bacterial organisms which are not members of the group. In such cases the specificity of the method relies on the specific binding of the probe to the target region, and determining whether the target region is present will require the use of a probe that is specific for the target region. In these cases the primers may bind to regions of the smpB gene that are outside the target region. In such a case the target region may comprise one target sequence (e.g. the probe binding site).

Alternatively the primers are specific for a sequence in the target region, alone or in combination i.e. they bind to generate an amplicon only when the target region is present. In this case, the primers are specific for the group of bacterial organisms of interest, alone or in combination. In these cases the mere detection of an amplified product can be enough to determine that the target region is present, but optionally a probe that is specific for a sequence in the target region may be used. The use of such a probe facilitates multiplex methods and may increase specificity or sensitivity.

In other cases both of the primers and the probe are specific for the target region (e.g. in combination).

The target region therefore may comprise one, two or three sequences that are specific for the group of bacterial organisms to be detected, alone or in combination. In some cases only the combination of two or three of these sequences is specific to the group of bacterial organisms to be detected. These sequences are preferably 10 to 50 nucleotides in length, e.g. 11-45, 12-40, 13-35, 14-30, 15-25, 16-24, 17-23, 18-22 nucleotides in length.

Primers

The method of the invention will in general use primers to amplify a target region of the smpB gene. Such primers also form part of the invention. In one embodiment, the methods of the invention comprise an amplifying step, in which an amplicon of the smpB gene is amplified. Detection of the amplicon is used to determine whether or not the target region is present and in general the amplicon will comprise or consist of the target region. The amplicon is up to or at least 40, 50, 60, 70, 80, 90, 100, 110, 120, 130, 140, 150, 160, 170, 180, 190, 200, 250, 300, 350, 400 or 450 nucleotides in length (e.g. of the smpB gene), e.g. 50-200, 60-190, 70-180, 80-170, 90-160, 100-150 nucleotides (e.g. of the smpB gene).

The primers will be chosen to generate an amplicon that allows the determination of whether the target region is present and/or to generate an amplicon of optimal size.

Primers (e.g. for real-time PCR) will in general have one or more of the following properties (i) a G-C content of about 40-60% (e.g. 50-60%), (ii) a melting temperature of about 55-65° C. (e.g. 58-60° C.), (iii) a C or G at the 3' terminus (iv) melting temperatures for the primer pair that are within about 1-5° C. (e.g. 1-2° C.) of each other.

Probes

In one embodiment, the methods of the invention use a probe. The probe may detect the presence of the target region (e.g. in an amplicon). The probe thus binds to the amplicon and to the target region of the smpB gene. In a preferred embodiment, the probe binds to a target sequence. The probe is preferably specific for this sequence.

In general the probe is specific for a the target region, alone or in combination with one or both of the primers, but when one or both of the primers are specific for the target region, production of an amplicon alone may be enough to detect the presence of the target region in the sample. In this instance, the probe may bind to a region of the amplicon other than a target sequence. In some embodiments therefore the probe is not specific to the bacterial organism of interest.

When only a single amplification reaction is carried out and, the primers are specific for the target region, the probe needs only to detect the presence of the amplicon. In this instance, the primers may be bind to the target region and therefore bacterial organisms in which the target region is not present do not amplify the smpB gene. Accordingly in some embodiments, the probe can be non-specific to the target region. In some embodiments the probe may be a DNA intercalator dye. Other non-specific probes will be apparent to those skilled in the art.

The probe may be labelled, e.g. with a fluorescent marker and optionally a quencher.

The probe may bind to either strand of the target region or amplicon. Therefore to the extent that probe sequences are provided herein, it is clear that probes with a sequence that is the reverse complement of these probes can also be used.

Probes (e.g. for real-time PCR) will in general have one or more of the following properties (i) a G-C content of about 40-60% (e.g. 50-60%), (ii) a melting temperature of about 5-10° C. (e.g. 7-8° C.) higher than the melting temperature of the primers (iii) will not have a G at the 5' terminus.

Internal Amplification Control (IAC)

In one embodiment, the methods of the invention include the use of an Internal Amplification Control (IAC). An IAC is a control amplification and detection that is carried out in parallel with the amplification and detection of the target region. The IAC amplifies and detects an IAC target. In one embodiment IAC nucleic acid, e.g. DNA, comprising the IAC target is added to each reaction. In another embodiment cells comprising the IAC target are added to the reaction. The nucleic acid that is added may be bacterial or non-bacterial. The nucleic acid may be e.g. from a plasmid, bacteria or may be an artificially generated sequence (e.g. non naturally occurring), a synthetic construct.

In a multiplex real-time PCR with an IAC, a positive result must always be observed in at least one assay. If a positive signal is not observed in at least the IAC channel, the result suggests that the reaction was inhibited due to malfunction of the thermal cycler, incorrect PCR mixture, inhibitory substances and or/poor polymerase activity. Several types of IAC can be incorporated into a multiplex real-time PCR including competitive and non-competitive IAC's. In a competitive IAC the primary target and the IAC are co-amplified with one common set of primers in a PCR master mix. In such instances a positive signal will always be observed in the primary channel and depending on the concentration of template present, the IAC may or may not be detected. Alternatively a non-competitive IAC may be chosen for inclusion in a multiplex real-time PCR. In this instance the IAC and primary target(s) are amplified by different oligonucleotides. In a non-competitive approach, the IAC must always give a positive signal. Careful consideration must be paid to choosing which type of IAC is most appropriate for a specific application but will be obvious to those skilled in the art.

The IAC may be added to the reaction as isolated nucleic acid e.g. plasmid-derived. Alternatively, cells comprising the IAC may be added to the reaction. Preferably bacterial cells comprising the IAC are added to the reaction. Preferably a known quantity of IAC bacteria is added. In this instance, the IAC may be used to simultaneously monitor the efficacy of nucleic acid extraction. Preferably the nucleic acid is extracted from the IAC bacteria under similar or identical conditions to those nucleic acid of the group of bacterial organisms of interest, or are extracted simultaneously with the nucleic acid of the group of bacterial organisms of interest.

The use of an IAC gives the assay greater reliability as false negative results are reduced. Without an IAC, if amplification fails no signal will be produced. There is a danger that this result will be incorrectly interpreted as a negative result, indicating the absence of a particular bacterial organism in a sample. However, by using an IAC target in each reaction (e.g. amplifying it with IAC primers and detecting its amplification using an IAC probe), it can be verified that the amplification and detection steps are working. If only the IAC signal is detected, no bacterial organisms tested for are present in a sample. However, if no signals at all are detected, amplification failed and the test must be repeated.

In one embodiment the IAC may comprise or consist of a 16sRNA, lepA or ssrA sequence (e.g. as defined in any of [1], [2] or [3]), e.g. *Bacillus subtilis* ssrA, e.g. which can be detected using primers with the sequences SEQ ID NO: 7 and 8 and a probe with the sequence SEQ ID NO: 9.

In certain embodiments, the IAC may be amplified using primers which comprise or consist of SEQ ID NO: 35 and 36.

The presence or absence of the IAC may be determined using a probe comprising or consisting of SEQ ID NO: 42 or its reverse complement.

The IAC target region and any primers and/or probes are preferably compatible with those for determining the presence of the other target region(s).

Assay Methods

The method of the present invention preferably comprises the steps of amplification and detection of the target region. The method may additionally comprise DNA isolation. This can be performed using any technique known in the art from whichever sample is to be tested.

The method of determining the presence or absence of a bacterial organism in a sample comprises amplification and detection of a target region of the smpB gene, wherein detecting the presence of the target region indicates that a member of a group of bacterial organisms is present in said sample. The method will fail to amplify and/or detect the presence of the target region when the target region is absent from the sample. Absence of the target region in a sample indicates the absence of the relevant bacterial organism. If the target region is specific to one or more particular bacterial genus, species or subspecies, then detecting its presence indicates the presence of the one or more genus, species or subspecies.

The methods of the invention comprise amplification and detection of a target region in the smpB gene. Amplification and detection of the target region in the smpB gene is performed using primers and/or probes that are specific, alone or in combination, for the target region of the smpB gene in the group of bacterial organisms of interest.

The target region may be amplified using primers that are specific for one or more bacterial genus, species, subspecies or of interest. In this instance, the presence of amplified target region is sufficient to indicate the presence of the one or more bacterial genus, species, subspecies or of interest. A non-specific probe may then be used to detect the presence of the amplified target region. Preferably, a probe that is specific for the target region (e.g. specific for the target sequence) is used to detect the presence of the amplified target region.

Alternatively, the target region may be amplified by primers that are not specific for a particular bacterial genus, species, subspecies of interest. In this instance, a probe that is specific for the target region is used to detect the presence of the target region.

The target region may be detected using a probe(s) and primers that in combination are specific for the one or more particular bacterial genus, species, subspecies or of interest.

DNA Amplification

DNA amplification is preferably performed with the polymerase chain reaction (PCR). Other methods of amplification will be apparent to those skilled in the art. One or more pairs of primers is designed to amplify a sequence comprising or consisting of a target region. The primers anneal to the template and DNA polymerases are used to amplify the nucleic acid sequence between the primer annealing sites during thermal cycling. The presence of the amplified nucleic acid molecule targets is then detected. This can be done through the use of gel electrophoresis but in preferred embodiments of the invention, detection is performed with the use of labelled probes that bind to the amplified nucleic acid molecule targets, and are preferably specific for these sequences. Preferably, fluorescent probes are used in detection. A wide range of fluorescent dyes for labelling probes are available and include FAM, HEX, ROX, CY3, CY5, CY5.5, JOE, VIC, TAMRA and Texas Red and many more will be known to those skilled in the art. Quencher dyes such as Black Hole Quenchers (BHQs, e.g., BHQ1, 2 or 3) are preferably used in conjunction with the fluorescent probes.

In one embodiment, multiplex assays are used. When a multiplex assays is used, each probe preferably uses a different fluorescent marker with a different output wavelength so that amplification of all the different nucleic acid molecule targets can be detected at the same time, in a single reaction.

The present invention contemplates the use of any appropriate method for amplification of target regions. The method of amplification will in general be PCR. Real-time PCR (RT-PCR) is one example of this. In certain embodiments RT-PCR using fluorescent reporter probes is used. The use of the reporter probes significantly increases specificity, and enables quantification even in the presence of non-specific DNA amplification. Fluorescent probes are particularly suited to multiplex assays, as specific probes with different-coloured labels can be used. RT-PCR relies on a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of the Taq polymerase breaks the reporter-quencher proximity, and results in emission of fluorescence. An increase in the product targeted by the reporter probe at each PCR cycle therefore causes a proportional increase in fluorescence due to the breakdown of the probe and release of the reporter.

Further the methods of the invention may therefore be configured to allow quantitation, i.e. the method comprises determining the amount of a member of a group of bacterial organisms in a sample. This may be achieved e.g. by selecting appropriate parameters for amplification (e.g. the number of cycles of amplification).

Other appropriate methods of amplification are referred to below.

Also contemplated for use in the present invention is Nucleic Acid Sequence Based Amplification (NASBA). Nucleic acid sequence-based amplification (NASBA) is an isothermal amplification technique which uses three enzymes (RNase H, AMV reverse transcriptase and T7 RNA polymerase) working in concert at a low isothermal temperature (generally 41° C.). The product of a NASBA reaction is mainly single-stranded RNA, which can be detected by gel electrophoresis, enzyme-linked gel assay (ELGA) or electrochemiluminescent detection (ECL). Alternatively, NASBA products can be detected in real time using molecular beacons included in the reaction [49]. In microbial diagnostics, NASBA has been successfully combined with electrochemiluminescent (ECL), ELISA labelled dendrimer and molecular beacon-based methods to detect and identify viral and bacterial pathogens [50].

Also contemplated for use in the present invention is Rolling Circle Amplification (RCA). RCA describes a process of unidirectional nucleic acid replication that can rapidly synthesize multiple copies of circular molecules of DNA or RNA. RCA is a technology that is adaptable to an on-chip signal amplification format. RCA is well suited to solid phase formats such as microarrays for generating localized signals at specific microarray locations. This distinctive property of RCA should allow many assays to be performed simultaneously (multiplexing) without interference [51].

Also contemplated for use in the present invention is the Ligase Chain Reaction (LCR). LCR uses two complementary pairs of probes which, when the correct template is available, hybridize next to each other and then are ligated together. These ligated probes plus the original template serve as the template for the next cycle of hybridization and ligation. As subsequent cycles are performed, the amplification proceeds exponentially [52]. A commercially available kit using this technology is the LCx *M. tuberculosis* complex specific kit available from Abbott Diagnostics [53].

Further isothermal amplification technologies that are contemplated for use with the present invention and include signal mediated amplification of RNA technology (SMART), strand displacement amplification (SDA), loop mediated isothermal amplification (LAMP), isothermal multiple displacement amplification (IMDA), helicase-dependent amplification (HDA), single primer isothermal amplification (SIPA) and circular helicase dependent amplification (cHDA). As exemplified by SMART, the amplification method used with the invention may comprise signal amplification rather than target amplification.

Also contemplated for use in the present invention is Next Generation Sequencing (NGS). Next generation sequencing is a relatively new field of sequencing which allows for the rapid high throughput process. NGS has the capacity to generate gigabases of nucleotide sequence, depending on the instrument used, in a single run [54]. A recently described assay combines the use of real-time PCR in combination with pyrosequencing which allows for the rapid detection of MTC DNA in addition to sequencing of an 81-bp core region of the rpoB gene associated with rifampin resistance [55].

Multiplex PCR

The methods of the invention may utilise multiplex PCR assays wherein more than one nucleic acid molecule target or target region is amplified and detected in a single PCR, with the use of a plurality of probes and sets of primers. Multiple sets of primers are used; each specific for a different target region. Multiple different probes are used; each specific for an amplified nucleic acid molecule target or target region. Preferably, each probe is labelled differently, for example with different fluorophores, so that amplification of each target region can be detected independently but at the same time in the single multiplex reactions, for example through the use of different colour channels. In the detection phase, the presence or lack of a signal in the different channels, indicating the presence or absence of amplification of the different nucleic acid molecule targets, is used to determine the identity of the species in a sample.

Multiplex, RT-PCR methods are preferred.

A multiplex assay may detect a plurality of target regions. Each target region is specific to a group of bacterial organisms. A multiplex assay may therefore be suitable for determining the presence or absence of a member of one group of bacterial organisms, or may therefore be suitable for determining the presence or absence (e.g. simultaneously) of members of a plurality of groups of bacterial organisms. Where the presence or absence of members of a plurality of groups of microorganisms is detected, these groups may be one or a plurality of groups of the same classification level (subspecies, species or genus), at different classification levels or a combination thereof. For example the assay may simultaneously determine the presence or absence of members of one or a plurality of groups that are species, e.g. the presence or absence of a plurality of species that are in the same genus or a plurality of species that are in a plurality of genera. Alternatively the assay may simultaneously determine the presence or absence of members of one or a plurality of groups that are a species, and/or a subspecies (e.g. a species and a subspecies (e.g. of that or a different species).

In one embodiment, a multiplex assay may detect three target regions to simultaneously determine the presence or absence of two different groups of bacteria and an IAC. Preferably, an ssrA target region is used to determine the presence or absence of the *Legionella* genus, an smpB target region is used to determine the presence or absence of the *Legionella pneumophila* species.

The methods of the invention can be used to detect the presence or absence of bacterial organisms that cannot be cultured. The bacterial organisms may not be susceptible to culture for many reasons. In some cases, the bacterial organisms are not present in the sample in sufficient numbers to culture. These methods also have the advantage that they are quicker to use these methods that are reliant on culture.

The methods of the invention are highly sensitive as they comprise amplification of nucleic acid and are therefore able to detect the presence of very few bacterial cells in a sample. In certain embodiments, the methods of the invention are able to detect the presence of as few as 2, 3, 4, 5, 6, 7, 8, 9, 10, 12, 14, 16, 18, 20, 30, 40, 50, 100 genome equivalents per reaction in a sample. In certain embodiments, the lower limits of detection (LOD) is up to 15, 10, 7.5, 5, 3.75, 2.5, 1.25 genome equivalents per reaction.

Uses of the Invention

The methods and kits of the present invention can be used to perform various analyses. The invention therefore provides, in general, the use of a method or kit to analyse the nucleic acids present in a sample. Some of the types of analyses envisaged by the inventors are described below.

In one embodiment, the invention provides the use of the smpB gene as disclosed herein to identify the type of bacterial organism(s) present in a sample. For example, the invention provides a method for identifying the type of bacterial organism(s) present in a sample, the method comprising analysing nucleic acid in or obtained from the sample using an analysis method as described herein, and using the results of the analysis to identify the type of bacterial organism(s) present in the sample.

The methods of the invention may also be methods of determining the amount of a member of a group of bacterial organisms in a sample e.g. by using an analysis method as described herein, and using the results of the analysis to identify the amount of a member of a group of bacterial organism(s) present in the sample. Such methods may be adapted to enable quantitation.

The invention provides the use of a method or kit as disclosed herein to analyse a sample.

In another embodiment, the invention provides the use of a method or kit as disclosed herein to diagnose a disease or condition in a patient (e.g. a human patient). For example, the invention provides a method for diagnosing a disease or condition in a patient, comprising analysing the nucleic acid in a sample obtained from the patient using an analysis method as described herein, and using the results of the analysis to diagnose a disease or condition in the patient. In some embodiments, methods of diagnosis as described herein are performed in vitro on a sample taken from a patient.

In another embodiment, the invention provides the use of a method or kit as disclosed herein to select a therapeutic strategy or treatment regimen for treating a disease or condition in a patient. For example, the invention provides a method for selecting a therapeutic strategy or treatment regimen for treating a disease or condition in a patient (e.g. a human patient), comprising analysing a sample nucleic acid obtained from the patient using an analysis method as described herein, identifying the presence of a pathogenic species and using the results of the analysis to select a therapeutic strategy or treatment regimen for treating the disease or condition. These methods may be performed in vitro on a sample taken from a patient. The method may further comprise treating the patient with an appropriate therapeutic strategy or treatment regimen for treating the disease or condition.

In a further embodiment, the invention provides the use of a method or kit as disclosed herein to monitor progression or status of a disease or condition in a patient, e.g. to monitor a patient's response to treatment. The method may further comprise treating the patient with an appropriate therapeutic strategy or treatment regimen for treating the disease or condition, or modifying an existing therapeutic strategy or treatment regimen for treating the disease or condition.

The invention also provides the use of a method or kit as disclosed herein for biosurveillance, e.g. to detect or identify the presence of bacterial organisms in food, environmental or clinical product samples. For example, a method of monitoring a building for the presence or absence of a member of a group of bacterial organisms is provided. This may be performed routinely, e.g. to monitor the progression of an outbreak of bacterial contamination, or to determine the nature of a bacterial organism that is causing disease, or to identify the source of bacterial contamination.

The methods, assays and sequences of the present invention will also be useful in maintenance of research stocks of particular bacterial organisms. Due to the similarity between certain species, it was not easy, prior to the present invention, to identify or confirm the identity of a particular species kept as stocks in, for example, research laboratory situations.

The present invention will also be useful in other research situations, including monitoring the growth and survival of different bacterial organisms and, for example, the effectiveness of drug treatments and development of drug resistance.

The individual sequences identified and characterised herein and primers and probes directed to these sequences will also be useful a range of other applications, including, the development and use of microarray platforms.

A method of identifying a target region for a group of bacterial organisms is also provided. The method may comprise aligning the nucleotide sequences of the smpB genes from the organisms of interest, and identifying a target region, wherein the target region contains or more target sequences and the target sequences, alone or in combination are specific to the group of bacterial organisms to be detected. Alignment may be performed using methods known in the art such as ClustalW or Clustal Omega. The method may further comprise designing and generating suitable primers and probes for use in the methods of the invention. Criteria for designing suitable primers and probes are discussed elsewhere herein.

Kits, Primers and Probes

The present invention additionally provides kits suitable for use in the methods provided herein. The invention provides a kit comprising sets of primers and probes which are specific for the target regions disclosed herein.

In certain embodiments, the invention provides a kit comprising one or more sets of primers and probes specific for amplifying and detecting target regions as defined herein. Exemplary sets of primers and probe sequences are shown in Table 1. Kits (e.g. diagnostic kits) comprising suitable variants of these primers and probes as discussed elsewhere herein may also form part of the invention.

TABLE 1

Exemplary Primers and Probes

| Primers | Probe |
| --- | --- |
| SEQ ID NO: 3 and SEQ ID NO: 4 | SEQ ID NO: 5 |
| SEQ ID NO: 10 and SEQ ID NO: 12 | SEQ ID NO: 14 |
| SEQ ID NO: 15 and SEQ ID NO: 16 | SEQ ID NO: 17 |
| SEQ ID NO: 18 and SEQ ID NO: 19 | SEQ ID NO: 20 |
| SEQ ID NO: 21 and SEQ ID NO: 22 | SEQ ID NO: 23 |
| SEQ ID NO: 24 and SEQ ID NO: 25 | SEQ ID NO: 26 |
| SEQ ID NO: 27 and SEQ ID NO: 28 | SEQ ID NO: 29 |
| SEQ ID NO: 6 and SEQ ID NO: 11 | SEQ ID NO: 13 |
| SEQ ID NO: 35 and SEQ ID NO: 36 | SEQ ID NO: 42 |

Primers and probes for use in the methods of the invention are also part of the invention. Exemplary primer sequences are SEQ ID NO: 3 (e.g. SEQ ID NO: 37) and SEQ ID NO: 4; SEQ ID NO: 10 and SEQ ID NO:12 (e.g. SEQ ID NO: 38); SEQ ID NO: 15 and SEQ ID NO: 16; SEQ ID NO: 18 and SEQ ID NO: 19; SEQ ID NO: 21 and SEQ ID NO: 22; SEQ ID NO: 24 and SEQ ID NO: 25; SEQ ID NO: 27 and SEQ ID NO:28; and SEQ ID NO: 6 and SEQ ID NO: 11; and SEQ ID NO: 35 and SEQ ID NO: 36.

Exemplary probe sequences are SEQ ID NO: 5, SEQ ID NO: 14, SEQ ID NO: 17, SEQ ID NO: 20, SEQ ID NO: 23, SEQ ID NO: 26, SEQ ID NO: 29 and SEQ ID NO: 13 and SEQ ID NO: 42.

Suitable variants of these primers and probes as discussed elsewhere herein may also form part of the invention.

Groups of Bacterial Organisms

Exemplary groups of bacterial organisms are set out below. For each group of bacterial organisms set out below target regions and target sequences are defined and suitable exemplary primers and probes are provided. For each group of bacterial organisms the target region is a region that can be amplified and detected using the exemplified primers and probes, and conversely the primers and probes that are exemplified are in combination specific for the target region and hence specific for the group of bacterial organisms. In each case three target sequences are defined (which have the sequence of, or are complementary to the exemplified forward primer, the reverse primer and the probe sequences). As noted elsewhere the target sequence (and hence the primer/probe sequence) can be represented by a consensus sequence and the probe and/or primer sequences that are used in any of the methods of the invention may be a single probe/primer that has a sequence that conforms to the consensus sequence or a mixture of two or more (e.g. 2, 3, 4, 5, 6) probes/primers for each consensus sequence, each of which conforms to the consensus sequence.

The exemplified primers and probes are therefore examples of primers and probes that can be used in methods to determine the presence or absence of a member of the group of bacterial organisms. Other suitable probes and primers can be used, if they are probes which bind to, and preferably are specific for all or a portion of the defined target region (e.g. a target sequence or a portion thereof). Suitable variations of such probes and primers are discussed elsewhere herein. In each case suitable forward primers bind to and are specific for all or a portion of the sequence complementary to the exemplified forward primer. Suitable reverse primers bind to and are specific for all or a portion of the sequence complementary to the exemplified reverse primer. Suitable probes bind to and are specific for all or a portion of the sequence of the exemplified probe sequence, or a sequence complementary thereto. Preferably primers and/or probes that have nucleic acid sequences that comprise or consist of the sequence of the exemplified probes are used.

*Haemophilus influenzae*

In certain embodiments of the invention, the bacterial organism is *H. influenzae*. The invention thus provides a method for determining the presence or absence of *H. influenzae* in a sample, wherein the method comprises determining whether a target region of the *H. influenzae* smpB gene is present in said sample. The target region is specific to *H. influenzae* and is not present in other *Haemophilus* species.

The exemplary forward primer sequence for *H. influenzae* is SEQ ID NO: 3. The exemplary reverse primer sequence for *H. influenzae* is SEQ ID NO: 4. The exemplary probe sequence for *H. influenzae* is SEQ ID NO: 5.

In certain embodiments, the method comprises a multiplex PCR, e.g. a multiplex RT-PCR. In certain embodiments the multiplex PCR comprises the use of an IAC. In a preferred embodiment the IAC is a *Bacillus subtilis* ssrA sequence.

In a particularly preferred embodiment, the method comprises a multiplex RT-PCR in which the primers have the sequences SEQ ID NO: 3 (e.g. SEQ ID NO: 37) and 4 and the probe has the sequence SEQ ID NO: 5. In another preferred embodiment the method comprises a multiplex RT-PCR in which the primers have the sequences SEQ ID NOs: 3, 4, 7 and 8 and the probes have the sequences SEQ ID NOs: 5 and 9, to detect the presence or absence of *H. influenzae* in a sample.

*Legionella pneumophila*

In certain embodiments of the invention, the bacterial organism is *L. pneumophila*. The invention thus provides a method for determining the presence or absence of *L. pneumophila* in a sample, wherein the method comprises determining whether a target region of the *L. pneumophila* smpB gene is present in said sample. The target region is specific to *L. pneumophila* and all 16 serogroups of *L. pneumophila* can be detected in a single diagnostic assay based on smpB The exemplary forward primer sequence for *L. pneumophila* is SEQ ID NO: 10. The exemplary reverse primer sequence for *L. pneumophila* is SEQ ID NO: 12 (e.g. SEQ ID NO: 38). The exemplary probe sequence for *L. pneumophila* is SEQ ID NO: 14.

In certain embodiments, the method comprises a multiplex PCR, e.g. a multiplex RT-PCR. In certain embodiments the multiplex PCR comprises the use of an IAC. In certain embodiments the multiplex PCR additionally determines the presence or absence of a member of the *Legionella* genus (e.g. a *Legionella* species). In such a case this may be by determining whether a target region of the ssrA gene is present or absent. This target region may be amplified and detected using primers and probes with SEQ ID NOs: 32 and 33 and 34 (e.g. SEQ ID NO: 40 and 41 and 39). In a preferred embodiment the IAC comprises a sequence that can be detected using primers comprising sequences SEQ ID NOs: 35 and 36 and a probe with the sequence SEQ ID NO: 37. The multiplex may therefore involve determining the presence or absence of the smpB target region, the ssrA target region and the IAC.

In a particularly preferred embodiment, the method comprises a multiplex RT-PCR in which the primers have the sequences SEQ ID NOs: 10 and 12 and the probe has the sequence SEQ ID NO: 14. In another preferred embodiment the method additionally or alternatively comprises a multiplex RT-PCR in which the primers have the sequences SEQ ID NOs: 32 and 33 (e.g. SEQ ID NOs: 40 and 41) and the probe has the sequence SEQ ID NO: 34 (e.g. SEQ ID NO: 39) (to detect the presence or absence of a *Legionella* species in a sample). In a preferred embodiment the method additionally or alternatively comprises a multiplex RT-PCR in which the IAC comprises a sequence that can be detected using primers comprising the sequences SEQ ID NOs: 35 and 36 and a probe comprising the sequence SEQ ID NO: 42.

In a particularly preferred embodiment, the method comprises a multiplex RT-PCT in which the primers have the sequences SEQ ID NOs 10, 12, 40, 41, 35 and 36, and the probes have the sequences SEQ ID NO: 14, 39 and 42.

*Acinetobacter baumannii*

In certain embodiments of the invention, the bacterial organism is *A. baumannii*. The invention thus provides a method for determining the presence or absence of *A. baumannii* in a sample, wherein the method comprises determining whether a target region of the *A. baumannii* smpB gene is present in said sample. The target region is specific to *A. baumannii*.

The exemplary forward primer sequence for *A. baumannii* is SEQ ID NO: 15. The exemplary reverse primer sequence for *A. baumannii* is SEQ ID NO: 16. The exemplary probe sequence for *A. baumannii* is SEQ ID NO: 17.

*Listeria grayi*

In certain embodiments of the invention, the bacterial organism is *L. grayi*. The invention thus provides a method for determining the presence or absence of *L. grayi* in a sample, wherein the method comprises determining whether a target region of the *L. grayi* smpB gene is present in said sample. The target region is specific to *L. grayi*.

The exemplary forward primer sequence for *L. grayi* is SEQ ID NO: 18. The exemplary reverse primer sequence for *L. grayi* is SEQ ID NO: 19. The exemplary probe sequence for *L. grayi* is SEQ ID NO: 20.

*Mycoplasma pneumoniae*

In certain embodiments of the invention, the bacterial organism is *M. pneumoniae*. The invention thus provides a method for determining the presence or absence of *M. pneumoniae* in a sample, wherein the method comprises determining whether a target region of the *M. pneumoniae* smpB gene is present in said sample. The target region is specific to *M. pneumoniae*.

The exemplary forward primer sequence for *M. pneumoniae* is SEQ ID NO:21. The exemplary reverse primer sequence for *M. pneumoniae* is SEQ ID NO: 22. The exemplary probe sequence for *M. pneumoniae* is SEQ ID NO: 23

*Mycobacterium avium*

In certain embodiments of the invention, the bacterial organism is *M. avium* (including the subspecies *M. avium* paratuberculosis). The invention thus provides a method for determining the presence or absence of *M. avium* in a sample, wherein the method comprises determining whether a target region of the *M. avium* smpB gene is present in said sample. The target region is specific to *M. avium.*

The exemplary forward primer sequence for *M. avium* is SEQ ID NO: 24. The exemplary reverse primer sequence for *M. avium* is SEQ ID NO: 25. The exemplary probe sequence for *M. avium* is SEQ ID NO: 26

*Mycobacterium intracellularae*

In certain embodiments of the invention, the bacterial organism is *M. intracellularae*. The invention thus provides a method for determining the presence or absence of *M. intracellularae* in a sample, wherein the method comprises determining whether a target region of the *M. intracellularae* smpB gene is present in said sample. The target region is specific to *M. intracellularae.*

The exemplary forward primer sequence for *M. intracellularae* is SEQ ID NO:27. The exemplary reverse primer sequence for *M. intracellularae* is SEQ ID NO: 28. The exemplary probe sequence for *M. intracellularae* is SEQ ID NO: 29

*Mycobacterium tuberculosis* Complex (MTC)

In certain embodiments of the invention, the group of bacterial organisms is the MTC. The invention thus provides a method for determining the presence or absence of a member of the MTC in a sample, wherein the method comprises determining whether a target region of the MTC smpB gene is present in said sample. The target region is specific to the members of the MTC.

The exemplary forward primer sequence for the MTC is SEQ ID NO: 6. The exemplary reverse primer sequence for the MTC is SEQ ID NO: 11. The exemplary probe sequence for the MTC is SEQ ID NO: 13.

Definitions

As used herein, the following terms and phrases shall have the meanings set forth below. Unless defined otherwise, all technical and scientific terms used herein have the same meaning as commonly understood by one of ordinary skill in the art to which this invention belongs.

The articles "a" and "an" refer to one or to more than one (i.e., to at least one) of the grammatical object of the article. By way of example, "an element" means one element or more than one element.

The terms "comprise" and "comprising" are used in the inclusive, open sense, meaning that additional elements may be included.

The terms "consists" and "consisting of" are used in the exclusive, closed sense, meaning that no additional elements may be included.

The term "including" is used herein to mean "including but not limited to". "Including" and "including but not limited to" are used interchangeably.

The term "target region" defines a nucleotide sequence that can be used to identify a member of a group of bacterial organisms of interest. The target region may be specific to the group of bacterial organisms (e.g. to a particular bacterial genus, species, subspecies of interest, or a group thereof). In this context, the term "specific to" is used to indicate that the particular target region is present in the group of bacterial organisms of interest, but not present in other bacterial organisms (e.g. other bacterial genera, species, subspecies or groups thereof). For instance, a certain target region may be present in one bacterial genus but not present in other bacterial genera, present in one bacterial species (e.g. *Haemophilus influenzae*), but not present in other bacterial species (e.g. other *Haemophilus* species), present in one bacterial subspecies but not present in other bacterial subspecies but not present in other bacterial serogroups. The target region is in one embodiment found in all serogroups of a species or species of a genus. The nucleotide sequence of the target region allows a particular group of bacterial organisms to be specifically identified. The target region therefore acts as a specific identifier for the group of bacterial organisms. For example, in one embodiment the target region is found in all species of the MTC group of *Mycobacteria* but is not present in the other *Mycobacteria* groups (nontuberculosis *Mycobacteria* (NTM) and *Mycobacteria leprae*). In other words, because the target region is specific to the group of bacterial organisms of interest, detecting the presence of the target region indicates that a member of the group of interest is present.

When referring to target regions, the term "present in" is used herein to mean found in the genome of the group of bacterial organisms in question. Preferably the genomic sequences of the one or more target sequences in the members of a group of interest are identical, but the target sequences may differ in a limited number of positions (e.g. 1-10, 2-9, 3-8, 4-7, 4-6, or 1, 2 or less, 3 or less, 4 or less or 5 or less between the members of the group. In such cases the target sequence(s) may be represented by consensus sequence(s). The primers and/or probes that are used may be one primer/probe that conforms to the consensus sequence or may be a mixture of primers and probes, e.g. that each conform to the consensus sequence. Preferably each member of the group of bacterial organisms to be detected will have no more than 1, 2, 3, 4 or 5 nucleotides difference in the genomic sequence of the target sequence, as compared to the primer/probe that is directed to that target, or as compared to one of the primers/probes that is directed to that target sequence.

Target regions and target sequences are defined by reference to their nucleotide sequence, in a conventional manner, with reference to a single sequence. It will be understood that in the bacterial organism itself and in any amplicon that is generated and detected in the methods of the invention the target region may be present as a double stranded molecule, which also contains a sequence that is complementary to the sequences provided herein for the target regions and target sequences. The probes that are used in the invention may bind to either strand thereof.

By the term "specific for" is meant that primers or probes hybridize to a particular nucleic acid sequence in preference to other nucleic acid sequences. A probe or primer which is "specific for" a sequence preferentially hybridises to that sequence and a primer or probe is considered to be "specific for" a sequence if it binds to that sequence with greater affinity than another sequence. For example, the probe or primer may bind with 2-fold, 3-fold, 4-fold, 5-fold, six-fold, seven-fold, eight-fold, nine-fold, 10-fold, 15-fold, 20-fold, 30-fold, 30-fold, 40-fold, 50-fold, 60-fold, 70-fold, 80-fold, 90-fold, 100-fold, 200-fold, 300-fold, 400-fold, 500-fold, or 1000-fold greater affinity to the target sequence which it is "specific for" than to another sequence. The probe or primer may for example be specific for a target sequence that is found in the smpB gene of a bacterial organism of interest, compared to the smpB gene of another bacterial organism.

In certain embodiments, the probe or primer binds to the whole length of a sequence within or flanking the target region (e.g. a target sequence). In other embodiments, the probe or primer binds to a portion of this sequence (e.g. at least 99%, 98%, 97%, 96% 95%, 94%, 93%, 92%, 91%, 90% of this sequence). In general the probe or primer will bind to at least 10, 11, 12, 13, 14, 15, 16, 17, 18, 19, 20, 21, 22, 23, 24, 25 nucleotides (e.g. contiguous nucleotides) of this sequence. The probe or primer may bind to regions immediately upstream or downstream of this sequence (e.g. up to 10 or 15 nucleotides thereof), in addition to binding to at least a portion thereof.

The term "primer" is used herein to mean a nucleic acid molecule for use in assisting amplification of specific nucleic acid molecules. Primers hybridize specifically to a designed sequence and are "specific for" that sequence (e.g. a target sequence). Primers are preferably 100% complementary to the sequence to which they are targeted. However, primers may be less than completely complementary in sequence, and may be, for example, 99%, 98%, 97%, 96% 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70% or less complementary to the sequence to which they are targeted. Primers are preferably 1 to 100 base pairs long, more preferably 5-50 base pairs long and even more preferably, 10 to 30, 17-25, 18-24, 19-23, 20-22 base pairs long such as 10, 11, 12, 13, 14, 15, 16, 17, 18, 19, 20, 21, 22, 23, 24, 25, 26, 27, 28, 29 or 30 base pairs long.

Exemplary primers are provided herein and primers of the invention comprise or consist of these sequences (e.g. a sequence that conforms to the consensus sequence where a consensus sequence is used to define the exemplary primer), or comprise or consist of a portion thereof (e.g. at least 10, 11, 12, 13, 14, 15, 16, 17, 18, 19, 20 nucleotides thereof). Optionally this is in combination with any one or more of the features defined herein that relate to primers.

The term "probe" is used herein to mean nucleic acid molecules for the detection of specific nucleic acid molecules. Probes are designed to hybridize specifically to a designated sequence and are "specific for" that sequence (e.g. a target sequence). Probes are preferably 100% complementary to the sequences for which they are designed. However, probes may be less than completely complementary in sequence, and may be, for example, 99%, 98%, 97%, 96% 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70% or less complementary to the sequence to which they are targeted. Probes are preferably 1 to 100 base pairs long, more preferably 5-50 base pairs long and even more preferably, 10 to 30, 17-25, 18-24, 19-23, 20-22 base pairs long, such as 10, 11, 12, 13, 14, 15, 16, 17, 18, 19, 20, 21, 22, 23, 24, 25, 26, 27, 28, 29 or 30 base pairs long. Probes are preferably labelled to assist detection. Preferably, they are labelled with a fluorescent dye. Preferably they also comprise a quencher.

Exemplary probes are provided herein and probes of the invention comprise or consist of these sequences, (e.g. a sequence that conforms to the consensus sequence where a consensus sequence is used to define the exemplary probe) or the reverse complement thereof) or comprise or consist of a portion thereof (e.g. at least 10, 11, 12, 13, 14, 15, 16, 17, 18, 19, 20 nucleotides thereof). Optionally this is in combination with any one or more of the features defined herein that relate to probes.

The term "sample" is used herein to mean any substance in which a bacterial organism may be found. In one embodiment the sample is taken from a patient or subject. For example, the sample may be a sputum sample, a pus sample, a lung fluid sample, a lymph node sample, a pleural fluid sample, a pleural tissue sample, a blood sample, a plasma sample, a serum sample, a urine sample, a fecal sample, a tissue sample, or a saliva sample. The sample may be a clinical product sample (e.g. a blood, plasma or serum product). The sample may be a food (including drinking water) sample. The sample may also be an environmental sample such as a soil, water, air sample or a cleaning sample (e.g. adsorbed material from wiping a surface, for example with a swab). Cleaning samples from buildings such as schools, hospitals are further examples (e.g. from hospital equipment, rooms curtains, pillows, furniture and sinks).

Methods of the invention may therefore further comprise the step of obtaining the sample, and/or of isolating nucleic acid from the sample.

The term "nucleic acid" refers to any type of nucleic acid that may present in a bacterial organism, but is preferably DNA or RNA.

The term "multiplex nucleic acid amplification method" is used herein to mean a single reaction wherein two or more different nucleic acid molecules are amplified and preferably detected. In a multiplex PCR assay, this is a polymerase chain reaction and this is achieved with the use of more than one set of primers. The multiplex assays of the invention may amplify and detect a plurality of target regions. A "plurality" in any context means more than 1 and includes, for example, 2, 3, 4, 5, 6, 7, 8, 9, 10, 11, 12, 13, 14, 15 or more (e.g. 2-10, 3-7, 4-6). In certain embodiments the invention may require the performance of one or more separate "multiplex nucleic acid amplification methods". The methods are preferably carried out in vitro or ex vivo.

A "patient" or "subject" may mean either a human or non-human animal and is preferably a mammal, more preferably a human. The human may be a child or an adult.

"Sequence identity" and "complementary" may be determined by standard methods that are known in the art. Identity or complementarity with respect to a sequence is defined herein as the percentage of nucleotide in the given sequence that are identical with the reference nucleotide sequence after aligning the sequences and introducing gaps, if necessary, to achieve the maximum percent sequence identity. Regions of sequence conservation contain relatively high levels of sequence identity. Regions of sequence variation contain relatively low levels of sequence identity.

References to a percentage sequence identity or complementarity between two nucleotide sequences means that, when aligned, that percentage of nucleotides are the same or complementary in comparing the two sequences. This alignment and the percent homology or sequence identity can be determined using software programs known in the art, for example those described in section 7.7.18 of [56]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in [57].

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

EXAMPLES

Example 1—Real-Time PCR Assay for the Specific Detection of *Haemophilus influenzae*

In Silico Diagnostics Target Identification

There is currently no single nucleic acid diagnostics target described in the literature that can unambiguously identify *Haemophilus influenzae*. A number of gene targets including the ssrA and lepA and genes, which have previously been described in the literature as suitable bacterial species specific molecular diagnostics targets were evaluated in silico. A putative novel diagnostics gene target, smpB, was also evaluated in silico. These gene targets were chosen as they are either present in all bacteria sequenced to date and/or have previously been demonstrated to be suitable as bacterial species specific molecular based diagnostics targets [58, 59, 60, 61 and 62]

Publicly available nucleotide sequences for potential diagnostics targets, including the smpB gene, were retrieved from the National Center for Biotechnology Information (see the internet at www.ncbi.nlm.nih.gov), the functional gene pipeline and repository (see the internet at fungene.cme.msu.edu/) and the tmRNA website (see the internet at bioinformatics.sandia.gov/tmrna/cgi-bin/blast/index.php).

In silico analysis of each molecular target was performed following alignments of nucleotide sequences using Clustal Omega (see the internet at www.ebi.ac.uk/Tools/msa/clustalo/).

From this in silico analysis the ssrA and lepA genes were deemed unsuitable for further use due to the nucleotide sequence similarity observed between *H. influenzae* and other closely related *Haemophilus* species. However, the smpB gene demonstrated sufficient intragenic nucleotide sequence variation between closely related *Haemophilus* species to allow for the design of *Haemophilus influenzae* specific probes.

All publicly available and generated nucleotide sequences for *H. influenzae* sequences were subsequently aligned (FIG. 17A-17J) which demonstrated sufficient nucleotide similarity to design oligonucleotide primers and probes.

Real-Time PCR Primers and Hydrolysis Probe Design

All oligonucleotide primers used in this study were designed to have a melting temperature (Tm) of 58-61° C. and all oligonucleotide hydrolysis probes a Tm of 7-10° C. higher.

For the *H. influenzae* specific diagnostics assay, PCR primers *H. influenzae* smpB F1 and *H. influenzae* smpB R1 (Table 2) were designed to amplify a 160 bp fragment of the smpB gene. The *H. influenzae* probe was labelled with FAM and BHQ1. The internal amplification control (IAC) PCR primers, *Bacillus subtilis* F land *Bacillus subtilis* R1 (Table 2), were designed to amplify a 206 bp region of the *Bacillus subtilis* subsp. *spizizenii* str. W23 ssrA gene. The IAC probe was labelled with Cy5 and BHQ2.

TABLE 2

Oligonucleotide primers and probes developed in this study

| Name | Function | Sequence 5'-3' | SEQ ID | Accession number (Nucleotide position) |
|---|---|---|---|---|
| *H. influenzae* smpB F1 | Forward smpB real-time PCR assay primer | ATTAAATGTTGCATCAACGC | SEQ ID NO: 3 | HI0981 (213-232 bp) |
| *H. influenzae* smpB R1 | Reverse smpB real-time PCR assay primer | GACTTTTGCCCACGCAC | SEQ ID NO: 4 | HI0981 (356-372 bp) |
| *H. influenzae* smpB P1 | smpB real-time PCR Probe | FAM-ACGRTTTTACCATAGTTGCACTTTCTC-BHQ1 | SEQ ID NO: 5 | HI0981 (317-343 bp) |
| *Bacillus subtilis* F1 | Forward IAC primer | AACGTAGCATTAGCTGC | SEQ ID NO: 7 | HG519928.1 (111-127 bp) |
| *Bacillus subtilis* R1 | Reverse IAC primer | CTCATCTTCTTGCCTGC | SEQ ID NO: 8 | HG519928.1 (260-276 bp) |
| *Bacillus subtilis* P1 | IAC Probe | Cy5-CACATCCAAGTAGGCTACGCT-BHQ2 | SEQ ID NO: 9 | HG519928.1 (179-199 bp) |

Development of IAC for Real-Time PCR.

To avoid false negative results due to PCR inhibition, thermocycler malfunction and/or reagent problems, a non-competitive IAC assay, targeting the *B. subtilis* subsp. *spizizenii* str. W23 ssrA gene, was incorporated into the real-time PCR diagnostics assays [63]. This means that in order for a result to be considered valid using this assay, a positive signal must be obtained in the Cy5 detection channel on the LightCycler 480. If the IAC is not detected, the result is considered invalid and must be repeated. For the purposes of this study *B. subtilis* DNA was spiked into the PCR master mix to act as an internal control target.

Titration experiments were performed to determine the optimum level of *B. subtilis* DNA to incorporate per reaction to ensure that the IAC was always detected, yet have the least impact on diagnostics assay robustness. Five hundred cell equivalents of *B. subtilis* DNA per reaction was determined as the optimum concentration of IAC target DNA to include in the duplex real-time PCR assay.

Development of Duplex Real-Time PCR *H. influenzae* Diagnostics Assay

To demonstrate the specificity and sensitivity of the Duplex real-time PCR, reactions were carried out on the LightCycler 480 using the LightCycler 480 Probes Master kit (Roche Diagnostics, Basel, Switzerland). The optimised PCR mix contained 2×LightCycler 480 Probes Master (6.4 mM $MgCl_2$), *H. influenzae* forward and reverse primer (0.5 μM final conc.), FAM labelled probe (0.4 μM final conc.), IAC forward and reverse primer (0.25 μM final conc.), and Cy5 labelled probe (0.2 μM final conc.), template DNA (Target: 5 μl; IAC: 2 μl) adjusted to a final volume of 20 μl with the addition of nuclease free $dH_2O$. The *B. subtilis* internal control DNA was diluted to contain 500 genome equivalents per 2 μl and all other DNA used in this study was diluted to contain ~$10^4$ genome equivalents per 5 μl.

The cycling parameters consisted of 10 min incubation at 95° C. to activate the Taq, 50 cycles of 95° C. for 10 s and 63° C. for 30 s, followed by a single cooling step at 40° C. for 10 s. The temperature ramp rate on the LightCycler 480 was 4.4° C./s while heating and 2.2° C./s while cooling. A colour compensation file was generated, to avoid fluorescence leaking from channel to channel, prior to experimental analysis on the LightCycler 480, as per manufacturer's instructions.

Genomic DNA Isolation and Quantification.

Genomic DNA from *Haemophilus* isolates and clinical samples were isolated using a modified procedure combining mechanical lysis (IDI lysis kit; Becton Dickinson, Canada) and purification using a quick gDNA kit (Zymo Research, Irvine, Calif., USA). Briefly, a loop of culture was resuspended in 250 μl IDI lysis buffer. The suspension was transferred to a GeneOhm lysis tube and bead beaten (Mini-Bead-Beater-16; Stratech, United Kingdom) for 3 min After bead beating, 200 μl of the supernatant was transferred to a Zymo-Spin™ Column in a collection tube and steps 2 to 5 of the procedure for purification of total DNA from cell suspensions were followed, according to the manufacturer's instructions. For all other bacterial species tested, DNA was provided from stocks held within this laboratory (NADRL, Microbiology, NUIG).

Genomic DNA concentrations for all species and strains used in this study were determined using the Quant-iT™ dsDNA High-Sensitivity Assay Kit and the QubIT™ fluorometer (Invitrogen Corporation, California, USA), as per manufacturer's instructions. Prior to use, genomic DNA samples were stored at −20° C.

Bacterial Strains, Culture Media, and Growth Conditions.

A panel of 32 well characterised *Haemophilus* species and strains (Table 3) and 30 other bacteria (Table 4) were used. These species and strains were purchased from the German Collection of Microorganisms and Cell Cultures (Deutsche Sammlung von Mikroorganismen and Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom) and Culture Collection, University of Goteborg, (CCUG, Sweden). All *Haemophilus* species and strains were cultured on Columbia Chocolate Agar (Oxoid, Hampshire, UK) at 37° C. with 5% $CO_2$ for 18-24 hrs.

TABLE 3

*Haemophilus* species tested

| Bacteria | Collection |
|---|---|
| *H. haemoglobinophilus* | DSM 21241 |
| *H. actinomycetemcomitans* | DSM 8324 |
| *H. actinomycetemcomitans* | DSM 11122 |
| *H. avium* | DSM 18557 |
| *H. ducreyi* | DSM 8925 |
| *H. equigenitalis* | DSM 10668 |
| *H. parahaemolyticus* | DSM 21417 |
| *H. parahaemolyticus* | DSM 21451 |
| *H. parasuis* | DSM 21448 |
| *H. paracuniculus* | DSM 21452 |
| *H. pittmaniae* | DSM 17240 |
| *H. pittmaniae* | DSM 21203 |

TABLE 3-continued

*Haemophilus* species tested

| Bacteria | Collection |
|---|---|
| *H. segnis* | DSM 10977 |
| *H. haemolyticus* | CDC-M21127 |
| *H. haemolyticus* | CDC-M21621 |
| *H. haemolyticus* | CDC-M19501 |
| *H. haemolyticus* | NCTC 10839 |
| *H. haemolyticus* | NCTC 10659 |
| *H parainfluenzae* | NCTC 7857 |
| *H parainfluenzae* | NCTC 10665 |
| *H parainfluenzae* | NCTC 10672 |
| *H. influenzae aegyptus* | DSM 21187 |
| *H influenzae* (Type a) | NCTC 8465 |
| *H. influenzae* (Type b) | DSM 10001 |
| *H. influenzae* (Type b) | DSM 23393 |
| *H. influenzae* (Type b) | DSM4690 |
| *H influenzae* (Type c) | NCTC 8469 |
| *H influenzae* (Type d) | DSM11121 |
| *H influenzae* (Type e) | NCTC 8472 |
| *H. influenzae* (Type f) | DSM10000 |
| *H. influenzae* (Non Typeable) | DSM 9999 |
| *H influenzae* (Type unknown) | CCUG 53865 |

(DSM = The German Collection of Microorganisms; CDC = Centre for Disease Control; NCTC = National Collection of Type Cultures CCUG = Culture Collection, University of Göteborg, Sweden)

TABLE 4

Other Bacteria tested

| Bacteria | Collection |
|---|---|
| *Acinteobacter baumanii* | DSM 30007 |
| *Alcaligenes faecalis* | DSM 30030 |
| *Bordetella bronchiseptica* | DSM 13414 |
| *Bordetella parapertussis* | DSM 13415 |
| *Bordetella pertussis* | DSM 5571 |
| *Chlamydophila pneumoniae* | ATCC 53592 |
| *Citrobacter freundii* | DSM 30039 |
| *Enterobacter aerogenes* | DSM 30053 |
| *Enterococcus faecalis* | DSM 20371 |
| *Enterococcus faecium* | DSM 20477 |
| *Klebsiella oxytoca* | DSM 5175 |
| *Klebsiella pneumoniae ozaenae* | DSM 16358 |
| *Legionella pneumophila* subsp*pneumophila* | DSM 7513 |
| *Moraxella catarrhalis* | DSM 11994 |
| *Mycobacterium tuberculosis* | ABI 08-949-250 |
| *Mycoplasma buccale* | NCTC 10136 |
| *Mycoplasma pneumoniae* | ATCC 29342 |
| *Neisseria meningitidis* | NCTC10025 |
| *Proteus mirabilis* | DSM 4479 |
| *Pseudomonas aeruginosa* | DSM 50071 |
| *Serratia marcescens* | DSM 1608 |
| *Staphylococcus aureus* | NCTC 11965 |
| *Staphylococcus epidermidis* | DSM 20044 |
| *Stenotrophomonas maltophilia* | DSM 50170 |
| *Streptococcus oralis* | DSM 20627 |
| *Streptococcus pneumoniae* | NCTC 11865 |
| *Streptococcus salivarius* | DSM 20560 |
| *Streptococcus sanguinis* | DSM 20567 |
| *Burkholderia cepacia* | DSMZ 7288 |
| *Ureaplasma urealyticum* | NCTC 10177 |

(DSM = The German Collection of Microorganisms; ATCC = American Type Culture Collection; ABI = Advanced Biotechnologies; NCTC = National Collection of Type Cultures; CCUG = Culture Collection, University of Göteborg, Sweden)

Specificity and Sensitivity of the Diagnostic Assays

The specificity of the real-time PCR diagnostics assay developed in this study was confirmed using the specificity panel listed in Table 3 and Table 4. For inclusivity and exclusivity testing, each sample was tested in triplicate at a concentration of ~$1\times10^4$ genome equivalents. The smpB-based assay specifically detected all 11 *H. influenzae* isolates; conversely, no other species of the *Haemophilus* genus and other bacteria were detected. The specificity of the IAC assay was also tested against the *Haemophilus* and other bacterial panels and was specific for *B. subtilis* DNA. A typical representation of the amplification curves generated in each of the analysis channels for this duplex assay are provided in FIG. 1A-1B.

The lower limit of detection (LOD) of the assay developed was established using Probit regression analysis. With an estimated genome size of 1.8 million base pairs, each *H. influenzae* cell contains approximately 1.96 fg DNA [64,65]. Genomic DNA was quantified and twelve replicates of each of 15, 10, 7.5, 5, 3.75, 2.5, 1.25 and 0.5 *H. influenzae* genome equivalents were tested. LOD's of 6.38 were determined (95% probability). The IAC, at a concentration of 500 genome equivalents per reaction, was included in all samples during sensitivity testing and detected as expected.

Clinical Isolate Evaluation

To evaluate the performance of the duplex real-time PCR diagnostics assays developed in this study, a panel of 44 recent clinical isolates of the genus *Haemophilus* were collected (Table 5). These isolates were cultured from clinical samples (sputum n=29, endotracheal aspirate n=2, nasal swabs n=8, bronchoalveolar lavage n=2, eye swabs n=2 and unknown n=1) using standard laboratory procedures and identified using MALDI-TOF MS (Bruker Daltonics, Bremen Germany) and MALDI-Biotyper 3.1 software. In accordance with previously published guidelines, only scores of 1.9 or greater were considered reliable for species identification [66, 67]. MALDI-TOF MS reliably determined that 36 of these isolates were *H. influenzae* and the remaining 8 were other *Haemophilus* species.

The antimicrobial susceptibility of the isolates to ampicillin, amoxycillin-clavulanate, ceftriaxone, erythromycin, imipenem, moxifloxacin, tetracycline and trimethoprim-sulphamethoxazole was determined by E-test and results interpreted according to EUCAST guidelines [68]. All isolates were tested for beta-lactamase activity using cefinase paper disks (Becton Dickinson). The beta-lactamase variant in positive isolates was identified by PCR for $bla_{TEM}$ and $bla_{ROB}$ as described previously [69,70]. 21 of the 44 isolates were resistant to one or more antibiotics. The most common resistance phenotypes were; ampicillin (25%), trimethoprim-sulphamethoxazole (13.6%) and erythromycin (11.4%). 18.2% of isolates were positive for TEM beta-lactamase, ROB beta-lactamase was not detected in any isolates.

Subsequently, genomic DNA was isolated, as outlined above, from pure isolates of confirmed *Haemophilus* species (Table 5). These DNA samples were then tested blindly in triplicate with a *H. influenzae* real-time PCR diagnostics assay previously described in the literature targeting the fucK gene [12], which was used as the reference standard method for this study, and also the novel smpB real-time PCR diagnostics assay developed. This fucK assay was chosen as the reference standard for evaluation of clinical isolates and samples as it has previously been demonstrated to be highly specific and sensitive for the detection of *H. influenzae* from clinical samples [12]. For epidemiological purposes, any isolate which was determined to contain *H. influenzae* using the smpB real-time PCR assay, was also serotyped using a previously described real-time PCR approach [12].

Using the fucK and novel smpB real-time PCR diagnostics assay 33/44 and 36/44 clinical isolates were positive for *H. influenzae* respectively. The results were also compared to bacterial culture and subsequent MALDI-TOF MS identification. From this analysis, 100% concordance was observed with the MALDI-TOF MS and the smpB real-time PCR diagnostics assay identifying 36 samples as positive for *H. influenzae*. Using a previously developed capsular serotyping method, it was determined that all the *H. influenzae* isolates were non typeable.

For epidemiological purposes, the capsular serotype and mechanisms of antimicrobial resistance for each of these culture positive isolates that contained *H. influenzae* as determined by MALDI-TOF MS and the smpB diagnostics assay was also determined. All isolates were determined to be non typeable *H. influenzae* which is consistent with recent findings in Europe [6, 43]. The prevalence of antimicrobial resistance was similar to previous reports from the UK [44,45]. These results further validate the robustness of the smpB assay developed for this study as they demonstrate that this novel assay can reliably detect the predominant strains of *H. influenzae* that are commonly causing LRTI.

TABLE 5

Clinical isolates used in this study

| Clinical isolates numbers | Real-time PCR fucK | Real-time PCR smpB | MALDI TOF ID | Serotype | Antimicrobial Resistance Detected[a] | Beta-lactamase |
|---|---|---|---|---|---|---|
| n = 6 | *H. influenzae* | *H. influenzae* | *H. influenzae* | Nontypeable | SXT | −ve |
| n = 2 | *H. influenzae* | *H. influenzae* | *H. influenzae* | Nontypeable | AMP, ERY | TEM |
| n = 1 | *H. influenzae* | *H. influenzae* | *H. influenzae* | Nontypeable | AMP, CRO, TET | −ve |
| n = 1 | *H. influenzae* | *H. influenzae* | *H. influenzae* | Nontypeable | AMP, AMC | −ve |
| n = 1 | *H. influenzae* | *H. influenzae* | *H. influenzae* | Nontypeable | AMP, AMC, ERY | −ve |
| n = 1 | −ve | *H. influenzae* | *H. influenzae* | Nontypeable | AMP, TET | TEM |
| n = 5 | *H. influenzae* | *H. influenzae* | *H. influenzae* | Nontypeable | AMP | TEM |
| n = 17 | *H. influenzae* | *H. influenzae* | *H. influenzae* | Nontypeable | Not Detected | −ve |
| n = 2 | −ve | *H. influenzae* | *H. influenzae* | Nontypeable | Not Detected | −ve |
| n = 3 | −ve | −ve | *H. paraznfluenzae* | — | Not Detected | −ve |
| n = 1 | −ve | −ve | *H. paraznfluenzae* | — | CRO, MXF | −ve |
| n = 1 | −ve | −ve | *H. paraznfluenzae* | — | ERY | −ve |
| n = 1 | −ve | −ve | *H. parahaemolyticus* | — | Not Detected | −ve |
| n = 1 | −ve | −ve | *H. parahaemolyticus* | — | TET | −ve |
| n = 1 | −ve | −ve | *H. parahaemolyticus* | — | TET, ERY | −ve |

SXT = trimethoprim-sulphamethozazole,
AMP = ampicillin,
ERY = erythromycin,
CRO = ceftriaxone,
TET = tetracycline,
AMC = amoxycillin-clavulanate,
MXF = moxifloxacin.

Direct Clinical RTI Sample Evaluation

To demonstrate the suitability for using the assay developed in this study directly on clinical samples (sputum n=67, endotracheal aspirates n=19, bronchoalveolar lavage n=12), a panel of 98 anonymised surplus specimens (Table 6) from patients with lower respiratory tract infections (LRTIs) was collected. Using 200 μL of sample, ten-fold serial dilutions were carried out down to $10^{-5}$ in phosphate-buffered saline. Neat sample (50 μL) and each dilution were spread onto Colombia blood agar (CBA), Colombia agar with chocolated horse blood (CHOC) and Brilliance™ UTI Clarity™ (UTI) agar (Oxoid). CBA and UTI plates were incubated at 37° C. for 18 hours and CHOC plates in a 5% $CO_2$ environment at 37° C. for 18 hours. Distinct colonies were identified using MALDI-TOF MS (Bruker Microflex™ LT) using MALDI Biotyper version 3.1 with default settings. From 300 μL of the sample, total nucleic acid was isolated in accordance with the procedure outlined above (Genomic DNA isolation and quantification). Nucleic acid isolated from clinical samples were then blindly tested using the previously described fucK real-time PCR diagnostics assay and also the novel *H. influenzae* smpB real-time PCR diagnostics assay.

Results of the fucK and novel smpB real-time PCR diagnostics assays performed on total nucleic acid purified directly from specimens were compared with those obtained from the same specimens by traditional bacterial culture and MALDI-TOF MS identification. Using traditional culture methods all of the samples which contained *Haemophilus* species were determined to contain a minimum of $1\times10^4$ CFU/ml. The fucK and smpB real-time PCR diagnostics assays were concordant for 96 of the 98 samples tested, with both assays identifying *H. influenzae* in 39 of the LRTI samples. One additional sample was positive for *H. influenzae* using the fucK assay which was not detected by the smpB assay and another sample was positive for *H. influenzae* using the smpB assay but not detected using the fucK assay. Based on the MALDI-TOF MS results, both of these discordant samples contained *H. influenzae* (Table 6). This discordant result is likely due to the sensitivity of the fucK assay when compared to the smpB assay. From the literature the LoD of the fucK assay is ~2.5 cells whereas the LoD of the smpB assay presented here is 6.8 cells. One additional sample was positive for *H. influenzae* using the smpB assay which was not detected by the fucK assay which may be as a result of a deletion of the fucose operon [71]. For the remaining 57 isolates, 100% concordance was observed between the fucK and smpB real-time PCR diagnostics assays.

The overall results from the real-time PCR analysis were also compared to bacterial culture and MALDI-TOF MS identification. From this analysis, the results each both real-time PCR diagnostics assays and MALDI-TOF MS were concordant for 79/98 samples. The fucK and smpB real-time PCR diagnostics assay detected *H. influenzae* in an additional 14 clinical samples which had been identified as containing *H. parainfluenzae* or *H. parahaemolyticus* (n=7) or contained no *haemophilus* species (n=7) using bacterial culture and MALDI-TOF MS identification. There were also 3 isolates identified as *H. influenzae* using MALDI-TOF MS which were not detected using the fucK or the smpB real-time PCR diagnostics assay.

TABLE 6

Clinical Respiratory Tract samples

| Clinical sample numbers | fucK real-time assay ID | smpB real-time assay ID | MALDI-TOF ID |
|---|---|---|---|
| n = 25 | *H. influenzae* | *H. influenzae* | *H. influenzae* |
| n = 7 | *H. influenzae* | *H. influenzae* | *Haemophilus* species not detected |
| n = 1 | *H. influenzae* | -ve | *H. influenzae* |
| n = 1 | -ve | *H. influenzae* | *H. influenzae* |
| n = 3 | -ve | -ve | *H. influenzae* |
| n = 7 | *H. influenzae* | *H. influenzae* | *H. parainfluenzae* and/or *H. parahaemolyticius* |
| n = 13 | -ve | -ve | *H. parainfluenzae* and/or *H. parahaemolyticius* |
| n = 41 | -ve | -ve | *Haemophilus* species not detected |

The diagnostic method developed in this study is the first-described high performance internally controlled duplex PCR assay capable of rapidly detecting all serotypes of *H. influenzae* with no cross reaction observed with other culture collection and cultured clinical isolates of *Haemophilus* species. The method has been validated on a large panel of well-characterized culture collection isolates, culture positive patient isolates and directly on patient samples.

Example 2—Real-Time PCR *L pneumophila*

In Silico Analysis

Publicly available smpB Nucleotide sequence information was retrieved from the National Center for Biotechnology Information website (see the internet at www.ncbi.nlm-.nih.gov/) for *Legionella pneumophila* and aligned using ClustalW (see the internet at www.ebi.ac.uk/Tools/msa/clustalw2/) (FIG. 2). Partial gene sequence was also generated for a number of culture collection strains using the sequencing primers listed in Table 7 and then aligned (FIG. 3). All publicly available and generated nucleotide sequences for *Legionella pneumophila* sequences were subsequently aligned (FIG. 4) which demonstrated sufficient nucleotide similarity to design oligonucleotide primers and probes.

TABLE 7

Oligonucleotide primers and probes used in Example 2

| Name | Function | Sequence 5'-3' | SEQ ID |
|---|---|---|---|
| LgensmpB_F primer | Forward Seqeuncing | GATCAATACGAAGCAGGC | SEQ ID NO: 30 |
| LgensmpB_R primer | Reverse Seqeuncing | GCCATTCTCTGTCTTTGATC | SEQ ID NO: 31 |
| LegPneuF1 Forward Primer | Real-time PCR assay | CACGTGATAATMAAATACGGTG | SEQ ID NO: 10 |
| LegPneuR1 Reverse primer | Real-time PCR assay | TTCATCAAYAGCTTGCGYG | SEQ ID NO: 12 |

TABLE 7-continued

| Oligonucleotide primers and probes used in Example 2 | | | |
|---|---|---|---|
| Name | Function | Sequence 5'-3' | SEQ ID |
| LegPneuP3 Probe | Real-time PCR assay | ROX-CYGCATCCACTCATTTTATTCCTGAT-BHQ2 | SEQ ID NO: 14 |

Nucleotide Sequencing

To generate partial smpB nucleotide sequence for *L. pneumophila*, conventional PCR was performed using the sequencing primers outlined in Table 7 on the iCycler iQ thermal cycler (Bio-Rad Laboratories Inc., California, USA). All reactions were carried out in a final volume of 50 containing 5 μl 10× buffer (15 mM MgCl2), 1 μl forward and reverse primers (0.2 μM final conc.), 2 Taq DNA polymerase (1 U/μl, Roche Diagnostics, Basel, Switzerland), 1 μl dNTP mix [(10 mM deoxynucleoside triphosphate set (Roche Diagnostics)], 5 μl of template DNA and 35 μl nuclease free water (Applied Biosystems/Ambion, Texas, USA). The cycling parameters consisted of initial denaturation at 95° C. for 5 mins, followed by 35 cycles of denaturation at 95° C. (1 min), annealing at 50° C. (1 min), and extension at 72° C. (1 min), with a final elongation step at 72° C. for 10 min PCR products were visualised on a 1.5% agarose gel and subsequently purified using the High Pure PCR Product Purification Kit (Roche Diagnostics). Purified products were sent for sequencing externally (Sequiserve, Vaterstetten, Germany).

DNA Isolation and Quantification.

Genomic DNA from *Legionella* cultures were isolated using a modified procedure combining mechanical lysis (IDI lysis kit; Becton Dickenson, Canada) and purification using a quick gDNA kit (Zymo Research, Irvine, Calif., USA). Briefly, a loop of culture was resuspended in 250 ul idi lysis buffer. The suspension was transferred to a GeneOhm lysis tube and bead beaten (Mini-Bead-Beater-16; Stratech, United Kingdom) for 3 min After bead beating, 200 μl was transferred to a Zymo-Spin™ Column in a collection tube and steps 2 to 5 of the procedure for purification of total DNA from cell suspensions were followed, according to the manufacturer's instructions.

Bacterial Strains, Culture Media, and Growth Conditions.

A panel of 20 *Legionella pneumophila* strains and 41 other *Legionella* species were used in this study (Table 8 and Table 9). These species and strains were purchased from the German Collection of Microorganisms and Cell Cultures (Deutsche Sammlung von Mikroorganismen and Zellkulturen GmbH, DSMZ. Braunschweig, Germany), the National Collection of Type Cultures (NCTC, Public Health England, Salisbury, United Kingdom), American Type Culture Collection (ATCC, provided by LGC standards, Middlesex United Kingdom) and Culture Collection, University of Goteborg, (CCUG, Sweden). All *Legionella* species and strains were cultured on BCYE media at 37° C. 18-24 hrs or until sufficient growth was observed.

TABLE 8

| Legionella assay inclusivity panel | |
|---|---|
| Strain | Culture collection |
| *Legionella pneumophila* subsp.*pneumophila-1* | DSM 7513 |
| *Leg. pneumophila* subsp. *fraseri-4* | DSM 7514 |

TABLE 8-continued

| Legionella assay inclusivity panel | |
|---|---|
| Strain | Culture collection |
| *Leg. pneumophila* subsp. *pasculei-5* | DSM 7515 |
| *Legionella pneumophila* subsp. *pneumophila-1* | NCTC 11191 |
| *Legionella pneumophila* subsp. *pneumophila-2* | NCTC 11230 |
| *Legionella pneumophila* subsp. *pneumophila-1* | NCTC 11231 |
| *Legionella pneumophila* subsp. *pneumophila-3* | NCTC 11232 |
| *Legionella pneumophila* subsp. *pneumophila-1* | NCTC 11286 |
| *Legionella pneumophila* subsp. *pneumophila-6* | NCTC 11287 |
| *Legionella pneumophila* subsp. *pneumophila-1* | NCTC 11378 |
| *Legionella pneumophila* subsp. *pneumophila-1* | NCTC 11404 |
| *Legionella pneumophila* subsp. *pneumophila-5* | NCTC 11417 |
| Legionella pneumophila subsp. *pneumophila-7* | NCTC 11984 |
| *Legionella pneumophila* subsp. *pneumophila-8* | NCTC 11985 |
| *Legionella pneumophila* subsp. *pneumophila-9* | NCTC 11986 |
| *Legionella pneumophila* subsp. *pneumophila-10* | NCTC 12000 |
| *Legionella pneumophila* subsp. *pneumophila-14* | NCTC 12174 |
| *Legionella pneumophila* subsp. *pneumophila-11* | NCTC 12179 |
| *Legionella pneumophila* subsp. *pneumophila-12* | NCTC 12180 |
| *Legionella pneumophila* subsp. *pneumophila-13* | NCTC 12181 |
| *Legionella pneumophila* subsp. *pneumophila-1* | DSM 25019 |
| *Legionella pneumophila* subsp. *pneumophila-1* | DSM 25071 |
| *Legionella pneumophila* subsp. *pneumophila-1* | DSM 25199 |
| *Legionella pneumophila* subsp. *pneumophila-1* | DSM 25200 |
| *Legionella pneumophila* subsp. *pneumophila-1* | DSM 25213 |
| *Legionella pneumophila* subsp. *pneumophila-1* | DSM 27564 |

TABLE 9

| *Legionella* assay exclusivity panel | |
|---|---|
| Species | Culture collection number |
| *Legionella anisa* | DSM 17627 |
| *Legionella birminghamensis* | DSM 19232 |
| *Legionella. birminghamensis* | ATCC 700709 |
| *Legionella bozemanii* | NCTC 11975 |
| *Legionella bozemanii* | DSM 16523 |
| *Legionella cincinnatiensis* | DSM 19233 |
| *Legionella dumoffii* | DSM 17625 |
| *Legionella dumoffii* | ATCC 33343 |
| *Legionella erythra* | DSM 17644 |
| *Legionella feeleii-1* | DSM 17645 |
| *Legionella feelii-2* | NCTC 11978 |
| *Legionella gormanii* | DSM 16641 |
| *Legionella gormanii* | ATCC 43769 |
| *Legionella hackeliae-1* | DSM 19214 |
| *Legionella hackeliae-2* | NCTC 11980 |
| *Legionella jordanis* | DSM 19212 |
| *Legionella jordanis* | ATCC 700762 |
| *Legionella lansingensis* | DSM 19556 |
| *Legionella longbeachae-1* | DSM 10572 |
| *Legionella maceachemii* | DSM 16642 |
| *Legionella miodadei* | NCTC 11403 |
| *Legionella oakridgensis* | NCTC 11531 |
| *Legionella oakridgensis* | ATCC 700515 |
| *Legionella parisiensis* | DSM 19216 |
| *Legionella wadworthii* | NCTC 11532 |
| *Legionella cherrii* | DSM 19213 |
| *Legionella jamestowniensis* | DSM 19215 |
| *Legionella londoniensis* | DSM 21234 |
| *Legionella taurinsis* | CCUG 44901 |
| *Legionella moravica* | DSM 19234 |

TABLE 9-continued

| *Legionella* assay exclusivity panel | |
|---|---|
| Species | Culture collection number |
| *Legionella adelaidensis* | DSM 19888 |
| *Legionella donaldsonii* | ATCC BAA-693 |
| *Legionella gratiana* | DSM 21233 |
| *Legionella gresilensis* | DSM 21218 |
| *Legionella fairfieldensis* | NCTC 12488 |
| *Legionella israelensis* | DSM 19235 |
| *Legionella fallonii* | CCUG 43887 |
| *Legionella brunensis* | DSM 19236 |
| *Legionella busanensis* | ATCC BAA-518 |
| *Legionella quinlivanii* | NCTC 12434 |
| *Legionella rubrilicens* | DSM 11884 |
| *Burkholderia cepacia* | DSM 7522 |
| *Ralstonia pickettii* | DSM 6297 |
| *Serratia marcescens* | DSM 30121 |
| *Cupriavidus pauculus* | DSM 17313 |
| *Stenotrophomonas maltophilia* | DSM 21874 |
| *Pseudomonas maltophila* | DSM 50071 |
| *Klebsiella pneumoniae* | DSM 12059 |
| *Proteus mirabilis* | DSM 4479 |
| *Enterobacter aerogenes* | DSM 2969 |
| *Acinetobacter baumannii* | LMG 984 |
| *Staphylococcus aureus* | DSM 11822 |
| *Bacillus cereus* | DSM 30584 |
| *Clostridium difficile* | DSM 1296 |
| *Sphingomonas paucimobilis* | DSM 1098 |

Real-Time PCR

The *Legionella pneumophila* specific assay was then tested in a real-time PCR format against a panel of well characterised *Legionella* species to determine assay specificity (Inclusivity and Exclusivity testing) and suitability of smpB nucleotide sequence as a diagnostics marker.

Real-time PCR was performed on the LightCycler 480 Instrument (Roche Diagnostics) using the LightCycler® 480 Probes Master kit (Roche Diagnostics2×LightCycler 480 Probes Master (6.4 mM $MgCl_2$), forward and reverse primer (0.5 μM final conc.), FAM labelled probe (0.2 μM final conc.), template DNA (5 μl) and nuclease free $dH_2O$ to a final volume of 20 μl. The cycling parameters consisted of 10 min incubation at 95° C. to activate the Taq, 50 cycles of 95° C. for 10 s and 60° C. for 30 s, followed by a cooling step at 40° C. for 10 s. The temperature transition rate, referred to as the ramp rate on the LightCycler 480 was 4.4° C./s while heating and 2.2° C./s while cooling.

Figure 5:
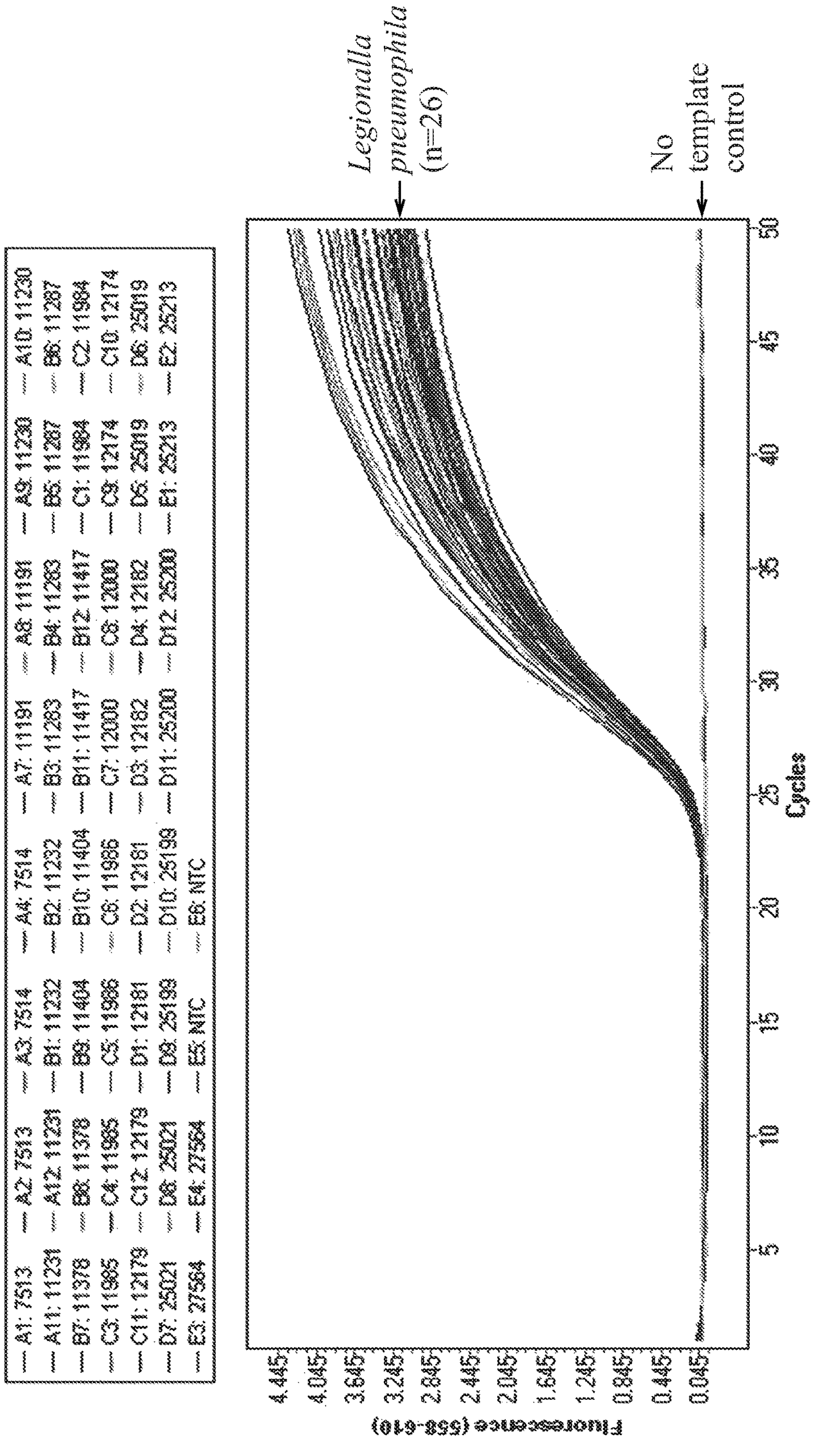
FIG. 5: Inclusivity testing of the *L. pneumophila* assay for detection of 26 strains of *L. pneumophila*. The no template control was not detected by the assay.
Figure 6:
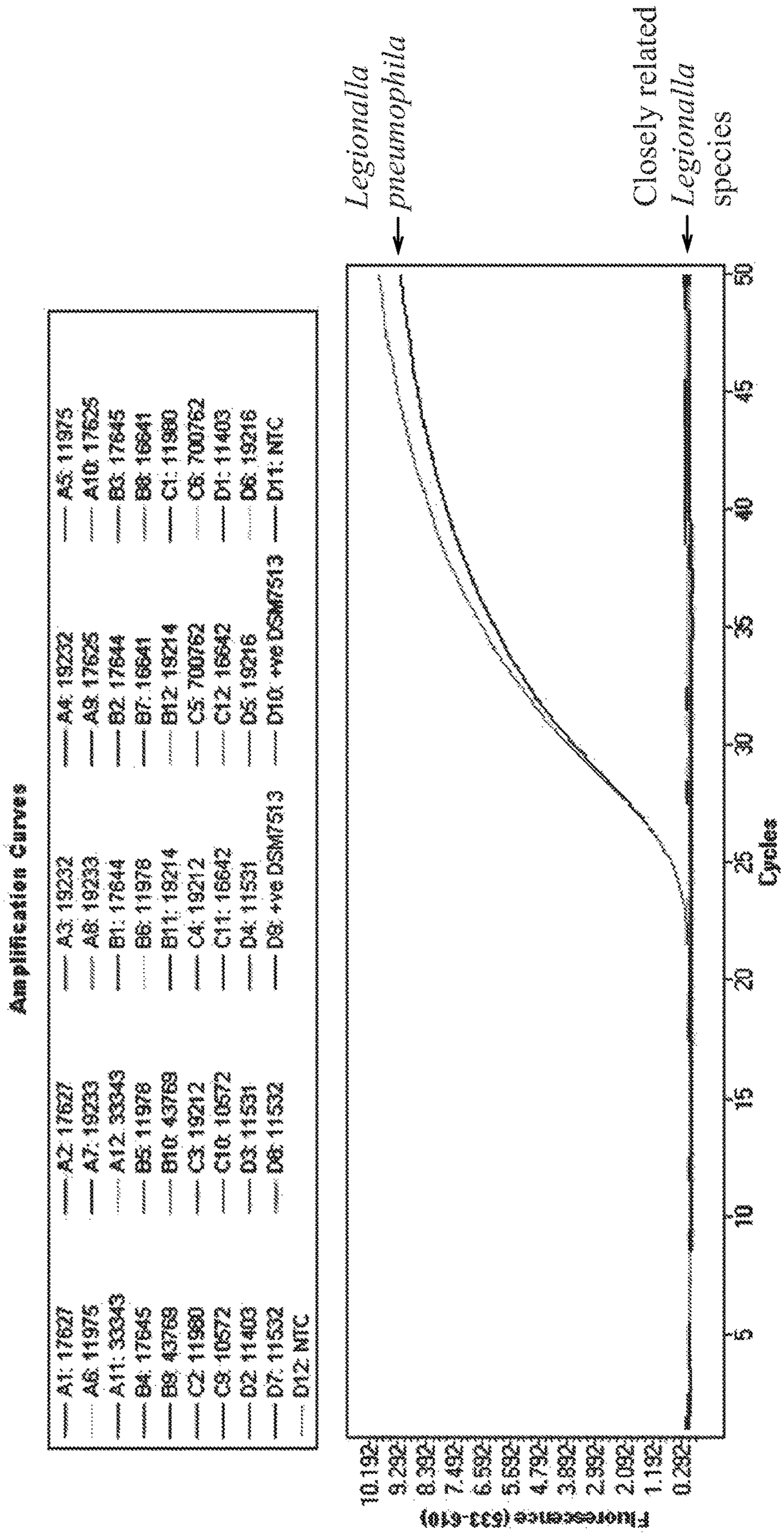
FIG. 6: Exclusivity testing for the *L. pneumophila* smpB assay. One *Legionella pneumophila* was detected by the assay and 16 closely related *Legionella* species were not detected by the assay.

As demonstrated below (FIG. 5), all 26 *Legionella pneumophila* strains were detected by the smpB assay. The remaining *Legionella* species and other bacteria (Table 9) were not detected by the assay (FIG. 6).

Conclusion

The real-time PCR assay described in this example is the first description of a real-time PCR diagnostics assay for the identification of *Legionella pneumophila* using the novel smpB diagnostics targets. This diagnostics assay takes approximately one hour to perform after genomic DNA extraction and purification.

Example 3—Real-Time PCR Assay for the Specific Detection of *Acinetobacter baumannii*

In Silico Analysis

Figure 8:
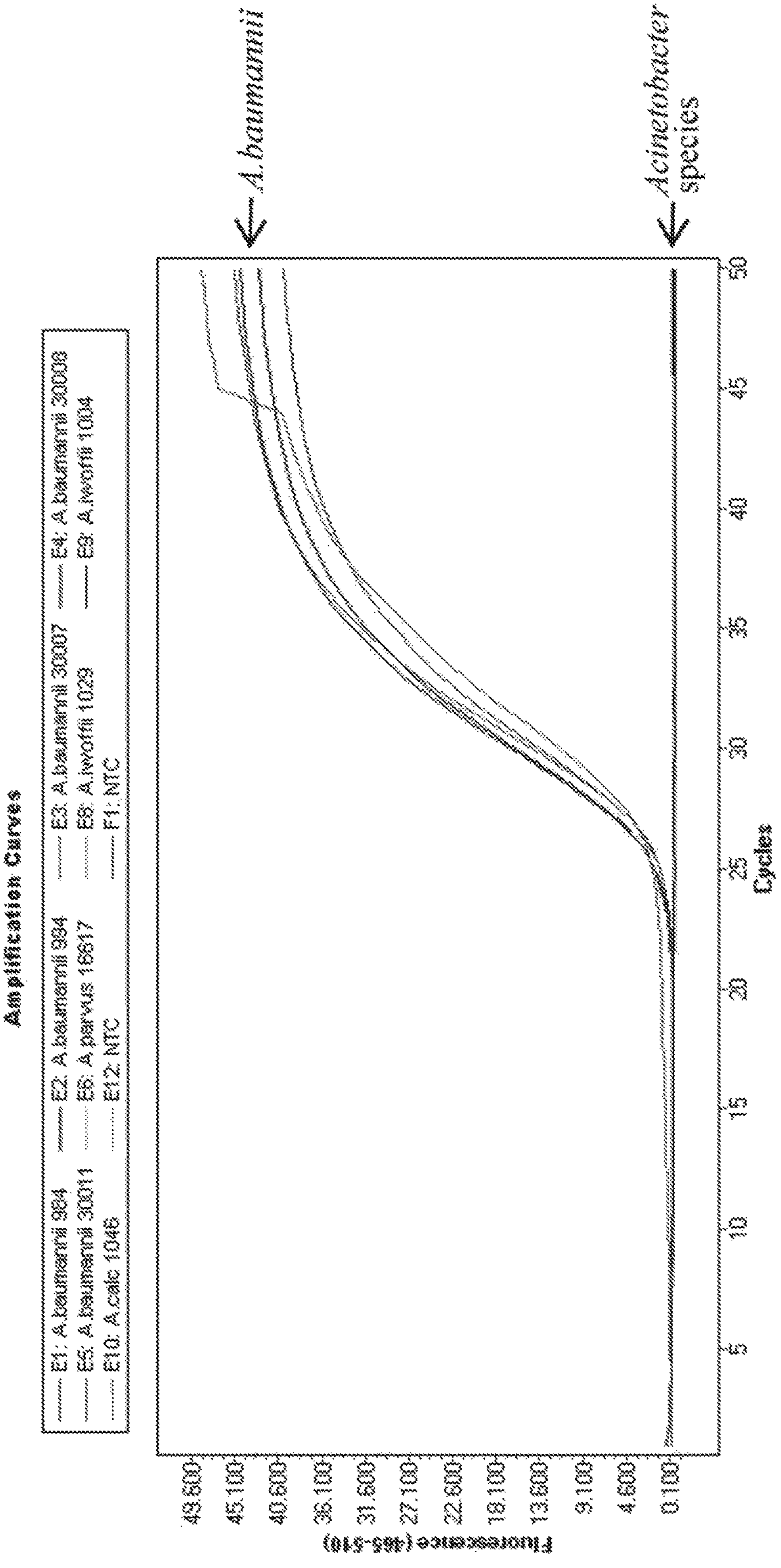
FIG. 8: Inclusivity testing *A. baumannii* specific smpB assay. 5 Strains *A. baumannii* detected. Exclusivity testing *A. baumannii* specific smpB assay. 4 other *Acinetobacter* species/strains not detected.

Publicly available smpB Nucleotide sequence information was retrieved from the National Center for Biotechnology Information website (see the internet at www.ncbi.nlm-.nih.gov/) for *Acinetobacter* species and aligned using ClustalW (see the internet at www.ebi.ac.uk/Tools/msa/clustalw2/) (FIG. 8). This demonstrated that sufficient nucleotide heterogeneity was present in the smpB gene to design oligonucleotide primers and probes specific for *A. baumanii* (Table 10).

TABLE 10

| Oligonucleotide primers and probes used in Example 3 | | | |
|---|---|---|---|
| Name | Function | Sequence 5'-3' | SEQ ID NO: |
| A.baum smpB F1 | Real-time PCR assay Forward Primer | TGGCATGTCTTTACTAGGCT | SEQ ID NO: 15 |
| A.baum smpB R1 | Real-time PCR assay Reverse primer | GCACAATATGTGTAGATGCAGA | SEQ ID NO: 16 |
| A.baum smpB P | Real-time PCR assay Probe | FAM-TGGTGCTCAGATTCAACCACTCC-BHQ1 | SEQ ID NO: 17 |

Bacterial Strains, Culture Media, and Growth Conditions.

A panel of 24 species were used in this study (Table 11 and Table 12). These species and strains were purchased from the German Collection of Microorganisms and Cell Cultures (Deutsche Sammlung von Mikroorganismen and Zellkulturen GmbH, DSMZ. Braunschweig, Germany), CBS-KNAW Fungal Biodiversity Centre, Utrecht, The Netherlands and the American Type Culture Collection (ATCC, provided by LGC standards, Middlesex United Kingdom). All *Acinetobacter* species and strains were cultured on nutrient agar media at 37° C. 18-24 hrs or until sufficient growth was observed.

TABLE 11

| *Acinetobacter* assay inclusivity panel |
|---|
| *Acinetobacter baumannii* LMG 984 |
| *Acinetobacter baumannii* LMG 994 |
| *Acinetobacter baumannii* DSM 30008 |
| *Acinetobacter baumannii* DSM 30011 |

TABLE 12

| *Acinetobacter* assay exclusivity panel |
| --- |
| *Klebsiella pneumoniae* DSM 12059 |
| *Proteus mirabilis* DSM 30116 |
| *Staphylococcus aureus* DSM 21705 |
| *Enterobacter aerogenes* DSM 12058 |
| *Burkholderia cepacia* DSM 7288 |
| *Ralstonia pickettii* DSM 6297 |
| *Serratia marcescens* DSM 1608 |
| *Sphingomonas paucimobilis* DSM 1098 |
| *Pseudomonas aeruginosa* DSM 50071 |
| *Stenotrophomonas maltophilia* DSM 50170 |
| *Candida albicans* CBS 562 |
| *Bacillus cereus* DSM 3648 |
| *Clostridium difficile* DSM 1296 |
| *Morganella morgannii* DSM 30164 |
| *Streptococcus bovis* DSM 20480 |
| *Aeromonas* hydro DSM 30015 |
| *Bacteroides fragilis* ATCC 25285 |
| *Campylobacter jejuni* DSM 4688 |
| *Citrobacter freundii* DSM 30039 |
| *Edwardsiella tarda* DSM 30052 |

DNA Isolation and Quantification

Total genomic DNA was isolated from overnight broth culture using the Quick-gDNA MiniPrep kit (Zymo Research, California, USA). Briefly, 1.5 ml of culture was centrifuged in a bench-top centrifuge at 18,000 g for two min. The supernatant was discarded and the pellet was resuspended in 400.mu.l Genomic Lysis Buffer by vortexing briefly, then incubated at room temperature for 5-10 min. Subsequently, steps 2-5 of the purification of total DNA from cell suspensions and proteinase K digested samples procedure were followed according to the manufacturer's guidelines (see the internet at www.zymoresearch.com/downloads/dl/file/id/18/d3006i.pdf).

Real-Time PCR

This *A. baumanii* specific assay was then tested in a real-time PCR format against a panel of well characterised bacterial to determine assay specificity (Inclusivity and Exclusivity testing) and suitability of smpB nucleotide sequence as a diagnostics marker.

Real-time PCR was performed on the LightCycler 480 Instrument (Roche Diagnostics) using the LightCycler® 480 Probes Master kit (Roche Diagnostics2×LightCycler 480 Probes Master (6.4 mM $MgCl_2$), forward and reverse primer (0.5 μM final conc.), FAM labelled probe (0.2 μM final conc.), template DNA (5 μl) and nuclease free $dH_2O$ to a final volume of 20 μl. The cycling parameters consisted of 10 min incubation at 95° C. to activate the Taq, 50 cycles of 95° C. for 10 s and 60° C. for 30 s, followed by a cooling step at 40° C. for 10 s. The temperature transition rate, referred to as the ramp rate on the LightCycler 480 was 4.4° C./s while heating and 2.2° C./s while cooling.

Figure 9:
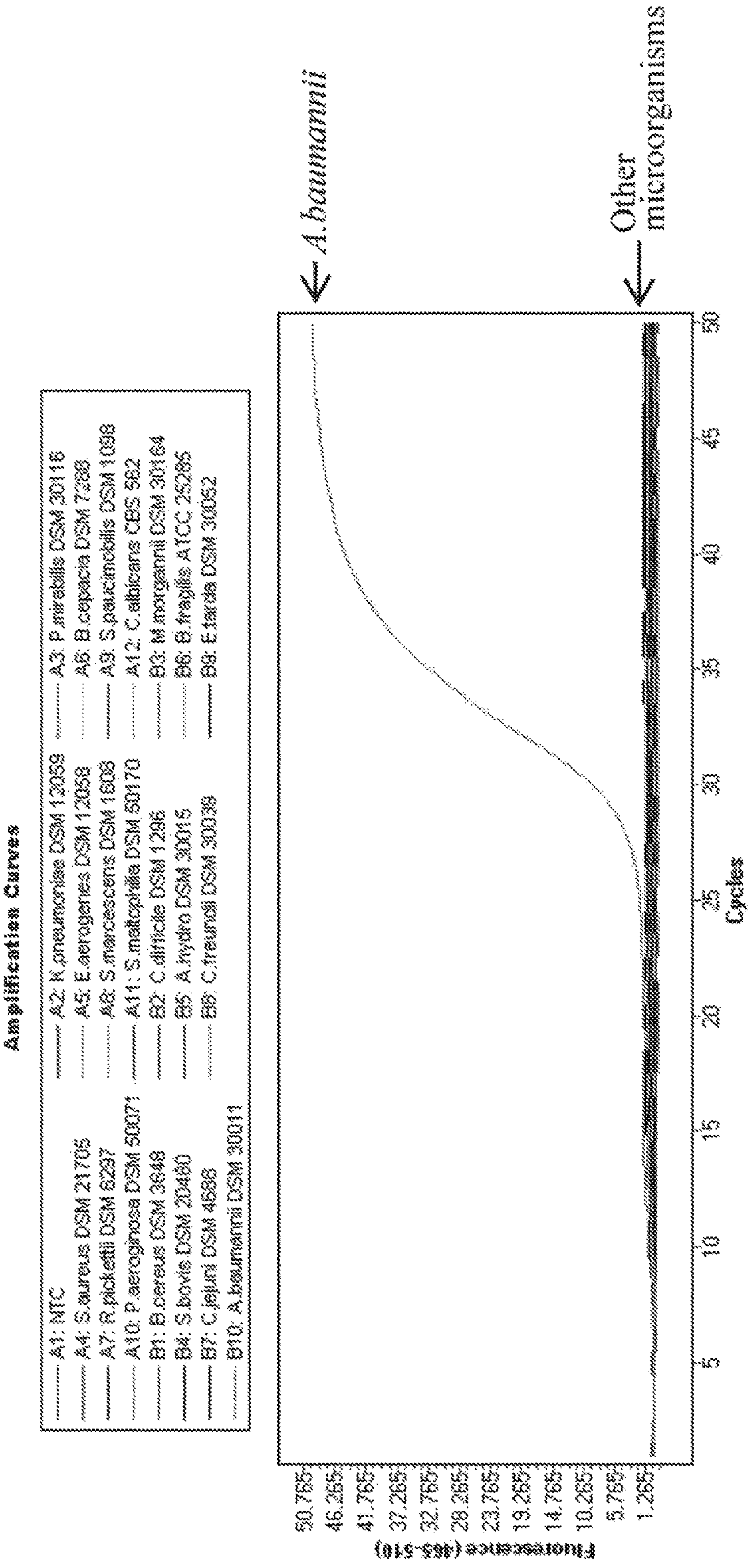
FIG. 9: Exclusivity testing *A. baumannii* specific smpB assay against 20 other microorganisms (Gram +ve, Gram −ve and fungal)

As demonstrated in FIG. 8, all 4 *A. baumani* strains were detected by the smpB assay. The remaining 20 bacterial species tested (Table 12) were not detected by the assay (FIG. 9).

Conclusion

The real-time PCR assay described in this example is the first description of a real-time PCR diagnostics assay for the identification of *A. baumanii* using the novel smpB diagnostics targets. This diagnostics assay takes approximately one hour to perform after genomic DNA extraction and purification.

Example 4—Real-Time PCR Assay for the Specific Detection of *Listeria grayi*

In Silico Analysis

Publicly available smpB Nucleotide sequence information was retrieved from the National Center for Biotechnology Information website (see the internet at www.ncbi.nlm.nih.gov/) for *Listeria* species and aligned using ClustalW (see the internet at www.ebi.ac.uk/Tools/msa/clustalw2/) (FIG. 10). This demonstrated that sufficient nucleotide heterogeneity was present in the smpB gene to design oligonucleotide primers and probes specific for *Listeria grayi* (Table 13).

TABLE 13

Oligonucleotide primers and probes used in Example 4

| Name | Function | Orientation 5'-3 | SEQ ID NO: |
| --- | --- | --- | --- |
| L.gra smpB F1 | *L. grayi* real-time assay forward primer | CGGCATTGTCTTGCAAG | SEQ ID NO: 18 |
| L.gra smpB R1 | *L. grayi* real-time assay reverse primer | GCTGATATGCATGTTGTGTA | SEQ ID NO: 19 |
| L.gra smpB PHEX2 | *L. grayi* real-time assay probe HEX | HEX-AGTTCACTCGTGCATTACGAAC-BHQ1 | SEQ ID NO: 20 |

Bacterial Strains.

A panel of 6 species were used in this example (Table 14 and Table 15)

TABLE 14

| *Listeria* inclusivity strains | |
| --- | --- |
| *Listeria grayi* | NCTC 10815 |
| *Listeria grayi murrayi* | NCTC 10812 |
| *Listeria grayi* DSM 20596 | DSM 20596 |

TABLE 15

| *Listeria* exclusivity strains | |
| --- | --- |
| *Listeria invanovii* | NCTC 11846 |
| *Listeria seelegeri* | NCTC 11856 |
| *Listeria welshimeri* | NCTC 11857 |

Real-Time PCR

This *L. grayi* specific assay was then tested in a real-time PCR format against a panel of well characterised bacterial to determine assay specificity (Inclusivity and Exclusivity testing) and suitability of smpB nucleotide sequence as a diagnostics marker.

Figure 11:
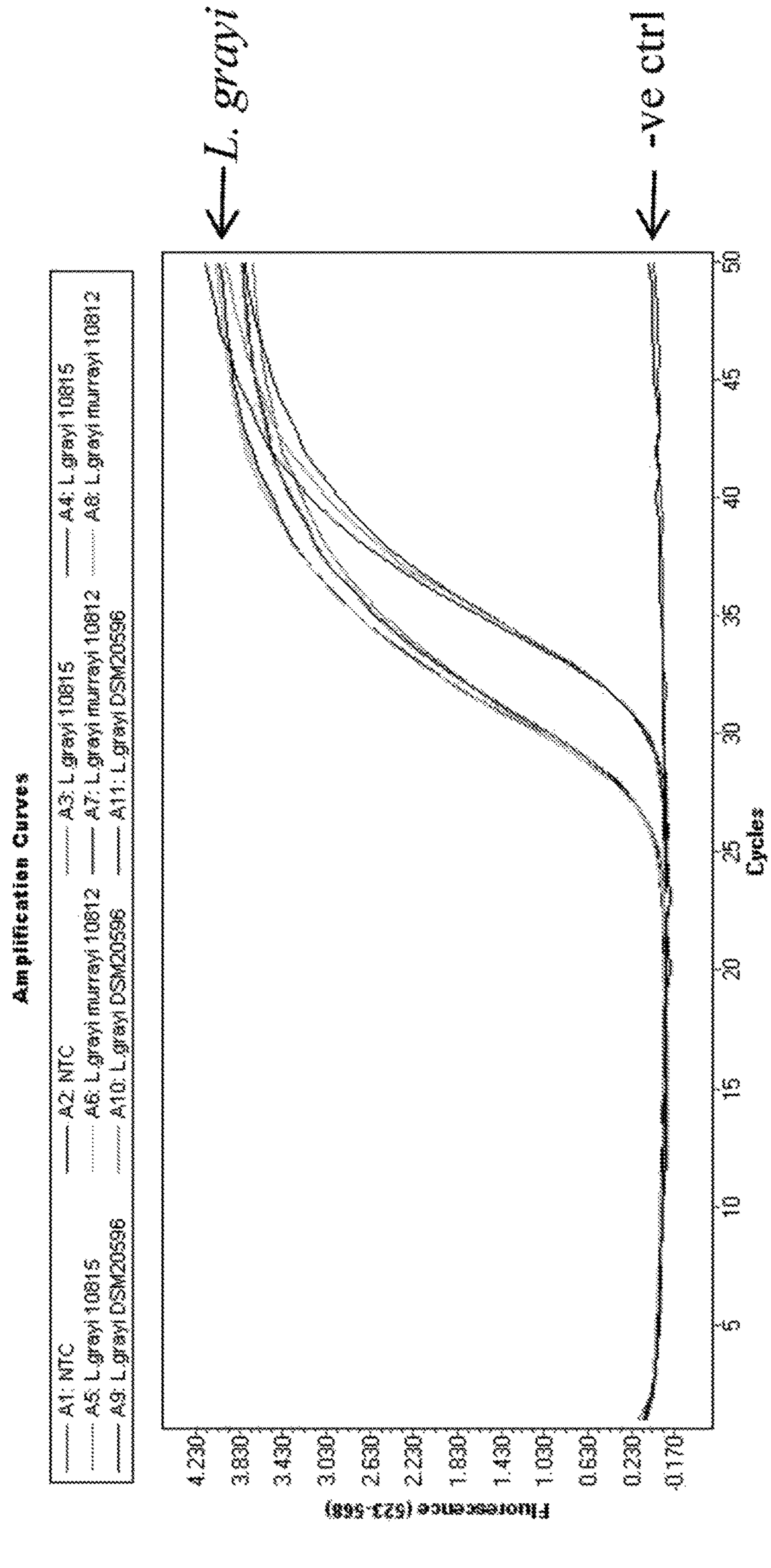
FIG. 11: Inclusivity testing *L. grayi* specific smpB assay. 3 Strains of *L. grayi* detected
Figure 12:
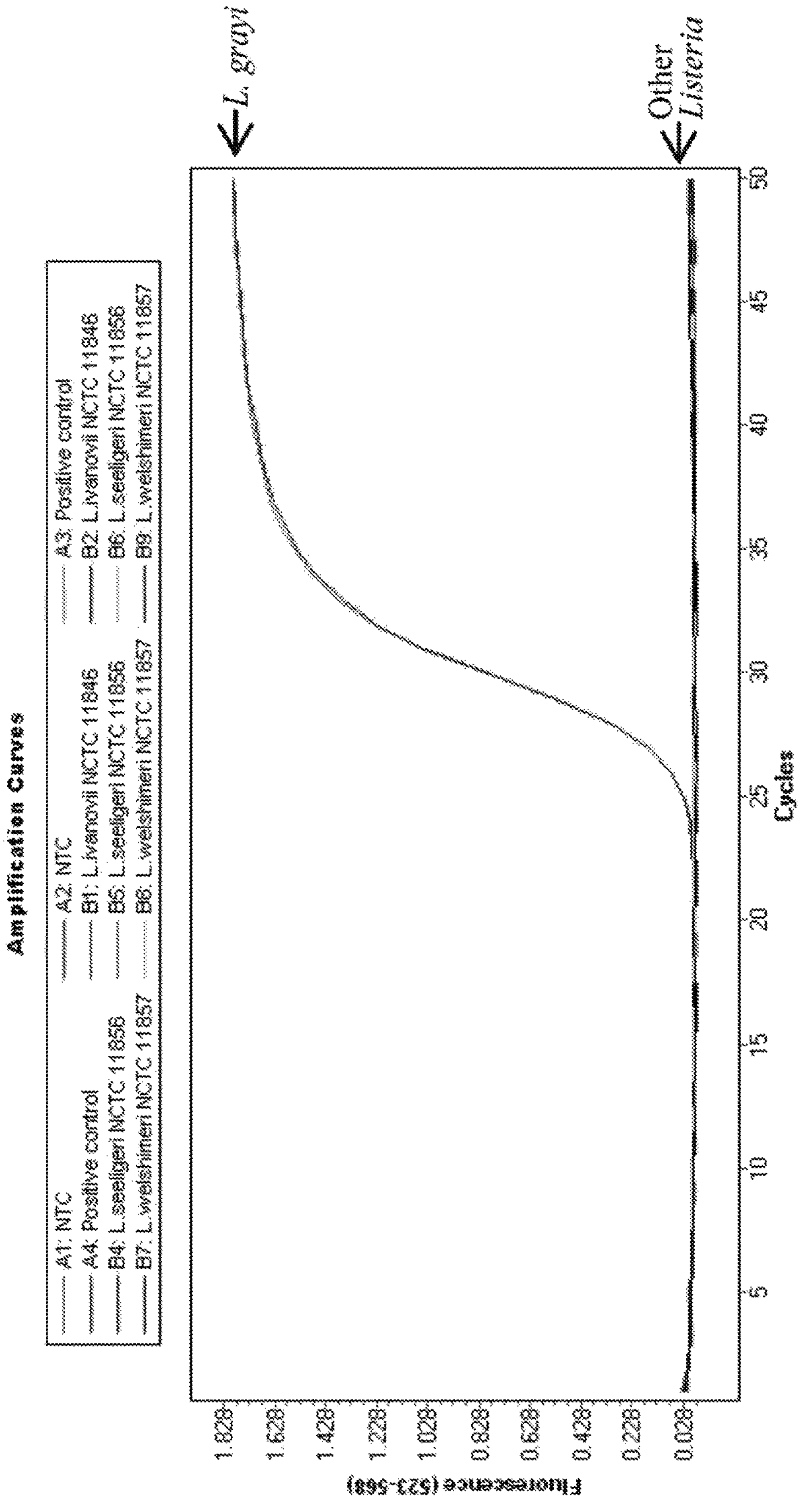
FIG. 12: Exclusivity testing *L. grayi* specific smpB assay. 3 other *Listeria* species/strains not detected.

As demonstrated in FIG. 11, all 3 *Listeria grayi* strains were detected by the smpB assay. The remaining 3 bacterial species tested (Table 15) were not detected by the assay (FIG. 12).

Conclusion

The real-time PCR assay described in this example is the first description of a real-time PCR diagnostics assay for the identification of *L. grayi* using the novel smpB diagnostics targets. This diagnostics assay takes approximately one hour to perform after genomic DNA extraction and purification.

Example 5—Real-Time PCR Assay for the Specific Detection of *Mycoplasma* Pneumonia In Silico Analysis Publicly available smpB Nucleotide sequence information was retrieved from the National Center for Biotechnology Information website (see the internet at www.ncbi.nlm-.nih.gov/) for *Mycoplasma* species and aligned using ClustalW (see the internet at www.ebi.ac.uk/Tools/msa/clustalw2/) (FIG. 13). This demonstrated that sufficient nucleotide heterogeneity was present in the smpB gene to design oligonucleotide primers and probes specific for *Mycoplasma* pneumonia (Table 16).

TABLE 16

Oligonucleotide primers and probes used in Example 5

| Name | Function | Orientation 5'-3' | SEQ ID NO: |
|---|---|---|---|
| Mpneu_F1 | *M. pneumoniae* real-time assay forward primer | TTAGCATTTCGCCCTATGC | SEQ ID NO:21 |
| Mpneu_R1 | *M. pneumoniae* real-time assay reverse primer | AGTCCTTCTTGCTTTTGGC | SEQ ID NO: 22 |
| Mpneu_P1 | *M. pneumoniae* real-time assay probe | FAM-CCACCCCTTCAAACGGGTGA-BHQ1 | SEQ ID NO: 23 |

Bacterial Strains.

A panel of 4 species were used in this example (Table 17).

TABLE 17

| *Mycoplasma penumoniae* inclusivity strains |
|---|
| *Mycoplasma pneumoniae* ATCC 15293 |
| *Mycoplasma pneumoniae* ATCC 15377 |
| *Mycoplasma pneumoniae* ATCC 29085 |
| *Mycoplasma pneumoniae* ATCC 29342 |

Real-Time PCR

This *Mycoplasma pneumoniae* specific assay was then tested in a real-time PCR format to determine the sensitivity of the smpB nucleotide sequence as a diagnostics marker.

Figure 14:
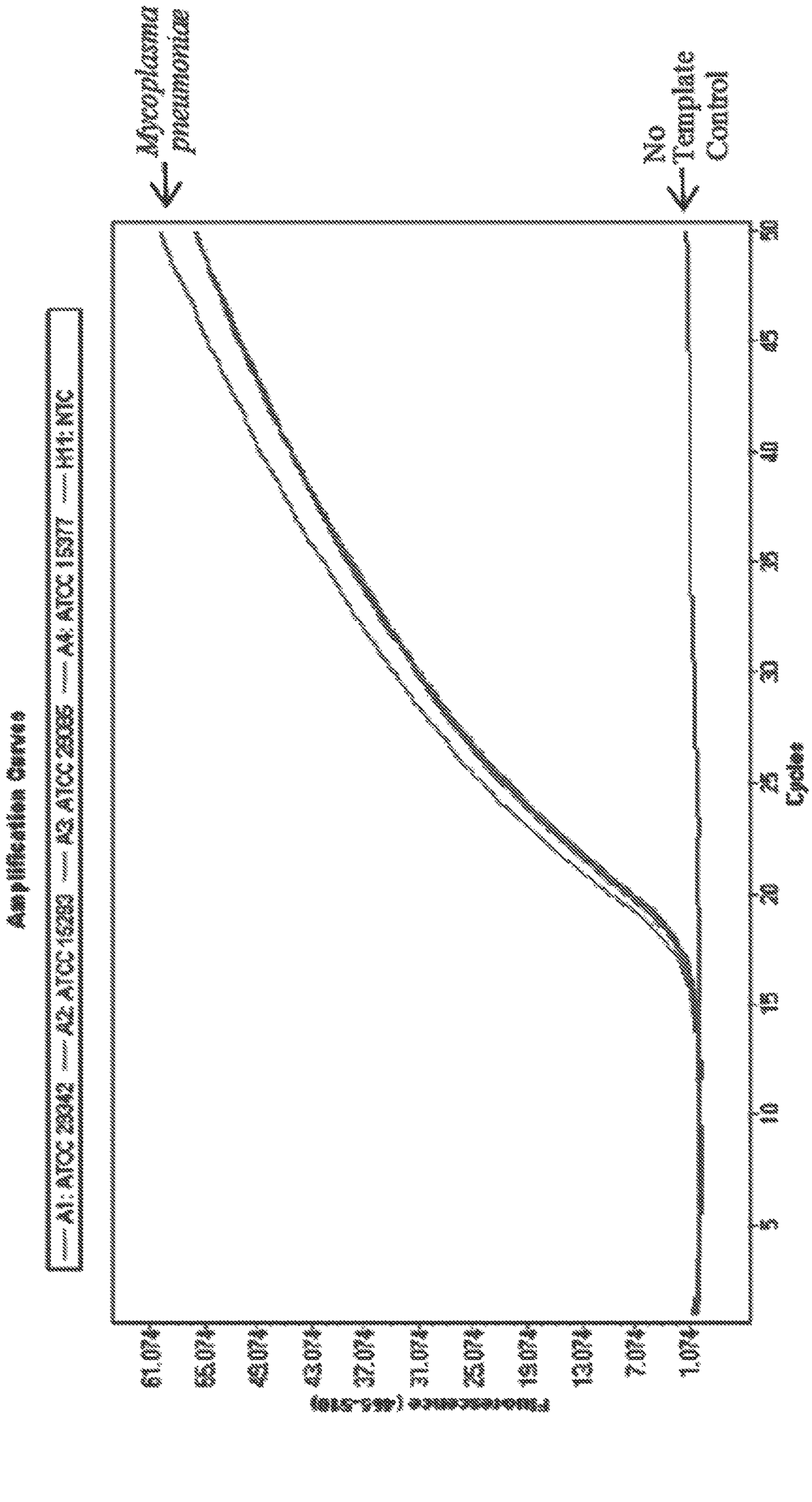
FIG. 14: Inclusivity testing of the assay for detection of 4 strains of *M. pneumoniae*. The no template control was not detected by the assay.
Figure 15:
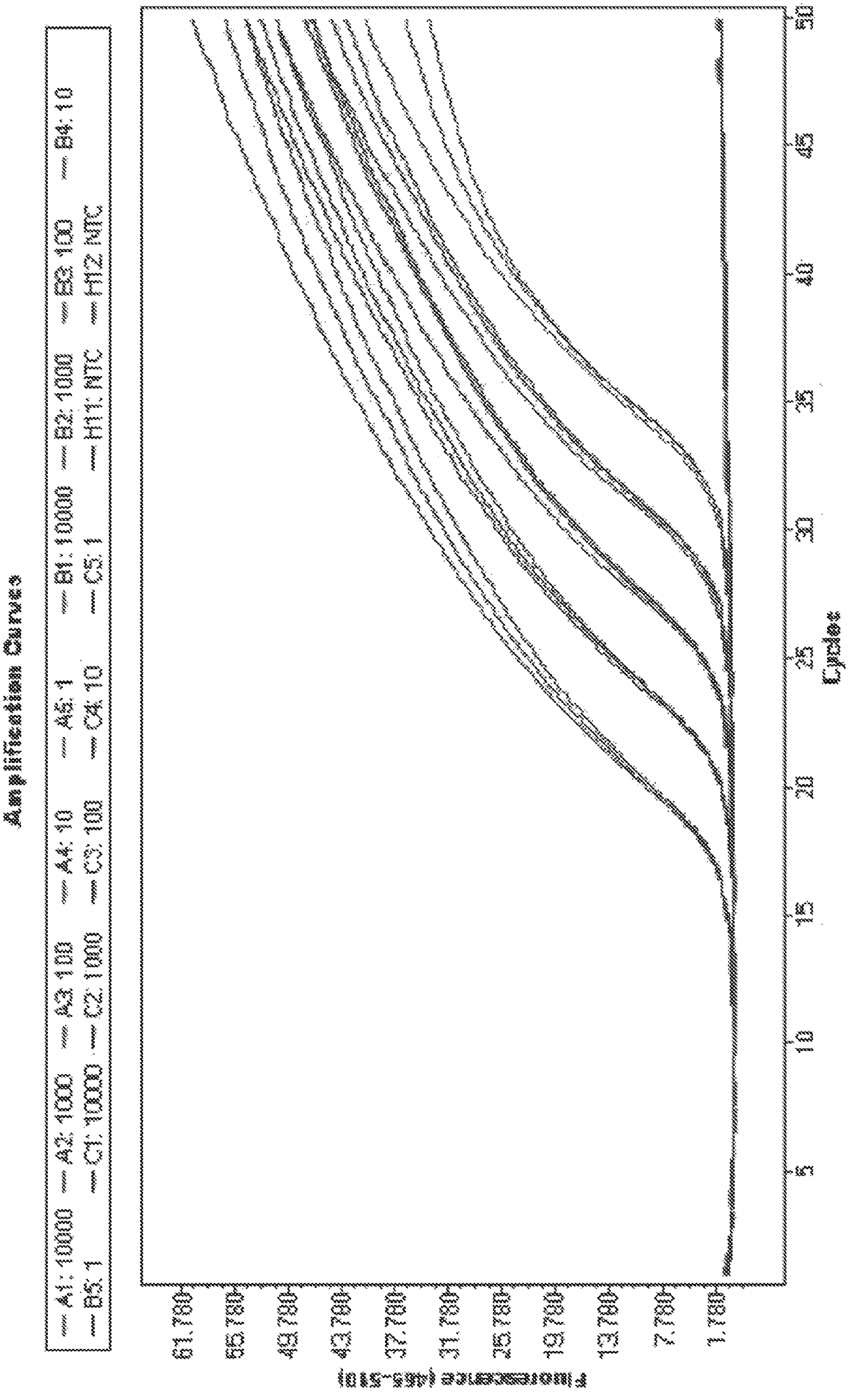
FIG. 15: Sensitivity testing on serial dilutions of *M. pneumoniae* with detection of 10000-1 cell equivalents
Figure 19:
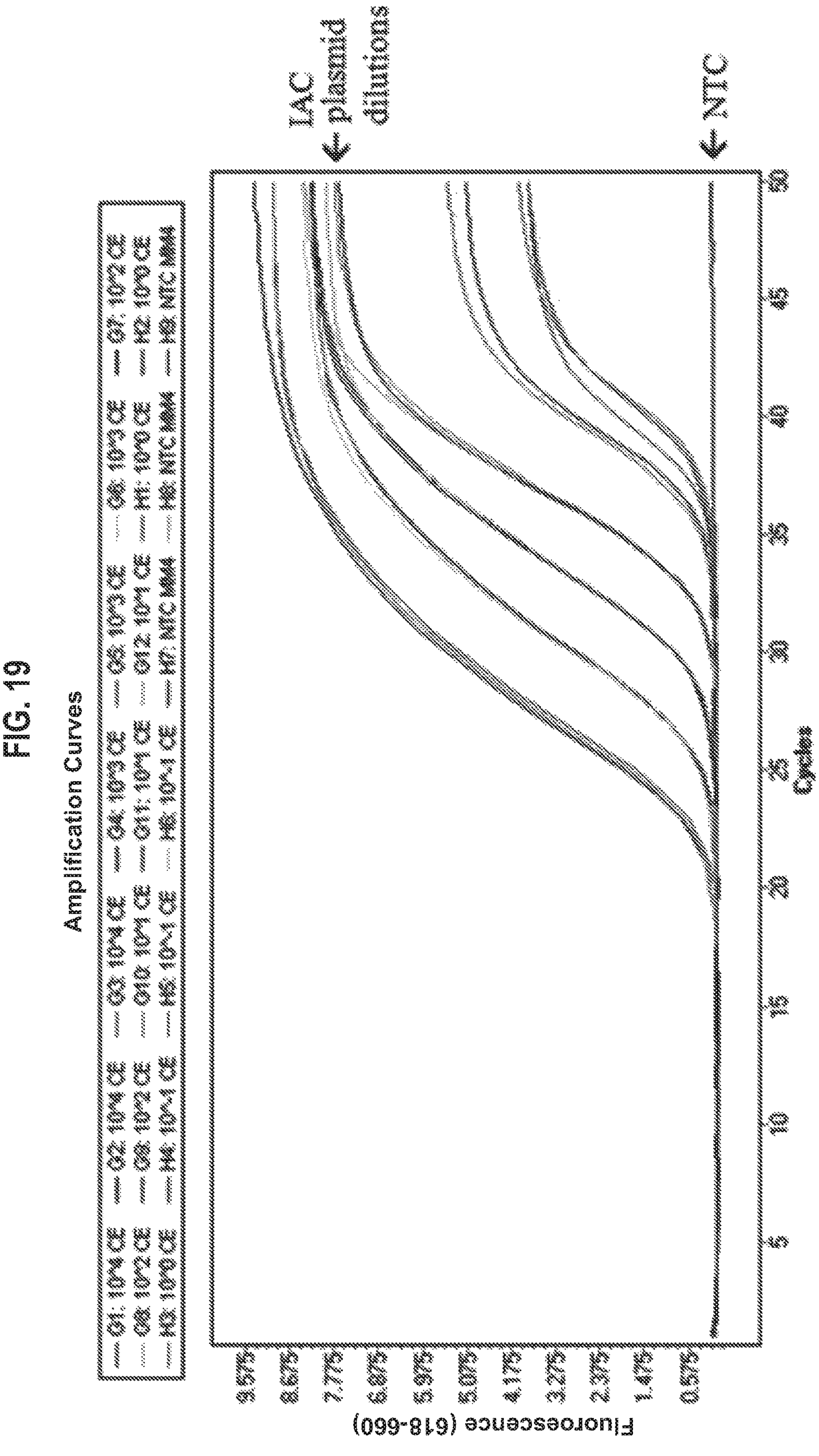
FIG. 19: Sensitivity testing on serial dilutions of plasmid PIAC DNA with detection of 10*4-0.1 cell equivalents

As demonstrated in FIG. 14, all 4 *Mycoplasma pneumoniae* strains were detected by the smpB assay. The sensitivity of the assay was demonstrated by testing serial dilutions of M pneumonia (FIG. 15).

Conclusion

The real-time PCR assay described in this example is the first description of a real-time PCR diagnostics assay for the identification of *Mycoplasma pneumoniae* using the novel smpB diagnostics targets. This diagnostics assay takes approximately one hour to perform after genomic DNA extraction and purification.

Example 6—Real-Time PCR Assay for the Specific Detection of *Mycobacterium avium, M Intracellulare* and the MTC In Silico Analysis Publicly available smpB Nucleotide sequence information was retrieved from the National Center for Biotechnology Information website (see the internet at www.ncbi.nlm-.nih.gov/) for *Myocbacterium* species and aligned using ClustalW (see the internet at www.ebi.ac.uk/Tools/msa/clustalw2/) (FIG. 16). This demonstrated that sufficient nucleotide heterogeneity was present in the smpB gene to design oligonucleotide primers and probes specific for *Mycobacterium avium, Mycobacterium intracellulare* and the *Mycobacterium tuberculosis* complex (MTC) (Table 18).

TABLE 18

| Oligonucleotide primers and probes used in Example 6. | | | |
|---|---|---|---|
| Name | Function | Orientation 5'-3' | SEQ ID NO: |
| M. av_avp FwP | *M. avium/M. avium paratuberculosis* forward primer | CGTTGCAAGGAACCGAGGT | SEQ ID NO: 24 |
| M. av_avp RvP | *M. avium/M. avium paratuberculosis* reverse primer | GTCGTGATTGGTCCAGCTACC | SEQ ID NO: 25 |
| M. av_avp P | *M. avium/M. avium paratuberculosis* probe | CAAGCGTCGTTAGCTGACGCGTTC | SEQ ID NO: 26 |
| M. int FwP | *M. intracellulare* forward primer | GCTGCAAGGCACCGAGGTC | SEQ ID NO: 27 |
| M. int RvP | *M. intracellulare* reverse primer | GTCATGATTGGTCCAGCTACC | SEQ ID NO: 28 |
| M. int P | *M. intracellulare* probe | CAAGCTTCGTTAGCTGACGCCTTC | SEQ ID NO: 29 |
| MTC FwP | MTC forward primer | CAAGGCACGGAGGTGAAGAGC | SEQ ID NO: 6 |
| MTC RvP | MTC reverse primer | CTCGTGGTTGGTCCAGCTGCC | SEQ ID NO: 11 |
| MTC_P | MTC probe | CAGGCGTCGCTGGCCGATTCGTTCGCCA | SEQ ID NO: 13 |

Example 7—Multiplex Real-Time PCR Assay for the Detection of *Legionella* Species and *Legionella pneumophila*

In Silico Analysis

Publicly available ssrA Nucleotide sequence information was retrieved from the National Center for Biotechnology Information website (see the internet at www.ncbinlm.nih.gov/) for *Legionella* species and aligned using ClustalW (see the internet at www.ebi.n.uk/Tools/msa/clustalw2/) (FIG. 18). This demonstrated that sufficient nucleotide heterogeneity was present in the ssrA gene to design oligonucleotide primers and probes specific for the *Legionella* species, (Table 19).

TABLE 19

| Oligonucleotide primers and probes used in Example 7. | | | |
|---|---|---|---|
| Name | Function | Orientation 5'-3' | SEQ ID NO: |
| Leg ssrA F1 | Forward Seqeuncing primer | TGCAAACGATGAAAACTTTGC | SEQ ID NO: 40 |
| Leg ssrA R1 | Real-time PCR assay Reverse primer | CTCTGCCTTTAGCTCTACATG | SEQ ID NO: 41 |
| Leg ssrA P3 | Real-time PCR assay Probe | Fam-YGGTATCGAATCAACGGTCATARRA-BHQ1 | SEQ ID NO: 39 |

The oligonucleotide primers and probes specific *Legionella pneumophila* of Example 2 were combined with the ssrA to produce a multiplex PCR assay that allows simultaneous identification of two bacterial organism groups: i) a *Legionella* species and ii) *Legionella pneumophila.*

Development of Triplex Real-Time PCR Assay for the Detection of *Legionella* Species and the Specific Identification of *Legionella pneumophila.*

To demonstrate the specificity of the triplex real-time PCR, reactions were carried out on the LightCycler 480 using the LightCycler 480 Probes Master kit (Roche Diagnostics, Basel, Switzerland). The optimised PCR mix contained 2×LightCycler 480 Probes Master (6.4 mM $MgCl_2$), *Legionella* species forward and reverse primer (0.5 μM final conc.), FAM labelled *Legionella* species probe (0.2 μM final conc.), *Legionella pneumophila* forward and reverse primer (0.5 μM final conc.), HEX labelled *Legionella pneumophila* probe (0.2 μM final conc.) IAC forward and reverse primer (0.5 μM final conc.), and Cy5 labelled IAC probe (0.2 μM final conc.), template DNA (Target: 5 μl; IAC: 2 μl) adjusted to a final volume of 20 μl with the addition of nuclease free $dH_2O$. The plasmid IAC DNA internal control DNA was diluted to contain 1000 genome equivalents per 2 μl and all other DNA used in this study was diluted to contain ~$10^4$ genome equivalents per 5

The cycling parameters consisted of 10 min incubation at 95° C. to activate the Taq, 50 cycles of 95° C. for 10 s and 63° C. for 30 s, followed by a single cooling step at 40° C. for 10 s. The temperature ramp rate on the LightCycler 480 was 4.4° C./s while heating and 2.2° C./s while cooling. A colour compensation file was generated, to avoid fluorescence leaking from channel to channel, prior to experimental analysis on the LightCycler 480, as per manufacturer's instructions.

Specificity of the Multiplex Diagnostic Assays

Figure 20A:
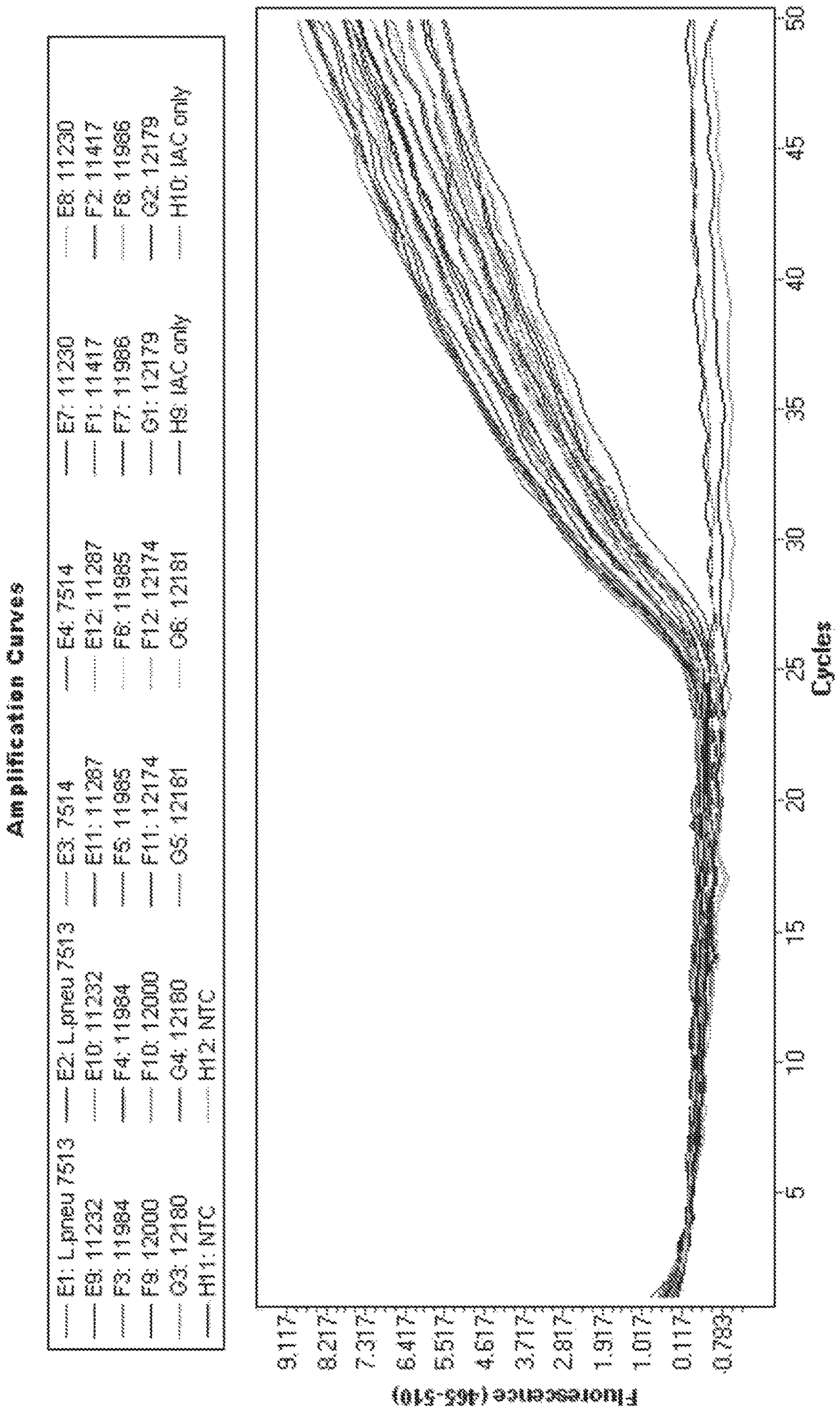
FIG. 20A-20C: Real-time amplification curves. The amplification curves generated in each of the analysis channels for the *Legionella* species, *Legionella* pneumonia and IAC triplex assay (ssrA, smpB and PIAC)
Figure 20B:
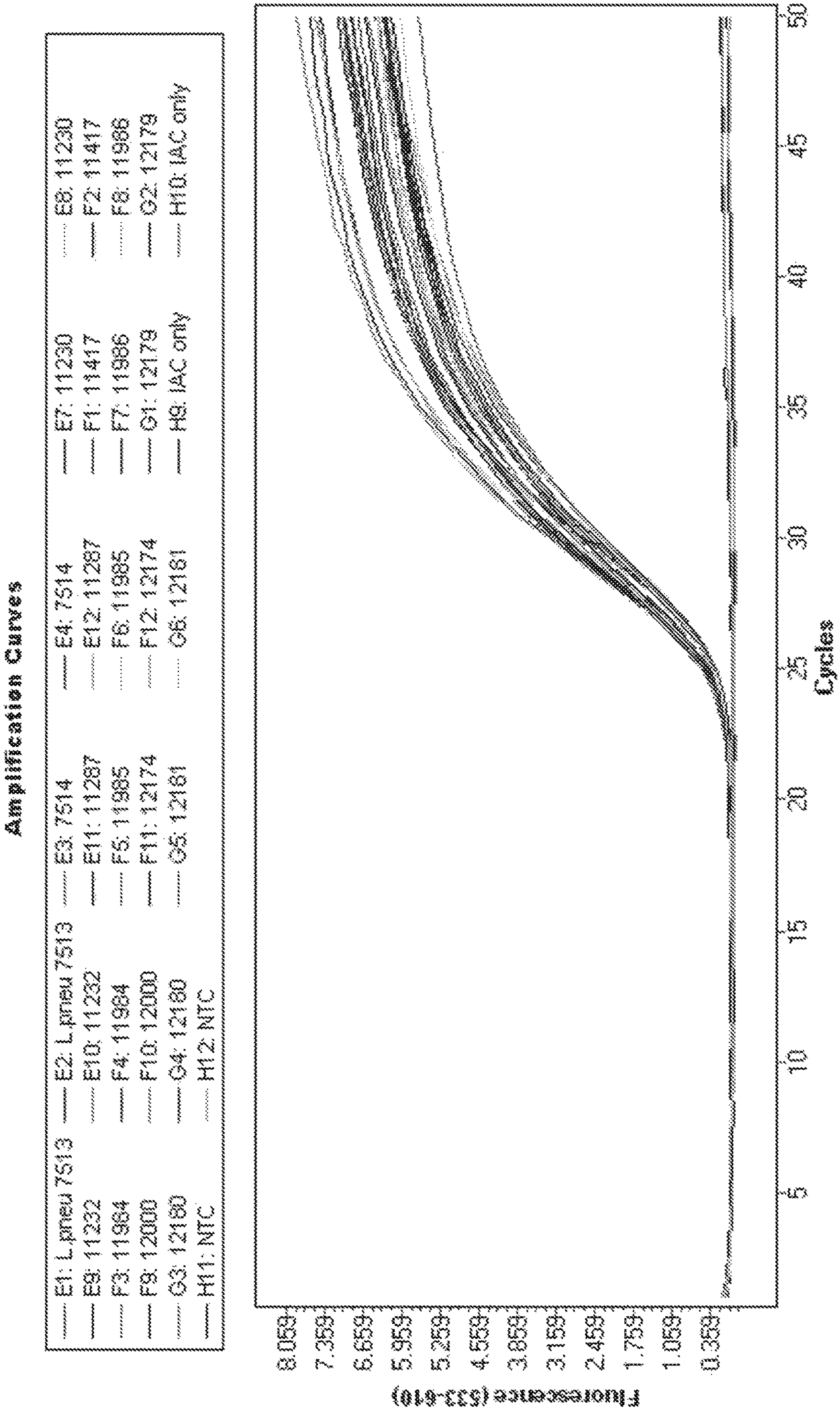
Figure 20C:
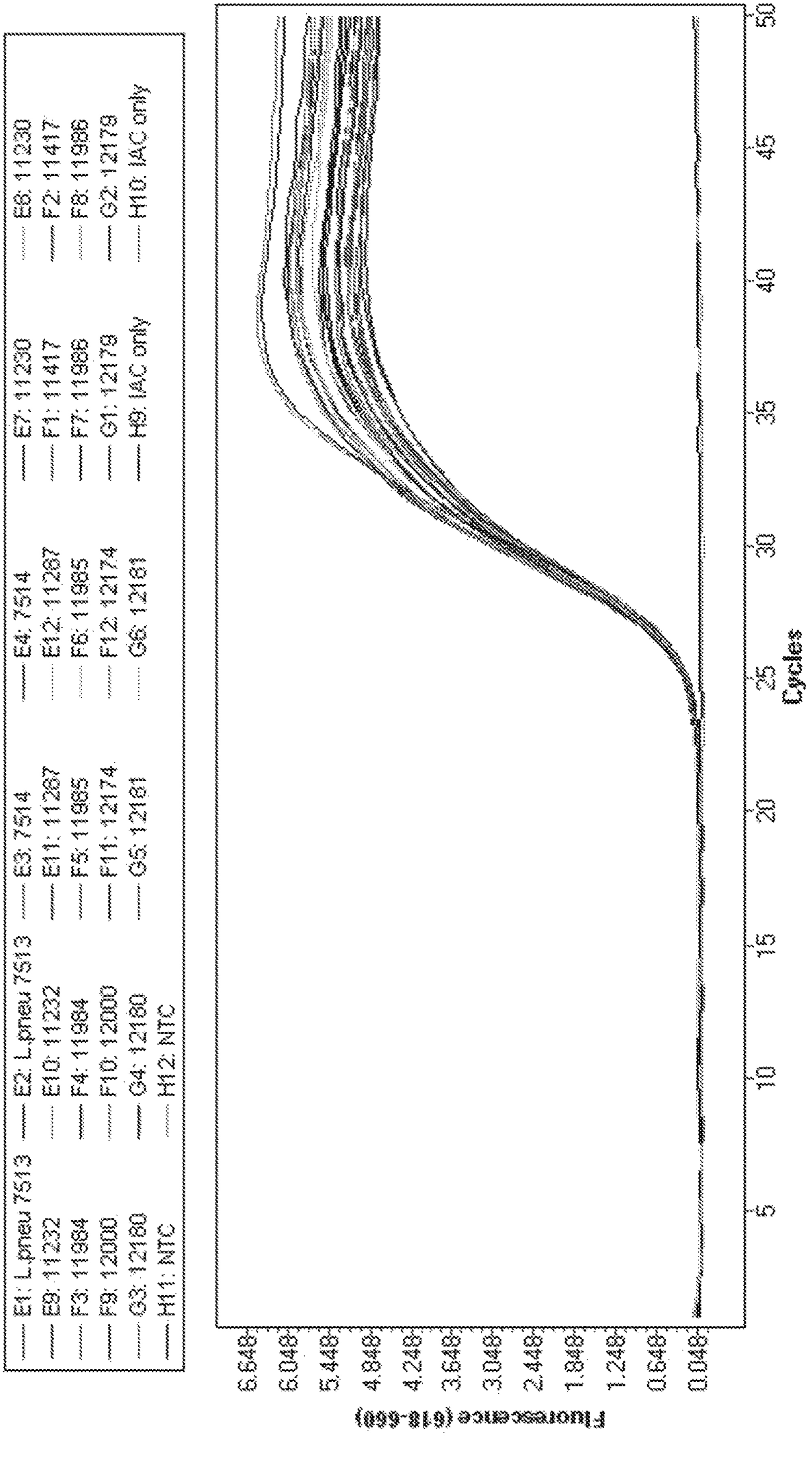

The specificity of the real-time PCR diagnostics assay developed in this study was confirmed using the specificity panel listed in Table 20. For inclusivity and exclusivity testing, each sample was tested in triplicate at a concentration of ~1×$10^4$ genome equivalents. The ssrA based *Legionella* assay detected all 26 species and strains of *Legionella* tested for; The IAC and no template controls were not detected by the assay (FIG. 20A). The smpB-based *L. pneumophila* specific assay detected all 19 *L. pneumophila* strains tested and did not detect the remaining 7 *Legionella* species. The IAC or no template controls were also not detected in this assay (FIG. 20A). The IAC, at a concentration of 100 genome equivalents, was detected in all samples tested (FIG. 20C).

Conclusion

The multiplex real-time PCR assay described in this example is the first description of a real-time PCR diagnostics assay for the detection of the *Legionella* species and specific identification of *Legionella pneumophila* using the combination of the ssrA and novel smpB diagnostics targets. This diagnostics assay takes approximately one hour to perform after genomic DNA extraction and purification.

Sequences

H.*influenzae* smpB nucleotide (Accession Number HI0981)-

SEQ ID NO: 1 atgacaaagaaaaaagtaaaacccaattcaaatactatcgcactaaataa acgtgcaagacacgattattttattgaagatgaaattgaagcaggtcttg aattacaaggctgggaagtcaaatctatgcgcgcaggcaaggcaaatatt agtgatagttatgttatttttaaaaatggcgaagcctttttattcggcgc aagcattcagccattaaatgttgcatcaacgcatattgtttgtgatccaa ctcgcactcgtaagttattgttaaataaacgcgaattagcatccctattt ggtaaagcaaaccgagacggttttaccatagttgcactttctctttattg gaaaagtgcgtgggcaaaagtcaaaatcggtttagccaaaggtaaaaaac aacaggataaacgtgatgatattaaagaacgtgaatggaaagtaacaaaa gatcgcattatgaaaaatgcacatcgaagatcttaa H.influenzae smpB protein (Accession Number HI0981)-

SEQ ID NO: 2

MTKKKVKPNSNTIALNKRARHDYFIEDEIEAGLELQGWEVKSMRAGKANI

SDSYVIFKNGEAFLFGASIQPLNVASTHIVCDPTRTRKLLLNKRELASLF

GKANRDGFTIVALSLYWKSAWAKVKIGLAKGKKQQDKRDDIKEREWKVTK

DRIMKNAHRRS

*H. influenzae* smpB F1-

SEQ ID NO: 3

ATTAAATGTYGCATCAACGC

*H. influenzae* smpB R1-

SEQ ID NO: 4

GACTTTTGCCCACGCAC

*H. influenzae* smpB P1-

SEQ ID NO: 5

ACGRTTTTACCATAGTTGCACTTTCTC

-continued

MTC FwP-

SEQ ID NO: 6

CAAGGCACGGAGGTGAAGAGC

*Bacillus subtilis* F1-

SEQ ID NO: 7

AACGTAGCATTAGCTGC

*Bacillus subtilis* R1-

SEQ ID NO: 8

CTCATCTTCTTGCCTGC

*Bacillus subtilis* P1-

SEQ ID NO: 9

CACATCCAAGTAGGCTACGCT

LegPneuF1-

SEQ ID NO: 10

CACGTGATAATMAAATACGGTG

MTC RvP-

SEQ ID NO: 11

CTCGTGGTTGGTCCAGCTGCC

LegPneuR1-

SEQ ID NO: 12

TTCATCAAYAGCTTGCGYG

MTC_P-

SEQ ID NO: 13

CAGGCGTCGCTGGCCGATTCGTTCGCCA egPneuP3-

SEQ ID NO: 14

CYGCATCCACTCATTTTATTCCTGAT

A.baum smpB F1-

SEQ ID NO: 15

TGGCATGTCTTTACTAGGCT

A.baum smpB R1-

SEQ ID NO: 16

GCACAATATGTGTAGATGCAGA

A.baum smpB P-

SEQ ID NO: 17

TGGTGCTCAGATTCAACCACTCC

L.gra smpB F1-

SEQ ID NO: 18

CGGCATTGTCTTGCAAG

L.gra smpB R1-

SEQ ID NO: 19

GCTGATATGCATGTTGTGTA

L.gra smpB PHEX2-

SEQ ID NO: 20

AGTTCACTCGTGCATTACGAAC

Mpneu_F1-

SEQ ID NO: 21

TTAGCATTTCGCCCTATGC

Mpneu_R-

SEQ ID NO: 22

AGTCCTTCTTGCTTTTGGC

Mpneu_P1-

SEQ ID NO: 23

CCACCCCTTCAAACGGGTGA

M av_avp FwP-

SEQ ID NO: 24

CGTTGCAAGGAACCGAGGT

M av_avp Rv-

SEQ ID NO: 25

GTCGTGATTGGTCCAGCTACC

-continued

M av_avp P-
SEQ ID NO: 26
CAAGCGTCGTTAGCTGACGCGTTC

M int FwP-
SEQ ID NO: 27
GCTGCAAGGCACCGAGGTC

M int RvP-
SEQ ID NO: 28
GTCATGATTGGTCCAGCTACC

M int P-
SEQ ID NO: 29
CAAGCTTCGTTAGCTGACGCCTTC

LgensmpB_
SEQ ID NO: 30
GATCAATACGAAGCAGGC

LgensmpB_R-
SEQ ID NO: 31
GCCATTCTCTGTCTTTGATC

Leg ssrA 1-
SEQ ID NO: 32
YGCAAAYRAWGMAAWSTTYGM

Leg ssrA R1-
SEQ ID NO: 33
CTCTGCCDTYAGHTCTACATG

Leg ssrA P3-
SEQ ID NO: 34
YGGTAYCGAATCAACGGTCATARRA

SIAC F2-
SEQ ID NO: 35
ATGCCAGTCAGCATAAGGA

SIAC R2-
SEQ ID NO: 36
CAGACCTCTGGTAGGATGTAC

*H. influenzae* smpB F1-
SEQ ID NO: 37
ATTAAATGTTGCATCAACGC

LegPneuR1-
SEQ ID NO: 38
TTCATCAATAGCTTGCGYG

Leg ssrA P3-
SEQ ID NO: 39
YGGTATCGAATCAACGGTCATARRA

Leg ssrA 1-
SEQ ID NO: 40
TGCAAACGATGAAAACTTTGC

Leg ssrA R1-
SEQ ID NO: 41
CTCTGCCTTTAGCTCTACATG

SIAC P1-
SEQ ID NO: 42
TCGGCACTACCGACACGAAC

SIAC_
SEQ ID NO: 43
ACCTCTAAGTAAGTGAGCGGTCGTGACATTATCCCTGATTTTCTCACTAC

TATTAGTACTCACGGCGCAATTCCACCACAGCCTTGTCTCGCCAGAATGC

CAGTCAGCATAAGGAAGAGCTCAAGGCAGGTCAACTCGCACTGTGAGGGT

CACATGGGCGTTCGGCACTACCGACACGAACCTCAGTTAGCGTACATCCT

ACCAGAGGTCTGTGGCCCCGTGGTCAAAAGTGCGGGTTTCGTATTTGCTG

CTCGTCAGTACTTTCAGAATCATGACCTGCACGGCAAAGAGACGCTTATT

-continued

ATGGAGCTCGACATGGCAATAACGCGACGAATCTACGTCACGACGAGAAT

AGTGTAAACGAAGCTGCTGACGGCGGAAGCGTCAAAGGGGTCTGTGAATT

GTTATTCGCGAAAAACATCCGTCCCCGTGGGGGATAGTCACCGACGCCGT

TTTATAGAAGCCTAGGGGAACAGGTTGGTTTAACTAGCTTAAGAAAGTAA

REFERENCES

1 WO 00/70086
2 WO 2010/003765
3 Janda et al. (2007) J. Clin. Microbiol. 45(9):2761-2764
4 Acinas et al. (2004) Journal of Bacteriology 186:2629-2635
5 Větrovský et al. (2013) PLoS ONE 8:e57923
6 Killan (1976) J. Gen. Microbiol. 93:9-62
7 McCrea et al. (2008) J. Clin. Microbiol. 46:406-416
8 Binks et al. (2012) PLoS One 7:e34083
9 Bruin et al. (2014) Eur. J. Clin. Microbiol. Infect. Dis. 33:279-284
10 Zhu et al. (2013) PLoS One 8:e56139
11 Theodore et al. (2012) J. Clin. Microbiol. 50:1422-1424
12 Meyler et al. (2012) Diagn. Microbiol. Infect. Dis. 74:356-362
13 Wang et al. (2011) Int. J. Med. Microbiol. 301:303-309
14 Marroufi et al. (2007) J. Clin. Microbiol. 45:2305-2308
15 McDade et al. (1977) The New England Journal of Medicine 297:1197-1203
16 Baumann P (1968) Journal of Bacteriology, 96(1):39-42.
17 Perez F et al. (2007) Antimicrobial Agents and Chemotherapy 51(10):3471-3484.
18 Cunha (2006) Clinical and Microbiology and Infection 12:12-24
19 Atkinson et al. (2008) Epidemiology, clinical manifestations, pathogenesis and laboratory detection of *Mycoplasma pneumoniae* infections, vol. 32
20 Von Baum et al. (2009) BMC Infectious Diseases 9:62
21 Daxboeck et al. (2003) Clinical microbiology and infection: the official publication of the European Society of Clinical Microbiology and Infectious Diseases
22 Covert et al. (1999) Applied and environmental microbiology 65:2492-2496
23 Falkinham (2009) Journal of Applied Microbiology 107: 356-367.
24 LiPuma (2010) Clinical Microbiology Reviews 23:299-323.
25 Hoefsloot et al. (2013) The Journal of Infection 66:542-545.
26 Marras et al. (2002) Clinics in chest medicine 23:553-567.
27 Griffith et al. (2007) American Journal of Respiratory and Critical Care Medicine 175:367-416.
28 Huang et al. (2011) The official publication of the International Society for Heart Transplantation 30:790-798.
29 Van de Werf et al. (2014) BMC infectious diseases 14:62.
30 Van Ingen et al. (2009) Thorax 64: 502-506.
31 Moore et al. (2010) BMC Public Health 10:1-6.
32 Cassidy et al. (2009) Clinical Infectious Disease 49:e124-e129.
33 Adjemian et al. (2012) American Journal of Respiratory and Critical Care Medicine 185:881-886.
34 David et al. (2013) Emerg Infect Dis. 2013; 19(11):1889-91.

35 Crago et al. (2014) The Journal of hospital infection 87:59-62.
36 Hussein et al. (2009) International journal of medical microbiology 299:281-290.
37 Health Protection Surveillance Centre Scientific Advisory Committee. (2014) Guideline for the Prevention of Infection from Water Systems in Healthcare Facilities.
38 Livni et al. (2008) The Journal of hospital infection 70:253-258.
39 Shin et al. (2007) The Journal of hospital infection 65:143-148.
40 Hoefsloot et al. (2013) European Repsiratory Journal 42(6):1604-13
41 Flint, J. L. et al. (2004). Proceedings of the National Academy of Sciences of the United States of America 101, 12598-12603.
42 Brosch et al (2002). A new evolutionary scenario for the *Mycobacterium tuberculosis* complex. Proceedings of the National Academy of Sciences of the United States of America 99, 3684-3689.
43 Kiers, A. et al (2008). The International Journal of Tuberculosis and Lung Disease 12, 1469-1473.
44 Huard, R. C et al. (2003). J Clin Microbiol 41, 1637-1650.
45 Karzai et al. (1999) EMBO J. 18(13):3793-3799
46 Karzai et al. (2000) Nat. Struct. Mol. Biol. 7:449-455
47 Dulebohn et al. (2006) J. Biol. Chem. 281:28536-28545
48 Gil et al. (2004) Microbiol. Mol. Biol. Rev. 68:518-537
49 Rodriguez-Lazaro et al. (2004) FEMS Microbiol. Lett. 237; 119-126
50 Scheler et al. (2009) BMC Biotechnology 9:45
51 Nallur et al. (2001) Nucl. Acids Res. 29; e118
52 Dille et al. (1993) J. Clin. Microbiol. 31:729-731
53 Tortoli et al. (1997) J. Clin. Microbiol. 35:2424-2426
54 Voelkerding et al. (2009) Clin. Chem. 55:641-658
55 Halse et al. J. Clin. Microbiol. 48:1182-1188
56 *Current Protocols in Molecular Biology* (F. M. Ausubel et al., eds., 1987) Supplement 30
57 Smith & Waterman (1981) Adv. App. Math. 2:482-489
58 Reddington et al. (2011) J. Clin. Microbiol. 49:651-657
59 Mignard et al. (2008) International Journal of Systematic and Evolutionary Microbiology 58:1432-441
60 O'Grady et al. (2008) Food Microbiology 25:75-84
61 Schonhuber et al. (2001) BMC Microbiol. 1:20
62 Qin et al. (2006) Cell 127:721-733
63 Hoorfar et al. (2004) J. Clin. Microbiol. 42:1863-1868
64 Fleischmann et al. (1995) Science 269:496-512
65 Yun et al. (2006) Nucleic Acids Res. 34:e85
66 Couturier et al. (2011) J. Clin. Microbiol. 49:1104-1106
67 Seng et al. (2009) Clin. Infect. Dis. 49:543-551
68 EUCAST (2014) The European Committee on Antimicrobial Susceptibility Testing. Breakpoint tables for interpretation of MICs and zone diameters. Version 4.0 (see the internet at www.eucast.org).
69 Enne et al. (2008) FEMS Microbiol. Lett. 278:193-199
70 San Millan et al. (2007) 51:2260-2264
71 Ridderberg et al. (2010) J. Med. Microbiol. 59:740-742

The invention claimed is:

1. A method for determining the presence of at least one member, or absence of all members of a group of bacterial organisms in a sample in which the presence or absence of the group of bacterial organisms is to be determined, wherein the method comprises determining whether a target region of the smpB gene, which codes for the RNA binding protein small protein B, is present in said sample, wherein the target region is specific to the group of bacterial organisms and comprises one or more target sequences that, alone or in combination, are specific to the group of organisms to be detected, wherein the method comprises a polymerase chain reaction (PCR), wherein amplification and detection is carried out using primers and probes that, alone or in combination, are specific for the target region, and wherein the presence of the target region indicates at least one member of the group of bacterial organisms is present in the sample and absence of the target region indicates that all members of the group of bacterial organisms are absent from the sample.

2. The method of claim 1, wherein the group of bacterial organisms is a genus or the group of bacterial organisms is a bacterial species.

3. The method of claim 1, wherein the group of bacterial organisms is the Non Tuberculosis *Mycobacteria* (NTM) or the *Mycobacterium tuberculosis* Complex (MTC).

4. The method of claim 1, wherein the target region is at least 20, 30, 40, 50, 60, 70, 80, 90, 100, 120, 140, 160, 180, 200, 250, 300, 350, or 400 nucleotides in length.

5. The method of claim 1, wherein the target region comprises three sequences that, in combination, are specific to the group of bacterial organisms to be detected.

6. The method of claim 1, wherein a probe that is conjugated to a marker is used.

7. The method of claim 1, wherein (i) the group of bacterial organisms is a species and a. the bacterial species is *Legionella pneumophila* and the target region can be detected using primers comprising SEQ ID NO: 10 and SEQ ID NO: 12 and a probe comprising SEQ ID NO: 14;

b. the bacterial species is *Acinetobacter baumannii* and the target region can be detected using primers comprising SEQ ID NO: 15 and SEQ ID NO: 16 and a probe comprising SEQ ID NO: 17;

c. the bacterial species is *Mycoplasma pneumoniae* and the target region can be detected using primers comprising SEQ ID NO: 21 and SEQ ID NO: 22 and a probe comprising SEQ ID NO: 23;

d. the bacterial species is *Mycobacterium avium* and the target region can be detected using primers comprising SEQ ID NO: 24 and SEQ ID NO: 25 and a probe comprising SEQ ID NO: 26;

e. the bacterial species is *Mycobacterium intracellulare* and the target region can be detected using primers comprising SEQ ID NO: 27 and SEQ ID NO: 28 and a probe comprising SEQ ID NO: 29;

f. the bacterial species is *Haemophilus influenzae* and the target region can be detected using primers comprising SEQ ID NO: 3 and SEQ ID NO: 4 and a probe comprising SEQ ID NO: 5;

g. the bacterial species is *Listeria grayi* and the target region can be detected using primers comprising SEQ ID NO: 18 and SEQ ID NO: 19 and a probe comprising SEQ ID NO: 20; or (ii) the group of bacterial organisms is the *Mycobacterium tuberculosis* complex and the target region can be detected using primers comprising SEQ ID NO: 6 and SEQ ID NO: 11 and a probe comprising SEQ ID NO: 13.

8. The method of claim 1, wherein the PCR produces an amplicon that is up to 40, 50, 60, 70, 80, 90, 100, 110, 120, 130, 140, 150, 160, 170, 180, 190, 200, 250, 300, 350, 400 or 450 nucleotides in length.

9. The method of claim 1, wherein (i) the group of bacterial organisms is a species and a. the bacterial species is *Legionella pneumophila* and the primers comprise SEQ ID NO: 10 and SEQ ID NO: 12;

b. the bacterial species is *Acinetobacter baumannii* and the primers comprise SEQ ID NO: 15 and SEQ ID NO: 16;

c. the bacterial species is *Mycoplasma pneumoniae* and the primers comprise SEQ ID NO: 21 and SEQ ID NO: 22;

d. the bacterial species is *Myocobacterium avium* and the primers comprise SEQ ID NO: 24 and SEQ ID NO: 25;

e. the bacterial species is *Mycobacterium intracellulare* and the primers comprise SEQ ID NO: 27 and SEQ ID NO: 28;

f. the bacterial species is *Haemophilus influenzae* and the primers comprise SEQ ID NO: 3 and SEQ ID NO: 4;

g. the bacterial species is *Listeria grayi* and the primers comprise SEQ ID NO: 18 and SEQ ID NO: 19; or (ii) the group of bacterial organisms is the *Mycobacterium tuberculosis* complex and the primers comprise SEQ ID NO: 6 and SEQ ID NO: 11.

10. The method of claim 1, wherein the method comprises a multiplex PCR, or the method comprises an Internal Amplification Control (IAC).

11. The method of claim 10, wherein the group of bacterial organisms is a species, wherein the bacterial species is *L. pneumophila*, said method further comprising determining the presence or absence of a member of the *Legionella* genus by determining whether a target region of the ssrA gene is present in said sample.

12. The method of claim 11, wherein the IAC comprises a sequence that can be amplified and detected using primers comprising SEQ ID NOs: 35 and 36 and a probe comprising SEQ ID NO: 42.

13. The method of claim 10, wherein the IAC comprises a target region of the ssrA gene which can be amplified and detected using primers comprising SEQ ID NO: 7 and SEQ ID NO: 8 and a probe comprising SEQ ID NO: 9.

14. The method of claim 1, wherein the sample is an environmental sample, a clinical sample, a food product sample or a clinical product sample.

15. The method of claim 1, wherein the sample is selected from the group consisting of a sputum sample, a pus sample, a lung fluid sample, a lymph node sample, a pleural fluid sample, a pleural tissue sample, a blood sample, a plasma sample, a serum sample, a urine sample, a fecal sample, a tissue sample, and a saliva sample.

16. The method of claim 2, wherein the bacterial species is selected from the group consisting of *Legionella pneumophila, Acinetobacter baumannii, Mycoplasma pneumoniae, Mycobacterium intracellulare, Mycobacterium avium, Haemophilus influenzae* and *Listeria grayi*, or the bacterial species is selected from the group consisting of *Legionella pneumophila, Acinetobacter baumannii* and *Haemophilus influenza.*

17. The method of claim 6, wherein the marker is a fluorescent marker.

18. The method of claim 9, wherein (i) the group of bacterial organisms is a species and a. the bacterial species is *Legionella pneumophila* and the probe comprises SEQ ID NO: 14;

b. the bacterial species is *Acinetobacter baumannii* and the probe comprises SEQ ID NO: 17;

c. the bacterial species is *Mycoplasma pneumoniae* and the probe comprises SEQ ID NO: 23;

d. the bacterial species is *Myocobacterium avium* and the probe comprises SEQ ID NO: 26;

e. the bacterial species is *Mycobacterium intracellulare* and the probe comprises SEQ ID NO: 29;

f. the bacterial species is *Haemophilus influenzae* and the probe comprises SEQ ID NO: 5;

g. the bacterial species is *Listeria grayi* and the probe comprises SEQ ID NO: 20; or (ii) the group of bacterial organisms is the *Mycobacterium tuberculosis* complex and the probe comprises SEQ ID NO: 13.

19. The method of claim 11, wherein the target region of the ssrA gene can be amplified and detected using primers comprising SEQ ID NO: 32 and 33 and a probe comprising SEQ ID NO: 34.

* * * * *